(12) United States Patent
Lim et al.

(10) Patent No.: US 9,554,742 B2
(45) Date of Patent: Jan. 31, 2017

(54) FLUID ANALYSIS SYSTEM

(71) Applicant: OptiScan Biomedical Corporation, Hayward, CA (US)

(72) Inventors: Eugene Lim, Lafayette, CA (US); Roger Tong, Berkeley, CA (US); Peter Rule, Los Altos Hills, CA (US); James R. Braig, Piedmont, CA (US); Richard Keenan, Livermore, CA (US); David N. Callicoat, Hayward, CA (US)

(73) Assignee: OptiScan Biomedical Corporation, Hayward, CA (US)

( * ) Notice: Subject to any disclaimer, the term of this patent is extended or adjusted under 35 U.S.C. 154(b) by 0 days.

(21) Appl. No.: 14/589,867

(22) Filed: Jan. 5, 2015

(65) Prior Publication Data

US 2015/0119663 A1  Apr. 30, 2015

Related U.S. Application Data

(63) Continuation-in-part of application No. 13/542,350, filed on Jul. 5, 2012, now Pat. No. 8,928,877, and a
(Continued)

(51) Int. Cl.
*G01N 33/48* (2006.01)
*A61B 5/157* (2006.01)
(Continued)

(52) U.S. Cl.
CPC ............. *A61B 5/157* (2013.01); *A61B 5/1427* (2013.01); *A61B 5/1455* (2013.01);
(Continued)

(58) Field of Classification Search
CPC .................................................... G01N 33/48
(Continued)

(56) References Cited

U.S. PATENT DOCUMENTS 2,797,149 A   6/1957 Skeggs
3,634,039 A   1/1972 Brondy
(Continued)

FOREIGN PATENT DOCUMENTS

EP   0470202   2/1992
EP   0483117   4/1992
(Continued)

OTHER PUBLICATIONS

International Search Report and Written Opinion for PCT Application No. PCT/US2012/045587, dated Sep. 24, 2012.
(Continued)

*Primary Examiner* — Roy M Punnoose
(74) *Attorney, Agent, or Firm* — Knobbe, Martens, Olson & Bear, LLP

(57) ABSTRACT

Systems and method are disclosed for determining a concentration of an analyte in a fluid (e.g., blood). The system can draw blood from a patient and deliver the blood to a sample cell. A particular component of the fluid (e.g., plasma) may be separated and/or positioned such that the concentration of the analyte is measured in the particular component of the fluid (e.g., plasma). The sample cell can include a sample container that has two window pieces. The system can have a fluid passage having a tip configured to mate with a multi-lumen catheter without leaking. The multi-lumen catheter can have proximal and distal ports. A fluid pressure system can be configured to periodically draw fluid from vasculature through a proximal intravascular opening and the proximal port while maintaining a low pressure and/or flow rate to thereby reduce risk of reversing the fluid flow in a vessel and drawing infusates upstream into another intravascular opening.

20 Claims, 53 Drawing Sheets

Related U.S. Application Data continuation-in-part of application No. 13/552,542, filed on Jul. 18, 2012, and a continuation-in-part of application No. 13/156,295, filed on Jun. 8, 2011, now Pat. No. 9,091,676, and a continuation-in-part of application No. 13/162,315, filed on Jun. 16, 2011, and a continuation-in-part of application No. 14/259,940, filed on Apr. 23, 2014, which is a continuation of application No. 13/068,121, filed on May 3, 2011, now Pat. No. 8,731,639, which is a continuation-in-part of application No. 12/804,336, filed on Jul. 20, 2010, now Pat. No. 8,731,638, application No. 14/589,867, which is a continuation-in-part of application No. 14/257,920, filed on Apr. 21, 2014, now Pat. No. 9,326,717, which is a continuation of application No. 12/804,336, filed on Jul. 20, 2010, now Pat. No. 8,731,638.

(60) Provisional application No. 61/505,025, filed on Jul. 6, 2011, provisional application No. 61/509,487, filed on Jul. 19, 2011, provisional application No. 61/353,186, filed on Jun. 9, 2010, provisional application No. 61/355,982, filed on Jun. 17, 2010, provisional application No. 61/330,812, filed on May 3, 2010, provisional application No. 61/227,040, filed on Jul. 20, 2009.

(51) Int. Cl.

| | | |
|---|---|---|
| *A61B 5/1455* | (2006.01) | |
| *A61B 5/15* | (2006.01) | |
| *G01N 33/49* | (2006.01) | |
| *A61B 5/00* | (2006.01) | |
| *A61B 5/155* | (2006.01) | |
| *A61B 5/145* | (2006.01) | |
| *A61B 5/1459* | (2006.01) | |
| *A61B 5/153* | (2006.01) | |
| *G01N 21/03* | (2006.01) | |
| *G01N 21/07* | (2006.01) | |
| *A61M 5/172* | (2006.01) | |
| *G06F 19/00* | (2011.01) | |
| *A61M 5/142* | (2006.01) | |
| *G01N 21/35* | (2014.01) | |
| *A61M 5/14* | (2006.01) | |
| *A61M 5/168* | (2006.01) | |

(52) U.S. Cl.
CPC ........ *A61B 5/1459* (2013.01); *A61B 5/14532* (2013.01); *A61B 5/153* (2013.01); *A61B 5/15003* (2013.01); *A61B 5/155* (2013.01); *A61B 5/150221* (2013.01); *A61B 5/150229* (2013.01); *A61B 5/150236* (2013.01); *A61B 5/150267* (2013.01); *A61B 5/150755* (2013.01); *A61B 5/150992* (2013.01); *A61B 5/6866* (2013.01); *A61M 5/1723* (2013.01); *G01N 21/03* (2013.01); *G01N 21/07* (2013.01); *G01N 33/491* (2013.01); *G06F 19/3468* (2013.01); *A61B 5/14546* (2013.01); *A61B 5/14552* (2013.01); *A61B 5/14557* (2013.01); *A61B 2562/0233* (2013.01); *A61B 2562/0238* (2013.01); *A61M 5/142* (2013.01); *A61M 5/1415* (2013.01); *A61M 5/16827* (2013.01); *A61M 2005/14208* (2013.01); *A61M 2205/12* (2013.01); *A61M 2205/128* (2013.01); *G01N 21/35* (2013.01); *G01N 2021/0346* (2013.01)

(58) Field of Classification Search
USPC .................................................. 356/246, 39
See application file for complete search history.

(56) References Cited

U.S. PATENT DOCUMENTS

| | | |
|---|---|---|
| 3,690,836 A | 9/1972 | Buissiere et al. |
| 3,751,173 A | 8/1973 | Sanz et al. |
| 3,787,124 A | 1/1974 | Lowy et al. |
| RE28,801 E | 5/1976 | Acker et al. |
| 4,028,056 A | 6/1977 | Snyder et al. |
| 4,036,210 A | 7/1977 | Campbell et al. |
| 4,061,469 A | 12/1977 | Du Bose |
| 4,088,448 A | 5/1978 | Lilja et al. |
| 4,092,233 A | 5/1978 | Clemens et al. |
| 4,151,845 A | 5/1979 | Clemens |
| 4,303,376 A | 12/1981 | Siekmann |
| 4,328,185 A | 5/1982 | Reasons et al. |
| 4,405,235 A | 9/1983 | Rossiter |
| 4,421,503 A | 12/1983 | Latham, Jr. et al. |
| 4,440,301 A | 4/1984 | Intengan |
| 4,447,150 A | 5/1984 | Heinemann |
| 4,519,792 A | 5/1985 | Dawe |
| 4,526,569 A | 7/1985 | Bernardi |
| 4,531,932 A | 7/1985 | Luppi et al. |
| 4,537,561 A | 8/1985 | Xanthopoulos |
| 4,569,589 A | 2/1986 | Neufeld |
| 4,573,968 A | 3/1986 | Parker |
| 4,613,322 A | 9/1986 | Edelson |
| 4,654,197 A | 3/1987 | Lilja et al. |
| 4,657,490 A | 4/1987 | Abbott |
| 4,657,529 A | 4/1987 | Prince et al. |
| 4,696,798 A | 9/1987 | Timgren |
| 4,734,260 A * | 3/1988 | Lautenschlager ...... G01N 21/03 117/72 |
| 4,753,776 A | 6/1988 | Hillman et al. |
| 4,756,884 A | 7/1988 | Hillman et al. |
| 4,758,228 A | 7/1988 | Williams |
| 4,761,381 A | 8/1988 | Blatt et al. |
| 4,786,394 A | 11/1988 | Enzer et al. |
| 4,790,640 A | 12/1988 | Nason |
| 4,798,589 A | 1/1989 | Tseo |
| 4,810,090 A | 3/1989 | Boucher et al. |
| 4,818,190 A | 4/1989 | Pelmulder et al. |
| 4,818,493 A | 4/1989 | Coville et al. |
| 4,840,542 A | 6/1989 | Abbott |
| 4,850,980 A | 7/1989 | Lentz et al. |
| 4,854,836 A | 8/1989 | Borsanyi |
| 4,863,425 A | 9/1989 | Slate et al. |
| 4,873,993 A | 10/1989 | Meserol et al. |
| 4,900,322 A | 2/1990 | Adams |
| 4,919,596 A | 4/1990 | Slate et al. |
| 4,940,527 A | 7/1990 | Kazlauskas et al. |
| 4,948,961 A | 8/1990 | Hillman et al. |
| 4,963,498 A | 10/1990 | Hillman et al. |
| 4,968,137 A | 11/1990 | Yount |
| 4,976,270 A | 12/1990 | Parl et al. |
| 5,004,923 A | 4/1991 | Hillman et al. |
| 5,029,583 A | 7/1991 | Meserol et al. |
| 5,036,198 A | 7/1991 | Spaeth |
| 5,039,492 A | 8/1991 | Saaski et al. |
| 5,039,617 A | 8/1991 | McDonald et al. |
| 5,045,473 A | 9/1991 | Cassaday et al. |
| 5,096,669 A | 3/1992 | Lauks et al. |
| 5,134,079 A | 7/1992 | Cusack et al. |
| 5,135,719 A | 8/1992 | Hillman et al. |
| 5,139,023 A | 8/1992 | Stanley et al. |
| 5,140,161 A | 8/1992 | Hillman et al. |
| 5,147,606 A | 9/1992 | Charlton et al. |
| 5,149,501 A | 9/1992 | Babson et al. |
| 5,164,598 A | 11/1992 | Hillman et al. |
| 5,165,406 A | 11/1992 | Wong et al. |
| 5,173,193 A | 12/1992 | Schembri |
| 5,186,844 A | 2/1993 | Burd et al. |
| 5,204,532 A | 4/1993 | Rosenthal |
| 5,209,904 A | 5/1993 | Forney et al. |

(56) References Cited

U.S. PATENT DOCUMENTS

| | | |
|---|---|---|
| 5,223,219 A | 6/1993 | Subramanian et al. |
| 5,271,815 A | 12/1993 | Wong |
| 5,273,517 A | 12/1993 | Barone |
| 5,279,150 A | 1/1994 | Katzer et al. |
| 5,286,454 A | 2/1994 | Nilsson et al. |
| 5,304,348 A | 4/1994 | Burd et al. |
| 5,371,020 A | 12/1994 | Frischauf |
| 5,380,665 A | 1/1995 | Cusack et al. |
| 5,430,542 A | 7/1995 | Shepherd |
| 5,437,635 A | 8/1995 | Fields et al. |
| 5,457,053 A | 10/1995 | Burd et al. |
| 5,470,757 A | 11/1995 | Gagnon et al. |
| 5,489,414 A | 2/1996 | Schreiber et al. |
| 5,567,869 A | 10/1996 | Hauch et al. |
| 5,582,184 A | 12/1996 | Erickson et al. |
| 5,609,572 A | 3/1997 | Lang |
| 5,627,041 A | 5/1997 | Shartle |
| 5,674,457 A | 10/1997 | Williamsson et al. |
| 5,681,529 A | 10/1997 | Taguchi et al. |
| 5,693,233 A | 12/1997 | Schembri |
| 5,697,899 A | 12/1997 | Hillman et al. |
| 5,700,695 A | 12/1997 | Yassinzadeh et al. |
| 5,714,123 A | 2/1998 | Sohrab |
| 5,714,390 A | 2/1998 | Hallowitz et al. |
| 5,746,217 A | 5/1998 | Erickson et al. |
| 5,750,998 A | 5/1998 | Goldman |
| 5,758,643 A | 6/1998 | Wong et al. |
| 5,776,078 A | 7/1998 | Wardlaw |
| 5,801,057 A | 9/1998 | Smart et al. |
| 5,804,048 A | 9/1998 | Wong et al. |
| 5,815,258 A | 9/1998 | Nakanishi |
| 5,817,007 A | 10/1998 | Fodgaard et al. |
| 5,827,746 A | 10/1998 | Duic |
| 5,879,310 A | 3/1999 | Sopp et al. |
| 5,902,253 A | 5/1999 | Pfeiffer et al. |
| 5,916,201 A | 6/1999 | Wilson, Jr. et al. |
| 5,944,660 A | 8/1999 | Kimball et al. |
| 5,948,695 A | 9/1999 | Douglas et al. |
| 5,971,941 A | 10/1999 | Simons et al. |
| 5,977,545 A | 11/1999 | Haar et al. |
| 6,017,318 A | 1/2000 | Gauthier et al. |
| 6,030,581 A | 2/2000 | Virtanen |
| 6,036,924 A | 3/2000 | Simons et al. |
| 6,040,578 A | 3/2000 | Malin et al. |
| 6,066,243 A | 5/2000 | Anderson et al. |
| 6,077,055 A | 6/2000 | Vilks |
| 6,084,660 A | 7/2000 | Shartle |
| 6,084,661 A | 7/2000 | Mendelson et al. |
| 6,101,406 A | 8/2000 | Hacker et al. |
| 6,102,872 A | 8/2000 | Doneen et al. |
| 6,162,639 A | 12/2000 | Douglas |
| 6,197,494 B1 | 3/2001 | Oberhardt |
| 6,200,287 B1 | 3/2001 | Keller et al. |
| 6,214,629 B1 | 4/2001 | Freitag et al. |
| 6,236,870 B1 | 5/2001 | Madarasz et al. |
| 6,261,065 B1 | 7/2001 | Nayak et al. |
| 6,261,519 B1 | 7/2001 | Harding et al. |
| 6,262,798 B1 | 7/2001 | Shepherd et al. |
| 6,271,045 B1 | 8/2001 | Douglas et al. |
| 6,285,448 B1 | 9/2001 | Kuenstner |
| 6,312,888 B1 | 11/2001 | Wong et al. |
| 6,327,031 B1 | 12/2001 | Gordon |
| 6,372,182 B1 | 4/2002 | Mauro et al. |
| 6,426,045 B1 | 7/2002 | Jeng et al. |
| 6,491,656 B1 | 12/2002 | Morris |
| 6,503,209 B2 | 1/2003 | Hakky et al. |
| 6,512,577 B1 | 1/2003 | Ozanich |
| 6,521,182 B1 | 2/2003 | Shartle et al. |
| 6,531,095 B2 | 3/2003 | Hammer et al. |
| 6,591,124 B2 | 7/2003 | Sherman et al. |
| 6,652,136 B2 | 11/2003 | Marziali |
| 6,653,091 B1 | 11/2003 | Dunn et al. |
| 6,694,157 B1 | 2/2004 | Stone et al. |
| 6,817,984 B2 | 11/2004 | Robinson et al. |
| 6,890,291 B2 | 5/2005 | Robinson et al. |
| 6,926,834 B2 | 8/2005 | Coville et al. |
| 6,958,809 B2 | 10/2005 | Sterling et al. |
| RE38,869 E | 11/2005 | Polaschegg et al. |
| 6,966,880 B2 | 11/2005 | Boecker et al. |
| 6,979,309 B2 | 12/2005 | Burbank et al. |
| 6,983,177 B2 | 1/2006 | Rule et al. |
| 6,989,891 B2 | 1/2006 | Braig et al. |
| 7,011,742 B2 | 3/2006 | Rosiello |
| 7,050,157 B2 | 5/2006 | Braig et al. |
| 7,061,593 B2 | 6/2006 | Braig et al. |
| 7,115,205 B2 | 10/2006 | Robinson et al. |
| 7,244,232 B2 | 7/2007 | Connelly et al. |
| 7,480,032 B2 | 1/2009 | Braig et al. |
| 7,531,098 B2 | 5/2009 | Robinson et al. |
| 7,608,042 B2 | 10/2009 | Goldberger et al. |
| 7,738,085 B2 | 6/2010 | Braig et al. |
| RE41,946 E | 11/2010 | Anderson et al. |
| 7,860,542 B2 | 12/2010 | Sterling et al. |
| 7,860,543 B2 | 12/2010 | Sterling et al. |
| 7,872,734 B2 | 1/2011 | Braig et al. |
| 8,197,770 B2 | 6/2012 | Gable et al. |
| 8,412,293 B2 | 4/2013 | Rule |
| 8,928,877 B2 * | 1/2015 | Lim ............... G01N 21/07 356/246 |
| 2001/0027269 A1 | 10/2001 | Tanaka |
| 2002/0002343 A1 | 1/2002 | Hung et al. |
| 2002/0010405 A1 | 1/2002 | Hung et al. |
| 2002/0066458 A1 | 6/2002 | Aliberto et al. |
| 2002/0076354 A1 | 6/2002 | Cohen |
| 2002/0106661 A1 | 8/2002 | Virtanen |
| 2002/0147423 A1 | 10/2002 | Burbank et al. |
| 2002/0160517 A1 | 10/2002 | Modzelewski et al. |
| 2003/0091477 A1 | 5/2003 | Paul et al. |
| 2003/0120210 A1 | 6/2003 | Worthen et al. |
| 2003/0221206 A1 | 11/2003 | Schatten et al. |
| 2003/0225336 A1 | 12/2003 | Callister et al. |
| 2004/0027659 A1 | 2/2004 | Messerschmidt et al. |
| 2004/0053322 A1 | 3/2004 | McDevitt et al. |
| 2004/0082899 A1 | 4/2004 | Mathias et al. |
| 2004/0127841 A1 | 7/2004 | Briggs |
| 2004/0132167 A1 | 7/2004 | Rule et al. |
| 2004/0132168 A1 | 7/2004 | Rule et al. |
| 2004/0147034 A1 | 7/2004 | Gore et al. |
| 2004/0167478 A1 | 8/2004 | Mooney et al. |
| 2004/0241736 A1 | 12/2004 | Hendee et al. |
| 2004/0249308 A1 | 12/2004 | Forssell |
| 2005/0036146 A1 | 2/2005 | Braig et al. |
| 2005/0037384 A1 | 2/2005 | Braig et al. |
| 2005/0038357 A1 | 2/2005 | Hartstein et al. |
| 2005/0094127 A1 | 5/2005 | O'Mahony et al. |
| 2005/0105095 A1 | 5/2005 | Pesach et al. |
| 2005/0106749 A1 | 5/2005 | Braig et al. |
| 2005/0203360 A1 | 9/2005 | Brauker et al. |
| 2005/0284815 A1 | 12/2005 | Sparks et al. |
| 2006/0004267 A1 | 1/2006 | Rule et al. |
| 2006/0009727 A1 | 1/2006 | O'Mahony et al. |
| 2006/0029923 A1 | 2/2006 | Togawa et al. |
| 2006/0189925 A1 | 8/2006 | Gable et al. |
| 2006/0189926 A1 | 8/2006 | Hall et al. |
| 2006/0195046 A1 | 8/2006 | Sterling et al. |
| 2006/0200070 A1 | 9/2006 | Callicoat et al. |
| 2006/0229531 A1 | 10/2006 | Goldberger et al. |
| 2006/0258522 A1 | 11/2006 | Cornay et al. |
| 2007/0060872 A1 | 3/2007 | Hall et al. |
| 2007/0083091 A1 | 4/2007 | Sterling et al. |
| 2007/0104616 A1 | 5/2007 | Keenan et al. |
| 2007/0129618 A1 | 6/2007 | Goldberger et al. |
| 2007/0142720 A1 | 6/2007 | Ridder et al. |
| 2007/0225675 A1 | 9/2007 | Robinson et al. |
| 2007/0240497 A1 | 10/2007 | Robinson et al. |
| 2007/0244381 A1 | 10/2007 | Robinson et al. |
| 2007/0244382 A1 | 10/2007 | Robinson et al. |
| 2008/0086042 A1 | 4/2008 | Brister et al. |
| 2008/0194964 A1 | 8/2008 | Randall et al. |
| 2009/0048535 A1 | 2/2009 | Robinson et al. |
| 2009/0048576 A1 | 2/2009 | Robinson et al. |
| 2009/0100944 A1 | 4/2009 | Newby |
| 2009/0156922 A1 | 6/2009 | Goldberger et al. |
| 2009/0156975 A1 | 6/2009 | Robinson et al. |

(56) References Cited

U.S. PATENT DOCUMENTS

| | | |
|---|---|---|
| 2009/0192409 A1 | 7/2009 | Wong et al. |
| 2010/0030137 A1 | 2/2010 | Hall et al. |
| 2010/0160854 A1 | 6/2010 | Gauthier |
| 2010/0204618 A1 | 8/2010 | Min et al. |
| 2010/0217238 A1 | 8/2010 | DeJournett |
| 2010/0273738 A1 | 10/2010 | Valcke et al. |
| 2010/0279405 A1 | 11/2010 | Peterson et al. |
| 2010/0331644 A1 | 12/2010 | Neale et al. |
| 2011/0009720 A1 | 1/2011 | Kunjan et al. |
| 2011/0208023 A1 | 8/2011 | Goodall et al. |
| 2011/0313318 A1 | 12/2011 | Rule et al. |
| 2013/0114068 A1* | 5/2013 | Lim .................. G01N 21/07 356/39 |
| 2014/0058235 A1 | 2/2014 | Le et al. |

FOREIGN PATENT DOCUMENTS

| | | |
|---|---|---|
| EP | 0488994 | 6/1992 |
| EP | 0549341 | 6/1993 |
| EP | 1491144 | 12/2004 |
| EP | 2251453 | 11/2010 |
| EP | 2251671 | 11/2010 |
| GB | 2128360 | 4/1984 |
| JP | 61 203947 | 9/1986 |
| JP | 03-012134 | 1/1991 |
| JP | 08-114539 | 5/1996 |
| JP | 2003-102710 | 4/2003 |
| WO | WO 93/00580 | 1/1993 |
| WO | WO 97/25608 | 7/1997 |
| WO | WO 98/35225 | 8/1998 |
| WO | WO 99/04041 | 8/1999 |
| WO | WO 99/52633 | 10/1999 |
| WO | WO 00/29847 | 5/2000 |
| WO | WO 01/53806 | 7/2001 |
| WO | WO 02/38201 | 5/2002 |
| WO | WO 02/39446 | 5/2002 |
| WO | WO 02/43866 | 6/2002 |
| WO | WO 02/46761 | 6/2002 |
| WO | WO 02/46762 | 6/2002 |
| WO | WO 03/016882 | 2/2003 |
| WO | WO 03/039362 | 5/2003 |
| WO | WO 2004/079343 | 9/2004 |
| WO | WO 2004/092715 | 10/2004 |
| WO | WO 2005/110601 | 11/2005 |
| WO | WO 2006/039310 | 4/2006 |

OTHER PUBLICATIONS

International Preliminary Report on Patentability for PCT Application No. PCT/US2012/045587, dated Jan. 7, 2014.
International Search Report and Written Opinion in App. No. PCT/US2011/040783, dated Oct. 18, 2011 in 18 pages.
Berger et al., "An Enhanced Algorithm for Linear Multivariate Calibration", Anal. Chem., No. 70, pp. 623-627, 1998.
Billman et. al., "Clinical Performance of an In line Ex-Vivo Point of Care Monitor: A Multicenter Study," Clinical Chemistry 48:11, pp. 2030-2043, 2002.
Finkielman et al., "Agreement Between Bedside Blood and Plasma Glucose Measurement in the ICU Settin!'.::i"; retrieved from http://www.chestiournal.orq; CHEST/127/5/May 2005.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
"Glucon Critical Care Blood Glucose Monitor", Glucon Inc., published no later than May 8, 2006 and possibly published as early as Oct. 9, 2001.
Widness et al., "Clinical Performance on an In-Line Point-of-Care Monitor in Neonates"; Pediatrics, vol. 106, No. 3, DD. 497-504, Sep. 2000.
Maser et al., "Use of arterial blood with bedside glucose reflectance meters in an intensive care unit: Are they accurate?", Critical Care Medicine, vol. 22, No. 4, 1994.
Petibois et al., "Glucose and lactate concentration determination on single microsamples by Fourier-transform infrared spectroscopy", J Lab Cln Med, vol. 35, No. 2, 1999.

* cited by examiner

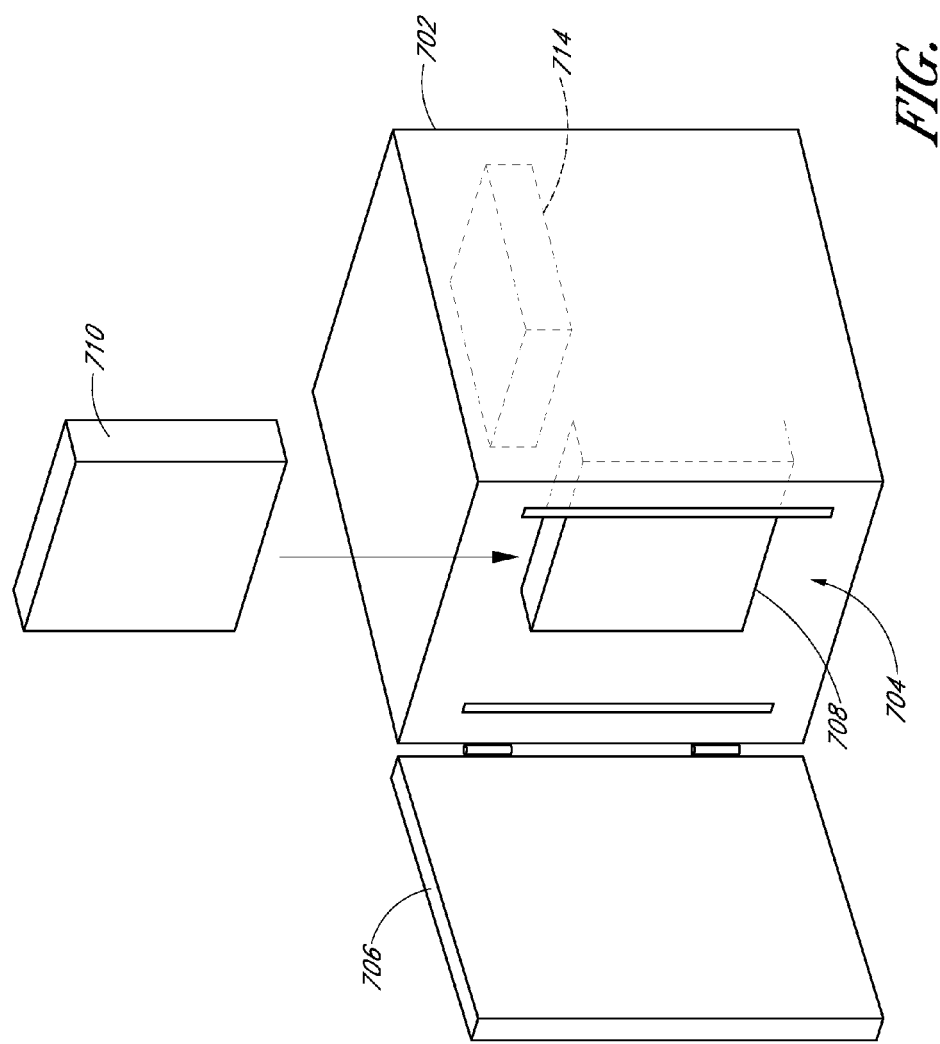

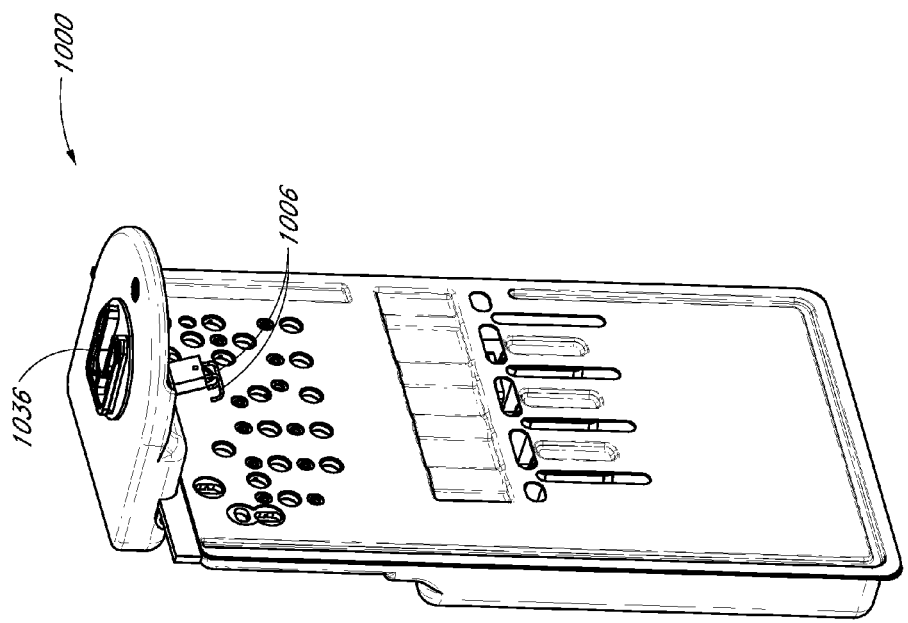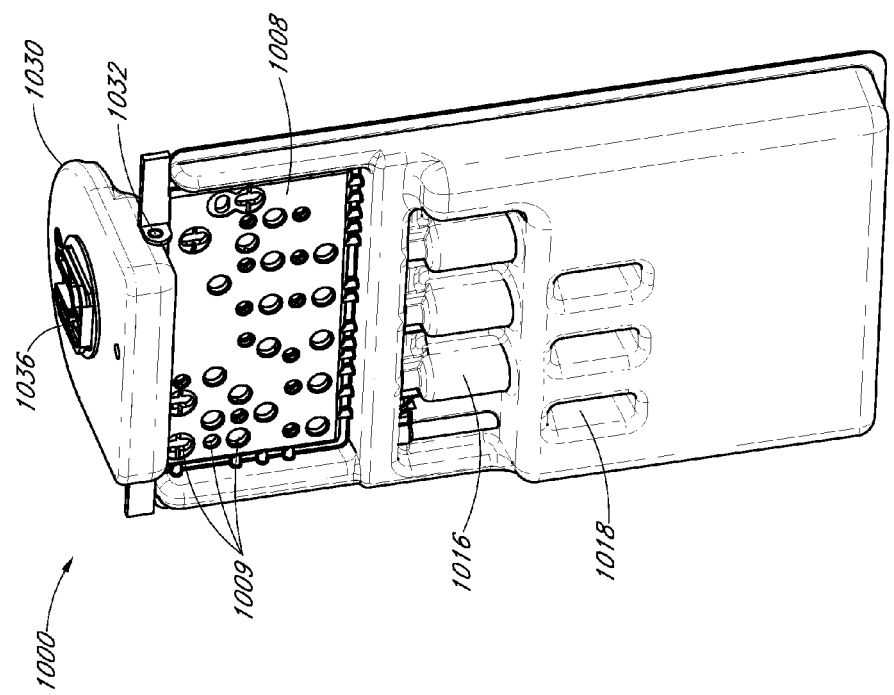
FIG. 10

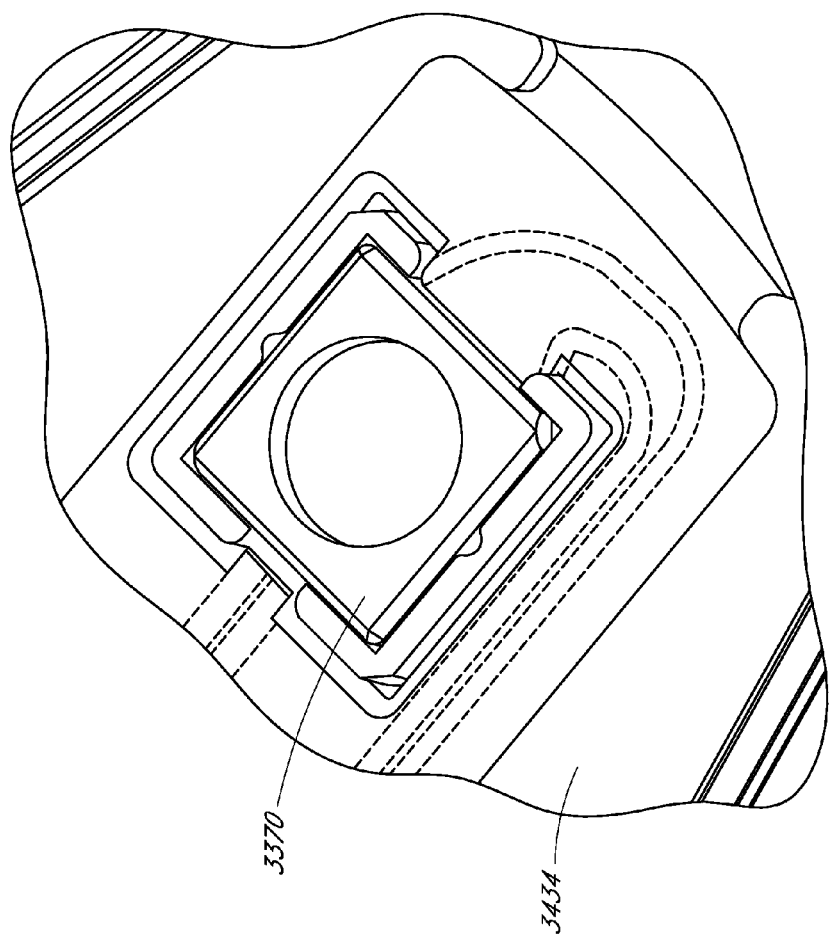

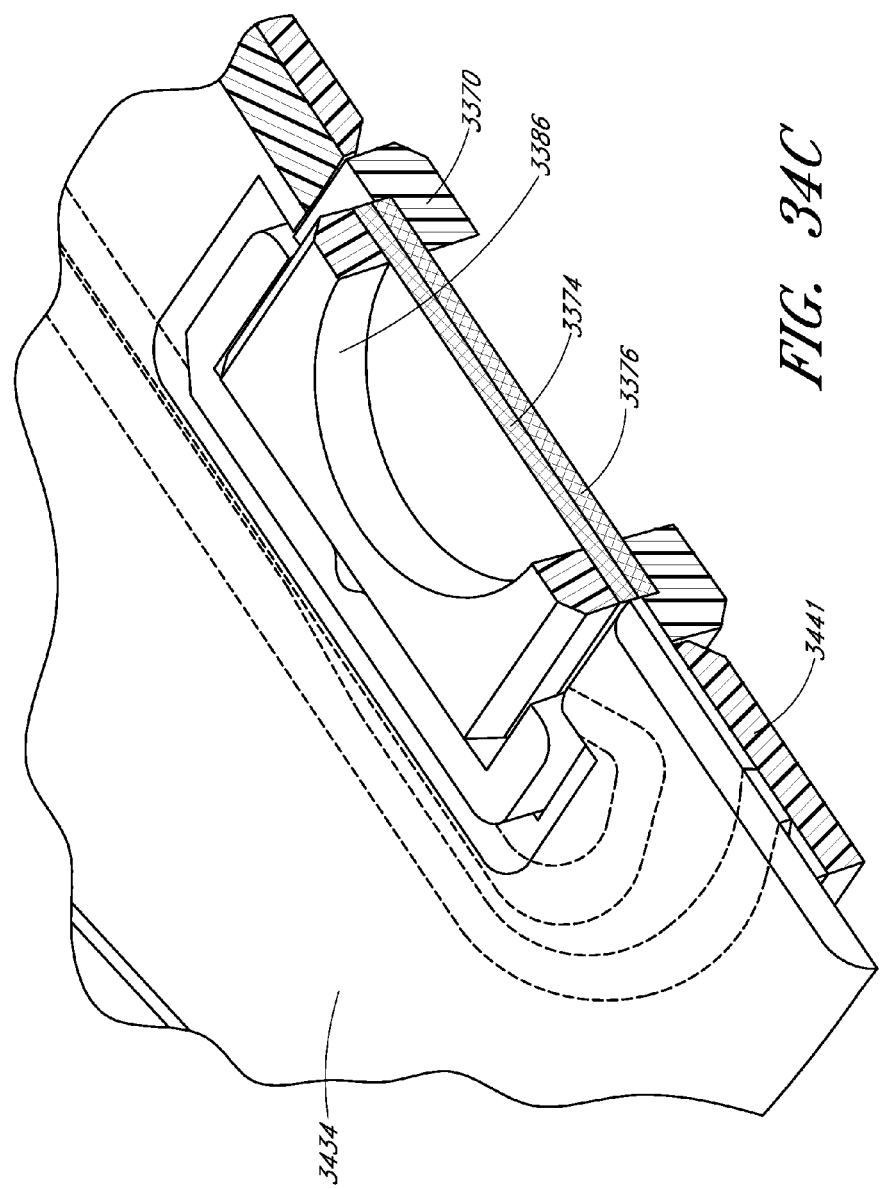

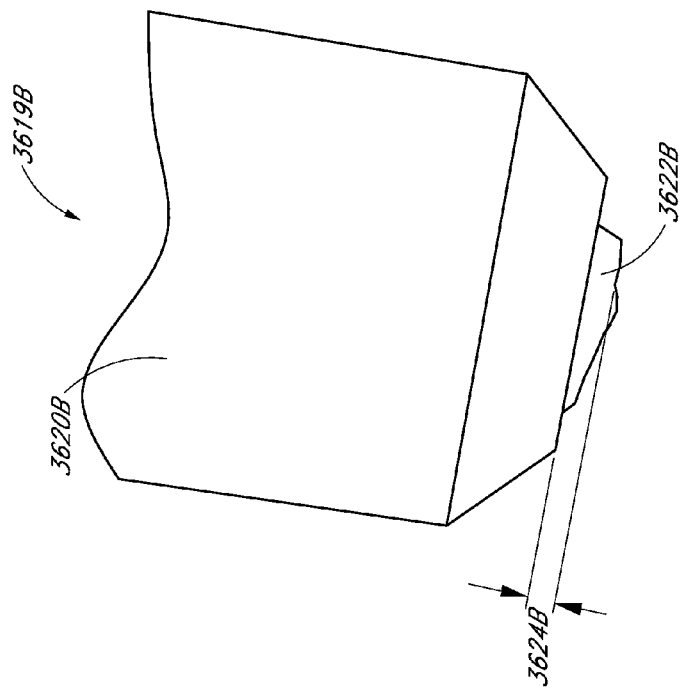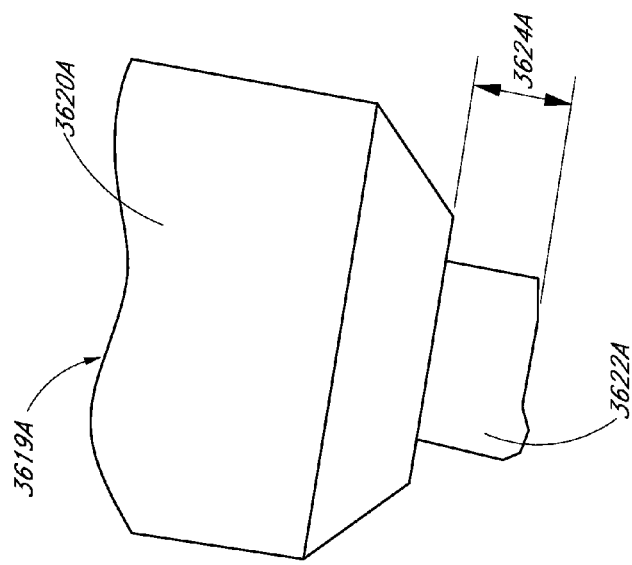
FIG. 36

FLUID ANALYSIS SYSTEM

CROSS-REFERENCE TO RELATED APPLICATIONS

This application is a continuation-in-part of U.S. patent application Ser. No. 13/542,350, filed on Jul. 5, 2012, and titled "SAMPLE CELL FOR FLUID ANALYSIS SYSTEM," which claims the benefit under 35 U.S.C. §119(e) of U.S. Provisional Patent Application No. 61/505,025, filed on Jul. 6, 2011, and titled "SAMPLE CELL FOR FLUID ANALYSIS SYSTEM."

This application is a continuation-in-part of U.S. patent application Ser. No. 13/552,542, filed on Jul. 18, 2012, and titled "METHOD AND APPARATUS FOR ANALYTE MEASUREMENTS USING CALIBRATION SETS," which claims the benefit under 35 U.S.C. §119(e) of U.S. Provisional Patent Application No. 61/509,487, filed on Jul. 19, 2011, and titled "METHOD AND APPARATUS FOR ANALYTE MEASUREMENTS USING MULTIPLE CALIBRATION SETS."

This application is a continuation-in-part of U.S. patent application Ser. No. 13/156,295, filed on Jun. 8, 2011, and titled "SYSTEMS AND METHODS FOR MEASURING MULTIPLE ANALYTES IN A SAMPLE," which claims the benefit under 35 U.S.C. §119(e) of U.S. Provisional Patent Application No. 61/353,186, filed on Jun. 9, 2010, and titled "SYSTEMS AND METHODS FOR MEASURING MULTIPLE ANALYTES IN A SAMPLE."

This application is a continuation-in-part of U.S. patent application Ser. No. 13/162,315, filed on Jun. 16, 2011, and titled "SYSTEMS AND METHODS TO REDUCE FLUID CONTAMINATION," which claims the benefit under 35 U.S.C. §119(e) of U.S. Provisional Patent Application No. 61/355,982, filed on Jun. 17, 2010, and titled "SYSTEMS AND METHODS TO REDUCE FLUID CONTAMINATION."

This application is a continuation-in-part of U.S. patent application Ser. No. 14/259,940, filed on Apr. 23, 2014, and titled "ADJUSTABLE CONNECTOR, IMPROVED FLUID FLOW AND REDUCED CLOTTING RISK," which is a continuation of U.S. patent application Ser. No. 13/068,121, filed on May 3, 2011, and titled "ADJUSTABLE CONNECTOR, IMPROVED FLUID FLOW AND REDUCED CLOTTING RISK," which claims the benefit under 35 U.S.C. §119(e) of U.S. Provisional Patent Application No. 61/330,812, filed on May 3, 2010, and titled "ADJUSTABLE CONNECTOR AND DEAD SPACE REDUCTION," and U.S. patent application Ser. No. 13/068,121 is a continuation-in-part of U.S. patent application Ser. No. 12/804,336, filed on Jul. 20, 2010, and titled "ADJUSTABLE CONNECTOR AND DEAD SPACE REDUCTION," which claims the benefit under 35 U.S.C. §119(e) of U.S. Provisional Patent Application No. 61/330,812, filed on May 3, 2010, and titled "ADJUSTABLE CONNECTOR AND DEAD SPACE REDUCTION," and U.S. Provisional Patent Application No. 61/227,040, filed on Jul. 20, 2009, and titled "ANALYTE DETECTION SYSTEM WITH A FLOW DIRECTOR."

This application is a continuation-in-part of U.S. patent application Ser. No. 14/257,920, filed on Apr. 21, 2014, and titled "ADJUSTABLE CONNECTOR AND DEAD SPACE REDUCTION," which is a continuation of U.S. patent application Ser. No. 12/804,336, filed on Jul. 20, 2010, and titled "ADJUSTABLE CONNECTOR AND DEAD SPACE REDUCTION," which claims the benefit under 35 U.S.C. §119(e) of U.S. Provisional Patent Application No. 61/330,812, filed on May 3, 2010, and titled "ADJUSTABLE CONNECTOR AND DEAD SPACE REDUCTION," and U.S. Provisional Patent Application No. 61/227,040, filed on Jul. 20, 2009, and titled "ANALYTE DETECTION SYSTEM WITH A FLOW DIRECTOR."

The entire contents of each of the above-identified applications are hereby made part of this specification as if set forth fully herein and incorporated by reference for all purposes, for all that each contains. Additionally, the entirety of U.S. Provisional Patent Application No. 61/954,530, filed Mar. 17, 2014, and titled "AUTOMATING IN-LINE OPTICAL MEASUREMENT IN MEDICAL FLUID SYSTEMS," is hereby made part of this specification as if set forth fully herein and incorporated by reference for all purposes, for all that it contains.

BACKGROUND

Field

Some embodiments of the disclosure relate generally to methods and devices for determining a concentration of an analyte in a sample, such as an analyte in a sample of bodily fluid, as well as methods and devices which can be used to support the making of such determinations. Some embodiments of the disclosure relate to a sample cell for holding a sample fluid. Various embodiments of the disclosure also relate to systems and methods to withdraw fluids (e.g. blood) through a port of a multi-lumen catheter such that the contamination from other ports is reduced Description of Related Art It is advantageous to measure the levels of certain analytes, such as glucose, in a bodily fluid, such as blood). This can be done, for example, in a hospital or clinical setting when there is a risk that the levels of certain analytes may move outside a desired range, which in turn can jeopardize the health of a patient. Currently known systems for analyte monitoring in a hospital or clinical setting may suffer from various drawbacks. For example, present fluid withdrawal techniques can result in fluid (e.g. blood) being withdrawn at a fast rate and/or at high pressures which can lead to contamination of the withdrawn blood particularly in multi-lumen catheters, where fluids from the other ports of the multi-lumen catheter can contaminate the withdrawn blood. Systems and methods described herein can reduce the contamination of the withdrawn fluid.

SUMMARY

Example embodiments described herein have several features, no single one of which is indispensible or solely responsible for their desirable attributes. Without limiting the scope of the claims, some of the advantageous features will now be summarized.

A cuvette is disclosed that includes a first window piece, a second window piece, and a spacer positioned between the first window piece and the second window piece to provide a gap between the first window piece and the second window piece. The cuvette can include a first clamshell piece and a second clamshell piece positioned on opposite sides of the window pieces, and the first and second clamshell pieces can be secured to each other to provide support to the first and second window pieces.

In various embodiments, a system for reducing contamination risk in drawing fluid from vasculature is described. The system comprises a tube configured to connect to a multi-lumen catheter. In various embodiments, the multi-lumen catheter can include a proximal port comprising an independent lumen that provides a fluid path between an extracorporeal opening and an intravascular opening that is positioned upstream when the multi-lumen catheter is inside a vessel having a fluid flow; a distal port comprising an independent lumen that provides a fluid path between the extracorporeal opening and the intravascular opening that is positioned downstream from the proximal port when the multi-lumen catheter is inside a vessel having a fluid flow; and a medial port comprising an independent lumen that provides a fluid path between the extracorporeal opening and the intravascular opening that is positioned between the proximal port and the distal port. In various embodiments, the distal and medial ports can each be configured to allow infusion of an infusate into the vessel from their intravascular openings downstream from the intravascular opening of the proximal port. In various embodiments, the tube can be configured to connect to the proximal port of the multi-lumen catheter without leaking. In various embodiments, the tube can have an inner lumen that is smaller than the inner lumen of the independent lumen of the proximal port. For example, the diameter of the inner lumen of the tube can be between approximately 0.01 inches and 0.04 inches. The system further comprises a fluid pressure system in fluid communication with the inner lumen of the tube that can be configured to create a pressure in the inner lumen that is automatically controlled to be less than 10 psi and/or provide a flow rate of between approximately 1 and 10 ml per minute such that the amount of contaminating infusate that is drawn into the intravascular opening of the proximal port is limited to less than 10 parts per million. The fluid pressure system may be configured to create a negative pressure in the inner lumen that is between approximately 40% and approximately 99% of the pressure in the vessel. The fluid pressure system may comprise a syringe pump.

A method for reducing contamination risk in drawing fluid from vasculature is described. The method comprises providing a tube that is configured to connect to a multi-lumen catheter. In various embodiments, the multi-lumen catheter can have a proximal port comprising an independent lumen that provides a fluid path between an extracorporeal opening and an intravascular opening that is positioned upstream when the multi-lumen catheter is inside a vessel having a fluid flow; a distal port comprising an independent lumen that provides a fluid path between the extracorporeal opening and the intravascular opening that is positioned downstream from the proximal port when the multi-lumen catheter is inside a vessel having a fluid flow; and a medial port comprising an independent lumen that provides a fluid path between the extracorporeal opening and the intravascular opening that is positioned between the proximal port and the distal port. In various embodiments, the distal and medial ports can each be configured to allow infusion of an infusate into the vessel from their intravascular openings downstream from the intravascular opening of the proximal port. In various embodiments, the tube can be configured to connect to the proximal port of the multi-lumen catheter without leaking. In various embodiments, the tube can have an inner lumen that is smaller than the inner lumen of the independent lumen of the proximal port. For example, the diameter of the inner lumen of the tube can be between approximately 0.01 inches and 0.04 inches. The method further comprises providing a fluid pressure system in fluid communication with the inner lumen of the tube and providing an automated system that is configured to automatically control the fluid pressure system and create a pressure in the inner lumen that is less than 10 psi and/or provide a flow rate of between approximately 1 and 10 ml per minute such that the amount of contaminating infusate that is drawn into the intravascular opening of the proximal port is limited to less than 10 parts per million. The automated system may control the fluid pressure system to create a negative pressure in the inner lumen that is between approximately 40% and approximately 99% of the pressure in the vessel. The fluid pressure system may comprise a syringe pump.

An apparatus for improving measurement accuracy in an analyte monitoring system and reducing fluid contamination risk is described. The apparatus may include a fluid passage with a tip configured to mate with a multi-lumen catheter without leaking. The multi-lumen catheter may have a proximal port communicating with a proximal port lumen that provides a fluid path to a proximal intravascular opening that is configured to open into a vessel having a fluid flow and a distal port communicating with a distal port lumen that is independent from and not in fluid communication with the proximal port lumen and that provides a fluid path to a distal intravascular opening that is configured to open into the vessel distal of and downstream from the proximal intravascular opening to infuse infusates. The apparatus may include a fluid pressure system in fluid communication with the fluid passage, the fluid pressure system configured to periodically automatically draw fluid from the vessel through the proximal intravascular opening and the proximal port and through the tip back into the fluid passage while maintaining a low pressure and/or flow rate to thereby reduce risk of reversing the fluid flow in the vessel and drawing infusates back upstream into the proximal intravascular opening. The apparatus may also have an analyzer configured to automatically analyze at least a portion of the drawn fluid, automatically achieving higher accuracy analysis at least in part as a result of the low pressure at which the fluid was drawn. The apparatus may be configured to reduce dilution errors due to withdrawal of infusates such that infusate does not cause more than a 20% difference in accuracy of an analyte reading that uses fluid drawn into the intravascular opening of the proximal port. The fluid passage may have an inner diameter of between approximately 0.01 inches and approximately 0.04 inches. The fluid pressure system may comprise a controller and a pressure monitor that provides feedback to the controller, the controller configured to maintain the withdrawal pressure below 99% of the pressure of blood in the vessel. A patient blood pressure monitor may provide feedback to the controller to allow a baseline for comparison to the withdrawal pressure. The pressure monitor may be configured to monitor the pressure at or near the proximal port. The fluid pressure system may be configured to maintain a constant rate for the majority of the time blood is being withdrawn through the proximal port. The fluid pressure system may be configured to adjust the withdrawal rate to be lower when infusates are being infused through the distal port A method for improving measurement accuracy in an analyte monitoring system and reducing fluid contamination risk is described. The method may comprise providing a tube configured to connect to a multi-lumen catheter without leaking, the multi-lumen catheter having an upstream port and a downstream port, each port having an independent lumen not in fluid communication with the other. The method may further comprise positioning the multi-lumen catheter in a patient's vessel such that the lumen of the upstream port opens into the vessel upstream of the lumen of the downstream port, providing an automated fluid pressure system configured to automatically maintain a low pressure and/or flow rate while drawing blood, connecting the automated fluid pressure system to the tube such that the system is in fluid communication with the upstream port and blood flow in the patient's vessel, and using the automated fluid pressure system to periodically draw blood in through the lumen of the upstream port while maintaining a low pressure and/or flow rate, thereby avoiding a reversal of blood flow in the patient's vessel and reducing the risk of contamination of a blood sample. The infusate may be infused into the vessel through the downstream port, and the method further comprising reducing the amount of infusate drawn into the lumen of the upstream catheter so that infusate does not cause more than a 20% difference in accuracy of an analyte reading of the blood drawn into the tube as compared to a reading of blood drawn when no infusate is being infused into the vessel. The automated fluid pressure system may comprise a syringe pump. The infusate may be periodically infused into the vessel through the downstream port, the method further comprising using the automated fluid pressure system to reduce the pressure and/or flow rate of withdrawn blood when infusion of infusate and blood withdrawal occur simultaneously. The method may also include determining the patient's blood pressure and using the automated fluid pressure system to maintain a withdrawal pressure that is less than the patient's blood pressure, thereby avoiding reversal of blood flow in the vessel.

BRIEF DESCRIPTION OF THE DRAWINGS

The following drawings and the associated descriptions are provided to illustrate embodiments of the present disclosure and do not limit the scope of the claims.

FIG. 7 is an oblique schematic depiction of an embodiment of a monitoring device.

FIG. 10 illustrates an embodiment of a removable cartridge that can interface with a monitoring device.

FIGS. 34A-C illustrate the cuvette of FIG. 33 incorporated into a rotor housing.

FIG. 36 illustrates ends of fluid nipples for use with a fluid interface in an analyte monitoring system.

Figure 1:
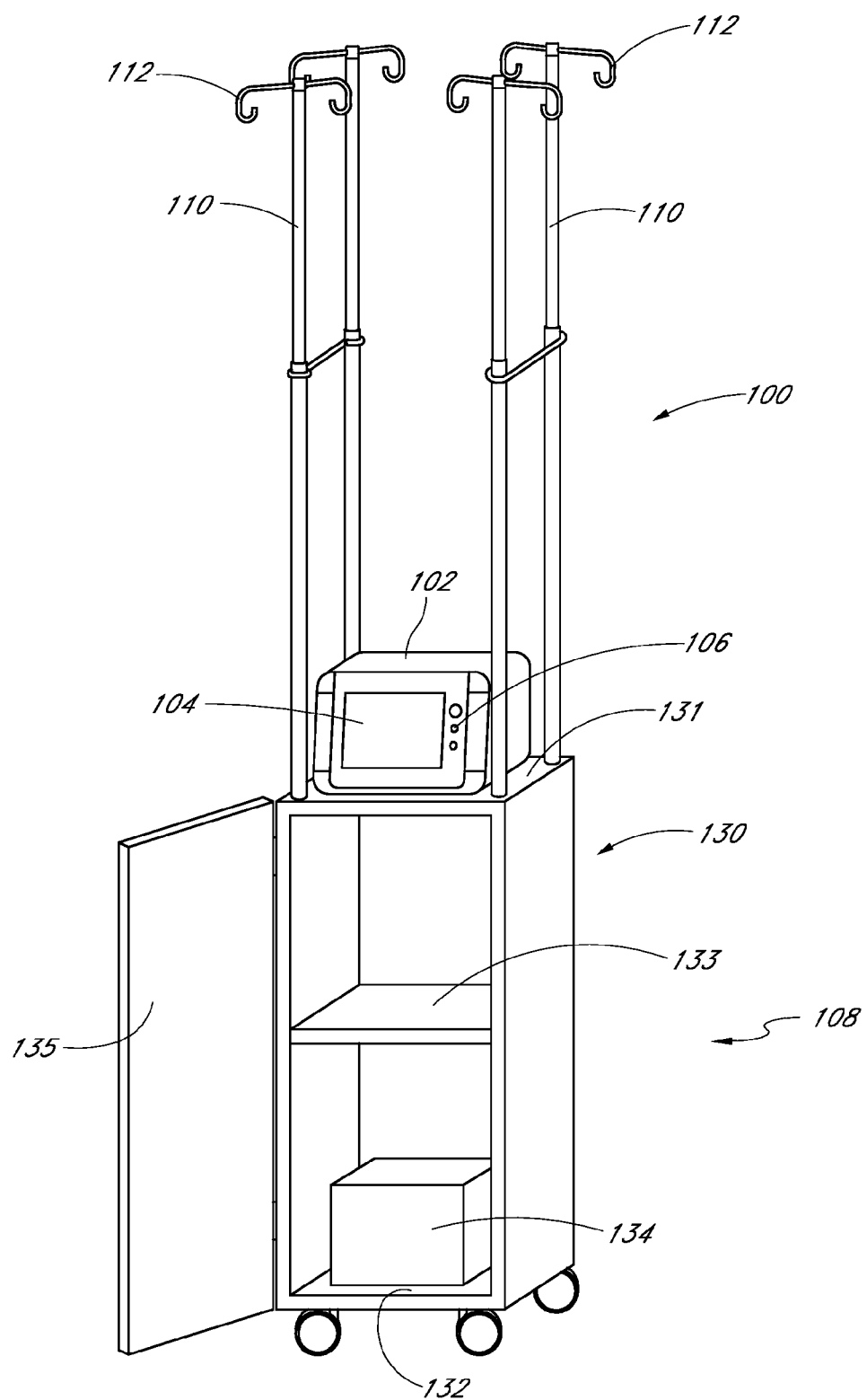
FIG. 1 shows an embodiment of an apparatus for withdrawing and analyzing fluid samples.

These and other features will now be described with reference to the drawings summarized above. The drawings and the associated descriptions are provided to illustrate embodiments and not to limit the scope of any claim. Throughout the drawings, reference numbers may be reused to indicate correspondence between referenced elements. In addition, where applicable, the first one or two digits of a reference numeral for an element can frequently indicate the figure number in which the element first appears.

DETAILED DESCRIPTION

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The systems and methods discussed herein can be used anywhere, including, for example, in laboratories, hospitals, healthcare facilities, intensive care units (ICUs), or residences. Moreover, the systems and methods discussed herein can be used for invasive techniques, as well as non-invasive techniques or techniques that do not involve a body or a patient such as, for example, in vitro techniques.

Analyte Monitoring Apparatus

FIG. 1 shows an embodiment of an apparatus 100 for withdrawing and analyzing fluid samples. The apparatus 100 includes a monitoring device 102. In some embodiments, the monitoring device 102 can be an "OptiScanner®" monitor available from OptiScan Biomedical Corporation of Hayward, Calif. In some embodiments, the device 102 can measure one or more physiological parameters, such as the concentration of one or more substance(s) in a sample fluid. The sample fluid can be, for example, whole blood from a patient 302 (see, e.g., FIG. 3) and/or a component of whole blood such as, e.g., blood plasma. In some embodiments, the device 100 can also deliver an infusion fluid to a patient.

In the illustrated embodiment, the monitoring device 102 includes a display 104 such as, for example, a touch-sensitive liquid crystal display. The display 104 can provide an interface that includes alerts, indicators, charts, and/or soft buttons. The device 102 also can include one or more inputs and/or outputs 106 that provide connectivity and/or permit user interactivity.

In the embodiment shown in FIG. 1, the device 102 is mounted on a stand 108. The stand 108 may comprise a cart such as, for example, a wheeled cart 130 as shown in FIG. 1. In some embodiments, the stand 108 is configured to roll on a wheeled pedestal 240 (shown in FIG. 2). The stand 108 advantageously can be easily moved and includes one or more poles 110 and/or hooks 112. The poles 110 and hooks 112 can be configured to accommodate other medical devices and/or implements, including, for example, infusion pumps, saline bags, arterial pressure sensors, other monitors and medical devices, and so forth. Some stands or carts may become unstable if intravenous (IV) bags, IV pumps, and other medical devices are hung too high on the stand or cart. In some embodiments, the apparatus 100 can be configured to have a low center of gravity, which may overcome possible instability. For example, the stand 108 can be weighted at the bottom to at least partially offset the weight of IV bags, IV pumps and medical devices that may be attached to the hooks 112 that are placed above the monitoring device 102. Adding weight toward the bottom (e.g., near the wheels) may help prevent the apparatus 100 from tipping over.

In some embodiments, the apparatus 100 includes the cart 130, which has an upper shelf 131 on which the monitoring device 102 may be placed (or attached) and a bottom shelf 132 on which a battery 134 may be placed (or attached). The battery 134 may be used as a main or backup power supply for the monitoring device 102 (which may additionally or alternatively accept electrical power from a wall socket). Two or more batteries are used in certain embodiments. The apparatus 100 may be configured so that the upper and lower shelves 131, 132 are close to ground level, and the battery provides counterweight. Other types of counterweights may be used. For example, in some embodiments, portions of the cart 130 near the floor (e.g., a lower shelf) are weighted, formed from a substantial quantity of material (e.g., thick sheets of metal), and/or formed from a relatively high-density metal (e.g., lead). In some embodiments the bottom shelf 132 is approximately 6 inches to 1 foot above ground level, and the upper shelf 131 is approximately 2 feet to 4 feet above ground level. In some embodiments the upper shelf 131 may be configured to support approximately 40 pounds (lbs), and the bottom shelf 132 may be configured to support approximately 20 lbs. One possible advantage of embodiments having such a configuration is that IV pumps, bags containing saline, blood and/or drugs, and other medical equipment weighing approximately 60 lbs, collectively, can be hung on the hooks 112 above the shelves without making the apparatus 100 unstable. The apparatus 100 may be moved by applying a horizontal force on the apparatus 100, for example, by pushing and/or pulling the poles 110. In many cases, a user may exert force on an upper portion of the apparatus 100, for example, close to shoulder-height. By counterbalancing the weight as described above, the apparatus 100 may be moved in a reasonably stable manner.

In the illustrated embodiment, the cart 130 includes the bottom shelf 132 and an intermediate shelf 133, which are enclosed on three sides by walls and on a fourth side by a door 135. The door 135 can be opened (as shown in FIG. 1) to provide access to the shelves 132, 133. In other embodiments, the fourth side is not enclosed (e.g., the door 135 is not used). Many cart variations are possible. In some embodiments the battery 134 can be placed on the bottom shelf 134 or the intermediate shelf 133.

Figure 2:
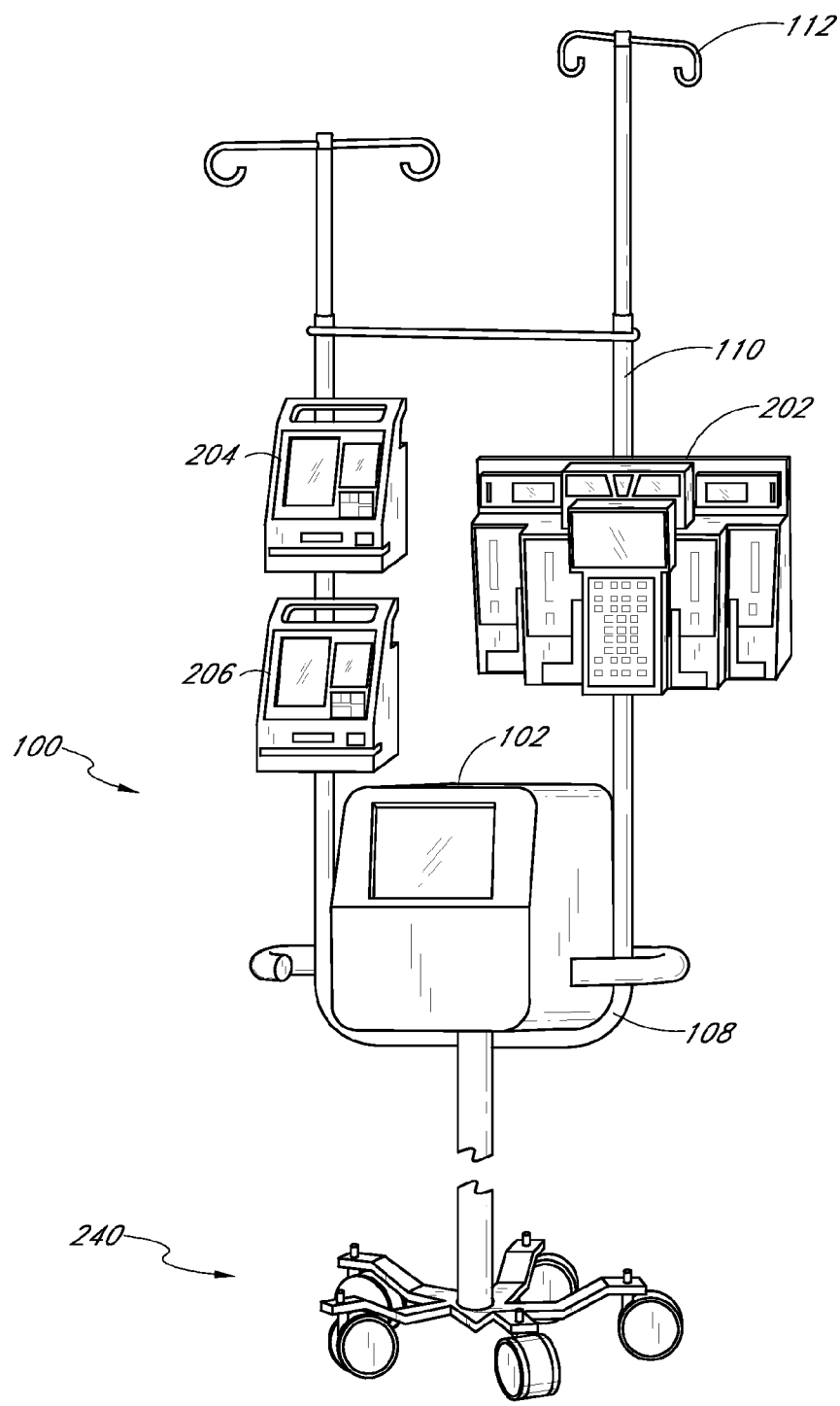
FIG. 2 illustrates how various other devices can be supported on or near an embodiment of apparatus illustrated in FIG. 1.

FIG. 2 illustrates how various other devices can be supported on or near the apparatus 100 illustrated in FIG. 1. For example, the poles 110 of the stand 108 can be configured (e.g., of sufficient size and strength) to accommodate multiple devices 202, 204, 206. In some embodiments, one or more COLLEAGUE® volumetric infusion pumps available from Baxter International Inc. of Deerfield, Ill. can be accommodated. In some embodiments, one or more Alaris® PC units available from Cardinal Health, Inc. of Dublin, Ohio can be accommodated. Furthermore, various other medical devices (including the two examples mentioned here), can be integrated with the disclosed monitoring device 102 such that multiple devices function in concert for the benefit of one or multiple patients without the devices interfering with each other.

Figure 3:
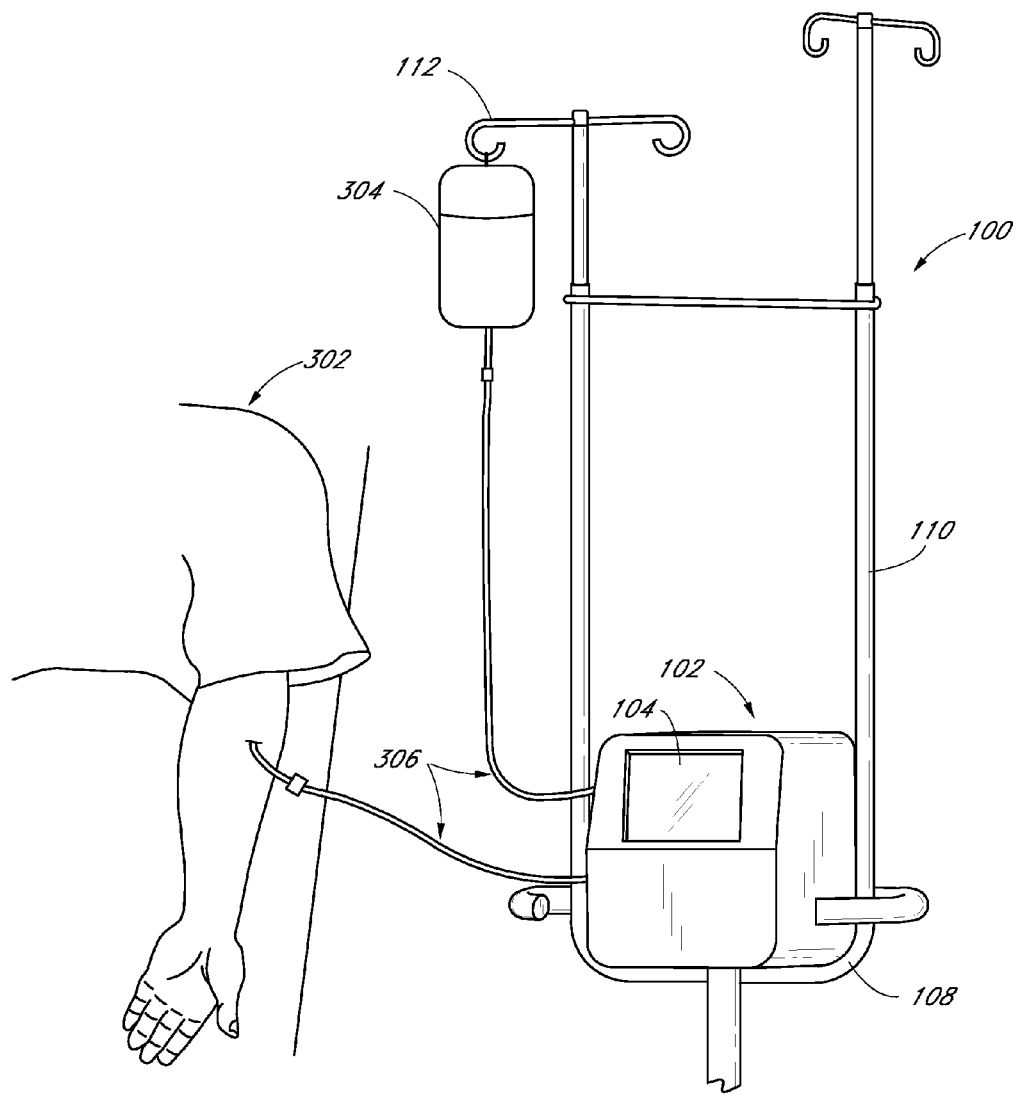
FIG. 3 illustrates an embodiment of the apparatus in FIG. 1 configured to be connected to a patient.
Figure 3A:
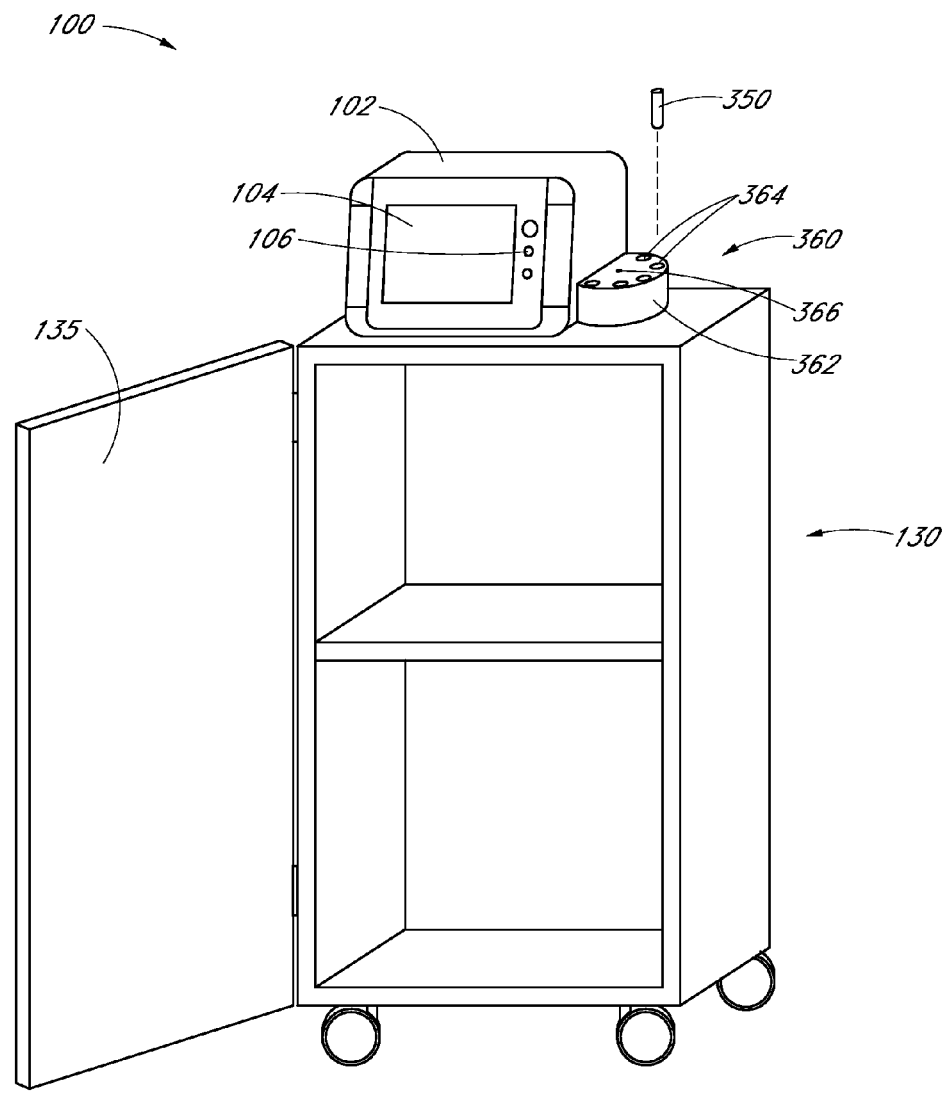
FIG. 3A illustrates an embodiment of the apparatus in FIG. 1 that is not configured to be connected to a patient but which receives a fluid sample from an extracorporeal fluid container such as, for example, a test tube. This embodiment of the apparatus advantageously provides in vitro analysis of a fluid sample.

FIG. 3 illustrates the apparatus 100 of FIG. 1 as it can be connected to a patient 302. The monitoring device 102 can be used to determine the concentration of one or more substances in a sample fluid. The sample fluid can come can come from the patient 302, as illustrated in FIG. 3, or the sample fluid can come from a fluid container, as illustrated in FIG. 3A. In some preferred embodiments, the sample fluid is whole blood.

In some embodiments (see, e.g., FIG. 3), the monitoring device 102 can also deliver an infusion fluid to the patient 302. An infusion fluid container 304 (e.g., a saline bag), which can contain infusion fluid (e.g., saline and/or medication), can be supported by the hook 112. The monitoring device 102 can be in fluid communication with both the container 304 and the sample fluid source (e.g., the patient 302), through tubes 306. The infusion fluid can comprise any combination of fluids and/or chemicals. Some advantageous examples include (but are not limited to): water, saline, dextrose, lactated Ringer's solution, drugs, and insulin.

The example monitoring device 102 schematically illustrated in FIG. 3 allows the infusion fluid to pass to the patient 302 and/or uses the infusion fluid itself (e.g., as a flushing fluid or a standard with known optical properties, as discussed further below). In some embodiments, the monitoring device 102 may not employ infusion fluid. The monitoring device 102 may thus draw samples without delivering any additional fluid to the patient 302. The monitoring device 102 can include, but is not limited to, fluid handling and analysis apparatuses, connectors, passageways, catheters, tubing, fluid control elements, valves, pumps, fluid sensors, pressure sensors, temperature sensors, hematocrit sensors, hemoglobin sensors, colorimetric sensors, gas (e.g., "bubble") sensors, fluid conditioning elements, gas injectors, gas filters, blood plasma separators, and/or communication devices (e.g., wireless devices) to permit the transfer of information within the monitoring device 102 or between the monitoring device 102 and a network.

In some embodiments, the apparatus 100 is not connected to a patient and may receive fluid samples from a container such as a decanter, flask, beaker, tube, cartridge, test strip, etc., or any other extracorporeal fluid source. The container may include a biological fluid sample such as, e.g., a body fluid sample. For example, FIG. 3A schematically illustrates an embodiment of the monitoring device 102 that is configured to receive a fluid sample from one or more test tubes 350. This embodiment of the monitoring device 102 is configured to perform in vitro analysis of a fluid (or a fluid component) in the test tube 350. The test tube 350 may comprise a tube, vial, bottle, or other suitable container or vessel. The test tube 350 may include an opening disposed at one end of the tube through which the fluid sample may be added prior to delivery of the test tube to the monitoring device 102. In some embodiments, the test tubes 350 may also include a cover adapted to seal the opening of the tube. The cover may include an aperture configured to permit a tube, nozzle, needle, pipette, or syringe to dispense the fluid sample into the test tube 350. The test tubes 350 may comprise a material such as, for example, glass, polyethylene, or polymeric compounds. In various embodiments, the test tubes 350 may be re-usable units or may be disposable, single-use units. In certain embodiments, the test tubes 350 may comprise commercially available low pressure/vacuum sample bottles, test bottles, or test tubes.

In the embodiment shown in FIG. 3A, the monitoring device 102 comprises a fluid delivery system 360 configured to receive a container (e.g., the test tube 350) containing a fluid sample and deliver the fluid sample to a fluid handling system (such as, e.g., fluid handling system 404 described below). In some embodiments, the fluid handling system delivers a portion of the fluid sample to an analyte detection system for in vitro measurement of one or more physiological parameters (e.g., an analyte concentration). Prior to measurement, the fluid handling system may, in some embodiments, separate the fluid sample into components, and a measurement may be performed on one or more of the components. For example, the fluid sample in the test tube 350 may comprise whole blood, and the fluid handling system may separate blood plasma from the sample (e.g., by filtering and/or centrifuging).

In the embodiment illustrated in FIG. 3A, the fluid delivery system 360 comprises a carousel 362 having one or more openings 364 adapted to receive the test tube 350. The carousel 362 may comprise one, two, four, six, twelve, or more openings 364. In the illustrated embodiment, the carousel 362 is configured to rotate around a central axis or spindle 366 so that a test tube 350 inserted into one of the openings 364 is delivered to the monitoring device 102. In certain embodiments, the fluid handling system of the monitoring device 102 comprises a sampling probe that is configured to collect a portion of the fluid sample from the test tube 350 (e.g., by suction or aspiration). The collected portion may then be transported in the device 102 as further described below (see, e.g., FIGS. 4-7). For example, in one embodiment suitable for use with whole blood, the collected portion of the whole blood sample is transported to a centrifuge for separation into blood plasma, a portion of the blood plasma is transported to an infrared spectroscope for measurement of one or more analytes (e.g., glucose), and the measured blood plasma is then transported to a waste container for disposal.

In other embodiments of the apparatus 100 shown in FIG. 3A, the fluid delivery system 360 may comprise a turntable, rack, or caddy adapted to receive the test tube 350. In yet other embodiments, the monitoring device 102 may comprise an inlet port adapted to receive the test tube 350. Additionally, in other embodiments, the fluid sample may be delivered to the apparatus 100 using a test cartridge, a test strip, or other suitable container. Many variations are possible.

In some embodiments, one or more components of the apparatus 100 can be located at another facility, room, or other suitable remote location. One or more components of the monitoring device 102 can communicate with one or more other components of the monitoring device 102 (or with other devices) by communication interface(s) such as, but not limited to, optical interfaces, electrical interfaces, and/or wireless interfaces. These interfaces can be part of a local network, internet, wireless network, or other suitable networks.

System Overview

Figure 4:
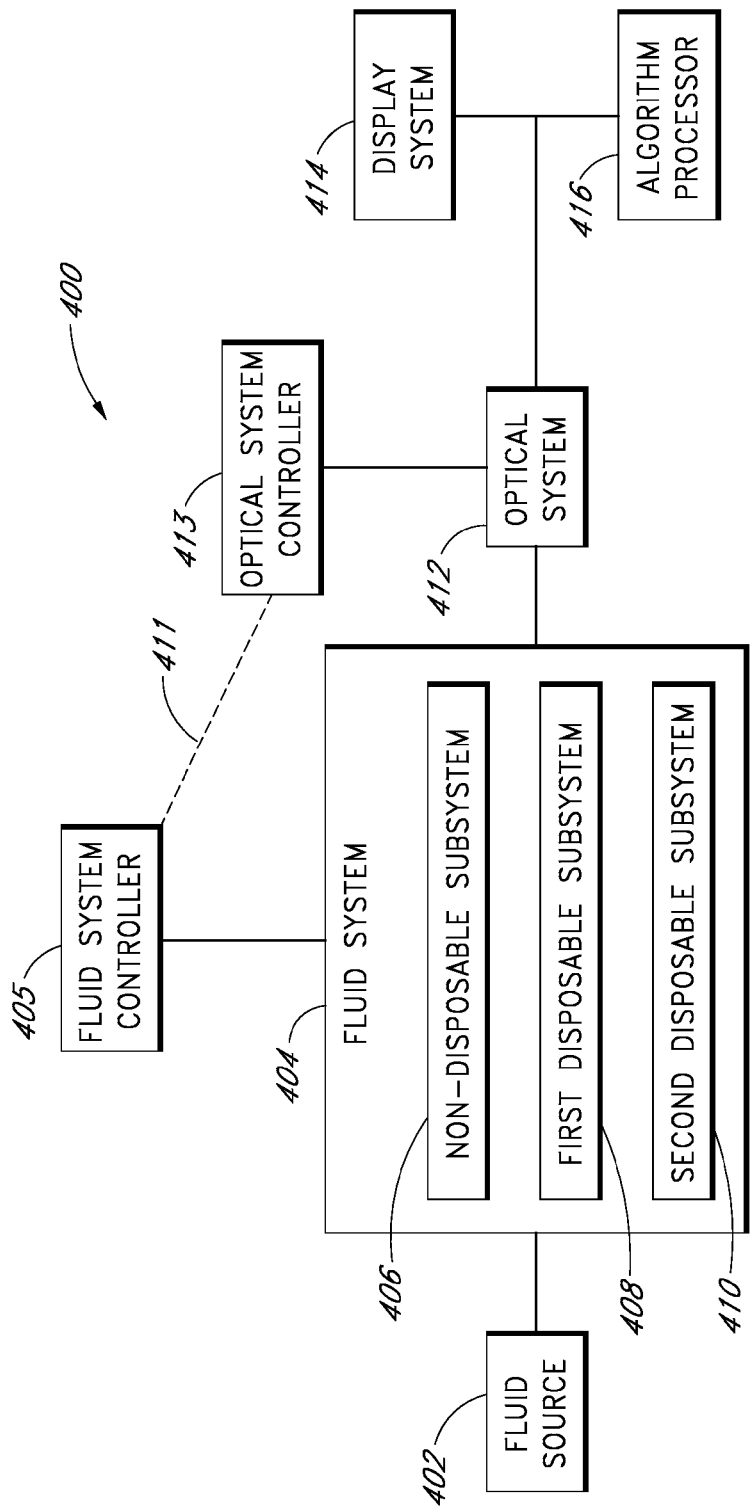
FIG. 4 is a block diagram of an embodiment of a system for withdrawing and analyzing fluid samples.

FIG. 4 is a block diagram of a system 400 for sampling and analyzing fluid samples. The monitoring device 102 can comprise such a system. The system 400 can include a fluid source 402 connected to a fluid-handling system 404. The fluid-handling system 404 includes fluid passageways and other components that direct fluid samples. Samples can be withdrawn from the fluid source 402 and analyzed by an optical system 412. The fluid-handling system 404 can be controlled by a fluid system controller 405, and the optical system 412 can be controlled by an optical system controller 413. The sampling and analysis system 400 can also include a display system 414 and an algorithm processor 416 that assist in fluid sample analysis and presentation of data.

In some embodiments, the sampling and analysis system 400 is a mobile point-of-care apparatus that monitors physiological parameters such as, for example, blood glucose concentration. Components within the system 400 that may contact fluid and/or a patient, such as tubes and connectors, can be coated with an antibacterial coating to reduce the risk of infection. Connectors between at least some components of the system 400 can include a self-sealing valve, such as a spring valve, in order to reduce the risk of contact between port openings and fluids, and to guard against fluid escaping from the system. Other components can also be included in a system for sampling and analyzing fluid in accordance with the described embodiments.

The sampling and analysis system 400 can include a fluid source 402 (or more than one fluid source) that contain(s) fluid to be sampled. The fluid-handling system 404 of the sampling and analysis system 400 is connected to, and can draw fluid from, the fluid source 402. The fluid source 402 can be, for example, a blood vessel such as a vein or an artery, a container such as a decanter, flask, beaker, tube, cartridge, test strip, etc., or any other corporeal or extracorporeal fluid source. For example, in some embodiments, the fluid source 402 may be a vein or artery in the patient 302 (see, e.g., FIG. 3). In other embodiments, the fluid source 402 may comprise an extracorporeal container 350 of fluid delivered to the system 400 for analysis (see, e.g., FIG. 3B). The fluid to be sampled can be, for example, blood, plasma, interstitial fluid, lymphatic fluid, or another fluid. In some embodiments, more than one fluid source can be present, and more than one fluid and/or type of fluid can be provided.

In some embodiments, the fluid-handling system 404 withdraws a sample of fluid from the fluid source 402 for analysis, centrifuges at least a portion of the sample, and prepares at least a portion of the sample for analysis by an optical sensor such as a spectrophotometer (which can be part of an optical system 412, for example). The sample can be optically measured both before and after centrifugation (e.g., so that an analyte more readily measurable in whole blood such as hemoglobin can be measured first, and then an analyte readily measured in plasma such as glucose can be measured). These functions can be controlled by a fluid system controller 405, which can also be integrated into the fluid-handling system 404. The fluid system controller 405 can also control the additional functions described below. In some embodiments, the sample can be withdrawn continuously or substantially continuously at certain time intervals (e.g., with a given period). The time intervals at which the sample is withdrawn can be periodic or aperiodic and range from approximately 1 minute to approximately 15 minutes (e.g., the sample can be withdrawn at time intervals of 1 minute, 5 minutes, 10 minutes or 15 minutes). In some embodiments, the sample can be withdrawn at discrete time intervals (e.g., once every 15 minutes, once every 30 minutes, once every 45 minutes, once every hour, etc.).

The duration of time over which the sample of fluid is withdrawn, referred to as "draw period", may be set to avoid clinical drawbacks, and/or it can be varied according to a health-care provider's wishes. For example, in some embodiments, fluid may be continuously withdrawn into the sampling and analysis system 400 over a draw period lasting approximately 10 seconds to approximately 5 minutes.

In some embodiments, the amount of sample withdrawn from the fluid source 402 can be small. For example, in some embodiments, the volume of sample withdrawn from the fluid source can be between approximately 1.0 ml and approximately 10.0 ml in a draw period (e.g. 2.0 ml-6.0 ml or 2.0 ml-8.0 ml of sample can be withdrawn in a draw period of approximately 1 minute). In some embodiments, the amount of sample withdrawn can be in the range of approximately 20 ml/day to approximately 500 ml/day. In some embodiments, the amount of sample withdrawn can be outside this range.

In some embodiments, at least a portion of the sample is returned to the fluid source 402. At least some of the sample, such as portions of the sample that are mixed with other materials or portions that are otherwise altered during the sampling and analysis process, or portions that, for any reason, are not to be returned to the fluid source 402, can also be placed in a waste bladder (not shown in FIG. 4). The waste bladder can be integrated into the fluid-handling system 404 or supplied by a user of the system 400. The fluid-handling system 404 can also be connected to a saline source, a detergent source, and/or an anticoagulant source, each of which can be supplied by a user, attached to the fluid-handling system 404 as additional fluid sources, and/or integrated into the fluid-handling system 404.

Components of the fluid-handling system 404 can be modularized into one or more non-disposable, disposable, and/or replaceable subsystems. In the embodiment shown in FIG. 4, components of the fluid-handling system 404 are separated into a non-disposable subsystem 406, a first disposable subsystem 408, and a second disposable subsystem 410.

The non-disposable subsystem 406 can include components that, while they may be replaceable or adjustable, do not generally require regular replacement during the useful lifetime of the system 400. In some embodiments, the non-disposable subsystem 406 of the fluid-handling system 404 includes one or more reusable valves and sensors. For example, the non-disposable subsystem 406 can include one or more valves (or non-disposable portions thereof), (e.g., pinch-valves, rotary valves, etc.), sensors (e.g., ultrasonic bubble sensors, non-contact pressure sensors, optical blood dilution sensors, etc). The non-disposable subsystem 406 can also include one or more pumps (or non-disposable portions thereof). For example, some embodiments can include pumps available from Hospira. In some embodiments, the components of the non-disposable subsystem 406 are not directly exposed to fluids and/or are not readily susceptible to contamination.

The first and second disposable subsystems 408, 410 can include components that are regularly replaced under certain circumstances in order to facilitate the operation of the system 400. For example, the first disposable subsystem 408 can be replaced after a certain period of use, such as a few days, has elapsed. Replacement may be necessary, for example, when a bladder within the first disposable subsystem 408 is filled to capacity. Such replacement may mitigate fluid system performance degradation associated with and/or contamination wear on system components.

In some embodiments, the first disposable subsystem 408 includes components that may contact fluids such as patient blood, saline, flushing solutions, anticoagulants, and/or detergent solutions. For example, the first disposable subsystem 408 can include one or more tubes, fittings, cleaner pouches and/or waste bladders. The components of the first disposable subsystem 408 can be sterilized in order to decrease the risk of infection and can be configured to be easily replaceable.

In some embodiments, the second disposable subsystem 410 can be designed to be replaced under certain circumstances. For example, the second disposable subsystem 410 can be replaced when the patient being monitored by the system 400 is changed. The components of the second disposable subsystem 410 may not need replacement at the same intervals as the components of the first disposable subsystem 408. For example, the second disposable subsystem 410 can include a sample holder and/or at least some components of a centrifuge, components that may not become filled or quickly worn during operation of the system 400. Replacement of the second disposable subsystem 410 can decrease or eliminate the risk of transferring fluids from one patient to another during operation of the system 400, enhance the measurement performance of system 400, and/or reduce the risk of contamination or infection.

In some embodiments, the sample holder of the second disposable subsystem 410 receives the sample obtained from the fluid source 402 via fluid passageways of the first disposable subsystem 408. The sample holder is a container that can hold fluid for the centrifuge and can include a window to the sample for analysis by a spectrometer. In some embodiments, the sample holder includes windows that are made of a material that is substantially transparent to electromagnetic radiation in the mid-infrared range of the spectrum. For example, the sample holder windows can be made of calcium fluoride.

An injector can provide a fluid connection between the first disposable subsystem 408 and the sample holder of the second disposable subsystem 410. In some embodiments, the injector can be removed from the sample holder to allow for free spinning of the sample holder during centrifugation.

In some embodiments, the components of the sample are separated by centrifuging for a period of time before measurements are performed by the optical system 412. For example, a fluid sample (e.g., a blood sample) can be centrifuged at a relatively high speed. The sample can be spun at a certain number of revolutions per minute (RPM) for a given length of time to separate blood plasma for spectral analysis. In some embodiments, the fluid sample is spun at about 7200 RPM. In some embodiments, the sample is spun at about 5000 RPM. In some embodiments, the fluid sample is spun at about 4500 RPM. In some embodiments, the fluid sample is spun at more than one rate for successive time periods. The length of time can be approximately 5 minutes. In some embodiments, the length of time is approximately 2 minutes. Separation of a sample into the components can permit measurement of solute (e.g., glucose) concentration in plasma, for example, without interference from other blood components. This kind of post-separation measurement, (sometimes referred to as a "direct measurement") has advantages over a solute measurement taken from whole blood because the proportions of plasma to other components need not be known or estimated in order to infer plasma glucose concentration. In some embodiments, the separated plasma can be analyzed electrically using one or more electrodes instead of, or in addition to, being analyzed optically. This analysis may occur within the same device, or within a different device. For example, in certain embodiments, an optical analysis device can separate blood into components, analyze the components, and then allow the components to be transported to another analysis device that can further analyze the components (e.g., using electrical and/or electrochemical measurements).

An anticoagulant, such as, for example, heparin can be added to the sample before centrifugation to prevent clotting. The fluid-handling system 404 can be used with a variety of anticoagulants, including anticoagulants supplied by a hospital or other user of the monitoring system 400. A detergent solution formed by mixing detergent powder from a pouch connected to the fluid-handling system 404 with saline can be used to periodically clean residual protein and other sample remnants from one or more components of the fluid-handling system 404, such as the sample holder. Sample fluid to which anticoagulant has been added and used detergent solution can be transferred into the waste bladder.

The system 400 shown in FIG. 4 includes an optical system 412 that can measure optical properties (e.g., transmission) of a fluid sample (or a portion thereof). In some embodiments, the optical system 412 measures transmission in the mid-infrared range of the spectrum. In some embodiments, the optical system 412 includes a spectrometer that measures the transmission of broadband infrared light through a portion of a sample holder filled with fluid. The spectrometer need not come into direct contact with the sample. As used herein, the term "sample holder" is a broad term that carries its ordinary meaning as an object that can provide a place for fluid. The fluid can enter the sample holder by flowing.

In some embodiments, the optical system 412 includes a filter wheel that contains one or more filters. In some embodiments, more than ten filters can be included, for example twelve or fifteen filters. In some embodiments, more than 20 filters (e.g., twenty-five filters) are mounted on the filter wheel. The optical system 412 includes a light source that passes light through a filter and the sample holder to a detector. In some embodiments, a stepper motor moves the filter wheel in order to position a selected filter in the path of the light. An optical encoder can also be used to finely position one or more filters. In some embodiments, one or more tunable filters may be used to filter light into multiple wavelengths. The one or more tunable filters may provide the multiple wavelengths of light at the same time or at different times (e.g., sequentially). The light source included in the optical system 412 may emit radiation in the ultraviolet, visible, near-infrared, mid-infrared, and/or far-infrared regions of the electromagnetic spectrum. In some embodiments, the light source can be a broadband source that emits radiation in a broad spectral region (e.g., from about 1500 nm to about 6000 nm). In other embodiments, the light source may emit radiation at certain specific wavelengths. The light source may comprise one or more light emitting diodes (LEDs) emitting radiation at one or more wavelengths in the radiation regions described herein. In other embodiments, the light source may comprise one or more laser modules emitting radiation at one or more wavelengths. The laser modules may comprise a solid state laser (e.g., a Nd:YAG laser), a semiconductor based laser (e.g., a GaAs and/or InGaAsP laser), and/or a gas laser (e.g., an Ar-ion laser). In some embodiments, the laser modules may comprise a fiber laser. The laser modules may emit radiation at certain fixed wavelengths. In some embodiments, the emission wavelength of the laser module(s) may be tunable over a wide spectral range (e.g., about 30 nm to about 100 nm). In some embodiments, the light source included in the optical system 412 may be a thermal infrared emitter. The light source can comprise a resistive heating element, which, in some embodiments, may be integrated on a thin dielectric membrane on a micromachined silicon structure. In one embodiment the light source is generally similar to the electrical modulated thermal infrared radiation source, IRSource™, available from the Axetris Microsystems division of Leister Technologies, LLC (Itasca, Ill.).

The optical system 412 can be controlled by an optical system controller 413. The optical system controller can, in some embodiments, be integrated into the optical system 412. In some embodiments, the fluid system controller 405 and the optical system controller 413 can communicate with each other as indicated by the line 411. In some embodiments, the function of these two controllers can be integrated and a single controller can control both the fluid-handling system 404 and the optical system 412. Such an integrated control can be advantageous because the two systems are preferably integrated, and the optical system 412 is preferably configured to analyze the very same fluid handled by the fluid-handling system 404. Indeed, portions of the fluid-handling system 404 (e.g., the sample holder described above with respect to the second disposable subsystem 410 and/or at least some components of a centrifuge) can also be components of the optical system 412. Accordingly, the fluid-handling system 404 can be controlled to obtain a fluid sample for analysis by optical system 412, when the fluid sample arrives, the optical system 412 can be controlled to analyze the sample, and when the analysis is complete (or before), the fluid-handling system 404 can be controlled to return some of the sample to the fluid source 402 and/or discard some of the sample, as appropriate.

Figure 24:
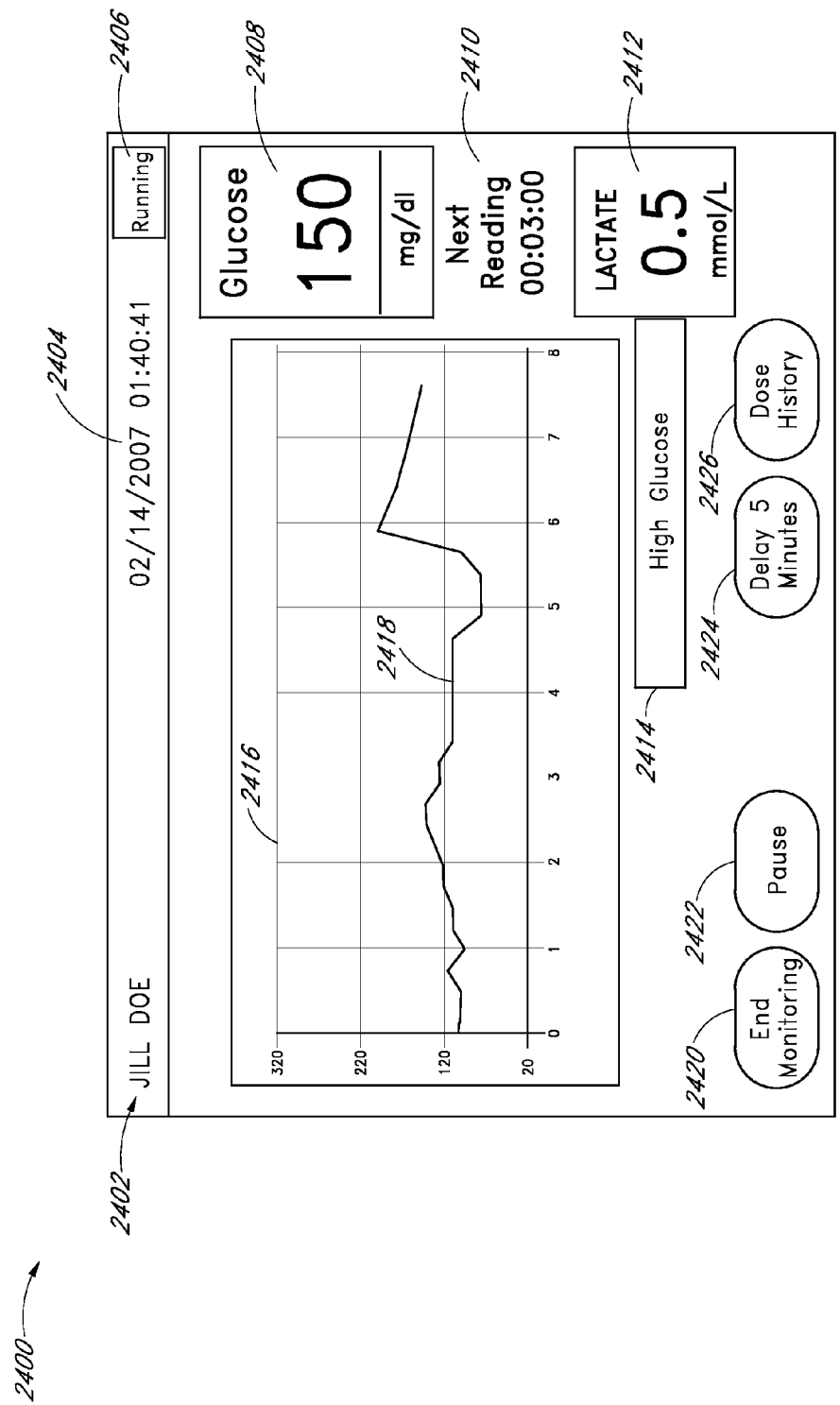
FIGS. 24 and 25 schematically illustrate the visual appearance of embodiments of a user interface for a system for withdrawing and analyzing fluid samples.
Figure 25:
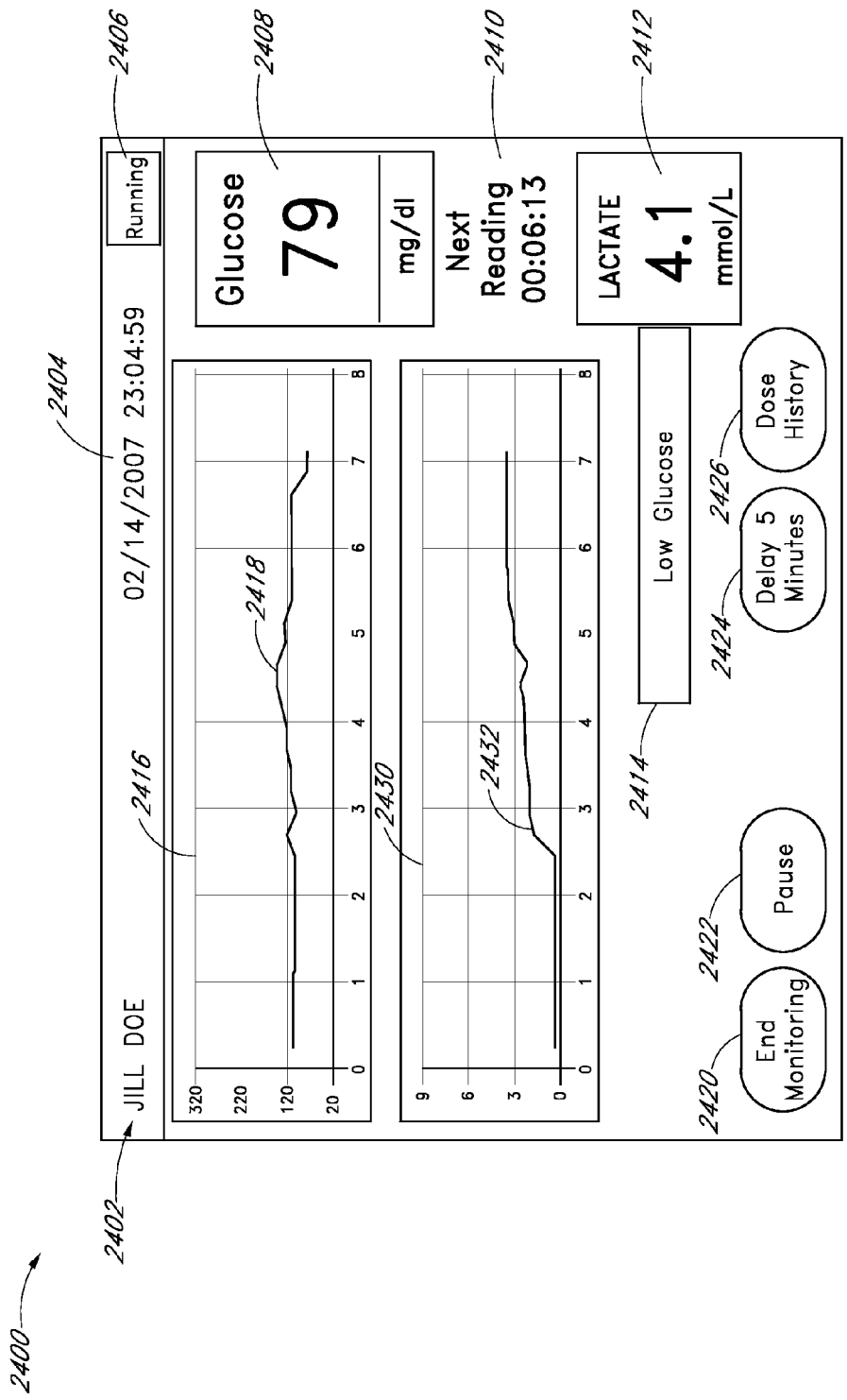

The system 400 shown in FIG. 4 includes a display system 414 that provides for communication of information to a user of the system 400. In some embodiments, the display 414 can be replaced by or supplemented with other communication devices that communicate in non-visual ways. The display system 414 can include a display processor that controls or produces an interface to communicate information to the user. The display system 414 can include a display screen. One or more parameters such as, for example, blood glucose concentration, system 400 operating parameters, and/or other operating parameters can be displayed on a monitor (not shown) associated with the system 400. An example of one way such information can be displayed is shown in FIGS. 24 and 25. In some embodiments, the display system 414 can communicate measured physiological parameters and/or operating parameters to a computer system over a communications connection.

The system 400 shown in FIG. 4 includes an algorithm processor 416 that can receive spectral information, such as optical density (OD) values (or other analog or digital optical data) from the optical system 412 and or the optical system controller 413. In some embodiments, the algorithm processor 416 calculates one or more physiological parameters and can analyze the spectral information. Thus, for example and without limitation, a model can be used that determines, based on the spectral information, physiological parameters of fluid from the fluid source 402. The algorithm processor 416, a controller that may be part of the display system 414, and any embedded controllers within the system 400 can be connected to one another with a communications bus.

Some embodiments of the systems described herein (e.g., the system 400), as well as some embodiments of each method described herein, can include a computer program accessible to and/or executable by a processing system, e.g., a one or more processors and memories that are part of an embedded system. Indeed, the controllers may comprise one or more computers and/or may use software. Thus, as will be appreciated by those skilled in the art, various embodiments may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, various embodiments may take the form of a method, an entirely hardware embodiment, an entirely software embodiment or an embodiment combining software and hardware aspects. Furthermore, any one or more of the disclosed methods (including but not limited to the disclosed methods of measurement analysis, interferent determination, and/or calibration constant generation) may be stored as one or more computer readable code segments or data compilations on a carrier medium. Any suitable computer readable carrier medium may be used including a magnetic storage device such as a diskette or a hard disk; a memory cartridge, module, card or chip (either alone or installed within a larger device); or an optical storage device such as a CD or DVD.

Fluid Handling System

Figure 5:
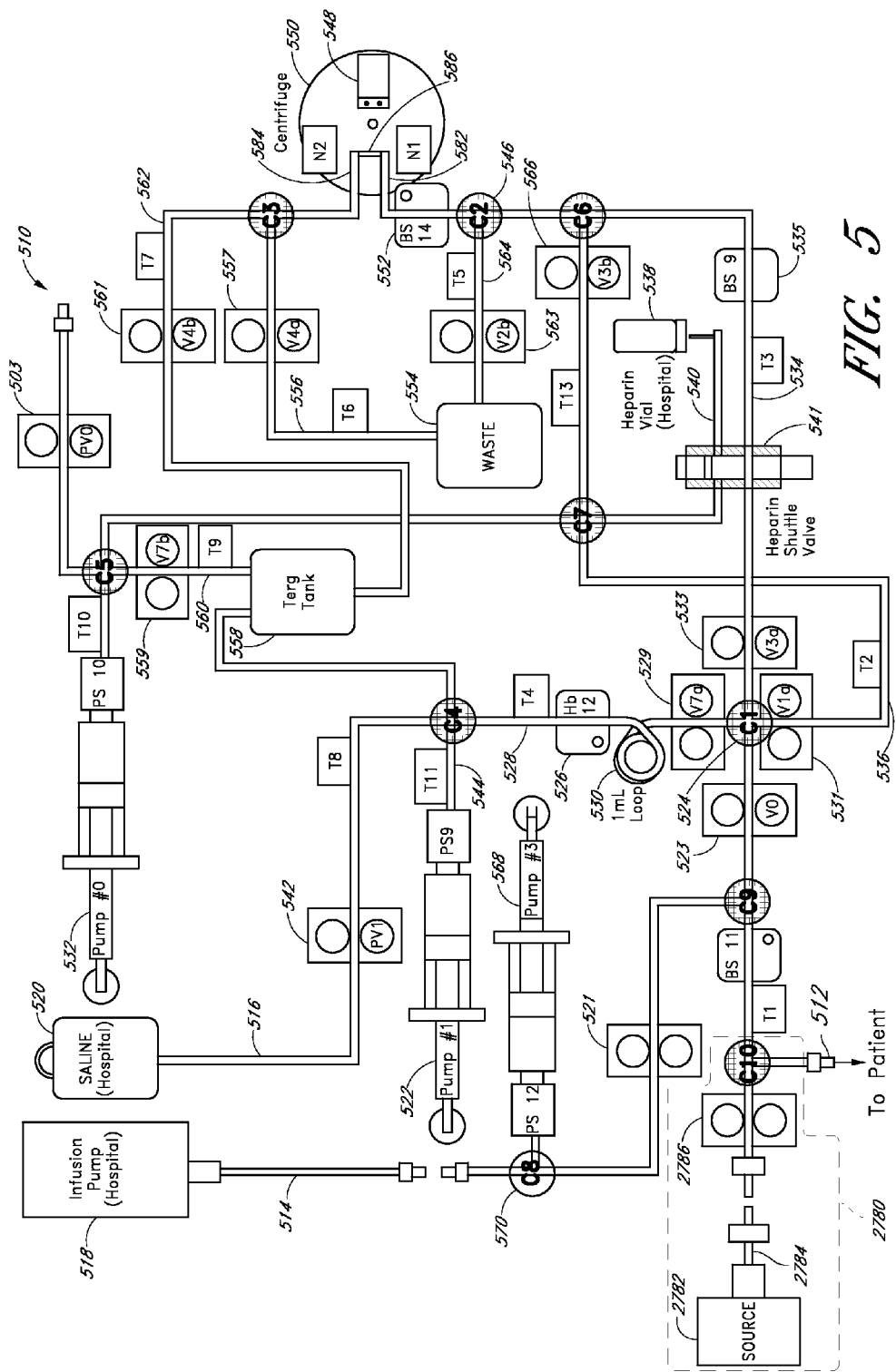
FIG. 5 schematically illustrates an embodiment of a fluid system that can be part of a system for withdrawing and analyzing fluid samples.

The generalized fluid-handling system 404 can have various configurations. In this context, FIG. 5 schematically illustrates the layout of an example embodiment of a fluid system 510. In this schematic representation, various components are depicted that may be part of a non-disposable subsystem 406, a first disposable subsystem 408, a second disposable subsystem 410, and/or an optical system 412. The fluid system 510 is described practically to show an example cycle as fluid is drawn and analyzed.

In addition to the reference numerals used below, the various portions of the illustrated fluid system 510 are labeled for convenience with letters to suggest their roles as follows: T# indicates a section of tubing. C# indicates a connector that joins multiple tubing sections. V# indicates a valve. BS# indicates a bubble sensor or ultrasonic air detector. N# indicates a needle (e.g., a needle that injects sample into a sample holder). PS# indicates a pressure sensor (e.g., a reusable pressure sensor). Pump# indicates a fluid pump (e.g., a syringe pump with a disposable body and reusable drive). "Hb 12" indicates a sensor for hemoglobin (e.g., a dilution sensor that can detect hemoglobin optically).

The term "valve" as used herein is a broad term and is used, in accordance with its ordinary meaning, to refer to any flow regulating device. For example, the term "valve" can include, without limitation, any device or system that can controllably allow, prevent, or inhibit the flow of fluid through a fluid passageway. The term "valve" can include some or all of the following, alone or in combination: pinch valves, rotary valves, stop cocks, pressure valves, shuttle valves, mechanical valves, electrical valves, electro-mechanical flow regulators, etc. In some embodiments, a valve can regulate flow using gravitational methods or by applying electrical voltages or by both.

The term "pump" as used herein is a broad term and is used, in accordance with its ordinary meaning, to refer to any device that can urge fluid flow. For example, the term "pump" can include any combination of the following: syringe pumps, peristaltic pumps, vacuum pumps, electrical pumps, mechanical pumps, hydraulic pumps, etc. Pumps and/or pump components that are suitable for use with some embodiments can be obtained, for example, from or through Hospira.

The function of the valves, pumps, actuators, drivers, motors (e.g., the centrifuge motor), etc. described below is controlled by one or more controllers (e.g., the fluid system controller 405, the optical system controller 413, etc.) The controllers can include software, computer memory, electrical and mechanical connections to the controlled components, etc.

At the start of a measurement cycle, most lines, including a patient tube 512 (T1), an Arrival sensor tube 528 (T4), an anticoagulant valve tube 534 (T3), and a sample cell 548 can be filled with saline that can be introduced into the system through the infusion tube 514 and the saline tube 516, and which can come from an infusion pump 518 and/or a saline bag 520. The infusion pump 518 and the saline bag 520 can be provided separately from the system 510. For example, a hospital can use existing saline bags and infusion pumps to interface with the described system. The infusion valve 521 can be open to allow saline to flow into the tube 512 (T1).

Before drawing a sample, the saline in part of the system 510 can be replaced with air. Thus, for example, the following valves can be closed: air valve 503 (PV0), the detergent tank valve 559 (V7b), 566 (V3b), 523 (V0), 529 (V7a), and 563 (V2b). At the same time, the following valves can be open: valves 531 (V1a), 533 (V3a) and 577 (V4a). Simultaneously, a second pump 532 (pump #0) pumps air through the system 510 (including tube 534 (T3), sample cell 548, and tube 556 (T6)), pushing saline through tube 534 (T3) and sample cell 548 into a waste bladder 554.

Next, a sample can be drawn. With the valves 542 (PV1), 559 (V7b), and 561 (V4b) closed, a first pump 522 (pump #1) is actuated to draw sample fluid to be analyzed (e.g. blood) from a fluid source (e.g., a laboratory sample container, a living patient, etc.) up into the patient tube 512 (T1). In various embodiments, the first pump 522 (pump #1) can be actuated at a rate such that the flow of blood in the catheter attached to the patient is about 4.0-8.0 ml/minute on average. The sample is drawn through the tube past the two flanking portions of the open pinch-valve 523 (V0), through the first connector 524 (C1), into the looped tube 530, past the arrival sensor 526 (Hb12), and into the arrival sensor tube 528 (T4). The arrival sensor 526 may be used to detect the presence of blood in the tube 528 (T4). For example in some embodiments, the arrival sensor 526 may comprise a hemoglobin sensor. In some other embodiments, the arrival sensor 526 may comprise a color sensor that detects the color of fluid flowing through the tube 528 (T4). During this process, the valve 529 (V7a) and 523 (V0) are open to fluid flow, and the valves 531 (V1a), 533 (V3a), 542 (PV1), 559 (V7b), and 561 (V4b) can be closed and therefore block (or substantially block) fluid flow by pinching the tube.

In some embodiments of fluid systems, for example those that are used in the hospital environment to periodically monitor the concentration of various analytes in a patient, the amount of sample of fluid withdrawn from the patient can be greater than approximately 600 ml/day. Withdrawing large blood sample volumes can be disadvantageous in patients who are critically ill or have significant blood loss. Thus it may be advantageous to provide systems and methods that can reduce the amount of withdrawn sample volume to between: approximately 500 ml/day–450 ml/day; approximately 450 ml/day–approximately 400 ml/day; approximately 400 ml/day–approximately 350 ml/day; approximately 350 ml/day–approximately 300 ml/day; approximately 300 ml/day–approximately 250 ml/day; approximately 250 ml/day–approximately 200 ml/day; approximately 200 ml/day–approximately 150 ml/day; and lower.

In some embodiments of the fluid system described herein, withdrawing low sample volumes (e.g. a few hundreds of milliliters per day) can be achieved by a combination of bubble sensors, pinch valves and low inner diameter tubing. For example, in some embodiments, the patient tube 512 and/or tube T1 (see FIGS. 5, 6) may comprise lower inner diameter tubing to allow reducing the amount of withdrawn sample. In some embodiments, the inner diameter of the patient tube 512 and/or tube T1 can be approximately 0.02 inches. In some embodiments, the inner diameter of the patient tube 512 and/or tube T1 can vary between 0.015 inches-0.02 inches. In some embodiments, the inner diameter of the patient tube 512 and/or tube T1 can vary between 0.02 inches-0.04 inches. Other values for the inner diameter of the patient tube 512 and/or tube T1 between 0.015 inches-0.04 inches are also possible.

In some embodiments of fluid systems, e.g., those providing continuous glucose monitoring, a sample of fluid is withdrawn periodically at certain intervals within a given time period. The duration of time over which the sample of fluid is withdrawn may be set to avoid clinical drawbacks, and/or it can be varied according to a health-care provider's wishes. In some embodiments, the duration of time over which the sample is withdrawn can be reduced and/or minimized. For example, in some embodiments, fluid may be continuously withdrawn into a monitoring system over a period of time lasting approximately 15 seconds to approximately 5 minutes, and that continuous withdrawal can take place at intervals of, for example, 15 minutes. In some embodiments, for every 15 minute time period, sample withdrawal may be minimized to last for a small fraction of that period (e.g., only 15 seconds to 5 minutes). Alternatively, it may be desirable to withdraw fluid over a longer period of time and/or at a lower flow rate, as discussed infra.

In continuous glucose monitoring systems where sample withdrawal time is minimized and/or sample volume is minimized, using a combination of low inner diameter tubing, pinch valves and sensors (e.g. hemoglobin sensors, color sensors, bubble sensors, etc.) can reduce the amount of sample withdrawn. For example, whereas in some cases an additional amount of sample is withdrawn—exceeding the bare minimum required for sample analysis and/or measurement—to provide for a margin of error, increasing precision can reduce the margin of error, thereby reducing a need for an additional amount of sample. Thus, a system that creates a more defined sample or more precisely detects the arrival of a sample can reduce the likelihood of errors and diminish the need for drawing additional sample fluid.

As described further below, injection of bubbles between slugs of fluid (e.g., blood, saline, sample, etc.) can help provide for greater accuracy and therefore smaller sample volumes. A bubble sensor can be used to sense the arrival of a sample with increased precision (e.g., by detecting the transition from air to liquid). This can reduce the amount of sample that is withdrawn (e.g., by reducing a need to draw additional sample volume as a precaution). Use of such techniques, for example, can allow the volume of sample fluid withdrawn to be in a range of between approximately 2 ml and approximately 6 ml in a certain interval of time (e.g., that interval can be the duration of a draw period, which can range from approximately 15 seconds to approximately 5 minutes, in some embodiments). In some embodiments the volume of sample withdrawn can lie outside this range, and the timer interval can be greater or lesser than the example provided.

Before drawing the sample, the tubes 512 (T1) and 528 (T4) are filled with saline and the hemoglobin (Hb) level is zero. The tubes that are filled with saline are in fluid communication with the sample source (e.g., the fluid source 402). The sample source can be the vessels of a living human or a pool of liquid in a laboratory sample container, for example. When the saline is drawn toward the first pump 522, fluid to be analyzed is also drawn into the system because of the suction forces in the closed fluid system. Thus, the first pump 522 draws a relatively continuous column of fluid that first comprises generally nondiluted saline, then a mixture of saline and sample fluid (e.g., blood), and then eventually nondiluted sample fluid. In the example illustrated here, the sample fluid is blood.

The arrival sensor 526 (Hb12) can detect and/or verify the presence of blood in the tubes. For example, in some embodiments, the arrival sensor 526 can determine the color of the fluid in the tubes. In some embodiments, the arrival sensor 526 (Hb12) can detect the level of Hemoglobin in the sample fluid. As blood starts to arrive at the arrival sensor 526 (Hb12), the sensed hemoglobin level rises. A hemoglobin level can be selected, and the system can be pre-set to determine when that level is reached. A controller such as the fluid system controller 405 of FIG. 4 can be used to set and react to the pre-set value, for example. In some embodiments, when the sensed hemoglobin level reaches the pre-set value, substantially undiluted sample is present at the first connector 524 (C1). The preset value can depend, in part, on the length and diameter of any tubes and/or passages traversed by the sample. In some embodiments, the pre-set value can be reached after approximately 2 mL of fluid (e.g., blood) has been drawn from a fluid source. A nondiluted sample can be, for example, a blood sample that is not diluted with saline solution, but instead has the characteristics of the rest of the blood flowing through a patient's body. A loop of tubing 530 (e.g., a 1-mL loop) can be advantageously positioned as illustrated to help insure that undiluted fluid (e.g., undiluted blood) is present at the first connector 524 (C1) when the arrival sensor 526 registers that the preset Hb threshold is crossed. The loop of tubing 530 provides additional length to the Arrival sensor tube 528 (T4) to make it less likely that the portion of the fluid column in the tubing at the first connector 524 (C1) has advanced all the way past the mixture of saline and sample fluid, and the nondiluted blood portion of that fluid has reached the first connector 524 (C1).

In some embodiments, when nondiluted blood is present at the first connector 524 (C1), a sample is mixed with an anticoagulant and is directed toward the sample cell 548. An amount of anticoagulant (e.g., heparin) can be introduced into the tube 534 (T3), and then the undiluted blood is mixed with the anticoagulant. A heparin vial 538 (e.g., an insertable vial provided independently by the user of the system 510) can be connected to a tube 540. An anticoagulant valve 541 (which can be a shuttle valve, for example) can be configured to connect to both the tube 540 and the anticoagulant valve tube 534 (T3). The valve can open the tube 540 to a suction force (e.g., created by the pump 532), allowing heparin to be drawn from the vial 538 into the valve 541. Then, the anticoagulant valve 541 can slide the heparin over into fluid communication with the anticoagulant valve tube 534 (T3). The anticoagulant valve 541 can then return to its previous position. Thus, heparin can be shuttled from the tube 540 into the anticoagulant valve tube 534 (T3) to provide a controlled amount of heparin into the tube 534 (T3).

With the valves 542 (PV1), 559 (V7b), 561 (V4b), 523 (V0), 531 (V1a), 566 (V3b), and 563 (V2b) closed, and the valves 529 (V7a) and 533 (V3a) open, first pump 522 (pump #1) pushes the sample from tube 528 (T4) into tube 534 (T3), where the sample mixes with the heparin injected by the anticoagulant valve 541 as it flows through the system 510. As the sample proceeds through the tube 534 (T3), the air that was previously introduced into the tube 534 (T3) is displaced. The sample continues to flow until a bubble sensor 535 (BS9) indicates a change from air to a liquid, and thus the arrival of a sample at the bubble sensor. In some embodiments, the volume of tube 534 (T3) from connector 524 (C1) to bubble sensor 535 (BS9) is a known and/or engineered amount, and may be approximately 500 μL, 200 μL or 100 μL, for example. In some embodiments, the volume of tube 534 (T3) from connector 524 (C1) to bubble sensor 535 (BS9) may be approximately less than 10 ml.

When bubble sensor 535 (BS9) indicates the presence of a sample, the remainder of the sampled blood can be returned to its source (e.g., the patient veins or arteries). The first pump 522 (pump #1) pushes the blood out of the Arrival sensor tube 528 (T4) and back to the patient by opening the valve 523 (V0), closing the valves 531 (V1a) and 533 (V3a), and keeping the valve 529 (V7a) open. The Arrival sensor tube 528 (T4) is preferably flushed with approximately 2 mL of saline. This can be accomplished by closing the valve 529 (V7a), opening the valve 542 (PV1), drawing saline from the saline source 520 into the tube 544, closing the valve 542 (PV1), opening the valve 529 (V7a), and forcing the saline down the Arrival sensor tube 528 (T4) with the pump 522. In some embodiments, less than two minutes elapse between the time that blood is drawn from the patient and the time that the blood is returned to the patient.

Following return of the unused patient blood sample, the sample is pushed up the anticoagulant valve tube 534 (T3), through the second connector 546 (C2), and into the sample cell 548, which can be located on the centrifuge rotor 550. This fluid movement is facilitated by the coordinated action (either pushing or drawing fluid) of the pump 522 (pump #1), the pump 532 (pump #0), and the various illustrated valves. In particular, valve 531 (V1a) can be opened, and valves 503 (PV0) and 559 (V7b) can be closed. Pump movement and valve position corresponding to each stage of fluid movement can be coordinated by one ore multiple controllers, such as the fluid system controller 405 of FIG. 4.

After the unused sample is returned to the patient, the sample can be divided into separate slugs before being delivered into the sample cell 548. Thus, for example, valve 533 (V3a) is opened, valves 566 (V3b), 523 (V0) and 529 (V7a) are closed, and the pump 532 (pump #0) uses air to push the sample toward sample cell 548. In some embodiments, the sample (for example, 200 μL or 100 μL) is divided into multiple (e.g., more than two, five, or four) "slugs" of sample, each separated by a small amount of air. As used herein, the term "slug" refers to a continuous column of fluid that can be relatively short. Slugs can be separated from one another by small amounts of air (or bubbles) that can be present at intervals in the tube. In some embodiments, the slugs are formed by injecting or drawing air into fluid in the first connector 546 (C2).

In some embodiments, when the leading edge of the sample reaches blood sensor 552 (BS14), a small amount of air (the first "bubble") is injected at a connector C6. This bubble helps define the first "slug" of liquid, which extends from the bubble sensor to the first bubble. In some embodiments, the valves 533 (V3a) and 566 (V3b) are alternately opened and closed to form a bubble at connector C6, and the sample is pushed toward the sample cell 548. Thus, for example, with pump 532 actuated, valve 566 V(3b) is briefly opened and valve 533 (V3a) is briefly closed to inject a first air bubble into the sample.

In some embodiments, the volume of the tube 534 (T3) from the connector 546 (C2) to the bubble sensor 552 (BS14) is less than the volume of tube 534 (T3) from the connector 524 (C1) to the bubble sensor 535 (BS9). Thus, for example and without limitation, the volume of the tube 534 (T3) from the connector 524 (C1) to the bubble sensor 535 (BS9) can be in the range of approximately 80 µL to approximately 120 µL, (e.g., 100 µL) and the volume of the tube 534 (T3) from the connector 546 (C2) to the bubble sensor 552 (BS14) can be in the range of approximately 5 µL to approximately 25 µL (e.g., 15 µL). In some embodiments, multiple blood slugs are created. For example, more than two blood slugs can be created, each having a different volume. In some embodiments, five blood slugs are created, each having approximately the same volume of approximately 20 µL each. In some embodiments, three blood slugs are created, the first two having a volume of 10 µL and the last having a volume of 20 µL. In some embodiments, four blood slugs are created; the first three blood slugs can have a volume of approximately 150 µL and the fourth can have a volume of approximately 35 µL.

A second slug can be prepared by opening the valve 533 (V3a), closing the valve 566 (V3b), with pump 532 (pump #0) operating to push the first slug through a first sample cell holder interface tube 582 (N1), through the sample cell 548, through a second sample cell holder interface tube 584 (N2), and toward the waste bladder 554. When the first bubble reaches the bubble sensor 552 (BS 14), the open/closed configurations of valves 533 (V3a) and 566 (V3b) are reversed, and a second bubble is injected into the sample, as before. A third slug can be prepared in the same manner as the second (pushing the second bubble to bubble sensor 552 (BS 14) and injecting a third bubble). After the injection of the third air bubble, the sample can be pushed through system 510 until the end of the sample is detected by bubble sensor 552 (BS 14). The system can be designed such that when the end of the sample reaches this point, the last portion of the sample (a fourth slug) is within the sample cell 548, and the pump 532 can stop forcing the fluid column through the anticoagulant valve tube 534 (T3) so that the fourth slug remains within the sample cell 548. Thus, the first three blood slugs can serve to flush any residual saline out the sample cell 548. The three leading slugs can be deposited in the waste bladder 554 by passing through the tube 556 (T6) and past the tube-flanking portions of the open pinch valve 557 (V4a).

In some embodiments, the fourth blood slug is centrifuged for a given length of time (e.g., more than 1 minute, five minutes, or 2 minutes, to take three advantageous examples) at a relatively fast speed (e.g., 7200 RPM, 5000 RPM, or 4500 RPM, to take three examples). Thus, for example, the sample cell holder interface tubes 582 (N1) and 584 (N2) disconnect the sample cell 548 from the tubes 534 (T3) and 562 (T7), permitting the centrifuge rotor 550 and the sample cell 548 to spin together. Spinning separates a sample (e.g., blood) into its components, isolates the plasma, and positions the plasma in the sample cell 548 for measurement. The centrifuge 550 can be stopped with the sample cell 548 in a beam of radiation (not shown) for analysis. The radiation, a detector, and logic can be used to analyze a portion of the sample (e.g., the plasma) spectroscopically (e.g., for glucose, lactate, or other analyte concentration). In some embodiments, some or all of the separated components (e.g., the isolated plasma) may be transported to a different analysis chamber. For example, another analysis chamber can have one or more electrodes in electrical communication with the chamber's contents, and the separated components may be analyzed electrically. At any suitable point, one or more of the separated components can be transported to the waste bladder 554 when no longer needed. In some chemical analysis systems and apparatus, the separated components are analyzed electrically. Analysis devices may be connected serially, for example, so that the analyzed substance from an optical analysis system (e.g., an "OptiScanner®" fluid analyzer) can be transferred to an independent analysis device (e.g., a chemical analysis device) for subsequent analysis. In certain embodiments, the analysis devices are integrated into a single system. Many variations are possible.

In some embodiments, portions of the system 510 that contain blood after the sample cell 548 has been provided with a sample are cleaned to prevent blood from clotting. Accordingly, the centrifuge rotor 550 can include two passageways for fluid that may be connected to the sample cell holder interface tubes 582 (N1) and 584 (N2). One passageway is sample cell 548, and a second passageway is a shunt 586. An embodiment of the shunt 586 is illustrated in more detail in FIG. 16 (see reference numeral 1586).

The shunt 586 can allow cleaner (e.g., a detergent such as tergazyme A) to flow through and clean the sample cell holder interface tubes without flowing through the sample cell 548. After the sample cell 548 is provided with a sample, the interface tubes 582 (N1) and 584 (N2) are disconnected from the sample cell 548, the centrifuge rotor 550 is rotated to align the shunt 586 with the interface tubes 582 (N1) and 584 (N2), and the interface tubes are connected with the shunt. With the shunt in place, the detergent tank 559 is pressurized by the second pump 532 (pump #0) with valves 561 (V4b) and 563 (V2b) open and valves 557 (V4a) and 533 (V3a) closed to flush the cleaning solution back through the interface tubes 582 (N1) and 584 (N2) and into the waste bladder 554. Subsequently, saline can be drawn from the saline bag 520 for a saline flush. This flush pushes saline through the Arrival sensor tube 528 (T4), the anticoagulant valve tube 534 (T3), the sample cell 548, and the waste tube 556 (T6). Thus, in some embodiments, the following valves are open for this flush: 529 (V7a), 533 (V3a), 557 (V4a), and the following valves are closed: 542 (PV1), 523 (V0), 531 (V1a), 566 (V3b), 563 (V2b), and 561 (V4b).

Following analysis, the second pump 532 (pump #0) flushes the sample cell 548 and sends the flushed contents to the waste bladder 554. This flush can be done with a cleaning solution from the detergent tank 558. In some embodiments, the detergent tank valve 559 (V7b) is open, providing fluid communication between the second pump 532 and the detergent tank 558. The second pump 532 forces cleaning solution from the detergent tank 558 between the tube-flanking portions of the open pinch valve 561 and through the tube 562 (T7). The cleaning flush can pass through the sample cell 548, through the second connector 546, through the tube 564 (T5) and the open valve 563 (V2b), and into the waste bladder 554.

Subsequently, the first pump 522 (pump #1) can flush the cleaning solution out of the sample cell 548 using saline in drawn from the saline bag 520. This flush pushes saline through the Arrival sensor tube 528 (T4), the anticoagulant valve tube 534 (T3), the sample cell 548, and the waste tube 556 (T6). Thus, in some embodiments, the following valves are open for this flush: 529 (V7a), 533 (V3a), 557 (V4a), and the following valves are closed: 542 (PV1), 523 (V0), 531 (V1a), 566 (V3b), 563 (V2b), and 561 (V4b).

When the fluid source is a living entity such as a patient, a low flow of saline (e.g., 1-5 mL/hr) is preferably moved through the patient tube 512 (T1) and into the patient to keep the patient's vessel open (e.g., to establish a keep vessel open, or "KVO" flow). This KVO flow can be temporarily interrupted when fluid is drawn into the fluid system 510. The source of this KVO flow can be the infusion pump 518, the third pump 568 (pump #3), or the first pump 522 (pump #1). In some embodiments, the infusion pump 518 can run continuously throughout the measurement cycle described above. This continuous flow can advantageously avoid any alarms that may be triggered if the infusion pump 518 senses that the flow has stopped or changed in some other way. In some embodiments, when the infusion valve 521 closes to allow pump 522 (pump #1) to withdraw fluid from a fluid source (e.g., a patient), the third pump 568 (pump #3) can withdraw fluid through the connector 570, thus allowing the infusion pump 518 to continue pumping normally as if the fluid path was not blocked by the infusion valve 521. If the measurement cycle is about two minutes long, this withdrawal by the third pump 568 can continue for approximately two minutes. Once the infusion valve 521 is open again, the third pump 568 (pump #3) can reverse and insert the saline back into the system at a low flow rate. Preferably, the time between measurement cycles is longer than the measurement cycle itself (for example, the time interval can be longer than ten minutes, shorter than ten minutes, shorter than five minutes, longer than two minutes, longer than one minute, etc.). Accordingly, the third pump 568 can insert fluid back into the system at a lower rate than it withdrew that fluid. This can help prevent an alarm by the infusion pump.

Figure 6:
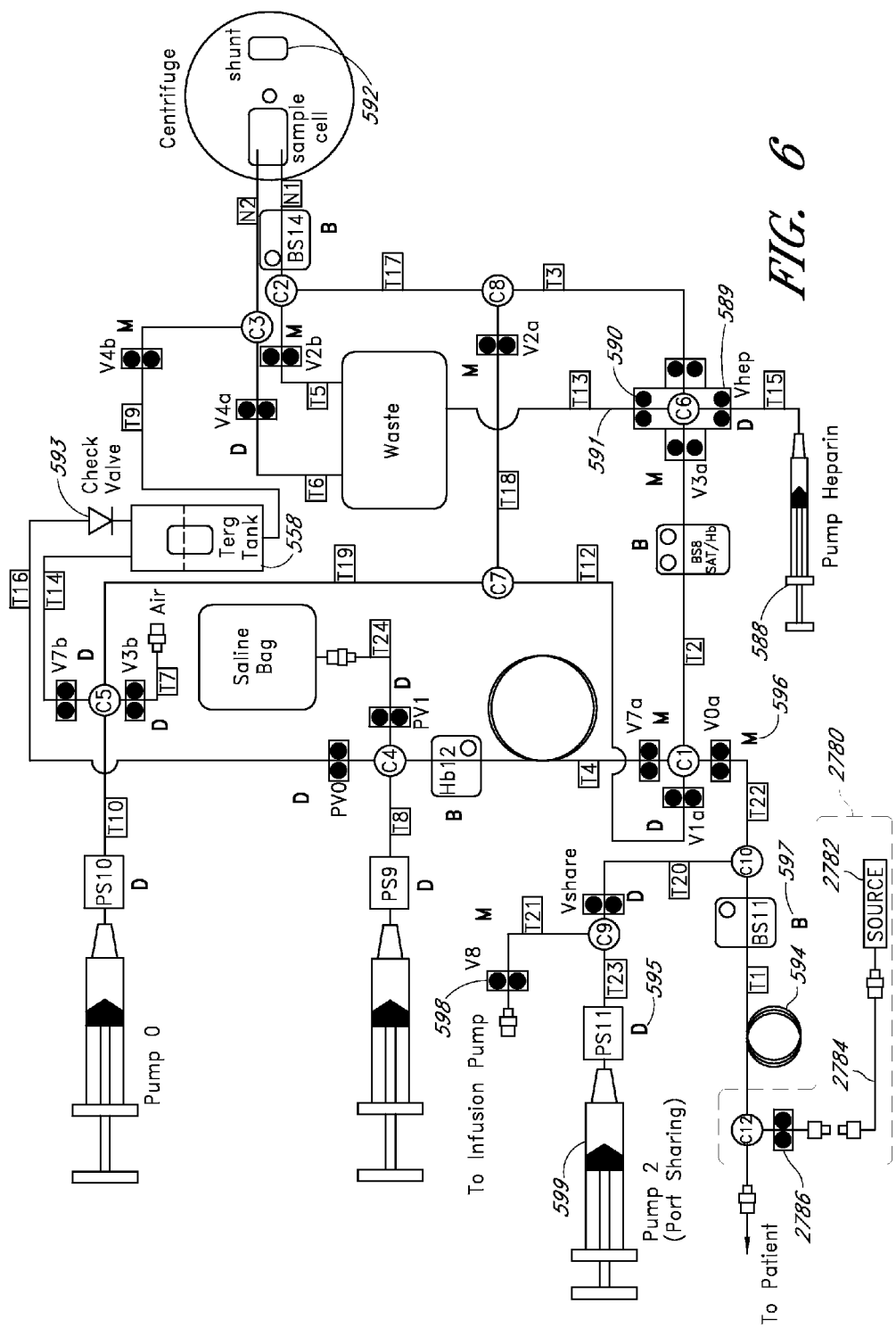
FIG. 6 schematically illustrates another embodiment of a fluid system that can be part of a system for withdrawing and analyzing fluid samples.

FIG. 6 schematically illustrates another embodiment of a fluid system that can be part of a system for withdrawing and analyzing fluid samples. In this embodiment, the anticoagulant valve 541 has been replaced with a syringe-style pump 588 (Pump Heparin) and a series of pinch valves around a junction between tubes. For example, a heparin pinch valve 589 (Vhep) can be closed to prevent flow from or to the pump 588, and a heparin waste pinch valve 590 can be closed to prevent flow from or to the waste container from this junction through the heparin waste tube 591. This embodiment also illustrates the shunt 592 schematically. Other differences from FIG. 5 include the check valve 593 located near the detergent tank 558 and the patient loop 594. The reference letters D, for example, the one indicated at 595, refer to components that are advantageously located on the door. The reference letters M, for example, the one indicated at 596, refer to components that are advantageously located on the monitor. The reference letters B, for example, the one indicated at 597, refer to components that can be advantageously located on both the door and the monitor.

In some embodiments, the system 400 (see FIG. 4), the apparatus 100 (see FIG. 1), or even the monitoring device 102 (see FIG. 1) itself can also actively function not only to monitor analyte levels (e.g., glucose), but also to change and/or control analyte levels. Thus, the monitoring device 102 can be both a monitoring and an infusing device. In some embodiments, the fluid handling system 510 can include an optional analyte control subsystem 2780 that will be further described below (see discussion of analyte control).

In certain embodiments, analyte levels in a patient can be adjusted directly (e.g., by infusing or extracting glucose) or indirectly (e.g., by infusing or extracting insulin). FIG. 6 illustrates one way of providing this function. The infusion pinch valve 598 (V8) can allow the port sharing pump 599 (compare to the third pump 568 (pump #3) in FIG. 5) to serve two roles. In the first role, it can serve as a "port sharing" pump. The port sharing function is described with respect to the third pump 568 (pump #3) of FIG. 5, where the third pump 568 (pump #3) can withdraw fluid through the connector 570, thus allowing the infusion pump 518 to continue pumping normally as if the fluid path was not blocked by the infusion valve 521. In the second role, the port sharing pump 599 can serve as an infusion pump. The infusion pump role allows the port sharing pump 599 to draw a substance (e.g., glucose, saline, etc.) from another source when the infusion pinch valve 598 is open, and then to infuse that substance into the system or the patient when the infusion pinch valve 598 is closed. This can occur, for example, in order to change the level of a substance in a patient in response to a reading by the monitor that the substance is too low. In some embodiments, one or more of the pumps may comprise a reversible infusion pump configured to interrupt the flow of the infusion fluid and draw a sample of blood for analysis.

In some embodiments, various components of the fluid system that may be part of a non-disposable (or less-frequently disposable) subsystem (e.g. 406), a first disposable subsystem (e.g. 408) or a second disposable subsystem (e.g. 410) may comprise fluid passageways (e.g. tubes) having different inner diameters. For example, in some embodiments of a fluid system that may be used to withdraw a sample of fluid from a patient for analysis, the inner diameter of the fluid passageway connected to the patient may be appropriately sized to withdraw the sample by applying reduced pressure and reduce the amount of sample withdrawn. For example, the amount of sample withdrawn into a fluid passageway in a certain interval of time depends on the cross-sectional area of the fluid passageway and the pressure applied to draw the sample. The amount of sample withdrawn in a certain interval of time in a fluid passageway having a small inner diameter will be smaller than the amount of sample withdrawn in a certain interval of time in a fluid passageway having a larger inner diameter assuming that the fluid flow speed of the sample is the same in both fluid passageways. The pressure required to draw a volume of sample in a fluid passageway having a small inner diameter is greater than the pressure required to draw the same volume of sample in a fluid passageway having a larger inner diameter in the same amount of time. Thus, appropriately choosing the inner diameter of the fluid passageway can strike a balance between the amount of sample withdrawn and the pressure used to withdraw the sample.

In some embodiments, the fluid system may comprise fluid passageways having a larger internal diameter. An advantage of fluid passageways with large internal diameter is that they can be used as a reservoir or a storage passageway for storing fluids (e.g. infusion fluid, fluid sample, treatment fluid, etc.). In some embodiments, a widened passage can allow an amount of fluid to be drawn with reduced pressure or can allow application of non-reduced pressure to draw the same amount of fluid more quickly.

In some embodiments, the fluid system may comprise fluid passageways having small inner diameter. A small inner diameter passageway has a smaller surface area which may be advantageous to reduce the amount of fluid that tends to adhere to the inner walls of the fluid passageways. In embodiments that use the same fluid passageway to transport different fluids at different times, reducing amount of fluid that tends to adhere to the inner walls of the fluid passageways is advantageous to reduce the amount of mixing between the different fluids. Fluid passageways with small inner diameter can also advantageously reduce the amount of fluids (e.g. infusion fluid, sample fluid or treatment fluid) that is used in the fluid system. Fluid passageways with small inner diameter can also advantageously reduce the flow rate of a fluid at the same pressure. This may reduce the risk of contamination, as discussed infra.

Figure 6A:
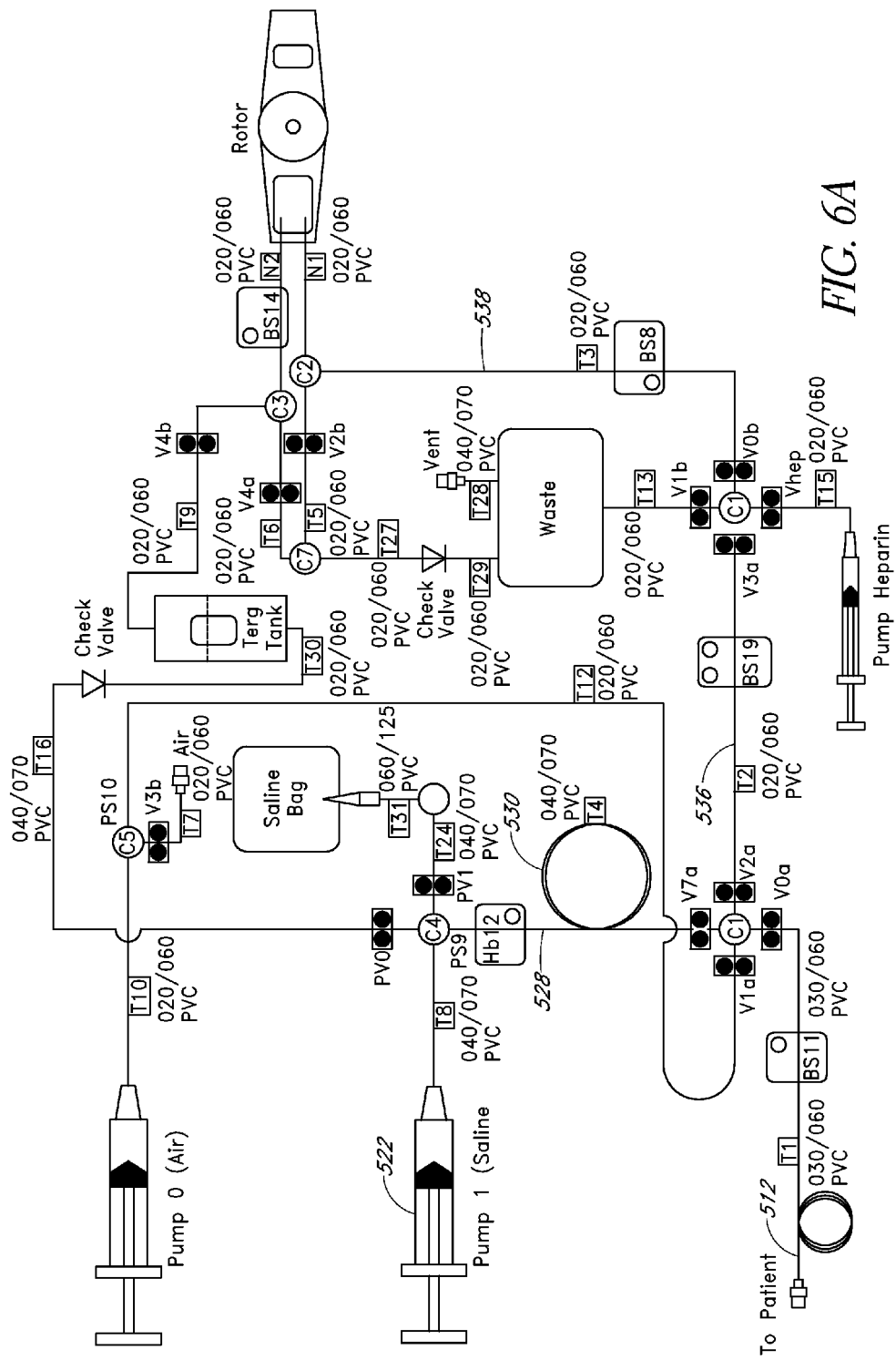
FIG. 6A schematically illustrates an embodiment of a fluid system having tubes of different internal diameters that can be part of a system for withdrawing and analyzing fluid samples.

FIG. 6A schematically illustrates an embodiment of a fluid system having tubes of different inner diameters that can be part of a system for withdrawing and analyzing fluid samples. The outer diameters of the various tubes (e.g. T1, T2, T3, etc.) in the embodiment illustrated in FIG. 6A may vary between approximately 0.06 inches and approximately 0.07 inches, while the inner diameter of the various tubes (e.g. T1, T2, T3, etc.) may vary between approximately 0.02 inches and approximately 0.04 inches. The various tubes (e.g. T1, T2, T3, etc.) in the embodiment illustrated in FIG. 6A may comprise PVC.

In the embodiment illustrated in FIG. 6A, the patient tube 512 and/or tube T1 may have an inner diameter of approximately 0.03 inches and an outer diameter of approximately 0.06 inches. The inner diameter of 0.03 inches is selected to withdraw a sample of fluid from the patient in a short amount of time by applying a reduced amount of pressure by the pump 522 (Pump 1) while still maintaining a low draw volume between approximately 100 ml/day to approximately 500 ml/day.

In the embodiment illustrated in FIG. 6A, the inner diameter of tubing 528 or T4 is selected to be approximately 0.04 inches so that the length of the loop 530 of the tubing 528 can be reduced, compared to a length of the same general volume and storage capacity having an inner diameter of less than approximately 0.04 inches. Indeed, altering the inner diameter of a tube in such a system can effectively reduce lengths and provide for more inexpensive manufacture, as well as reducing friction of fluid flow in the system, reducing pressure in portions of the flow path, etc. For example, increasing the inner diameter of the tubing 528 from 0.02 inches to 0.04 inches can allow the length of the loop 530 required to store approximately 1 ml of fluid to be reduced from approximately 17 feet to approximately 4 feet. A reduction in the length of the loop 530 provides space-saving and other benefits.

The inner diameter of the tubing 536 or T2 and tubing 538 or T3 is approximately 0.02 inches in the embodiment illustrated in FIG. 6A. In some embodiments, tubings 536 and 538 may communicate the sample to the sample cell 548 for analysis and may be periodically flushed, e.g., with saline. Having small inner diameters for tubings 536 and 538 can reduce the amount of mixing between saline and the sample which can lead to less sample dilution. Having smaller inner diameters for tubings 536 and 538 can also advantageously reduce the amount of saline required for flushing and/or the amount of sample transferred to the sample cell 548.

Mechanical/Fluid System Interface

FIG. 7 is an oblique schematic depiction of a modular monitoring device 700, which can correspond to the monitoring device 102. The modular monitoring device 700 includes a body portion 702 having a receptacle 704, which can be accessed by moving a movable portion 706. The receptacle 704 can include connectors (e.g., rails, slots, protrusions, resting surfaces, etc.) with which a removable portion 710 can interface. In some embodiments, portions of a fluidic system that directly contact fluid are incorporated into one or more removable portions (e.g., one or more disposable cassettes, sample holders, tubing cards, etc.). For example, a removable portion 710 can house at least a portion of the fluid system 510 described previously, including portions that contact sample fluids, saline, detergent solution, and/or anticoagulant.

In some embodiments, a non-disposable fluid-handling subsystem 708 is disposed within the body portion 702 of the monitoring device 700. The first removable portion 710 can include one or more openings that allow portions of the non-disposable fluid-handling subsystem 708 to interface with the removable portion 710. For example, the non-disposable fluid-handling subsystem 708 can include one or more pinch valves that are designed to extend through such openings to engage one or more sections of tubing. When the first removable portion 710 is present in a corresponding first receptacle 704, actuation of the pinch valves can selectively close sections of tubing within the removable portion. The non-disposable fluid-handling subsystem 708 can also include one or more sensors that interface with connectors, tubing sections, or pumps located within the first removable portion 710. The non-disposable fluid-handling subsystem 708 can also include one or more actuators (e.g., motors) that can actuate moveable portions (e.g., the plunger of a syringe) that may be located in the removable portion 710. A portion of the non-disposable fluid-handling subsystem 708 can be located on or in the moveable portion 706 (which can be a door having a slide or a hinge, a detachable face portion, etc.).

In the embodiment shown in FIG. 7, the monitoring device 700 includes an optical system 714 disposed within the body portion 702. The optical system 714 can include a light source and a detector that are adapted to perform measurements on fluids within a sample holder (not shown). The light source may comprise a fixed wavelength light source and/or a tunable light source. The light source may comprise one or more sources including, for example, broadband sources, LEDs, and lasers. In some embodiments, the sample holder comprises a removable portion, which can be associated with or disassociated from the removable portion 710. The sample holder can include an optical window through which the optical system 714 can emit radiation for measuring properties of a fluid in the sample holder. The optical system 714 can include other components such as, for example, a power supply, a centrifuge motor, a filter wheel, and/or a beam splitter.

In some embodiments, the removable portion 710 and the sample holder are adapted to be in fluid communication with each other. For example, the removable portion 710 can include a retractable injector that injects fluids into a sample holder. In some embodiments, the sample holder can comprise or be disposed in a second removable portion (not shown). In some embodiments, the injector can be retracted to allow the centrifuge to rotate the sample holder freely.

The body portion 702 of the monitoring device 700 can also include one or more connectors for an external battery (not shown). The external battery can serve as a backup emergency power source in the event that a primary emergency power source such as, for example, an internal battery (not shown) is exhausted.

FIG. 7 shows an embodiment of a system having subcomponents illustrated schematically. By way of a more detailed (but nevertheless non-limiting) example, FIG. 8 and FIG. 9 show more details of the shape and physical configuration of a sample embodiment.

Figure 8:
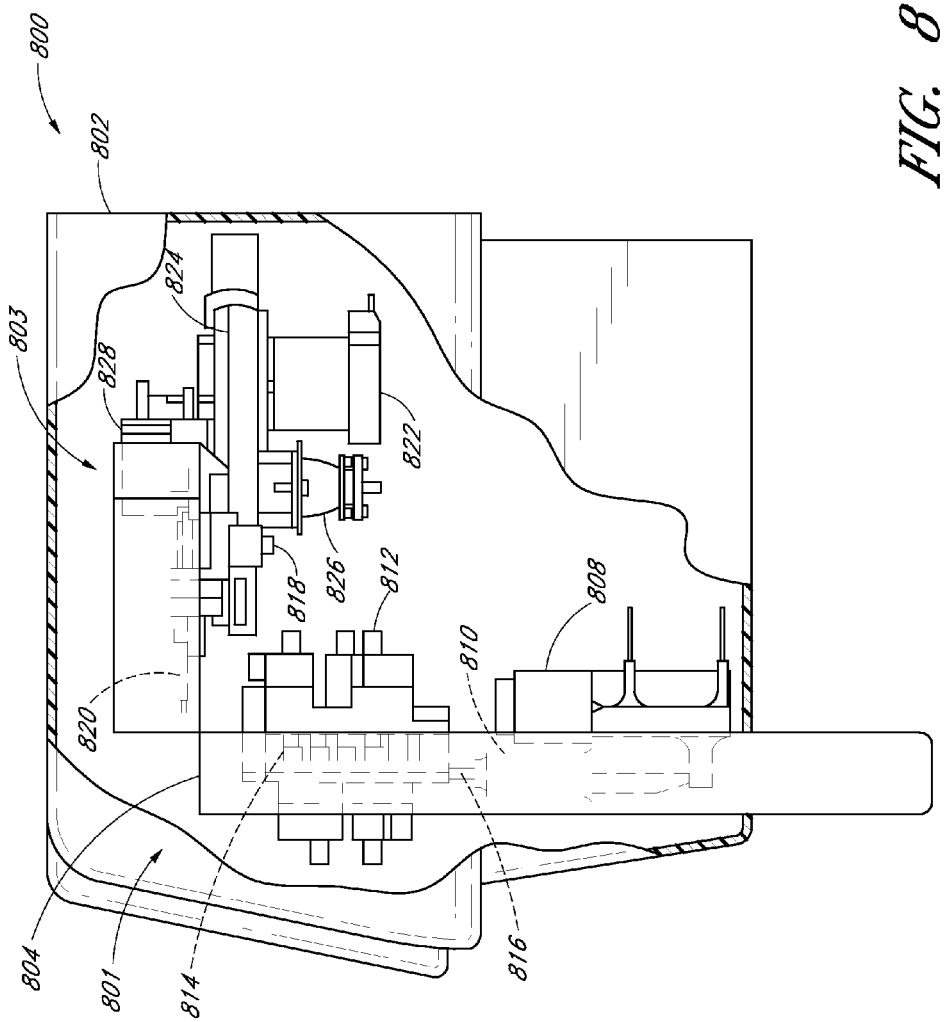
FIG. 8 shows a cut-away side view of an embodiment of a monitoring device.
Figure 9:
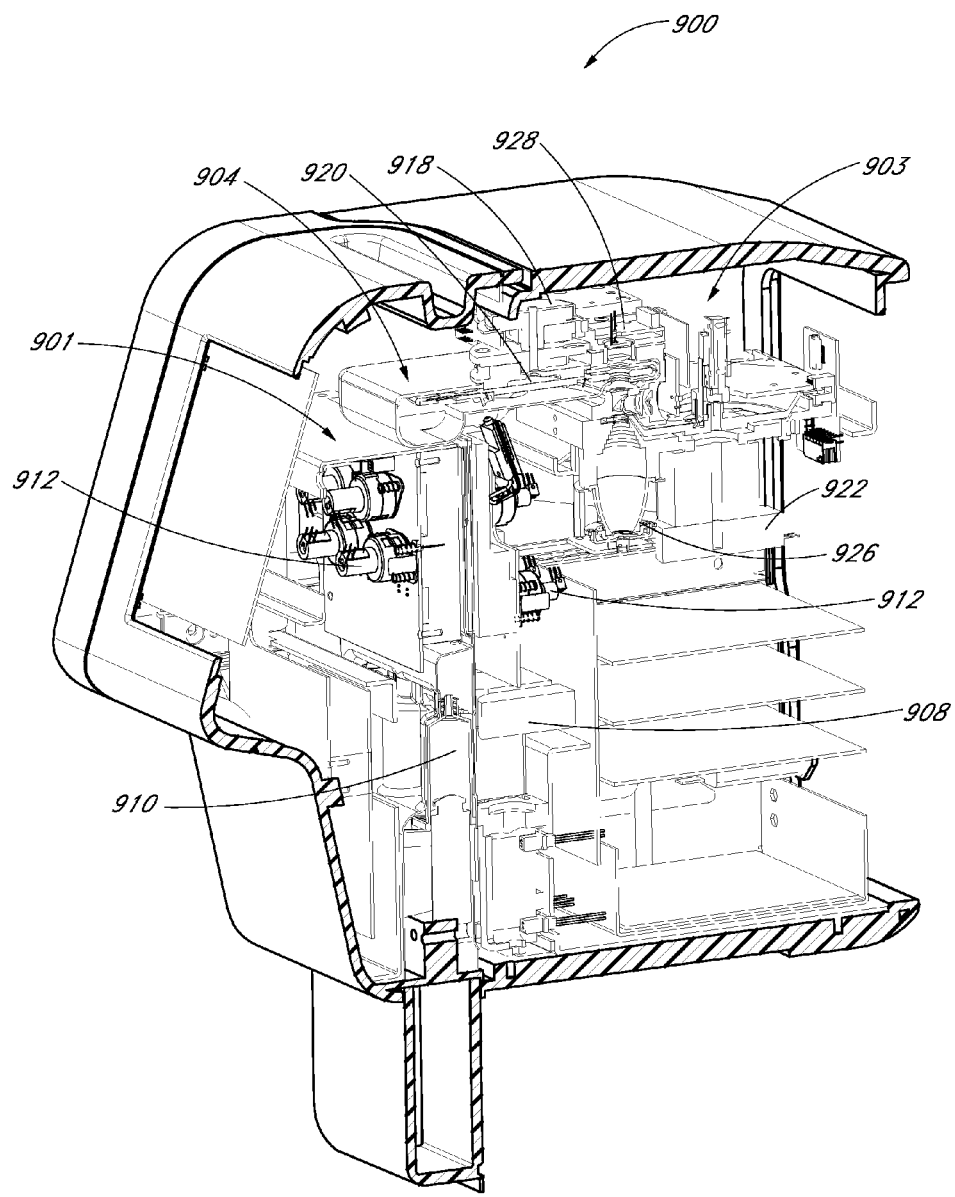
FIG. 9 shows a cut-away perspective view of an embodiment of a monitoring device.

FIG. 8 shows a cut-away side view of a monitoring device 800 (which can correspond, for example, to the device 102 shown in FIG. 1). The device 800 includes a casing 802. The monitoring device 800 can have a fluid system. For example, the fluid system can have subsystems, and a portion or portions thereof can be disposable, as schematically depicted in FIG. 4. As depicted in FIG. 8, the fluid system is generally located at the left-hand portion of the casing 802, as indicated by the reference 801. The monitoring device 800 can also have an optical system. In the illustrated embodiment, the optical system is generally located in the upper portion of the casing 802, as indicated by the reference 803. Advantageously, however, the fluid system 801 and the optical system 803 can both be integrated together such that fluid flows generally through a portion of the optical system 803, and such that radiation flows generally through a portion of the fluid system 801.

Depicted in FIG. 8 are examples of ways in which components of the device 800 mounted within the casing 802 can interface with components of the device 800 that comprise disposable portions. Not all components of the device 800 are shown in FIG. 8. A disposable portion 804 having a variety of components is shown in the casing 802. In some embodiments, one or more actuators 808 housed within the casing 802, operate syringe bodies 810 located within a disposable portion 804. The syringe bodies 810 are connected to sections of tubing 816 that move fluid among various components of the system. The movement of fluid is at least partially controlled by the action of one or more pinch valves 812 positioned within the casing 802. The pinch valves 812 have arms 814 that extend within the disposable portion 804. Movement of the arms 814 can constrict a section of tubing 816.

In some embodiments, a sample cell holder 820 can engage a centrifuge motor 818 mounted within the casing 802 of the device 800. A filter wheel motor 822 disposed within the housing 802 rotates a filter wheel 824, and in some embodiments, aligns one or more filters with an optical path. An optical path can originate at a source 826 within the housing 802 that can be configured to emit a beam of radiation (e.g., infrared radiation, visible radiation, ultraviolet radiation, etc.) through the filter and the sample cell holder 820 and to a detector 828. A detector 828 can measure the optical density of the light when it reaches the detector.

FIG. 9 shows a cut-away perspective view of an alternative embodiment of a monitoring device 900. Many features similar to those illustrated in FIG. 8 are depicted in this illustration of an alternative embodiment. A fluid system 901 can be partially seen. The disposable portion 904 is shown in an operative position within the device. One of the actuators 808 can be seen next to a syringe body 910 that is located within the disposable portion 904. Some pinch valves 912 are shown next to a fluid-handling portion of the disposable portion 904. In this figure, an optical system 903 can also be partially seen. The sample holder 920 is located underneath the centrifuge motor 918. The filter wheel motor 922 is positioned near the radiation source 926, and the detector 928 is also illustrated.

FIG. 10 illustrates two views of a cartridge 1000 that can interface with a fluid system such as the fluid system 510 of FIG. 5. The cartridge 1000 can be configured for insertion into a receptacle of the device 800 of FIG. 8 and/or the device 900 shown in FIG. 9. In some embodiments, the cartridge 1000 can comprise a portion that is disposable and a portion that is reusable. In some embodiments, the cartridge 1000 can be disposable. The cartridge 1000 can fill the role of the removable portion 710 of FIG. 7, for example. In some embodiments, the cartridge 1000 can be used for a system having only one disposable subsystem, making it a simple matter for a health care provider to replace and/or track usage time of the disposable portion. In some embodiments, the cartridge 1000 includes one or more features that facilitate insertion of the cartridge 1000 into a corresponding receptacle. For example, the cartridge 1000 can be shaped so as to promote insertion of the cartridge 1000 in the correct orientation. The cartridge 1000 can also include labeling or coloring affixed to or integrated with the cartridge's exterior casing that help a handler insert the cartridge 1000 into a receptacle properly.

The cartridge 1000 can include one or more ports for connecting to material sources or receptacles. Such ports can be provided to connect to, for example, a saline source, an infusion pump, a sample source, and/or a source of gas (e.g., air, nitrogen, etc.). The ports can be connected to sections of tubing within the cartridge 1000. In some embodiments, the sections of tubing are opaque or covered so that fluids within the tubing cannot be seen, and in some embodiments, sections of tubing are transparent to allow interior contents (e.g., fluid) to be seen from outside.

Figure 15:
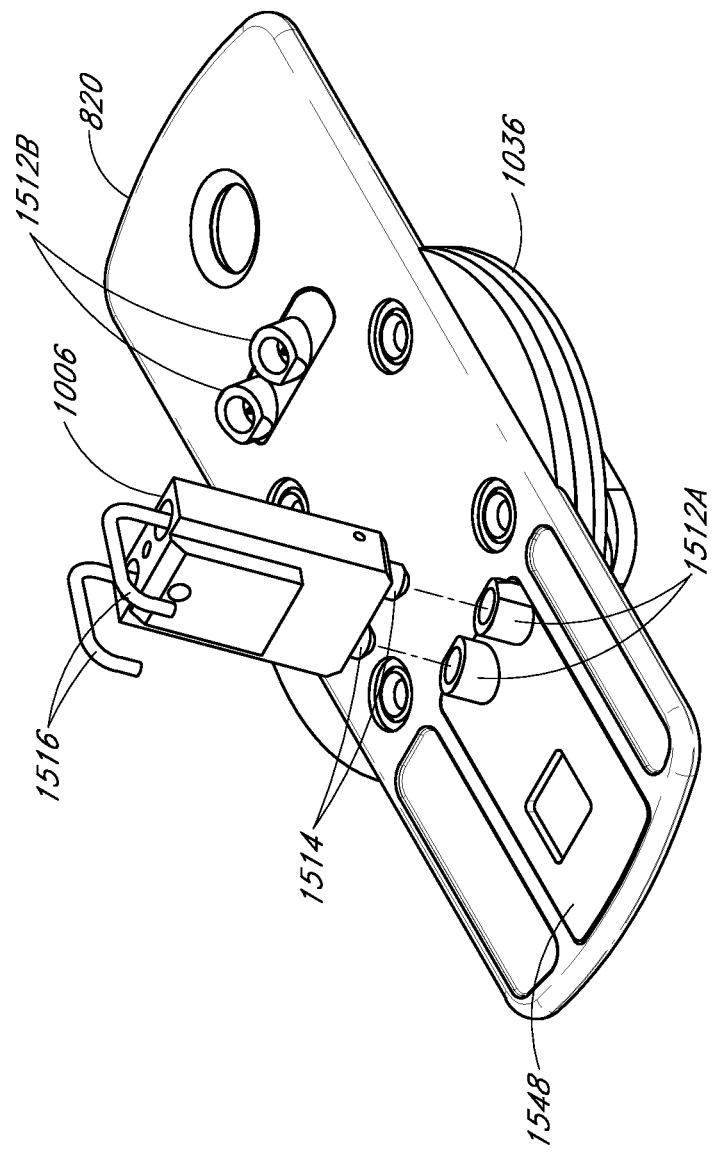
FIG. 15 shows an underneath perspective view of a sample cell holder attached to a centrifuge interface, with a view of an interface with a sample injector.

The cartridge 1000 shown in FIG. 10 can include a sample injector 1006. The sample injector 1006 can be configured to inject at least a portion of a sample into a sample holder (see, e.g., the sample cell 548), which can also be incorporated into the cartridge 1000. The sample injector 1006 can include, for example, the sample cell holder interface tubes 582 (N1) and 584 (N2) of FIG. 5, embodiments of which are also illustrated in FIG. 15.

The housing of the cartridge 1000 can include a tubing portion 1008 containing within it a card having one or more sections of tubing. In some embodiments, the body of the cartridge 1000 includes one or more apertures 1009 through which various components, such as, for example, pinch valves and sensors, can interface with the fluid-handling portion contained in the cartridge 1000. The sections of tubing found in the tubing portion 1008 can be aligned with the apertures 1009 in order to implement at least some of the functionality shown in the fluid system 510 of FIG. 5.

The cartridge 1000 can include a pouch space (not shown) that can comprise one or more components of the fluid system 510. For example, one or more pouches and/or bladders can be disposed in the pouch space (not shown). In some embodiments, a cleaner pouch and/or a waste bladder can be housed in a pouch space. The waste bladder can be placed under the cleaner pouch such that, as detergent is removed from the cleaner pouch, the waste bladder has more room to fill. The components placed in the pouch space (not shown) can also be placed side-by-side or in any other suitable configuration.

The cartridge 1000 can include one or more pumps 1016 that facilitate movement of fluid within the fluid system 510. Each of the pump housings 1016 can contain, for example, a syringe pump having a plunger. The plunger can be configured to interface with an actuator outside the cartridge 1000. For example, a portion of the pump that interfaces with an actuator can be exposed to the exterior of the cartridge 1000 housing by one or more apertures 1018 in the housing.

The cartridge 1000 can have an optical interface portion 1030 that is configured to interface with (or comprise a portion of) an optical system. In the illustrated embodiment, the optical interface portion 1030 can pivot around a pivot structure 1032. The optical interface portion 1030 can house a sample holder (not shown) in a chamber that can allow the sample holder to rotate. The sample holder can be held by a centrifuge interface 1036 that can be configured to engage a centrifuge motor (not shown). When the cartridge 1000 is being inserted into a system, the orientation of the optical interface portion 1030 can be different than when it is functioning within the system.

In some embodiments, the cartridge 1000 is designed for single patient use. The cartridge 1000 may also be disposable and/or designed for replacement after a period of operation. For example, in some embodiments, if the cartridge 1000 is installed in a continuously operating monitoring device that performs four measurements per hour, the waste bladder may become filled or the detergent in the cleaner pouch depleted after about three days. The cartridge 1000 can be replaced before the detergent and waste bladder are exhausted. In some embodiments, a portion of the cartridge 1000 can be disposable while another portion of the cartridge 1000 is disposable, but lasts longer before being discarded. In some embodiments, a portion of the cartridge 1000 may not be disposable at all. For example, a portion thereof may be configured to be cleaned thoroughly and reused for different patients. Various combinations of disposable and less- or non-disposable portions are possible.

The cartridge 1000 can be configured for easy replacement. For example, in some embodiments, the cartridge 1000 is designed to have an installation time of only minutes. For example, the cartridge can be designed to be installed in less than about five minutes, or less than two minutes. During installation, various fluid lines contained in the cartridge 1000 can be primed by automatically filling the fluid lines with saline. The saline can be mixed with detergent powder from the cleaner pouch in order to create a cleaning solution.

The cartridge 1000 can also be designed to have a relatively brief shut down time. For example, the shut down process can be configured to take less than about fifteen minutes, or less than about ten minutes, or less than about five minutes. The shut down process can include flushing the patient line; sealing off the insulin pump connection, the saline source connection, and the sample source connection; and taking other steps to decrease the risk that fluids within the used cartridge 1000 will leak after disconnection from the monitoring device.

Some embodiments of the cartridge 1000 can comprise a flat package to facilitate packaging, shipping, sterilizing, etc. Advantageously, however, some embodiments can further comprise a hinge or other pivot structure. Thus, as illustrated, an optical interface portion 1030 can be pivoted around a pivot structure 1032 to generally align with the other portions of the cartridge 1000. The cartridge can be provided to a medical provider sealed in a removable wrapper, for example.

In some embodiments, the cartridge 1000 is designed to fit within standard waste containers found in a hospital, such as a standard biohazard container. For example, the cartridge 1000 can be less than one foot long, less than one foot wide, and less than two inches thick. In some embodiments, the cartridge 1000 is designed to withstand a substantial impact, such as that caused by hitting the ground after a four foot drop, without damage to the housing or internal components. In some embodiments, the cartridge 1000 is designed to withstand significant clamping force applied to its casing. For example, the cartridge 1000 can be built to withstand five pounds per square inch of force without damage. In some embodiments, the cartridge 1000 can be designed to be less sturdy and more biodegradable. In some embodiments, the cartridge 1000 can be formed and configured to withstand more or less than five pounds of force per square inch without damage. In some embodiments, the cartridge 1000 is non pyrogenic and/or latex free.

Figure 11:
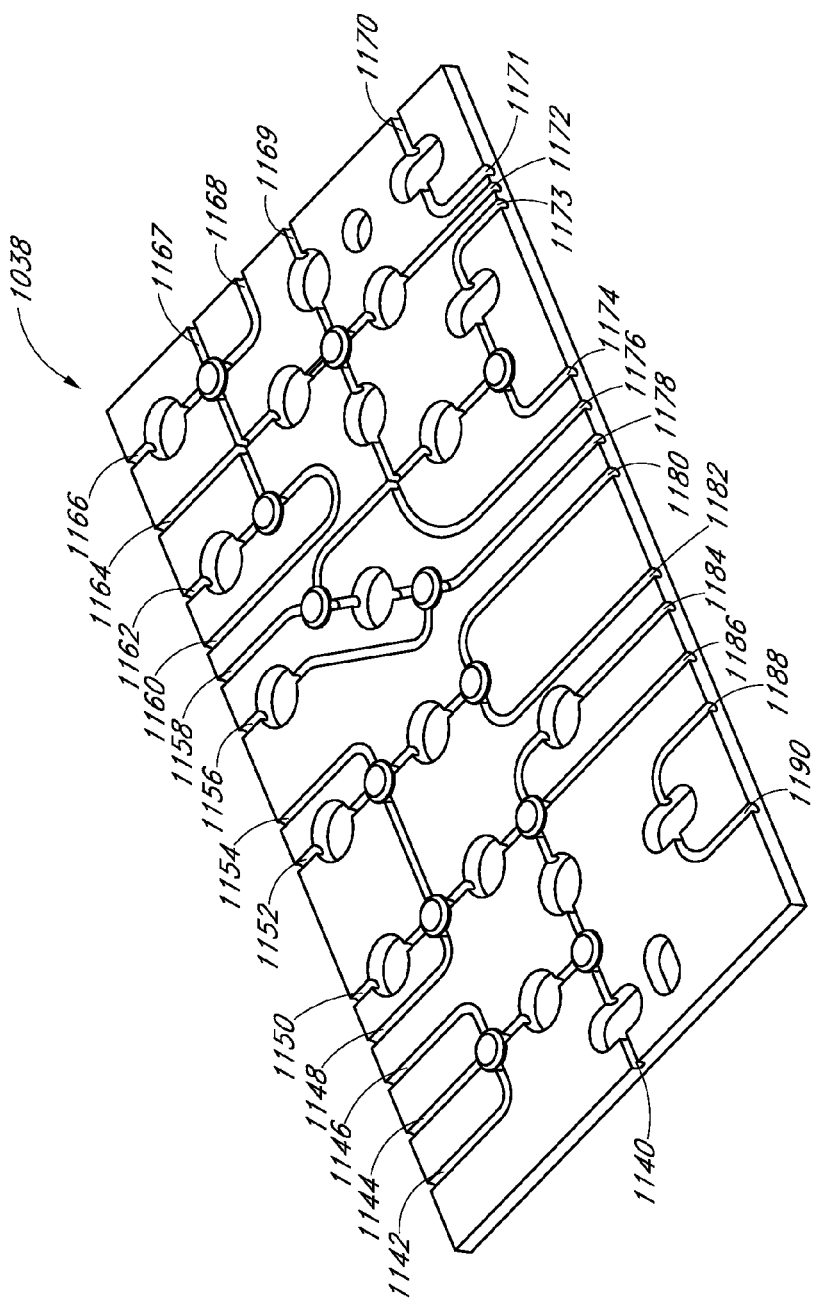
FIG. 11 illustrates an embodiment of a fluid routing card that can be part of the removable cartridge of FIG. 10.

FIG. 11 illustrates an embodiment of a fluid-routing card 1038 that can be part of the removable cartridge of FIG. 10. For example, the fluid-routing card 1038 can be located generally within the tubing portion 1008 of the cartridge 1000. The fluid-routing card 1038 can contain various passages and/or tubes through which fluid can flow as described with respect to FIG. 5 and/or FIG. 6, for example. Thus, the illustrated tube opening openings can be in fluid communication with the following fluidic components, for example:

| Tube Opening Reference Numeral | Can Be In Fluid Communication With |
| --- | --- |
| 1142 | third pump 568 (pump #3) |
| 1144 | infusion pump 518 |
| 1146 | Presx |
| 1148 | air pump |
| 1150 | Vent |
| 1152 | detergent (e.g., tergazyme) source or waste tube |
| 1154 | Presx |
| 1156 | detergent (e.g., tergazyme) source or waste tube |
| 1158 | waste receptacle |
| 1160 | first pump 522 (pump #1) (e.g., a saline pump) |
| 1162 | saline source or waste tube |
| 1164 | anticoagulant (e.g., heparin) pump (see FIG. 6) and/or shuttle valve |
| 1166 | detergent (e.g., tergazyme) source or waste tube |
| 1167 | Presx |
| 1168 | Arrival sensor tube 528 (T4) |
| 1169 | tube 536 (T2) |
| 1170 | Arrival sensor tube 528 (T4) |
| 1171 | Arrival sensor tube 528 (T4) |
| 1172 | anticoagulant (e.g., heparin) pump |
| 1173 | T17 (see FIG. 6) |
| 1174 | Sample cell holder interface tube 582 (N1) |
| 1176 | anticoagulant valve tube 534 (T3) |
| 1178 | Sample cell holder interface tube 584 (N2) |
| 1180 | T17 (see FIG. 6) |
| 1182 | anticoagulant valve tube 534 (T3) |
| 1184 | Arrival sensor tube 528 (T4) |
| 1186 | tube 536 (T2) |
| 1188 | anticoagulant valve tube 534 (T3) |
| 1190 | anticoagulant valve tube 534 (T3) |

The depicted fluid-routing card 1038 can have additional openings that allow operative portions of actuators and/or valves to protrude through the fluid-routing card 1038 and interface with the tubes.

Figure 12:
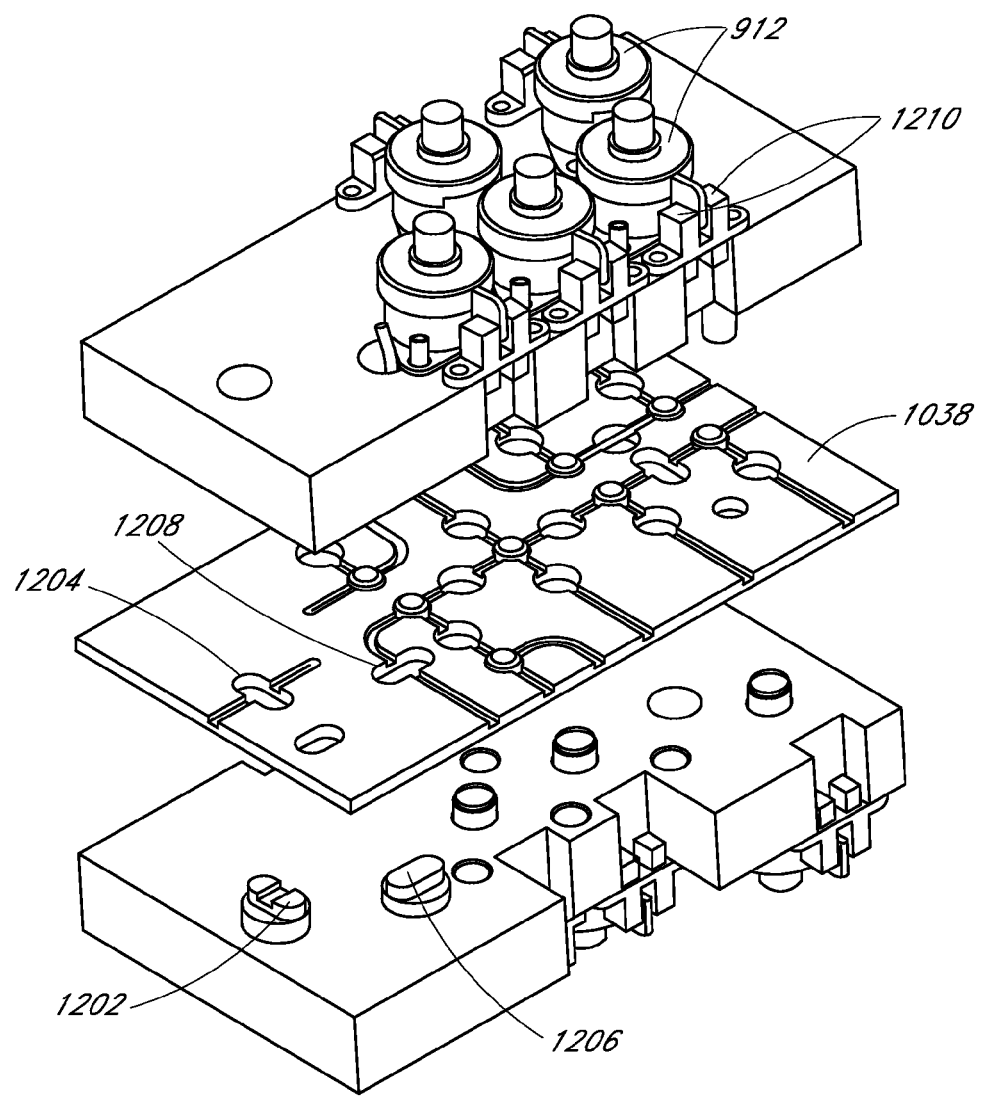
FIG. 12 illustrates how non-disposable actuators can interface with the fluid routing card of FIG. 11.

FIG. 12 illustrates how actuators, which can sandwich the fluid-routing card 1038 between them, can interface with the fluid-routing card 1038 of FIG. 11. Pinch valves 812 can have an actuator portion that protrudes away from the fluid-routing card 1038 containing a motor. Each motor can correspond to a pinch platen 1202, which can be inserted into a pinch platen receiving hole 1204. Similarly, sensors, such as a bubble sensor 1206 can be inserted into receiving holes (e.g., the bubble sensor receiving hole 1208). Movement of the pinch valves 812 can be detected by the position sensors 1210.

Figure 13:
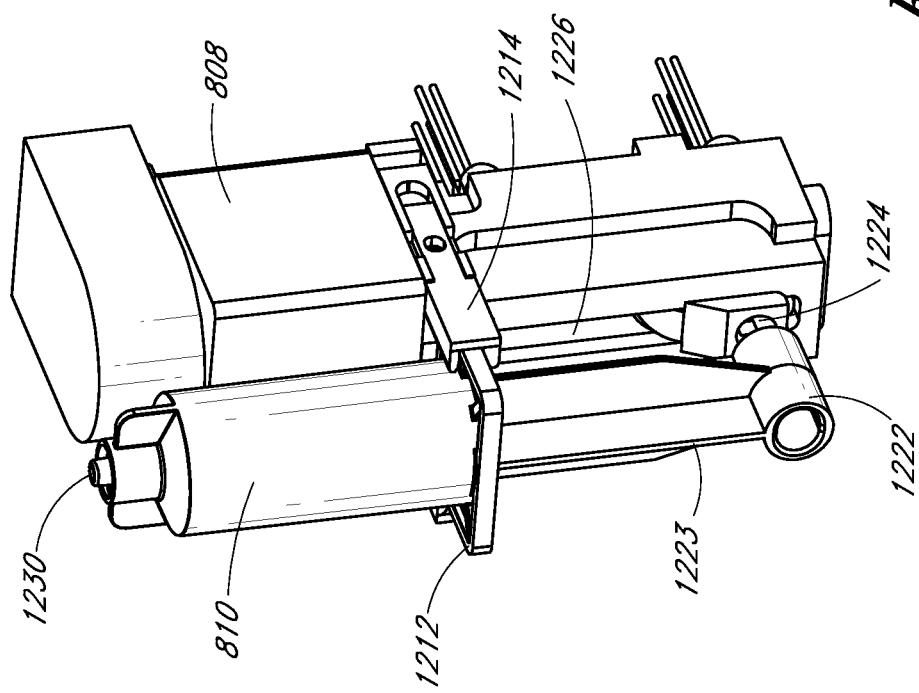
FIG. 13 illustrates a modular pump actuator connected to a syringe housing that can form a portion of a removable cartridge.

FIG. 13 illustrates an actuator 808 that is connected to a corresponding syringe body 810. The actuator 808 is an example of one of the actuators 808 that is illustrated in FIG. 8 and in FIG. 9, and the syringe body 810 is an example of one of the syringe bodies 810 that are visible in FIG. 8 and in FIG. 9. A ledge portion 1212 of the syringe body 810 can be engaged (e.g., slid into) a corresponding receiving portion 1214 in the actuator 808. In some embodiments, the receiving portion 1214 can slide outward to engage the stationary ledge portion 1212 after the disposable cartridge 804 is in place. Similarly, a receiving tube 1222 in the syringe plunger 1223 can be slide onto (or can receive) a protruding portion 1224 of the actuator 808. The protruding portion 1224 can slide along a track 1226 under the influence of a motor inside the actuator 808, thus actuating the syringe plunger 1223 and causing fluid to flow into or out of the syringe tip 1230.

Figure 14:
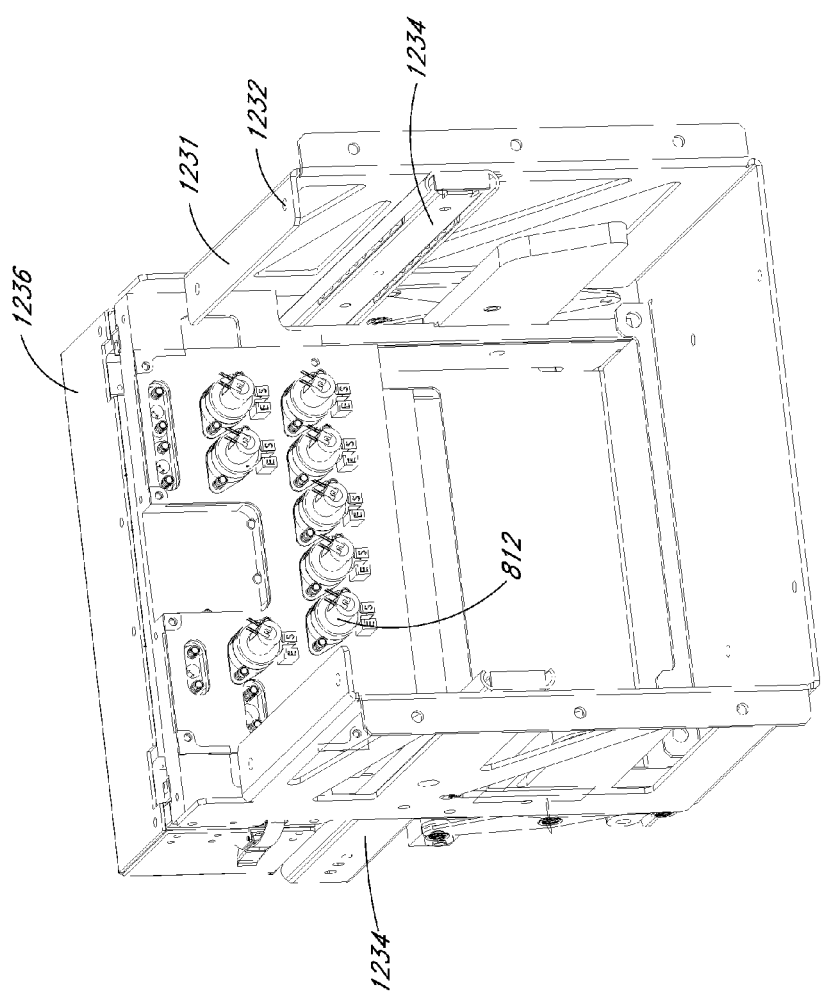
FIG. 14 shows a rear perspective view of internal scaffolding and some pinch valve pump bodies.

FIG. 14 shows a rear perspective view of internal scaffolding 1231 and the protruding bodies of some pinch valves 812. The internal scaffolding 1231 can be formed from metal and can provide structural rigidity and support for other components. The scaffolding 1231 can have holes 1232 into which screws can be screwed or other connectors can be inserted. In some embodiments, a pair of sliding rails 1234 can allow relative movement between portions of an analyzer. For example, a slidable portion 1236 (which can correspond to the movable portion 706, for example) can be temporarily slid away from the scaffolding 1231 of a main unit in order to allow an insertable portion (e.g., the cartridge 804) to be inserted.

FIG. 15 shows an underneath perspective view of the sample cell holder 820, which is attached to the centrifuge interface 1036. The sample cell holder 820 can have an opposite side (see FIG. 17) that allows it to slide into a receiving portion of the centrifuge interface 1036. The sample cell holder 820 can also have receiving nubs 1512A that provide a pathway into a sample cell 1548 held by the sample cell holder 820. Receiving nubs 1512B can provide access to a shunt 1586 (see FIG. 16) inside the sample cell holder 820. The receiving nubs 1512A and 1512B can receive and or dock with fluid nipples 1514. The fluid nipples 1514 can protrude at an angle from the sample injector 1006, which can in turn protrude from the cartridge 1000 (see FIG. 10). The tubes 1516 shown protruding from the other end of the sample injector 1006 can be in fluid communication with the sample cell holder interface tubes 582 (N1) and 584 (N2) (see FIG. 5 and FIG. 6), as well as 1074 and 1078 (see FIG. 11).

Figure 16:
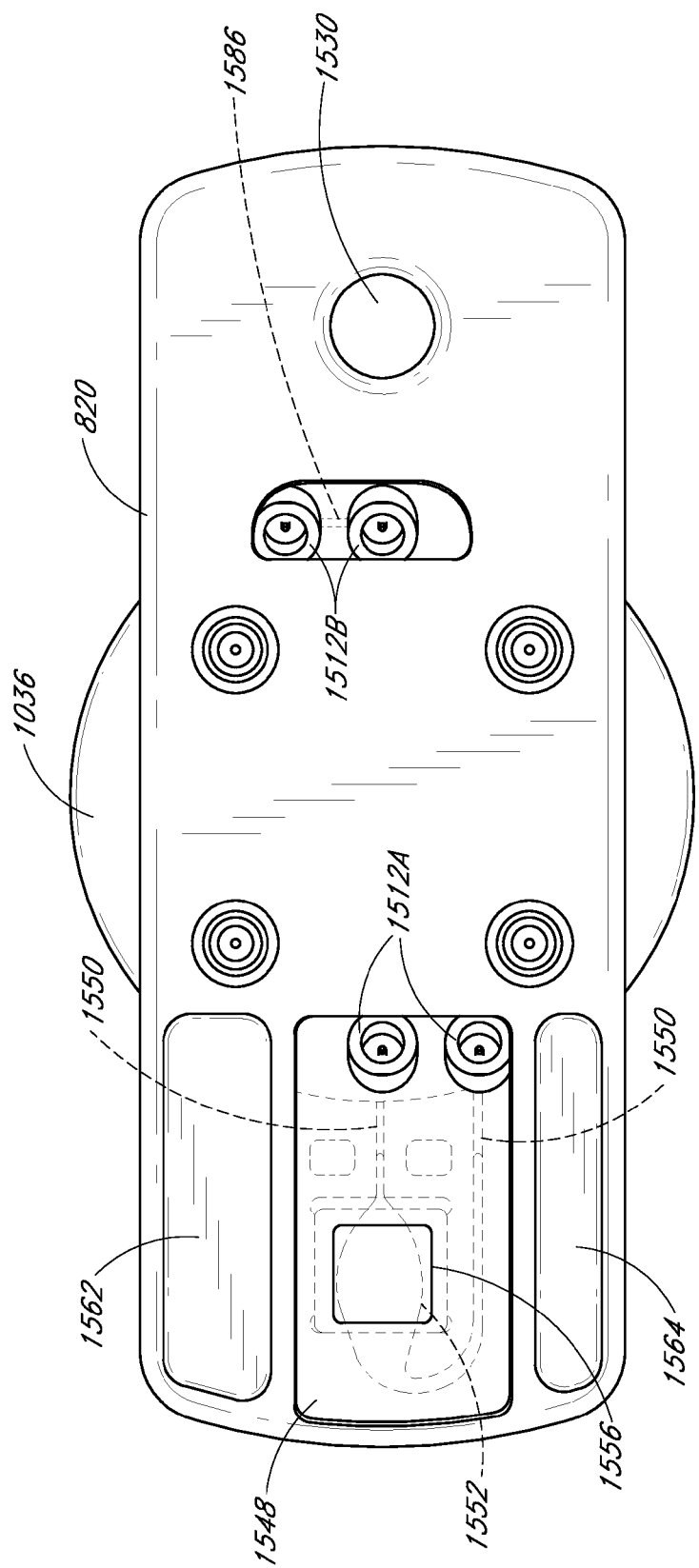
FIG. 16 shows a plan view of a sample cell holder with hidden and/or non-surface portions illustrated using dashed lines.

FIG. 16 shows a plan view of the sample cell holder 820 with hidden and/or non-surface portions illustrated using dashed lines. The receiving nubs 1512A communicate with passages 1550 inside the sample cell 1548 (which can correspond, for example to the sample cell 548 of FIG. 5). The passages widen out into a wider portion 1552 that corresponds to a window 1556. The window 1556 and the wider portion 1552 can be configured to house the sample when radiation is emitted along a pathlength that is generally non-parallel to the sample cell 1548. The window 1556 can allow calibration of the instrument with the sample cell 1548 in place, even before a sample has arrived in the wider portion 1552.

An opposite opening 1530 can provide an alternative optical pathway between a radiation source and a radiation detector (e.g., the radiation source 826 of FIG. 18) and may be used, for example, for obtaining a calibration measurement of the source and detector without an intervening window or sample. Thus, the opposite opening 1530 can be located generally at the same radial distance from the axis of rotation as the window 1556.

The receiving nubs 1512B communicate with a shunt passage 1586 inside the sample cell holder 820 (which can correspond, for example to the shunt 586 of FIG. 5).

Other features of the sample cell holder 820 can provide balancing properties for even rotation of the sample cell holder 820. For example, the wide trough 1562 and the narrower trough 1564 can be sized or otherwise configured so that the weight and/or mass of the sample cell holder 820 is evenly distributed from left to right in the view of FIG. 16, and/or from top to bottom in this view of FIG. 16.

Figure 17:
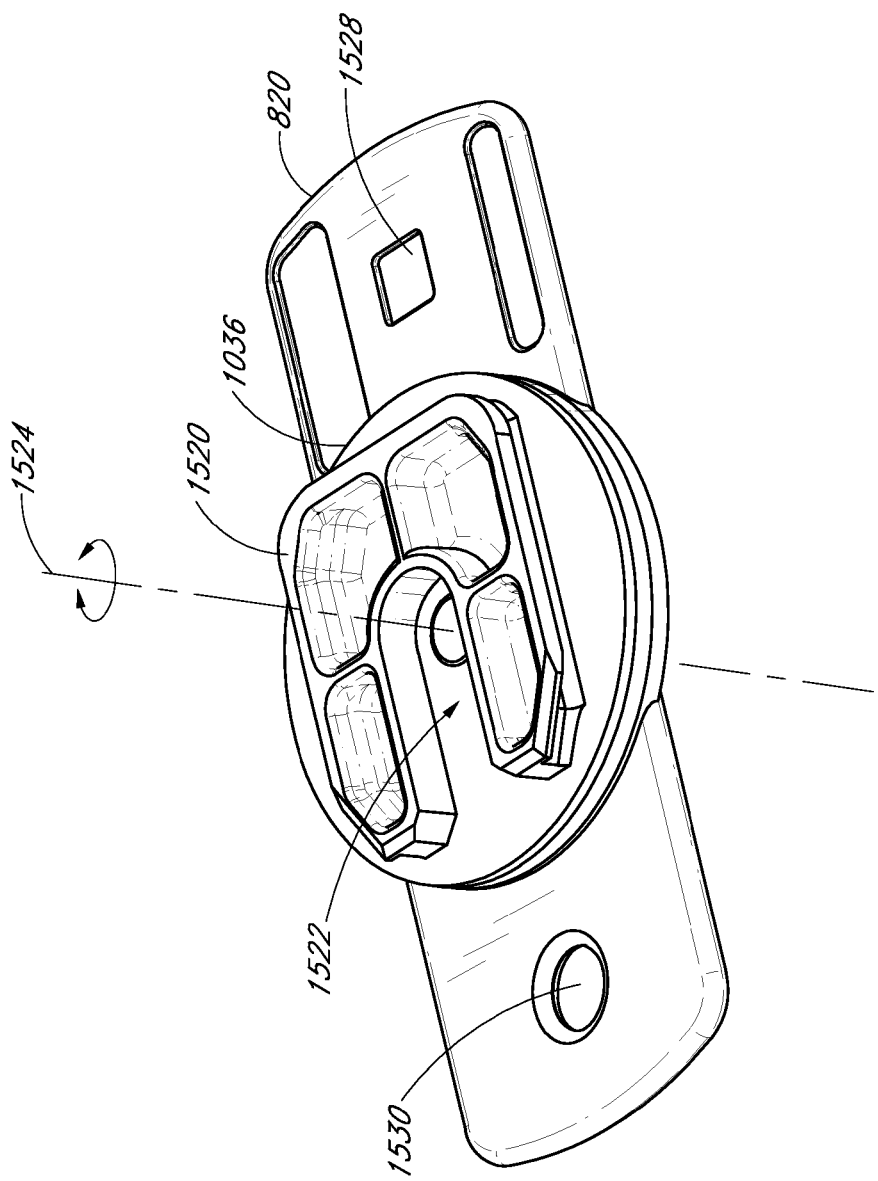
FIG. 17 shows a top perspective view of the centrifuge interface connected to the sample holder.

FIG. 17 shows a top perspective view of the centrifuge interface 1036 connected to the sample cell holder 820. The centrifuge interface 1036 can have a bulkhead 1520 with a rounded slot 1522 into which an actuating portion of a centrifuge can be slid from the side. The centrifuge interface 1036 can thus be spun about an axis 1524, along with the sample cell holder 820, causing fluid (e.g., whole blood) within the sample cell 1548 to separate into concentric strata, according to relative density of the fluid components (e.g., plasma, red blood cells, buffy coat, etc.), within the sample cell 1548. The sample cell holder 820 can be transparent, or it can at least have transparent portions (e.g., the window 1556 and/or the opposite opening 1530) through which radiation can pass, and which can be aligned with an optical pathway between a radiation source and a radiation detector (see, e.g., FIG. 20). In addition, a round opening 1530 through centrifuge rotor 1520 provides an optical pathway between the radiation source and radiation detector and may be used, for example, for obtaining a calibration measurement of the source and detector without an intervening window or sample.

Figure 18:
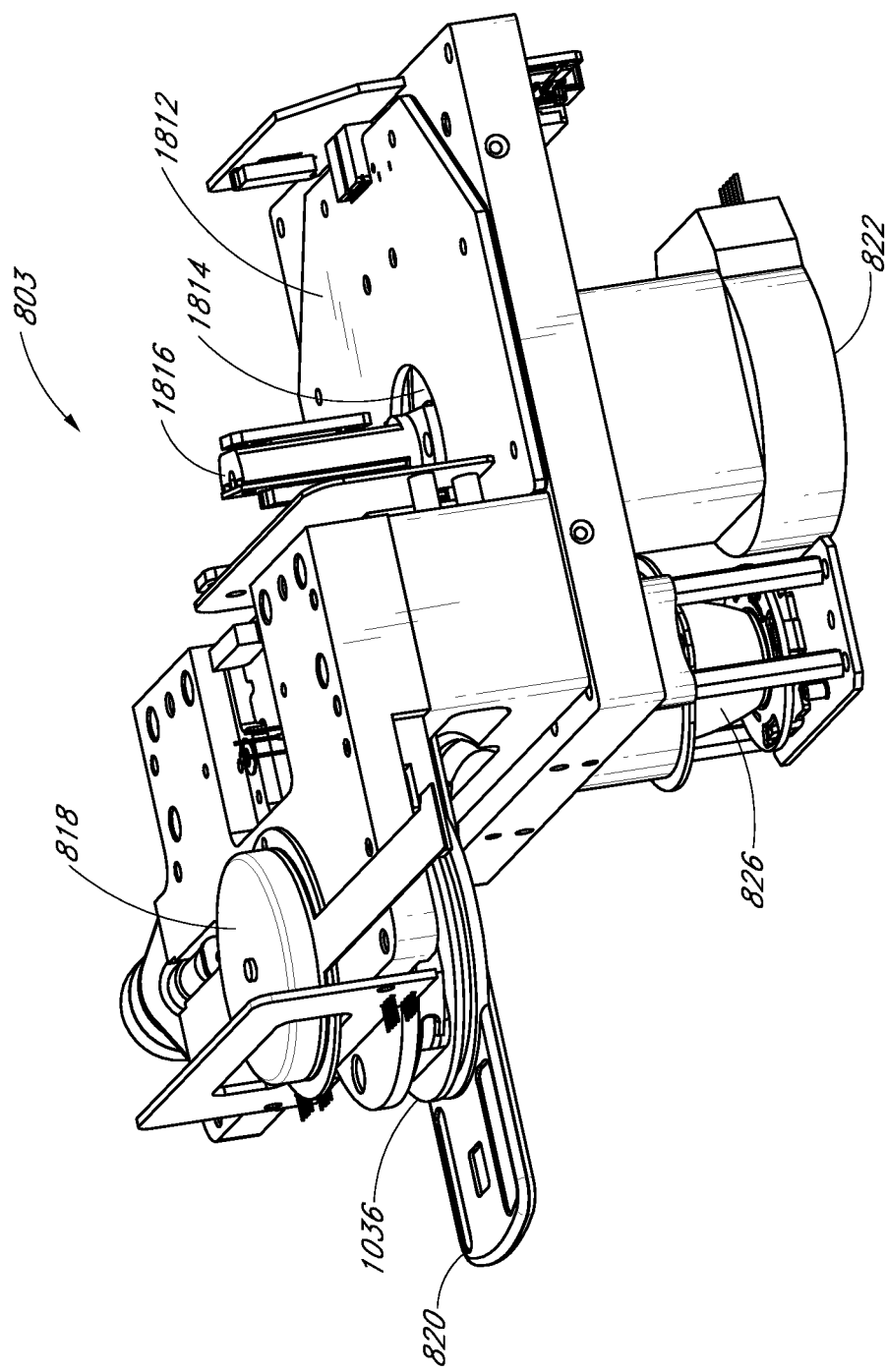
FIG. 18 shows a perspective view of an example optical system.

FIG. 18 shows a perspective view of an example optical system 803. Such a system can be integrated with other systems as shown in FIG. 9, for example. The optical system 803 can fill the role of the optical system 412, and it can be integrated with and/or adjacent to a fluid system (e.g., the fluid-handling system 404 or the fluid system 801). The sample cell holder 820 can be seen attached to the centrifuge interface 1036, which is in turn connected to, and rotatable by the centrifuge motor 818. A filter wheel housing 1812 is attached to the filter wheel motor 822 and encloses a filter wheel 1814. A protruding shaft assembly 1816 can be connected to the filter wheel 1814. The filter wheel 1814 can have multiple filters (see FIG. 19). The radiation source 826 is aligned to transmit radiation through a filter in the filter wheel 1814 and then through a portion of the sample cell holder 820. Transmitted and/or reflected and/or scattered radiation can then be detected by a radiation detector.

Figure 19:
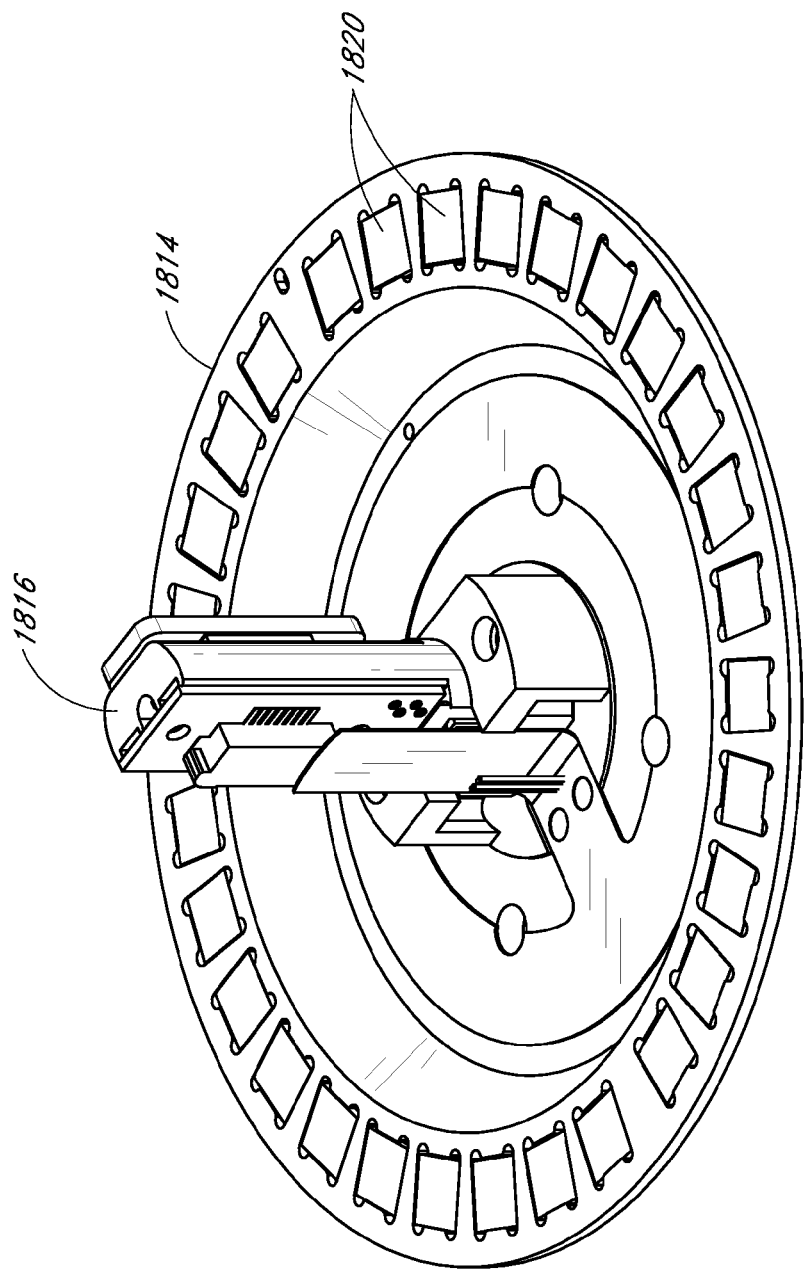
FIG. 19 shows a filter wheel that can be part of the optical system of FIG. 18.

FIG. 19 shows a view of the filter wheel 1814 when it is not located within the filter wheel housing 1812 of the optical system 803. Additional features of the protruding shaft assembly 1816 can be seen, along with multiple filters 1820. In some embodiments, the filters 1820 can be removably and/or replaceably inserted into the filter wheel 1814.

Spectroscopic System

As described above with reference to FIG. 4, the system 400 comprises the optical system 412 for analysis of a fluid sample. In various embodiments, the optical system 412 comprises one or more optical components including, for example, a spectrometer, a photometer, a reflectometer, or any other suitable device for measuring optical properties of the fluid sample. The optical system 412 may perform one or more optical measurements on the fluid sample including, for example, measurements of transmittance, absorbance, reflectance, scattering, and/or polarization. The optical measurements may be performed in one or more wavelength ranges including, for example, infrared (IR) and/or optical wavelengths. As described with reference to FIG. 4 (and further described below), the measurements from the optical system 412 are communicated to the algorithm processor 416 for analysis. For example, In some embodiments the algorithm processor 416 computes concentration of analyte(s) (and/or interferent(s)) of interest in the fluid sample. Analytes of interest include, e.g., glucose and lactate in whole blood or blood plasma.

Figure 20:
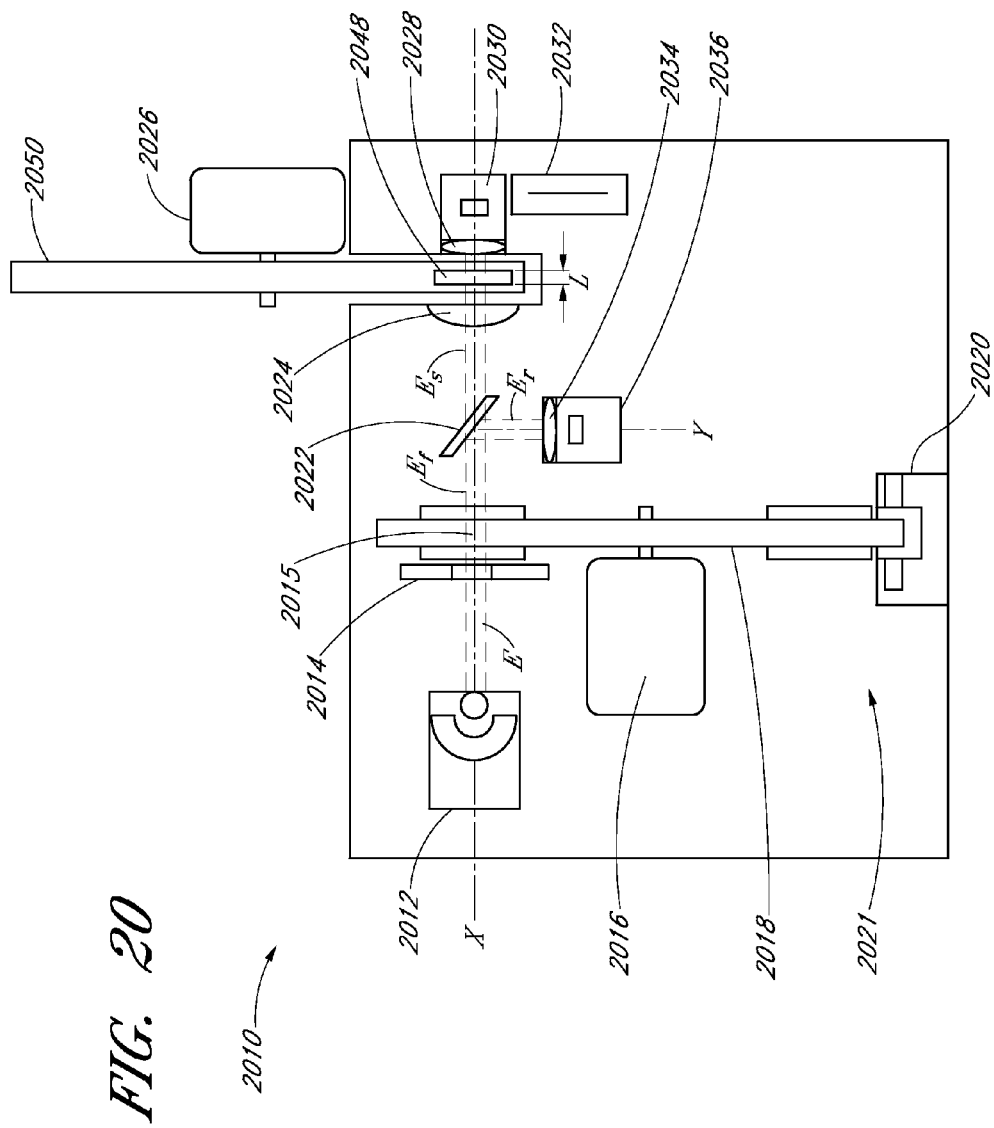
FIG. 20 schematically illustrates an embodiment of an optical system that comprises a spectroscopic analyzer adapted to measure spectra of a fluid sample.

FIG. 20 schematically illustrates an embodiment of the optical system 412 that comprises a spectroscopic analyzer 2010 adapted to measure spectra of a fluid sample such as, for example, blood or blood plasma. The analyzer 2010 comprises an energy source 2012 disposed along an optical axis X of the analyzer 2010. When activated, the energy source 2012 generates an electromagnetic energy beam E, which advances from the energy source 2012 along the optical axis X. In some embodiments, the energy source 2012 comprises an infrared energy source, and the energy beam E comprises an infrared beam. In some embodiments, the infrared energy beam E comprises a mid-infrared energy beam or a near-infrared energy beam. In some embodiments, the energy beam E can include optical and/or radio frequency wavelengths.

The energy source 2012 may comprise a broad-band and/or a narrow-band source of electromagnetic energy. In some embodiments, the energy source 2012 comprises optical elements such as, e.g., filters, collimators, lenses, mirrors, etc., that are adapted to produce a desired energy beam E. For example, in some embodiments, the energy beam E is an infrared beam in a wavelength range between about 2 µm and 20 µm. In some embodiments, the energy beam E comprises an infrared beam in a wavelength range between about 4 µm and 10 µm. In the infrared wavelength range, water generally is the main contributor to the total absorption together with features from absorption of other blood components, particularly in the 6 µm-10 µm range. The 4 µm to 10 µm wavelength band has been found to be advantageous for determining glucose concentration, because glucose has a strong absorption peak structure from about 8.5 µm to 10 µm, whereas most other blood components have a relatively low and flat absorption spectrum in the 8.5 µm to 10 µm range. Two exceptions are water and hemoglobin, which are interferents in this range.

The energy beam E may be temporally modulated to provide increased signal-to-noise ratio (S/N) of the measurements provided by the analyzer 2010 as further described below. For example, in some embodiments, the beam E is modulated at a frequency of about 10 Hz or in a range from about 1 Hz to about 30 Hz. A suitable energy source 2012 may be an electrically modulated thin-film thermoresistive element such as the HawkEye IR-50 available from Hawkeye Technologies of Milford, Conn.

As depicted in FIG. 20, the energy beam E propagates along the optical axis X and passes through an aperture 2014 and a filter 2015 thereby providing a filtered energy beam $E_f$. The aperture 2014 helps collimate the energy beam E and can include one or more filters adapted to reduce the filtering burden of the filter 2015. For example, the aperture 2014 may comprise a broadband filter that substantially attenuates beam energy outside a wavelength band between about 4 µm to about 10 µm. The filter 2015 may comprise a narrow-band filter that substantially attenuates beam energy having wavelengths outside of a filter passband (which may be tunable or user-selectable in some embodiments). The filter passband may be specified by a half-power bandwidth ("HPBW"). In some embodiments, the filter 2015 may have an HPBW in a range from about 0.1 µm to about 2 µm, or 0.01 µm to about 1 µm. In some embodiments, the bandwidths are in a range from about 0.2 µm to 0.5 µm, or 0.1 µm to 0.35 µm. Other filter bandwidths may be used. The filter 2015 may comprise a varying-passband filter, an electronically tunable filter, a liquid crystal filter, an interference filter, and/or a gradient filter. In some embodiments, the filter 2015 comprises one or a combination of a grating, a prism, a monochromer, a Fabry-Perot etalon, and/or a polarizer. Other optical elements may be utilized as well.

In the embodiment shown in FIG. 20, the analyzer 2010 comprises a filter wheel assembly 2021 configured to dispose one or more filters 2015 along the optical axis X. The filter wheel assembly 2021 comprises a filter wheel 2018, a filter wheel motor 2016, and a position sensor 2020. The filter wheel 2018 may be substantially circular and have one or more filters 2015 or other optical elements (e.g., apertures, gratings, polarizers, mirrors, etc.) disposed around the circumference of the wheel 2018. In some embodiments, the number of filters 2015 in the filter wheel 2016 may be, for example, 1, 2, 5, 10, 15, 20, 25, or more. The motor 2016 is configured to rotate the filter wheel 2018 to dispose a desired filter 2015 (or other optical element) in the energy beam E so as to produce the filtered beam $E_f$. In some embodiments, the motor 2016 comprises a stepper motor. The position sensor 2020 determines the angular position of the filter wheel 2016, and communicates a corresponding filter wheel position signal to the algorithm processor 416, thereby indicating which filter 2015 is in position on the optical axis X. In various embodiments, the position sensor 2020 may be a mechanical, optical, and/or magnetic encoder. An alternative to the filter wheel 2018 is a linear filter translated by a motor. The linear filter can include an array of separate filters or a single filter with properties that change along a linear dimension.

The filter wheel motor 2016 rotates the filter wheel 2018 to position the filters 2015 in the energy beam E to sequentially vary the wavelengths or the wavelength bands used to analyze the fluid sample. In some embodiments, each individual filter 2015 is disposed in the energy beam E for a dwell time during which optical properties in the passband of the filter are measured for the sample. The filter wheel motor 2016 then rotates the filter wheel 2018 to position another filter 2015 in the beam E. In some embodiments, 25 narrow-band filters are used in the filter wheel 2018, and the dwell time is about 2 seconds for each filter 2015. A set of optical measurements for all the filters can be taken in about 2 minutes, including sampling time and filter wheel movement. In some embodiments, the dwell time may be different for different filters 2015, for example, to provide a substantially similar S/N ratio for each filter measurement. Accordingly, the filter wheel assembly 2021 functions as a varying-passband filter that allows optical properties of the sample to be analyzed at a number of wavelengths or wavelength bands in a sequential manner.

In some embodiments of the analyzer 2010, the filter wheel 2018 includes 25 finite-bandwidth infrared filters having a Gaussian transmission profile and full-width half-maximum (FWHM) bandwidth of 28 $cm^{-1}$ corresponding to a bandwidth that varies from 0.14 µm at 7.08 µm to 0.28 µm at 10 µm. The central wavelength of the filters are, in microns: 7.082, 7.158, 7.241, 7.331, 7.424, 7.513, 7.605, 7.704, 7.800, 7.905, 8.019, 8.150, 8.271, 8.598, 8.718, 8.834, 8.969, 9.099, 9.217, 9.346, 9.461, 9.579, 9.718, 9.862, and 9.990.

With further reference to FIG. 20, the filtered energy beam $E_f$ propagates to a beamsplitter 2022 disposed along the optical axis X. The beamsplitter 2022 separates the filtered energy beam $E_f$ into a sample beam $E_s$ and a reference beam $E_r$. The reference beam $E_r$ propagates along a minor optical axis Y, which in this embodiment is substantially orthogonal to the optical axis X. The energies in the sample beam $E_s$ and the reference beam $E_r$ may comprise any suitable fraction of the energy in the filtered beam $E_f$. For example, in some embodiments, the sample beam $E_s$ comprises about 80%, and the reference beam $E_r$ comprises about 20%, of the filtered beam energy $E_f$. A reference detector 2036 is positioned along the minor optical axis Y. An optical element 2034, such as a lens, may be used to focus or collimate the reference beam $E_r$ onto the reference detector 2036. The reference detector 2036 provides a reference signal, which can be used to monitor fluctuations in the intensity of the energy beam E emitted by the source 2012. Such fluctuations may be due to drift effects, aging, wear, or other imperfections in the source 2012. The algorithm processor 416 may utilize the reference signal to identify changes in properties of the sample beam $E_s$ that are attributable to changes in the emission from the source 2012 and not to the properties of the fluid sample. By so doing, the analyzer 2010 may advantageously reduce possible sources of error in the calculated properties of the fluid sample (e.g., concentration). In other embodiments of the analyzer 2010, the beamsplitter 2022 is not used, and substantially all of the filtered energy beam $E_f$ propagates to the fluid sample.

As illustrated in FIG. 20, the sample beam $E_s$ propagates along the optical axis X, and a relay lens 2024 transmits the sample beam $E_s$ into a sample cell 2048 so that at least a fraction of the sample beam $E_s$ is transmitted through at least a portion of the fluid sample in the sample cell 2048. A sample detector 2030 is positioned along the optical axis X to measure the sample beam $E_s$ that has passed through the portion of the fluid sample. An optical element 2028, such as a lens, may be used to focus or collimate the sample beam $E_s$ onto the sample detector 2030. The sample detector 2030 provides a sample signal that can be used by the algorithm processor 416 as part of the sample analysis.

In the embodiment of the analyzer 2010 shown in FIG. 20, the sample cell 2048 is located toward the outer circumference of the centrifuge wheel 2050 (which can correspond, for example, to the sample cell holder 820 described herein). The sample cell 2048 preferably comprises windows that are substantially transmissive to energy in the sample beam $E_s$. For example, in implementations using mid-infrared energy, the windows may comprise calcium fluoride. As described herein with reference to FIG. 5, the sample cell 2048 is in fluid communication with an injector system that permits filling the sample cell 2048 with a fluid sample (e.g., whole blood) and flushing the sample cell 2048 (e.g., with saline or a detergent). The injector system may disconnect after filling the sample cell 2048 with the fluid sample to permit free spinning of the centrifuge wheel 2050.

The centrifuge wheel 2050 can be spun by a centrifuge motor 2026. In some embodiments of the analyzer 2010, the fluid sample (e.g., a whole blood sample) is spun at a certain number of revolutions per minute (RPM) for a given length of time to separate blood plasma for spectral analysis. In some embodiments, the fluid sample is spun at about 7200 RPM. In some embodiments, the fluid sample is spun at about 5000 RPM or 4500 RPM. In some embodiments, the fluid sample is spun at more than one rate for successive time periods. The length of time can be approximately 5 minutes. In some embodiments, the length of time is approximately 2 minutes. In some embodiments, an anticlotting agent such as heparin may be added to the fluid sample before centrifuging to reduce clotting. With reference to FIG. 20, the centrifuge wheel 2050 is rotated to a position where the sample cell 2048 intercepts the sample beam $E_s$, allowing energy to pass through the sample cell 2048 to the sample detector 2030.

The embodiment of the analyzer 2010 illustrated in FIG. 20 advantageously permits direct measurement of the concentration of analytes in the plasma sample rather than by inference of the concentration from measurements of a whole blood sample. An additional advantage is that relatively small volumes of fluid may be spectroscopically analyzed. For example, in some embodiments the fluid sample volume is between about 1 μL and 80 μL and is about 25 μL in some embodiments. In some embodiments, the sample cell 2048 is disposable and is intended for use with a single patient or for a single measurement.

In some embodiments, the reference detector 2036 and the sample detector 2030 comprise broadband pyroelectric detectors. As known in the art, some pyroelectric detectors are sensitive to vibrations. Thus, for example, the output of a pyroelectric infrared detector is the sum of the exposure to infrared radiation and to vibrations of the detector. The sensitivity to vibrations, also known as "microphonics," can introduce a noise component to the measurement of the reference and sample energy beams $E_r$, $E_s$ using some pyroelectric infrared detectors. Because it may be desirable for the analyzer 2010 to provide high signal-to-noise ratio measurements, such as, e.g., S/N in excess of 100 dB, some embodiments of the analyzer 2010 utilize one or more vibrational noise reduction apparatus or methods. For example, the analyzer 2010 may be mechanically isolated so that high S/N spectroscopic measurements can be obtained for vibrations below an acceleration of about 1.5 G.

In some embodiments of the analyzer 2010, vibrational noise can be reduced by using a temporally modulated energy source 2012 combined with an output filter. In some embodiments, the energy source 2012 is modulated at a known source frequency, and measurements made by the detectors 2036 and 2030 are filtered using a narrowband filter centered at the source frequency. For example, in some embodiments, the energy output of the source 2012 is sinusoidally modulated at 10 Hz, and outputs of the detectors 2036 and 2030 are filtered using a narrow bandpass filter of less than about 1 Hz centered at 10 Hz. Accordingly, microphonic signals that are not at 10 Hz are significantly attenuated. In some embodiments, the modulation depth of the energy beam E may be greater than 50% such as, for example, 80%. The duty cycle of the beam may be between about 30% and 70%. The temporal modulation may be sinusoidal or any other waveform. In embodiments utilizing temporally modulated energy sources, detector output may be filtered using a synchronous demodulator and digital filter. The demodulator and filter are software components that may be digitally implemented in a processor such as the algorithm processor 416. Synchronous demodulators, coupled with low pass filters, are often referred to as "lock in amplifiers."

The analyzer 2010 may also include a vibration sensor 2032 (e.g., one or more accelerometers) disposed near one (or both) of the detectors 2036 and 2030. The output of the vibration sensor 2032 is monitored, and suitable actions are taken if the measured vibration exceeds a vibration threshold. For example, in some embodiments, if the vibration sensor 2032 detects above-threshold vibrations, the system discards any ongoing measurement and "holds off" on performing further measurements until the vibrations drop below the threshold. Discarded measurements may be repeated after the vibrations drop below the vibration threshold. In some embodiments, if the duration of the "hold off" is sufficiently long, the fluid in the sample cell 2030 is flushed, and a new fluid sample is delivered to the cell 2030 for measurement. The vibration threshold may be selected so that the error in analyte measurement is at an acceptable level for vibrations below the threshold. In some embodiments, the threshold corresponds to an error in glucose concentration of 5 mg/dL. The vibration threshold may be determined individually for each filter 2015.

Certain embodiments of the analyzer 2010 include a temperature system (not shown in FIG. 20) for monitoring and/or regulating the temperature of system components (such as the detectors 2036, 2030) and/or the fluid sample. Such a temperature system can include temperature sensors, thermoelectrical heat pumps (e.g., a Peltier device), and/or thermistors, as well as a control system for monitoring and/or regulating temperature. In some embodiments, the control system comprises a proportional-plus-integral-plus-derivative (PID) control. For example, in some embodiments, the temperature system is used to regulate the temperature of the detectors 2030, 2036 to a desired operating temperature, such as 35 degrees Celsius.

Optical Measurement

The analyzer 2010 illustrated in FIG. 20 can be used to determine optical properties of a substance in the sample cell 2048. The substance can include whole blood, plasma, saline, water, air or other substances. In some embodiments, the optical properties include measurements of an absorbance, transmittance, and/or optical density in the wavelength passbands of some or all of the filters 2015 disposed in the filter wheel 2018. As described above, a measurement cycle comprises disposing one or more filters 2015 in the energy beam E for a dwell time and measuring a reference signal with the reference detector 2036 and a sample signal with the sample detector 2030. The number of filters 2015 used in the measurement cycle will be denoted by N, and each filter 2015 passes energy in a passband around a center wavelength $\lambda_i$, where i is an index ranging over the number of filters (e.g., from 1 to N). The set of optical measurements from the sample detector 2036 in the passbands of the N filters 2015 provide a wavelength-dependent spectrum of the substance in the sample cell 2048. The spectrum will be denoted by $C_s(\lambda_i)$, where $C_s$ may be a transmittance, absorbance, optical density, or some other measure of an optical property of the substance. In some embodiments, the spectrum is normalized with respect to one or more of the reference signals measured by the reference detector 2030 and/or with respect to spectra of a reference substance (e.g., air or saline). The measured spectra are communicated to the algorithm processor 416 for calculation of the concentration of the analyte(s) of interest in the fluid sample.

In some embodiments, the analyzer 2010 performs spectroscopic measurements on the fluid sample (known as a "wet" reading) and on one or more reference samples. For example, an "air" reading occurs when the sample detector 2036 measures the sample signal without the sample cell 2048 in place along the optical axis X. (This can occur, for example, when the opposite opening 1530 is aligned with the optical axis X). A "water" or "saline" reading occurs when the sample cell 2048 is filled with water or saline, respectively. The algorithm processor 416 may be programmed to calculate analyte concentration using a combination of these spectral measurements.

In some embodiments, a pathlength corrected spectrum is calculated using wet, air, and reference readings. For example, the transmittance at wavelength denoted by $T_i$, may be calculated according to $T_i = (S_i(\text{wet})/R_i(\text{wet}))/(S_i(\text{air})/R_i(\text{air}))$, where $S_i$ denotes the sample signal from the sample detector 2036 and $R_i$ denotes the corresponding reference signal from the reference detector 2030. In some embodiments, the algorithm processor 416 calculates the optical density, $OD_i$, as a logarithm of the transmittance, e.g., according to $OD_i = -\text{Log}(T_i)$. In one implementation, the analyzer 2010 takes a set of wet readings in each of the N filter passbands and then takes a set of air readings in each of the N filter passbands. In other embodiments, the analyzer 2010 may take an air reading before (or after) the corresponding wet reading.

The optical density $OD_i$ is the product of the absorption coefficient at wavelength $\lambda_i$, $\alpha_i$, times the pathlength L over which the sample energy beam $E_s$ interacts with the substance in the sample cell 2048, e.g., $OD_i = \alpha_i L$. The absorption coefficient $\alpha_i$ of a substance may be written as the product of an absorptivity per mole times a molar concentration of the substance. FIG. 20 schematically illustrates the pathlength L of the sample cell 2048. The pathlength L may be determined from spectral measurements made when the sample cell 2048 is filled with a reference substance. For example, because the absorption coefficient for water (or saline) is known, one or more water (or saline) readings can be used to determine the pathlength L from measurements of the transmittance (or optical density) through the cell 2048. In some embodiments, several readings are taken in different wavelength passbands, and a curve-fitting procedure is used to estimate a best-fit pathlength L. The pathlength L may be estimated using other methods including, for example, measuring interference fringes of light passing through an empty sample cell 2048.

The pathlength L may be used to determine the absorption coefficients of the fluid sample at each wavelength. Molar concentration of an analyte of interest can be determined from the absorption coefficient and the known molar absorptivity of the analyte. In some embodiments, a sample measurement cycle comprises a saline reading (at one or more wavelengths), a set of N wet readings (taken, for example, through a sample cell 2048 containing saline solution), followed by a set of N air readings (taken, for example, through the opposite opening 1530). As discussed above, the sample measurement cycle can be performed in a given length of time that may depend, at least in part, on filter dwell times. For example, the measurement cycle may take five minutes when the filter dwell times are about five seconds. In some embodiments, the measurement cycle may take about two minutes when the filter dwell times are about two seconds. After the sample measurement cycle is completed, a detergent cleaner may be flushed through the sample cell 2048 to reduce buildup of organic matter (e.g., proteins) on the windows of the sample cell 2048. The detergent is then flushed to a waste bladder.

In some embodiments, the system stores information related to the spectral measurements so that the information is readily available for recall by a user. The stored information can include wavelength-dependent spectral measurements (including fluid sample, air, and/or saline readings), computed analyte values, system temperatures and electrical properties (e.g., voltages and currents), and any other data related to use of the system (e.g., system alerts, vibration readings, S/N ratios, etc.). The stored information may be retained in the system for a time period such as, for example, 30 days. After this time period, the stored information may be communicated to an archival data storage system and then deleted from the system. In some embodiments, the stored information is communicated to the archival data storage system via wired or wireless methods, e.g., over a hospital information system (HIS).

Analyte Analysis

The algorithm processor 416 (FIG. 4) (or any other suitable processor or processors) may be configured to receive from the analyzer 2010 the wavelength-dependent optical measurements $Cs(\lambda_i)$ of the fluid sample. In some embodiments, the optical measurements comprise spectra such as, for example, optical densities $OD_i$ measured in each of the N filter passbands centered around wavelengths $\lambda_i$. The optical measurements $Cs(\lambda_i)$ are communicated to the processor 416, which analyzes the optical measurements to detect and quantify one or more analytes in the presence of interferents. In some embodiments, one or more poor quality optical measurements $Cs(\lambda_i)$ are rejected (e.g., as having a S/N ratio that is too low), and the analysis performed on the remaining, sufficiently high-quality measurements. In another embodiment, additional optical measurements of the fluid sample are taken by the analyzer 2010 to replace one or more of the poor quality measurements.

Interferents can comprise components of a material sample being analyzed for an analyte, where the presence of the interferent affects the quantification of the analyte. Thus, for example, in the spectroscopic analysis of a sample to determine an analyte concentration, an interferent could be a compound having spectroscopic features that overlap with those of the analyte, in at least a portion of the wavelength range of the measurements. The presence of such an interferent can introduce errors in the quantification of the analyte. More specifically, the presence of one or more interferents can affect the sensitivity of a measurement technique to the concentration of analytes of interest in a material sample, especially when the system is calibrated in the absence of, or with an unknown amount of, the interferent.

Independently of or in combination with the attributes of interferents described above, interferents can be classified as being endogenous (i.e., originating within the body) or exogenous (i.e., introduced from or produced outside the body). As an example of these classes of interferents, consider the analysis of a blood sample (or a blood component sample or a blood plasma sample) for the analyte glucose. Endogenous interferents include those blood components having origins within the body that affect the quantification of glucose, and can include water, hemoglobin, blood cells, and any other component that naturally occurs in blood. Exogenous interferents include those blood components having origins outside of the body that affect the quantification of glucose, and can include items administered to a person, such as medicaments, drugs, foods or herbs, whether administered orally, intravenously, topically, etc.

Independently of or in combination with the attributes of interferents described above, interferents can comprise components which are possibly, but not necessarily, present in the sample type under analysis. In the example of analyzing samples of blood or blood plasma drawn from patients who are receiving medical treatment, a medicament such as acetaminophen is possibly, but not necessarily, present in this sample type. In contrast, water is necessarily present in such blood or plasma samples.

Certain disclosed analysis methods are particularly effective if each analyte and interferent has a characteristic signature in the measurement (e.g., a characteristic spectroscopic feature), and if the measurement is approximately affine (e.g., includes a linear term and an offset) with respect to the concentration of each analyte and interferent. In such methods, a calibration process is used to determine a set of one or more calibration coefficients and a set of one or more optional offset values that permit the quantitative estimation of an analyte. For example, the calibration coefficients and the offsets may be used to calculate an analyte concentration from spectroscopic measurements of a material sample (e.g., the concentration of glucose in blood plasma). In some of these methods, the concentration of the analyte is estimated by multiplying the calibration coefficient by a measurement value (e.g., an optical density) to estimate the concentration of the analyte. Both the calibration coefficient and measurement can comprise arrays of numbers. For example, in some embodiments, the measurement comprises spectra $C_s(\lambda_i)$ measured at the wavelengths $\lambda_i$, and the calibration coefficient and optional offset comprise an array of values corresponding to each wavelength $\lambda_i$. In some embodiments, as further described below, a hybrid linear analysis (HLA) technique is used to estimate analyte concentration in the presence of a set of interferents, while retaining a high degree of sensitivity to the desired analyte. The data used to accommodate the set of possible interferents can include (a) signatures of each of the members of the family of potential additional substances and (b) a typical quantitative level at which each additional substance, if present, is likely to appear. In some embodiments, the calibration coefficient (and optional offset) are adjusted to minimize or reduce the sensitivity of the calibration to the presence of interferents that are identified as possibly being present in the fluid sample.

In some embodiments, the analyte analysis method uses a set of training spectra each having known analyte concentration and produces a calibration that minimizes the variation in estimated analyte concentration with interferent concentration. The resulting calibration coefficient indicates sensitivity of the measurement to analyte concentration. The training spectra need not include a spectrum from the individual whose analyte concentration is to be determined. That is, the term "training" when used in reference to the disclosed methods does not require training using measurements from the individual whose analyte concentration will be estimated (e.g., by analyzing a bodily fluid sample drawn from the individual).

Several terms are used herein to describe the analyte analysis process. The term "Sample Population" is a broad term and includes, without limitation, a large number of samples having measurements that are used in the computation of calibration values (e.g., calibration coefficients and optional offsets). In some embodiments, the term Sample Population comprises measurements (such as, e.g., spectra) from individuals and may comprise one or more analyte measurements determined from those same individuals. Additional demographic information may be available for the individuals whose sample measurements are included in the Sample Population. For an embodiment involving the spectroscopic determination of glucose concentration, the Sample Population measurements may include a spectrum (measurement) and a glucose concentration (analyte measurement).

Various embodiments of Sample Populations may be used in various embodiments of the systems and methods described herein. Several examples of Sample Populations will now be described. These examples are intended to illustrate certain aspects of possible Sample Population embodiments but are not intended to limit the types of Sample Populations that may be generated. In certain embodiments, a Sample Population may include samples from one or more of the example Sample Populations described below.

In some embodiments of the systems and methods described herein, one or more Sample Populations are included in a "Population Database." The Population Database may be implemented and/or stored on a computer-readable medium. In certain embodiments, the systems and methods may access the Population Database using wired and/or wireless techniques. Certain embodiments may utilize several different Population Databases that are accessible locally and/or remotely. In some embodiments, the Population Database includes one or more of the example Sample Populations described below. In some embodiments, two or more databases can be combined into a single database, and in other embodiments, any one database can be divided into multiple databases.

An example Sample Population may comprise samples from individuals belonging to one or more demographic groups including, for example, ethnicity, nationality, gender, age, etc. Demographic groups may be established for any suitable set of one or more distinctive factors for the group including, for example, medical, cultural, behavioral, biological, geographical, religious, and genealogical traits. For example, in certain embodiments, a Sample Population includes samples from individuals from a specific ethnic group (e.g., Caucasians, Hispanics, Asians, African Americans, etc.). In another embodiment, a Sample Population includes samples from individuals of a specific gender or a specific race. In some embodiments, a Sample Population includes samples from individuals belonging to more than one demographic group (e.g., samples from Caucasian women).

Another example Sample Population can comprise samples from individuals having one or more medical conditions. For example, a Sample Population may include samples from individuals who are healthy and unmedicated (sometimes referred to as a Normal Population). In some embodiments, the Sample Population includes samples from individuals having one or more health conditions (e.g., diabetes). In some embodiments, the Sample Population includes samples from individuals taking one or more medications. In certain embodiments, Sample Population includes samples from individuals diagnosed to have a certain medical condition or from individuals being treated for certain medical conditions or some combination thereof. The Sample Population may include samples from individuals such as, for example, ICU patients, maternity patients, and so forth.

An example Sample Population may comprise samples that have the same interferent or the same type of interferents. In some embodiments, a Sample Population can comprise multiple samples, all lacking an interferent or a type of interferent. For example, a Sample Population may comprise samples that have no exogenous interferents, that have one or more exogenous interferents of either known or unknown concentration, and so forth. The number of interferents in a sample depends on the measurement and analyte(s) of interest, and may number, in general, from zero to a very large number (e.g., greater than 300). All of the interferents typically are not expected to be present in a particular material sample, and in many cases, a smaller number of interferents (e.g., 0, 1, 2, 5, 10, 15, 20, or 25) may be used in an analysis. In certain embodiments, the number of interferents used in the analysis is less than or equal to the number of wavelength-dependent measurements N in the spectrum $C_s(\lambda_i)$.

Certain embodiments of the systems and methods described herein are capable of analyzing a material sample using one or more Sample Populations (e.g., accessed from the Population Database). Certain such embodiments may use information regarding some or all of the interferents which may or may not be present in the material sample. In some embodiments, a list of one or more possible interferents, referred to herein as forming a "Library of Interferents," can be compiled. Each interferent in the Library can be referred to as a "Library Interferent." The Library Interferents may include exogenous interferents and endogenous interferents that may be present in a material sample. For example, an interferent may be present due to a medical condition causing abnormally high concentrations of the exogenous and endogenous interferents. In some embodiments, the Library of Interferents may not include one or more interferents that are known to be present in all samples. Thus, for example, water, which is a glucose interferent for many spectroscopic measurements, may not be included in the Library of Interferents. In certain embodiments, the systems and methods use samples in the Sample Population to train calibration methods.

The material sample being measured, for example a fluid sample in the sample cell 2048, may also include one or more Library Interferents which may include, but is not limited to, an exogenous interferent or an endogenous interferent. Examples of exogenous interferent can include medications, and examples of endogenous interferents can include urea in persons suffering from renal failure. In addition to components naturally found in the blood, the ingestion or injection of some medicines or illicit drugs can result in very high and rapidly changing concentrations of exogenous interferents.

In some embodiments, measurements of a material sample (e.g., a bodily fluid sample), samples in a Sample Population, and the Library Interferents comprise spectra (e.g., infrared spectra). The spectra obtained from a sample and/or an interferent may be temperature dependent. In some embodiments, it may be beneficial to calibrate for temperatures of the individual samples in the Sample Population or the interferents in the Library of Interferents. In some embodiments, a temperature calibration procedure is used to generate a temperature calibration factor that substantially accounts for the sample temperature. For example, the sample temperature can be measured, and the temperature calibration factor can be applied to the Sample Population and/or the Library Interferent spectral data. In some embodiments, a water or saline spectrum is subtracted from the sample spectrum to account for temperature effects of water in the sample.

In other embodiments, temperature calibration may not be used. For example, if Library Interferent spectra, Sample Population spectra, and sample spectra are obtained at approximately the same temperature, an error in a predicted analyte concentration may be within an acceptable tolerance. If the temperature at which a material sample spectrum is measured is within, or near, a temperature range (e.g., several degrees Celsius) at which the plurality of Sample Population spectra are obtained, then some analysis methods may be relatively insensitive to temperature variations. Temperature calibration may optionally be used in such analysis methods.

Figure 21:
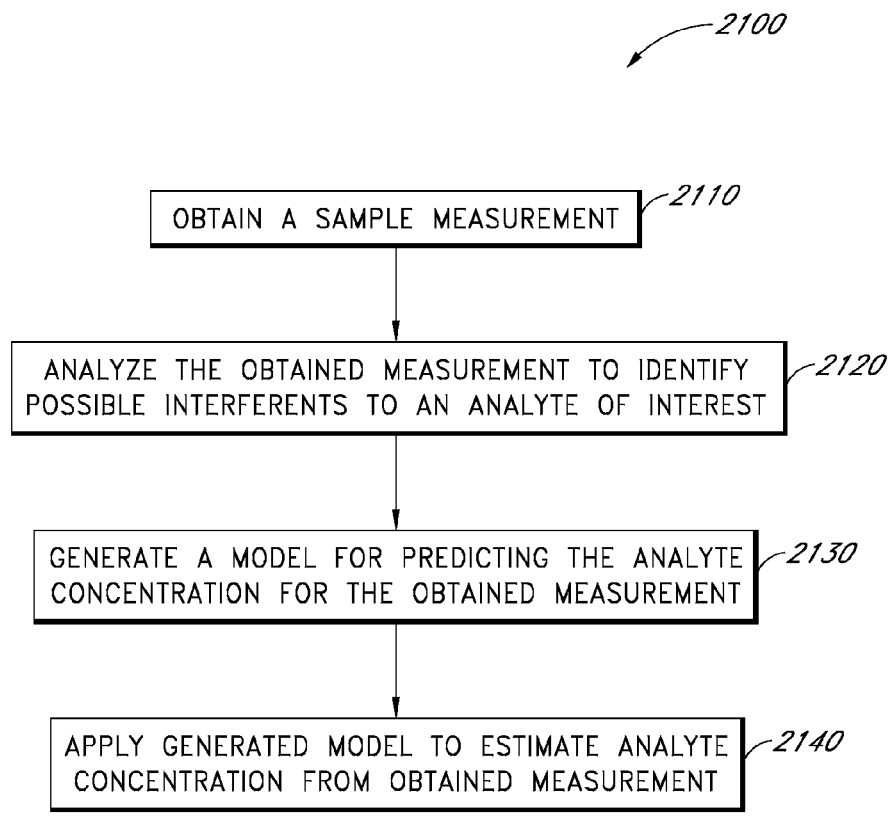
FIG. 21 is a flowchart that schematically illustrates an embodiment of a method for estimating the concentration of an analyte in the presence of interferents.

Systems and Methods for Estimating Analyte Concentration in the Presence of Interferents FIG. 21 is a flowchart that schematically illustrates an embodiment of a method 2100 for estimating the concentration of an analyte in the presence of interferents. In block 2110, a measurement of a sample is obtained, and in block 2120 data relating to the obtained measurement is analyzed to identify possible interferents to the analyte. In block 2130, a model is generated for predicting the analyte concentration in the presence of the identified possible interferents, and in block 2140 the model is used to estimate the analyte concentration in the sample from the measurement. In certain embodiments of the method 2100, the model generated in block 2130 is selected to reduce or minimize the effect of identified interferents that are not present in a general population of which the sample is a member.

An example embodiment of the method 2100 of FIG. 21 for the determination of an analyte (e.g., glucose) in a blood sample will now be described. This example embodiment is intended to illustrate various aspects of the method 2100 but is not intended as a limitation on the scope of the method 2100 or on the range of possible analytes. In this example, the sample measurement in block 2110 is an absorption spectrum, $C_s(\lambda_i)$, of a measurement sample S that has, in general, one analyte of interest, glucose, and one or more interferents.

In block 2120, a statistical comparison of the absorption spectrum of the sample S with a spectrum of the Sample Population and combinations of individual Library Interferent spectra is performed. The statistical comparison provides a list of Library Interferents that are possibly contained in sample S and can include either no Library Interferents or one or more Library Interferents. In this example, in block 2130, one or more sets of spectra are generated from spectra of the Sample Population and their respective known analyte concentrations and known spectra of the Library Interferents identified in block 2120. In block 2130, the generated spectra are used to calculate a model for predicting the analyte concentration from the obtained measurement. In some embodiments, the model comprises one or more calibration coefficients $\kappa(\lambda_i)$ that can be used with the sample measurements $C_s(\lambda_i)$ to provide an estimate of the analyte concentration, $g_{est}$. In block 2140, the estimated analyte concentration is determined form the model generated in block 2130. For example, in some embodiments of HLA, the estimated analyte concentration is calculated according to a linear formula: $g_{est} = \kappa(\lambda_i) \cdot C_s(\lambda_i)$. Because the absorption measurements and calibration coefficients may represent arrays of numbers, the multiplication operation indicated in the preceding formula may comprise a sum of the products of the measurements and coefficients (e.g., an inner product or a matrix product). In some embodiments, the calibration coefficient is determined so as to have reduced or minimal sensitivity to the presence of the identified Library Interferents.

Figure 22:
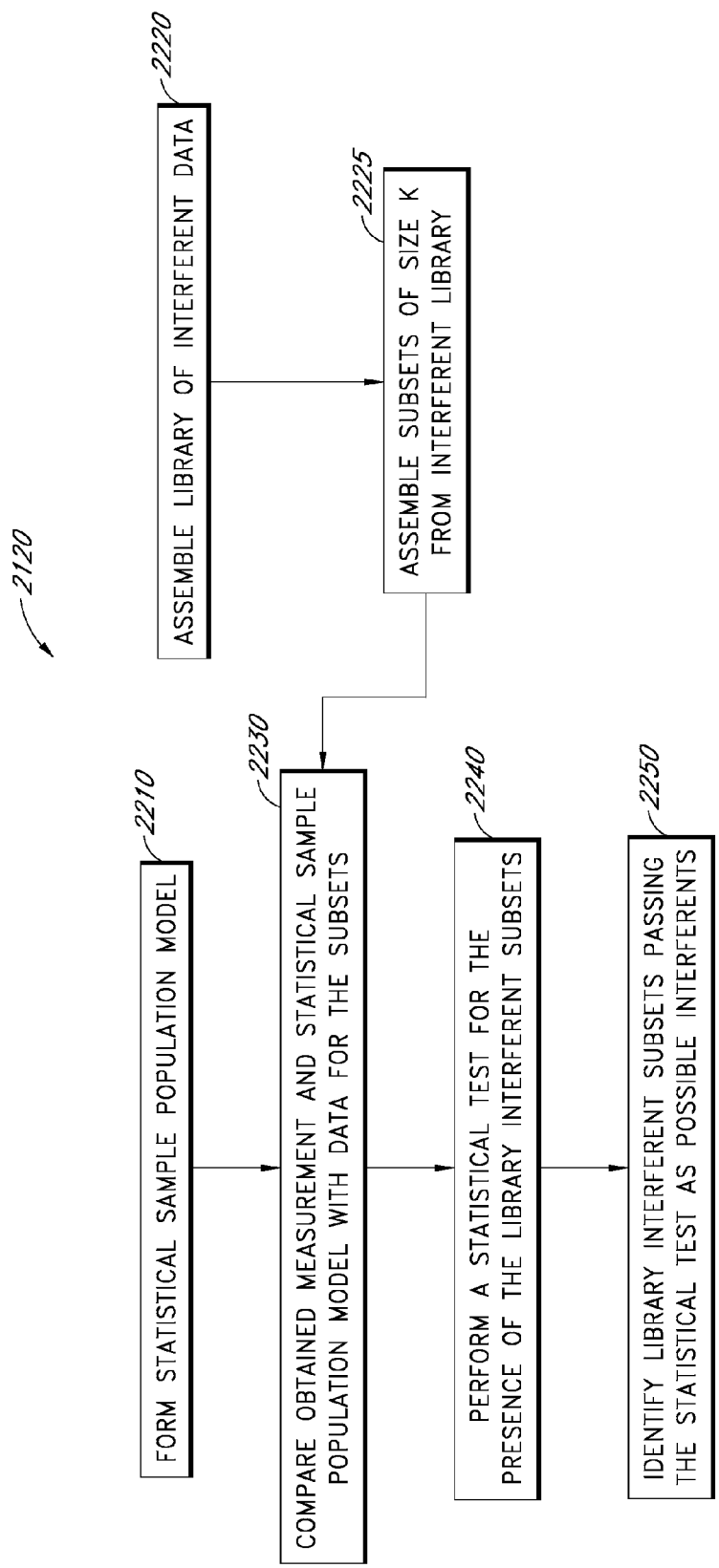
FIG. 22 is a flowchart that schematically illustrates an embodiment of a method for performing a statistical comparison of the absorption spectrum of a sample with the spectrum of a sample population and combinations of individual library interferent spectra.

An example embodiment of block 2120 of the method 2100 will now be described with reference to FIG. 22. In this example, block 2120 includes forming a statistical Sample Population model (block 2210), assembling a library of interferent data (block 2220), assembling all subsets of size K of the library interferents (block 2225), comparing the obtained measurement and statistical Sample Population model with data for each set of interferents from an interferent library (block 2230), performing a statistical test for the presence of each interferent from the interferent library (block 2240), and identifying possible interferents that pass the statistical test (block 2250). The size K of the subsets may be an integer such as, for example, 1, 2, 3, 4, 5, 6, 10, 16, or more. The acts of block 2220 can be performed once or can be updated as necessary. In certain embodiments, the acts of blocks 2230, 2240, and 2250 are performed sequentially for all subsets of Library Interferents that pass the statistical test (block 2240). In this example, in block 2210, a Sample Population Database is formed that includes a statistically large Sample Population of individual spectra taken over the same wavelength range as the sample spectrum, $C_s(\lambda_i)$. The Database also includes an analyte concentration corresponding to each spectrum. For example, if there are P Sample Population spectra, then the spectra in the Database can be represented as $C=\{C_1, C_2, \ldots, C_P\}$, and the analyte concentration corresponding to each spectrum can be represented as $g=\{g_1, g_2, \ldots, g_P\}$. In some embodiments, the Sample Population does not have any of the Library Interferents present, and the material sample has interferents contained in the Sample Population and one or more of the Library Interferents.

In some embodiments of block 2210, the statistical sample model comprises a mean spectrum and a covariance matrix calculated for the Sample Population. For example, if each spectrum measured at N wavelengths $\lambda_i$ is represented by an N×1 array, C, then the mean spectrum, $\mu$, is an N×1 array having values at each wavelength averaged over the range of spectra in the Sample Population. The covariance matrix, V, is calculated as the expected value of the deviation between C and $\mu$ and can be written as $V=E((C-\mu)(C-\mu)^T)$ where $E(\bullet)$ represents the expected value and the superscript T denotes transpose. In other embodiments, additional statistical parameters may be included in the statistical model of the Sample Population spectra.

Additionally, a Library of Interferents may be assembled in block 2220. A number of possible interferents can be identified, for example, as a list of possible medications or foods that might be ingested by the population of patients at issue. Spectra of these interferents can be obtained, and a range of expected interferent concentrations in the blood, or other expected sample material, can be estimated. In certain embodiments, the Library of Interferents includes, for each of "M" interferents, the absorption spectrum normalized to unit interferent concentration of each interferent, $IF=\{IF_1, IF_2, \ldots, IF_M\}$, and a range of concentrations for each interferent from $Tmax=\{Tmax_1, Tmax_2, \ldots, Tmax_M\}$ to $Tmin=\{Tmin_1, Tmin_2, \ldots, Tmin_M\}$. Information in the Library may be assembled once and accessed as needed. For example, the Library and the statistical model of the Sample Population may be stored in a storage device associated with the algorithm processor 416 (see, FIG. 4).

Continuing in block 2225, the algorithm processor 416 assembles one or more subsets comprising a number K of spectra taken from the Library of Interferents. The number K may be an integer such as, for example, 1, 2, 3, 4, 5, 6, 10, 16, or more. In some embodiments, the subsets comprise all combinations of the M Library spectra taken K at a time. In these embodiments, the number of subsets having K spectra is $M!/(K!(M-K)!)$, where ! represents the factorial function.

Continuing in block 2230, the obtained measurement data (e.g., the sample spectrum) and the statistical Sample Population model (e.g., the mean spectrum and the covariance matrix) are compared with data for each subset of interferents determined in block 2225 in order to determine the presence of possible interferents in the sample (block 2240). In some embodiments, the statistical test for the presence of an interferent subset in block 2240 comprises determining the concentrations of each subset of interferences that minimize a statistical measure of "distance" between a modified spectrum of the material sample and the statistical model of the Sample Population (e.g., the mean µ and the covariance V). The term "concentration" used in this context refers to a computed value, and, in some embodiments, that computed value may not correspond to an actual concentration. The concentrations may be calculated numerically. In some embodiments, the concentrations are calculated by algebraically solving a set of linear equations. The statistical measure of distance may comprise the well-known Mahalanobis distance (or square of the Mahalanobis distance) and/or some other suitable statistical distance metric (e.g., Hotelling's T-square statistic). In certain implementations, the modified spectrum is given by $C'_s(T)=C_s-IF \cdot T$ where $T=(T_1, T_2, \ldots T_K)^T$ is a K-dimensional column vector of interferent concentrations and $IF=\{IF_1, IF_2, \ldots IF_K\}$ represents the K interferent absorption spectra of the subset. In some embodiments, concentration of the $i^{th}$ interferent is assumed to be in a range from a minimum value, $Tmin_i$, to a maximum value, $Tmax_i$. The value of $Tmin_i$ may be zero, or may be a value between zero and $Tmax_i$, such as a fraction of $Tmax_i$, or may be a negative value. Negative values represent interferent concentrations that are smaller than baseline interferent values in the Sample Population.

In block 2250, a list of a number $N_S$ of possible interferent subsets $\xi$ may be identified as the particular subsets that pass one or more statistical tests (in block 2240) for being present in the material sample. One or more statistical tests may be used, alone or in combination, to identify the possible interferents. For example, if a statistical test indicates that an $i^{th}$ interferent is present in a concentration outside the range $Tmin_i$ to $Tmax_i$, then this result may be used to exclude the $i^{th}$ interferent from the list of possible interferents. In some embodiments, only the single most probable interferent subset is included on the list, for example, the subset having the smallest statistical distance (e.g., Mahalanobis distance). In an embodiment, the list includes the subsets $\xi$ having statistical distances smaller than a threshold value. In certain embodiments, the list includes a number $N_S$ of subsets having the smallest statistical distances, e.g., the list comprises the "best" candidate subsets. The number $N_S$ may be any suitable integer such as 10, 20, 50, 100, 200, or more. An advantage of selecting the "best" $N_S$ subsets is reduced computational burden on the algorithm processor 416. In some embodiments, the list includes all the Library Interferents. In certain such embodiments, the list is selected to comprise combinations of the $N_S$ subsets taken L at a time. For example, in some embodiments, pairs of subsets are taken (e.g., L=2). An advantage of selecting pairs of subsets is that pairing captures the most likely combinations of interferents and the "best" candidates are included multiple times in the list of possible interferents. In embodiments in which combinations of L subsets are selected, the number of combinations of subsets in the list of possible interferent subsets is $N_S!/(L!(N_S-L)!)$.

In other embodiments, the list of possible interferent subsets $\xi$ is determined using a combination of some or all of the above criteria. In another embodiment, the list of possible interferent subsets $\xi$ includes each of the subsets assembled in block 2225. Many selection criteria are possible for the list of possible interferent subsets $\xi$.

Figure 23:
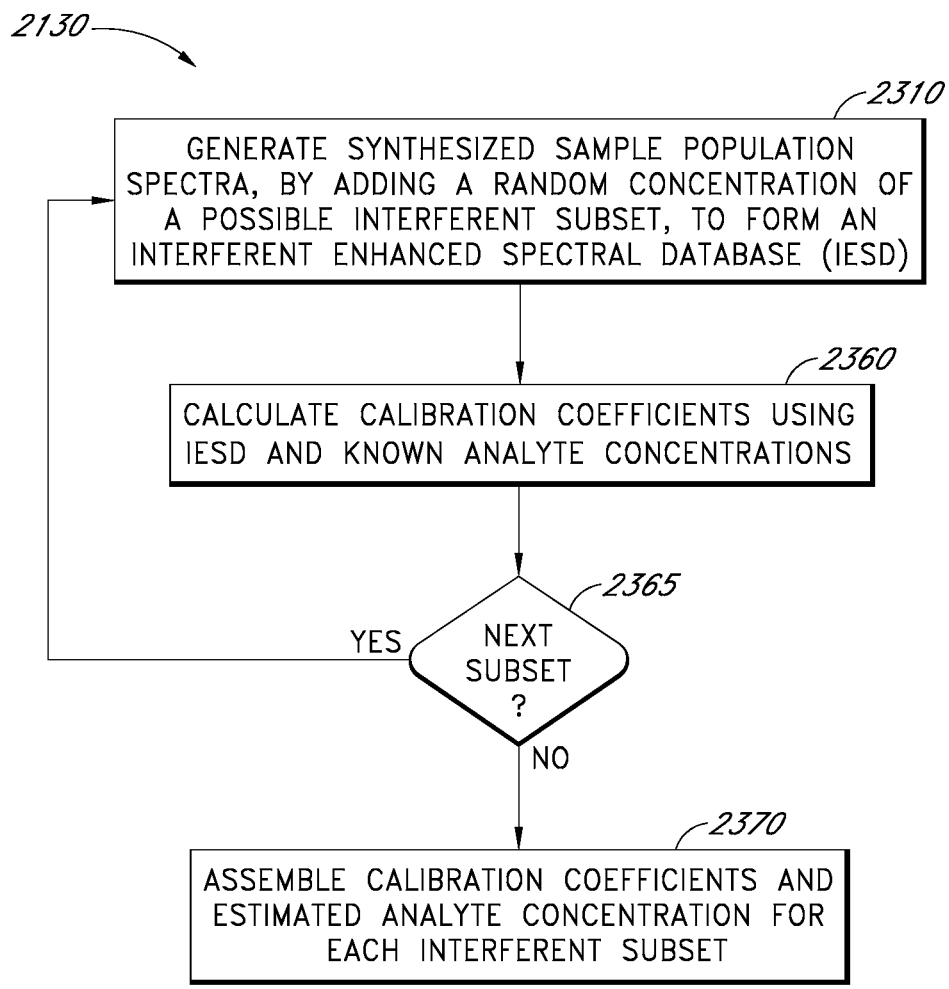
FIG. 23 is a flowchart that schematically illustrates an example embodiment of a method for estimating analyte concentration in the presence of the possible interferents.

Returning to FIG. 21, the method 2100 continues in block 2130 where analyte concentration is estimated in the presence of the possible interferent subsets $\xi$ determined in block 2250. FIG. 23 is a flowchart that schematically illustrates an example embodiment of the acts of block 2130. In block 2310, synthesized Sample Population measurements are generated to form an Interferent Enhanced Spectral Database (IESD). In block 2360, the IESD and known analyte concentrations are used to generate calibration coefficients for the selected interferent subset. As indicated in block 2365, blocks 2310 and 2360 may be repeated for each interferent subset $\xi$ identified in the list of possible interferent subsets (e.g., in block 2250 of FIG. 22). In this example embodiment, when all the interferent subsets $\xi$ have been processed, the method continues in block 2370, wherein an average calibration coefficient is applied to the measured spectra to determine a set of analyte concentrations.

In one example embodiment for block 2310, synthesized Sample Population spectra are generated by adding random concentrations of each interferent in one of the possible interferent subsets $\xi$. These spectra are referred to herein as an Interferent-Enhanced Spectral Database or IESD. In one example method, the IESD is formed as follows. A plurality of Randomly-Scaled Single Interferent Spectra (RSIS) are formed for each interferent in the interferent subset $\xi$. Each RSIS is formed by combinations of the interferent having spectrum IF multiplied by the maximum concentration Tmax, which is scaled by a random factor between zero and one. In certain embodiments, the scaling places the maximum concentration at the $95^{th}$ percentile of a log-normal distribution in order to generate a wide range of concentrations. In some embodiments, the log-normal distribution has a standard deviation equal to half of its mean value.

In this example method, individual RSIS are then combined independently and in random combinations to form a large family of Combination Interferent Spectra (CIS), with each spectrum in the CIS comprising a random combination of RSIS, selected from the full set of identified Library Interferents. An advantage of this method of selecting the CIS is that it produces adequate variability with respect to each interferent, independently across separate interferents.

The CIS and replicates of the Sample Population spectra are combined to form the IESD. Since the interferent spectra and the Sample Population spectra may have been obtained from measurements having different optical pathlengths, the CIS may be scaled to the same pathlength as the Sample Population spectra. The Sample Population Database is then replicated R times, where R depends on factors including the size of the Database and the number of interferents. The IESD includes R copies of each of the Sample Population spectra, where one copy is the original Sample Population Data, and the remaining R-1 copies each have one randomly chosen CIS spectra added. Accordingly, each of the IESD spectra has an associated analyte concentration from the Sample Population spectra used to form the particular IESD spectrum. In some embodiments, a 10-fold replication of the Sample Population Database is used for 130 Sample Population spectra obtained from 58 different individuals and 18 Library Interferents. A smaller replication factor may be used if there is greater spectral variety among the Library Interferent spectra, and a larger replication factor may be used if there is a greater number of Library Interferents.

After the IESD is generated in block 2310, in block 2360, the IESD spectra and the known, random concentrations of the subset interferents are used to generate a calibration coefficient for estimating the analyte concentration from a sample measurement. The calibration coefficient is calculated in some embodiments using a hybrid linear analysis (HLA) technique. In certain embodiments, the HLA technique uses a reference analyte spectrum to construct a set of spectra that are free of the desired analyte, projecting the analyte's spectrum orthogonally away from the space spanned by the analyte-free calibration spectra, and normalizing the result to produce a unit response. Further description of embodiments of HLA techniques may be found in, for example, "Measurement of Analytes in Human Serum and Whole Blood Samples by Near-Infrared Raman Spectroscopy," Chapter 4, Andrew J. Berger, Ph. D. thesis, Massachusetts Institute of Technology, 1998, and "An Enhanced Algorithm for Linear Multivariate Calibration," by Andrew J. Berger, et al., Analytical Chemistry, Vol. 70, No. 3, Feb. 1, 1998, pp. 623-627, the entirety of each of which is hereby incorporated by reference herein. In other embodiments, the calibration coefficients may be calculated using other techniques including, for example, regression techniques such as, for example, ordinary least squares (OLS), partial least squares (PLS), and/or principal component analysis.

In block 2365, the processor 416 determines whether additional interferent subsets ξ remain in the list of possible interferent subsets. If another subset is present in the list, the acts in blocks 2310-2360 are repeated for the next subset of interferents using different random concentrations. In some embodiments, blocks 2310-2360 are performed for only the most probable subset on the list.

The calibration coefficient determined in block 2360 corresponds to a single interferent subset β from the list of possible interferent subsets and is denoted herein as a single-interferent-subset calibration coefficient $\kappa_{avg}(\xi)$. In this example method, after all subsets ξ have been processed, the method continues in block 2370, in which the single-interferent-subset calibration coefficient is applied to the measured spectra $C_s$ to determine an estimated, single-interferent-subset analyte concentration, $g(\xi)=\kappa_{avg}(\xi)\cdot C_s$, for the interferent subset ξ. The set of the estimated, single-interferent-subset analyte concentrations $g(\xi)$ for all subsets in the list may be assembled into an array of single-interferent-subset concentrations. As noted above, in some embodiments the blocks 2310-2370 are performed once for the most probable single-interferent-subset on the list (e.g., the array of single-interferent analyte concentrations has a single member).

Returning to block 2140 of FIG. 21, the array of single-interferent-subset concentrations, $g(\xi)$, is combined to determine an estimated analyte concentration, $g_{est}$, for the material sample. In certain embodiments, a weighting function $p(\xi)$ is determined for each of the interferent subsets ξ on the list of possible interferent subsets. The weighting functions may be normalized such that $\Sigma p(\xi)=1$, where the sum is over all subsets ξ that have been processed from the list of possible interferent subsets. In some embodiments, the weighting functions can be related to the minimum Mahalanobis distance or an optimal concentration. In certain embodiments, the weighting function $p(\xi)$, for each subset ξ is selected to be a constant, e.g., $1/N_S$ where $N_S$ is the number of subsets processed from the list of possible interferent subsets. In other embodiments, other weighting functions $p(\xi)$ can be selected.

In certain embodiments, the estimated analyte concentration, $g_{est}$, is determined (in block 2140) by combining the single-interferent-subset estimates, $g(\xi)$, and the weighting functions, $p(\xi)$, to generate an average analyte concentration. The average concentration may be computed according to $g_{est}=\Sigma g(\xi)p(\xi)$, where the sum is over the interferent subsets processed from the list of possible interferent subsets. In some embodiments, the weighting function $p(\xi)$ is a constant value for each subset (e.g., a standard arithmetic average is used for determining average analyte concentration). By testing the above described example method on simulated data, it has been found that the average analyte concentration advantageously has errors that may be reduced in comparison to other methods (e.g., methods using only a single most probable interferent).

Although the flowchart in FIG. 21 schematically illustrates an embodiment of the method 2100 performed with reference to the blocks 2110-2140 described herein, in other embodiments, the method 2100 can be performed differently. For example, some or all of the blocks 2110-2140 can be combined, performed in a different order than shown, and/or the functions of particular blocks may be reallocated to other blocks and/or to different blocks. Embodiments of the method 2100 may utilize different blocks than are shown in FIG. 21.

For example, in some embodiments of the method 2100, the calibration coefficient is computed without synthesizing spectra and/or partitioning the data into calibration sets and test sets. Such embodiments are referred to herein as "Parameter-Free Interferent Rejection" (PFIR) methods. In one example embodiment using PFIR, for each of the possible interferent subsets ξ, the following calculations may be performed to compute an estimate of a calibration coefficient for each subset ξ. An average concentration may be estimated according to $g_{est}=\Sigma g(\xi)p(\xi)$, where the sum is over the interferent subsets processed from the list of possible interferent subsets.

An example of an alternative embodiment of block 2130 includes the following steps and calculations.

Step 1: For a subset's $N_{IF}$ interferents, form a scaled interferent spectra matrix. In certain embodiments, the scaled interferent spectra matrix is the product of an interferent spectral matrix, IF, multiplied by an interferent concentration matrix, $T_{max}$, and can be written as: IF $T_{max}$. In certain such embodiments, the interferent concentration matrix $T_{max}$ is a diagonal matrix having entries given by the maximum plasma concentrations for the various interferents.

Step 2: Calculate a covariance for the interferent component. If X denotes the IESD, the covariance of X, cov(X), is defined as the expectation $E((X-\text{mean}(X))(X-\text{mean}(X))^T)$ and is $$cov(X) \approx XX^T/(N-1) - \text{mean}(X)\text{mean}(X)^T.$$

As described above, the IESD (e.g., X) is obtained as a combination of Sample Population Spectra, C, with Combination Interferent Spectra (CIS): $X_j=C_j+IF_j\xi_j$, therefore the covariance is:

$$cov(X) \approx CC^T/(N-1) + IF\Xi\Xi^T IF^T/(N-1) - \text{mean}(X)\text{mean}(X)^T,$$

which can be written as, $$cov(X) \approx cov(C) + IF cov(\Xi) IF^T.$$

If the weights in the weighting matrix Ξ are independent and identically distributed, the covariance of Ξ, cov(Ξ), is a diagonal matrix having along the diagonal the variance, v, of the samples in Ξ. The last equation may be written as $$cov(X) \approx V_0 + v\Phi,$$

where $V_0$ is the covariance of the original sample population and Φ is the covariance of the IF spectral set.

Step 3: The group's covariance may be at least partially corrected for the presence of a single replicate of the Sample Population spectra with the IESD as formed from $N_{IF}$ replicates of the Sample Population Spectra with Combined Interferent Spectra. This partial correction may be achieved by multiplying the second term in the covariance formula given above by a correction factor ρ:

$$V=V_0+\rho v\Phi,$$

where ρ is a scalar weighting function that depends on the number of interferents in the group. In some embodiments, the scalar weighting function is $\rho=N_{IF}/(N_{IF}+1)$. In certain embodiments, the variance v of the weights is assumed to be the variance of a log-normal random variable having a 95th percentile at a value of 1.0, and a standard deviation equal to half of the mean value.

Step 4: The eigenvectors and the corresponding eigenvalues of the covariance matrix V are determined using any suitable linear algebraic methods. The number of eigenvectors (and eigenvalues) is equal to the number of wavelengths L in the spectral measurements. The eigenvectors may be sorted based on decreasing order of their corresponding eigenvalues.

Step 5: The matrix of eigenvectors is decomposed so as to provide an orthogonal matrix Q. For example, in some embodiments, a QR-decomposition is performed, thereby yielding the matrix Q having orthonormal columns and rows.

Step 6: The following matrix operations are performed on the orthogonal matrix Q. For n=2 to L−1, the product $P^{\parallel}_n = Q(:,1:n)Q(:,1:n)^T$ is calculated, where Q(:,1:n) denotes the submatrix comprising the first n columns of the full matrix Q. The orthogonal projection, $P^{\perp}_n$, away from the space spanned by Q(:,1:n) is determined by subtracting $P^{\parallel}_n$ from the L×L identity matrix I. The $n^{th}$ calibration vector is then determined from $\kappa_n = P^{\perp}_n \alpha_X / \alpha_X^T P^{\perp}_n \alpha_X$, and the $n^{th}$ error variance $E_n$ is determined as the projection of the full covariance V onto the subspace spanned by $\kappa_n$ as follows: $E_n = \kappa_n^T V \kappa_n$.

The steps 4-6 of this example are an embodiment of the HLA technique.

In some embodiments, the calibration coefficient κ is selected as the calibration vector corresponding to the minimum error variance $E_n$. Thus, for example, the average group calibration coefficient κ may be found by searching among all the error variances for the error variance $E_n$ that has the minimum value. The calibration coefficient is then selected as the $n^{th}$ calibration vector $\kappa_n$ corresponding to the minimum error variance $E_n$. In other embodiments, the calibration coefficient is determined by averaging some or all of the calibration vectors $\kappa_n$.

Examples of Algorithm Results and Effects of Sample Population

Embodiments of the above-described methods have been used to estimate blood plasma glucose concentrations in humans. Four example experiments will now be described. The population of individuals from whom samples were obtained for analysis (estimation of glucose concentration) will be referred to as the "target population." Infrared spectra obtained from the target population will be referred to as the "target spectra." In the four example experiments, the target population included 41 intensive care unit (ICU) patients. Fifty-five samples were obtained from the target population.

Example Experiment 1

In this example experiment, a partial least squares (PLS) regression method was applied to the infrared target spectra of the target patients' blood plasma to obtain the glucose estimates. In example experiment 1, estimated glucose concentration was not corrected for effects of interferents. The Sample Population used for the analysis included infrared spectra and independently measured glucose concentrations for 92 individuals selected from the general population. This Sample Population will be referred to as a "Normal Population."

Example Experiment 2

In example experiment 2, an embodiment of the Parameter-Free Interferent Rejection (PFIR) method was used to estimate glucose concentration for the same target population of patients in example experiment 1. The Sample Population was the Normal Population. In this example, calibration for Library Interferents was applied to the measured target spectra. The Library of Interferents included spectra of the 59 substances listed below:

Acetylsalicylic Acid
Ampicillin Sulbactam
Azithromycin
Aztreonam
Bacitracin
Benzyl Alcohol
Calcium Chloride
Calcium Gluconate
Cefazolin
Cefoparazone
Cefotaxime Sodium
Ceftazidime
Ceftriaxone
D_Sorbitol
Dextran
Ertapenem
Ethanol
Ethosuximide
Glycerol
Heparin
Hetastarch
Human Albumin
Hydroxy Butyric Acid
Imipenem Cilastatin
Iohexol
L_Arginine
Lactate Sodium
Magnesium Sulfate
Maltose
Mannitol
Meropenem
Oxylate Potassium
Phenytoin
Phosphates Potassium
Piperacillin
Piperacillin Tazobactam
PlasmaLyteA
Procaine HCl
Propylene Glycol
Pyrazinamide
Pyruvate Sodium
Pyruvic Acid
Salicylate Sodium
Sodium Acetate
Sodium Bicarbonate
Sodium Chloride
Sodium Citrate
Sodium Thiosulfate
Sulfadiazine
Urea
Uric Acid
Voriconazole
Xylitol
Xylose
PC 1 of Saline covariance
PC 2 of Saline covariance
PC 3 of Saline covariance
PC 4 of Saline covariance
ICU/Normal difference spectrum In some embodiments, the calibration data set is determined according to two criteria: the calibration method itself (e.g., HLA, PLS, OLS, PFIR) and the intended application of the method. The calibration data set may comprise spectra and corresponding analyte levels derived from a set of plasma samples from the Sample Population. In some embodiments, e.g., those where an HLA calibration method is used, the calibration data set may also include spectra of the analyte of interest.

In the example experiments 1 and 2, the Sample Population was the Normal Population. Thus, samples were drawn from a population of normal individuals who did not have identifiable medical conditions that might affect the spectra of their plasma samples. For example, the sample plasma spectra typically did not show effects of high levels of medications or other substances (e.g., ethanol), or effects of chemicals that are indicative of kidney or liver malfunction.

In some embodiments, an analysis method may calibrate for deviations from the distribution defined by the calibration plasma spectra by identifying a "base" set of interferent spectra likely to be responsible for the deviation. The analysis method may then recalibrate with respect to an enhanced spectral data set. In some embodiments, the enhancement can be achieved by including the identified interferent spectra into the calibration plasma spectra. When it is anticipated that the target population may have been administered significant amounts of substances not present in the samples of the calibration set, or when the target population have many distinct interferents, estimation of the interferents present in the target spectrum may be subject to a large degree of uncertainty. In some cases, this may cause analyte estimation to be subject to errors.

Accordingly, in certain embodiments, the calibration data set may be enhanced beyond the base of "normal" samples to include a population of samples intended to be more representative of the target population. The enhancement of the calibration set may be generated, in some embodiments, by including samples from a sufficiently diverse range of individuals in order to represent the range of likely interferents (both in type and in concentration) and/or the normal variability in underlying plasma characteristics. The enhancement may, additionally or alternatively, be generated by synthesizing interferent spectra having a range of concentrations as described above (see, e.g., discussion of block 2310 in FIG. 23). Using the enhanced calibration set may reduce the error in estimating the analyte concentration in the target spectra.

Example Experiments 3 and 4

Example experiments 3 and 4 use the analysis methods of example experiments 1 and 2, respectively (PLS without interferent correction and PFIR with interferent correction). However, example experiments 3 and 4 use a Sample Population having blood plasma spectral characteristics different from the Normal Population used in example experiments 1 and 2. In example experiments 3 and 4, the Sample Population was modified to include spectra of both the Normal Population and spectra of an additional population of 55 ICU patients. These spectra will be referred to as the "Normal+Target Spectra." In experiments 3 and 4, the ICU patients included Surgical ICU patients, Medical ICU patients as well as victims of severe trauma, including a large proportion of patients who had suffered major blood loss. Major blood loss may necessitate replacement of the patient's total blood volume multiple times during a single day and subsequent treatment of the patient via electrolyte and/or fluid replacement therapies. Major blood loss may also require administration of plasma-expanding medications. Major blood loss may lead to significant deviations from the blood plasma spectra representative of a Normal Population. The population of 55 ICU patients (who provided the Target Spectra) has some similarities to the individuals for whom the analyses in experiments 1-4 were performed (e.g., all were ICU patients), but in these experiments, target spectra from individuals in the target population were not included in the Target Spectra.

Results of example experiments 1-4 are shown in the following table. The glucose concentrations estimated from the analysis method were compared to independently determined glucose measurements to provide an average prediction error and a standard deviation of the average prediction error. The table demonstrates that independent of the Sample Population used (e.g., either the Normal Population or the Normal+Target Population), calibrating for interferents reduces both the average prediction error and the standard deviation (e.g., compare the results for experiment 2 to the results for experiment 1 and compare the results for experiment 4 to the results for experiment 3). The table further demonstrates that independent of the analysis method used (e.g., either PLS or PFIR), using a Sample Population with more similarity to the target population (e.g., the Normal+Target Population) reduces both the average prediction error and the standard deviation (e.g., compare the results for experiment 3 to the results for experiment 1 and compare the results for experiment 4 to the results for experiment 2).

| Example Experiment No. | Interferent Calibration | Sample Population | Average Prediction Error (mg/dL) | Standard Deviation (mg/dL) |
|---|---|---|---|---|
| 1 | NO | Normal | 126 | 164 |
| 2 | YES | Normal | −6.8 | 23.2 |
| 3 | NO | Normal + Target | 8.2 | 16.9 |
| 4 | YES | Normal + Target | 1.32 | 12.6 |

Accordingly, embodiments of analysis methods that use a Sample Population that includes both normal spectra and spectra from individuals similar to those of the target population and that calibrate for possible interferents provide a good match between the estimated glucose concentration and the measured glucose concentration. As discussed above, a suitable Sample Population may be assembled from the Population Database in order to include normal spectra plus suitable target spectra from individuals that match a desired target population including, for example, ICU patients, trauma patients, a particular demographic group, a group having a common medical condition (e.g., diabetes), and so forth.

User Interface

The system 400 can include a display system 414, for example, as depicted in FIG. 4. The display system 414 may comprise an input device including, for example, a keypad or a keyboard, a mouse, a touchscreen display, and/or any other suitable device for inputting commands and/or information. The display system 414 may also include an output device including, for example, an LCD monitor, a CRT monitor, a touchscreen display, a printer, and/or any other suitable device for outputting text, graphics, images, videos, etc. In some embodiments, a touchscreen display is advantageously used for both input and output.

The display system 414 can include a user interface 2400 by which users can conveniently and efficiently interact with the system 400. The user interface 2400 may be displayed on the output device of the system 400 (e.g., the touchscreen display). In some embodiments, the user interface 2400 is implemented and/or stored as one or more code modules, which may be embodied in hardware, firmware, and/or software.

FIGS. 24 and 25 schematically illustrate the visual appearance of embodiments of the user interface 2400. The user interface 2400 may show patient identification information 2402, which can include patient name and/or a patient ID number. The user interface 2400 also can include the current date and time 2404. An operating graphic 2406 shows the operating status of the system 400. For example, as shown in FIGS. 24 and 25, the operating status is "Running," which indicates that the system 400 is fluidly connected to the patient ("Jill Doe") and performing normal system functions such as infusing fluid and/or drawing blood. The user interface 2400 can include one or more analyte concentration graphics 2408, 2412, which may show the name of the analyte and its last measured concentration. For example, the graphic 2408 in FIG. 24 shows "Glucose" concentration of 150 mg/dL, while the graphic 2412 shows "Lactate" concentration of 0.5 mmol/L. The particular analytes displayed and their measurement units (e.g., mg/dL, mmol/L, or other suitable unit) may be selected by the user. The size of the graphics 2408, 2412 may be selected to be easily readable out to a distance such as, e.g., 30 feet. The user interface 2400 may also include a next-reading graphic 2410 that indicates the time until the next analyte measurement is to be taken. In FIG. 24, the time until next reading is 3 minutes, whereas in FIG. 25, the time is 6 minutes, 13 seconds.

The user interface 2400 can include an analyte concentration status graphic 2414 that indicates status of the patient's current analyte concentration compared with a reference standard. For example, the analyte may be glucose, and the reference standard may be a hospital ICU's tight glycemic control (TGC). In FIG. 24, the status graphic 2414 displays "High Glucose," because the glucose concentration (150 mg/dL) exceeds the maximum value of the reference standard. In FIG. 25, the status graphic 2414 displays "Low Glucose," because the current glucose concentration (79 mg/dL) is below the minimum reference standard. If the analyte concentration is within bounds of the reference standard, the status graphic 2414 may indicate normal (e.g., "Normal Glucose"), or it may not be displayed at all. The status graphic 2414 may have a background color (e.g., red) when the analyte concentration exceeds the acceptable bounds of the reference standard.

The user interface 2400 can include one or more trend indicators 2416 that provide a graphic indicating the time history of the concentration of an analyte of interest. In FIGS. 24 and 25, the trend indicator 2416 comprises a graph of the glucose concentration (in mg/dL) versus elapsed time (in hours) since the measurements started. The graph includes a trend line 2418 indicating the time-dependent glucose concentration. In other embodiments, the trend line 2418 can include measurement error bars and may be displayed as a series of individual data points. In FIG. 25, the glucose trend indicator 2416 is shown as well as a trend indicator 2430 and trend line 2432 for the lactate concentration. In some embodiments, a user may select whether none, one, or both trend indicators 2416, 2418 are displayed. In some embodiments, one or both of the trend indicators 2416, 2418 may appear only when the corresponding analyte is in a range of interest such as, for example, above or below the bounds of a reference standard.

The user interface 2400 can include one or more buttons 2420-2426 that can be actuated by a user to provide additional functionality or to bring up suitable context-sensitive menus and/or screens. For example, in the embodiments shown in FIG. 24 and FIG. 25, four buttons 2420-2426 are shown, although fewer or more buttons are used in other embodiments. The button 2420 ("End Monitoring") may be pressed when one or more removable portions (see, e.g., 710 of FIG. 7) are to be removed. In many embodiments, because the removable portions 710, 712 are not reusable, a confirmation window appears when the button 2420 is pressed. If the user is certain that monitoring should stop, the user can confirm this by actuating an affirmative button in the confirmation window. If the button 2420 were pushed by mistake, the user can select a negative button in the confirmation window. If "End Monitoring" is confirmed, the system 400 performs appropriate actions to cease fluid infusion and blood draw and to permit ejection of a removable portion (e.g., the removable portion 710).

The button 2422 ("Pause") may be actuated by the user if patient monitoring is to be interrupted but is not intended to end. For example, the "Pause" button 2422 may be actuated if the patient is to be temporarily disconnected from the system 400 (e.g., by disconnecting the tubes 306). After the patient is reconnected, the button 2422 may be pressed again to resume monitoring. In some embodiments, after the "Pause" button 2422 has been pressed, the button 2422 displays "Resume."

The button 2424 ("Delay 5 Minutes") causes the system 400 to delay the next measurement by a delay time period (e.g., 5 minutes in the depicted embodiments). Actuating the delay button 2424 may be advantageous if taking a reading would be temporarily inconvenient, for example, because a health care professional is attending to other needs of the patient. The delay button 2424 may be pressed repeatedly to provide longer delays. In some embodiments, pressing the delay button 2424 is ineffective if the accumulated delay exceeds a maximum threshold. The next-reading graphic 2410 automatically increases the displayed time until the next reading for every actuation of the delay button 2424 (up to the maximum delay).

The button 2426 ("Dose History") may be actuated to bring up a dosing history window that displays patient dosing history for an analyte or medicament of interest. For example, in some embodiments, the dosing history window displays insulin dosing history of the patient and/or appropriate hospital dosing protocols. A nurse attending the patient can actuate the dosing history button 2426 to determine the time when the patient last received an insulin dose, the last dosage amount, and/or the time and amount of the next dosage. The system 400 may receive the patient dosing history via wired or wireless communications from a hospital information system.

In other embodiments, the user interface 2400 can include additional and/or different buttons, menus, screens, graphics, etc. that are used to implement additional and/or different functionalities.

Related Components

Figure 26:
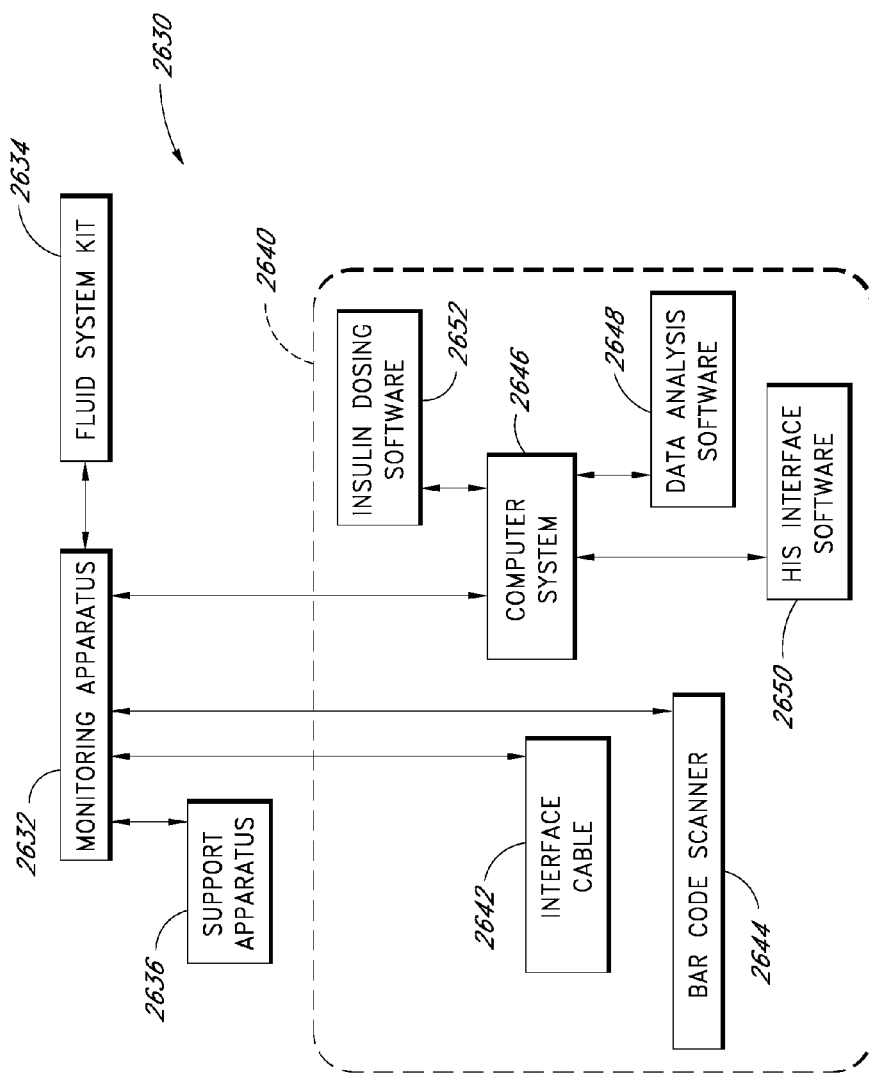
FIG. 26 schematically depicts various components and/or aspects of a patient monitoring system and the relationships among the components and/or aspects.

FIG. 26 schematically depicts various components and/or aspects of a patient monitoring system 2630 and how those components and/or aspects relate to each other. In some embodiments, the monitoring system 2630 can be the apparatus 100 for withdrawing and analyzing fluid samples. Some of the depicted components can be included in a kit containing a plurality of components. Some of the depicted components, including, for example, the components represented within the dashed rounded rectangle 2640 of FIG. 26, are optional and/or can be sold separately from other components.

The patient monitoring system 2630 shown in FIG. 26 includes a monitoring apparatus 2632. The monitoring apparatus 2632 can be the monitoring device 102, shown in FIG. 1 and/or the system 400 of FIG. 4. The monitoring apparatus 2632 can provide monitoring of physiological parameters of a patient. In some embodiments, the monitoring apparatus 2632 measures glucose and/or lactate concentrations in the patient's blood. In some embodiments, the measurement of such physiological parameters is substantially continuous. The monitoring apparatus 2632 may also measure other physiological parameters of the patient. In some embodiments, the monitoring apparatus 2632 is used in an intensive care unit (ICU) environment. In some embodiments, one monitoring apparatus 2632 is allocated to each patient room in an ICU.

The patient monitoring system 2630 can include an optional interface cable 2642. In some embodiments, the interface cable 2642 connects the monitoring apparatus 2632 to a patient monitor (not shown). The interface cable 2642 can be used to transfer data from the monitoring apparatus 2632 to the patient monitor for display. In some embodiments, the patient monitor is a bedside cardiac monitor having a display that is located in the patient room (see, e.g., the user interface 2400 shown in FIG. 24 and FIG. 25.) In some embodiments, the interface cable 2642 transfers data from the monitoring apparatus 2632 to a central station monitor and/or to a hospital information system (HIS). The ability to transfer data to a central station monitor and/or to a HIS may depend on the capabilities of the patient monitor system.

In the embodiment shown in FIG. 26, an optional bar code scanner 2644 is connected to the monitoring apparatus 2632. In some embodiments, the bar code scanner 2644 is used to enter patient identification codes, nurse identification codes, and/or other identifiers into the monitoring apparatus 2632. In some embodiments, the bar code scanner 2644 contains no moving parts. The bar code scanner 2644 can be operated by manually sweeping the scanner 2644 across a printed bar code or by any other suitable means. In some embodiments, the bar code scanner 2644 includes an elongated housing in the shape of a wand.

The patient monitoring system 2630 includes a fluid system kit 2634 connected to the monitoring apparatus 2632. In some embodiments, the fluid system kit 2634 includes fluidic tubes that connect a fluid source to an analytic subsystem. For example, the fluidic tubes can facilitate fluid communication between a blood source or a saline source and an assembly including a sample holder and/or a centrifuge. In some embodiments, the fluid system kit 2634 includes many of the components that enable operation of the monitoring apparatus 2632. In some embodiments, the fluid system kit 2634 can be used with anti-clotting agents (such as heparin), saline, a saline infusion set, a patient catheter, a port sharing IV infusion pump, and/or an infusion set for an IV infusion pump, any or all of which may be made by a variety of manufacturers. In some embodiments, the fluid system kit 2634 includes a monolithic housing that is sterile and disposable. In some embodiments, at least a portion of the fluid system kit 2634 is designed for single patient use. For example, the fluid system kit 2634 can be constructed such that it can be economically discarded and replaced with a new fluid system kit 2634 for every new patient to which the patient monitoring system 2630 is connected. In addition, at least a portion of the fluid system kit 2634 can be designed to be discarded after a certain period of use, such as a day, several days, several hours, three days, a combination of hours and days such as, for example, three days and two hours, or some other period of time. Limiting the period of use of the fluid system kit 2634 may decrease the risk of malfunction, infection, or other conditions that can result from use of a medical apparatus for an extended period of time.

In some embodiments, the fluid system kit 2634 includes a connector with a luer fitting for connection to a saline source. The connector may be, for example, a three-inch pigtail connector. In some embodiments, the fluid system kit 2634 can be used with a variety of spikes and/or IV sets used to connect to a saline bag. In some embodiments, the fluid system kit 2634 also includes a three-inch pigtail connector with a luer fitting for connection to one or more IV pumps. In some embodiments, the fluid system kit 2634 can be used with one or more IV sets made by a variety of manufacturers, including IV sets obtained by a user of the fluid system kit 2634 for use with an infusion pump. In some embodiments, the fluid system kit 2634 includes a tube with a low dead volume luer connector for attachment to a patient vascular access point. For example, the tube can be approximately seven feet in length and can be configured to connect to a proximal port of a cardiovascular catheter. In some embodiments, the fluid system kit 2634 can be used with a variety of cardiovascular catheters, which can be supplied, for example, by a user of the fluid system kit 2634.

As shown in FIG. 26, the monitoring apparatus 2632 is connected to a support apparatus 2636, such as an IV pole. The support apparatus 2636 can be customized for use with the monitoring apparatus 2632. A vendor of the monitoring apparatus 2632 may choose to bundle the monitoring apparatus 2632 with a custom support apparatus 2636. In some embodiments, the support apparatus 2636 includes a mounting platform for the monitoring apparatus 2632. The mounting platform can include mounts that are adapted to engage threaded inserts in the monitoring apparatus 2632. The support apparatus 2636 can also include one or more cylindrical sections having a diameter of a standard IV pole, for example, so that other medical devices, such as IV pumps, can be mounted to the support apparatus. The support apparatus 2636 can also include a clamp adapted to secure the apparatus to a hospital bed, an ICU bed, or another variety of patient conveyance device.

In the embodiment shown in FIG. 26, the monitoring apparatus 2632 is electrically connected to an optional computer system 2646. The computer system 2646 can comprise one or multiple computers, and it can be used to communicate with one or more monitoring devices. In an ICU environment, the computer system 2646 can be connected to at least some of the monitoring devices in the ICU. The computer system 2646 can be used to control configurations and settings for multiple monitoring devices (for example, the system can be used to keep configurations and settings of a group of monitoring devices common). The computer system 2646 can also run optional software, such as data analysis software 2648, HIS interface software 2650, and insulin dosing software 2652.

In some embodiments, the computer system 2646 runs optional data analysis software 2648 that organizes and presents information obtained from one or more monitoring devices. In some embodiments, the data analysis software 2648 collects and analyzes data from the monitoring devices in an ICU. The data analysis software 2648 can also present charts, graphs, and statistics to a user of the computer system 2646.

In some embodiments, the computer system 2646 runs optional hospital information system (HIS) interface software 2650 that provides an interface point between one or more monitoring devices and an HIS. The HIS interface software 2650 may also be capable of communicating data between one or more monitoring devices and a laboratory information system (LIS).

In some embodiments, the computer system 2646 runs optional insulin dosing software 2652 that provides a platform for implementation of an insulin dosing regimen. In some embodiments, the hospital tight glycemic control protocol is included in the software. The protocol allows computation of proper insulin doses for a patient connected to a monitoring device 2646. The insulin dosing software 2652 can communicate with the monitoring device 2646 to ensure that proper insulin doses are calculated.

Analyte Control and Monitoring

In some embodiments, it may be advantageous to control a level of an analyte (e.g., glucose) in a patient using an embodiment of an analyte detection system described herein. Although certain examples of glucose control are described below, embodiments of the systems and methods disclosed herein may be used to monitor and/or control other analytes (e.g., lactate).

For example, diabetic individuals control their glucose levels by administration of insulin. If a diabetic patient is admitted to a hospital or ICU, the patient may be in a condition in which he or she cannot self-administer insulin. Advantageously, embodiments of the analyte detection systems disclosed herein may be used to control the level of glucose in the patient. Additionally, it has been found that a majority of patients admitted to the ICU exhibit hyperglycemia without having diabetes. In such patients it may be beneficial to monitor and control their blood glucose level to be within a particular range of values. Further, it has been shown that tightly controlling blood glucose levels to be within a stringent range may be beneficial to patients undergoing surgical procedures.

A patient admitted to the ICU or undergoing surgery may be administered a variety of drugs and fluids such as Hetastarch, intravenous antibiotics, intravenous glucose, intravenous insulin, intravenous fluids such as saline, etc., which may act as interferents and make it difficult to determine the blood glucose level. Moreover, the presence of additional drugs and fluids in the blood stream may require different methods for measuring and controlling blood glucose level. Also, the patient may exhibit significant changes in hematocrit levels due to blood loss or internal hemorrhage, and there can be unexpected changes in the blood gas level or a rise in the level of bilirubin and ammonia levels in the event of an organ failure. Embodiments of the systems and methods disclosed herein advantageously may be used to monitor and control blood glucose (and/or other analytes) in the presence of possible interferents to estimation of glucose and for patients experiencing health problems.

In some environments, Tight Glycemic Control (TGC) can include: (1) substantially continuous monitoring (which can include periodic monitoring, at relatively frequent intervals of every 1, 5, 15, 30, 45, and/or 60 minutes, for example) of glucose levels; (2) determination of substances that tend to increase glucose levels (e.g., sugars such as dextrose) and/or decrease glucose levels (e.g., insulin); and/or (3) responsive delivery of one or more of such substances, if appropriate under the controlling TGC protocol. For example, one possible TGC protocol can be achieved by controlling glucose within a relatively narrow range (for example between 70 mg/dL to 110 mg/dL). As will be further described, in some embodiments, TGC may be achieved by using an analyte monitoring system to make continuous and/or periodic but frequent measurements of glucose levels.

In some embodiments, the analyte detection system schematically illustrated in FIGS. 4, 5, and 6 may be used to regulate the concentration of one or more analytes in the sample in addition to determining and monitoring the concentration of the one or more analytes. In some cases, the analyte detection system may be used in an ICU to monitor (and/or control) analytes that may be present in patients experiencing trauma. In some implementations, the concentration of the analytes is regulated to be within a certain range. The range may be predetermined (e.g., according to a hospital protocol or a physician's recommendation), or the range may be adjusted as conditions change.

In an example of glycemic control, a system can be used to determine and monitor the concentration of glucose in the sample. If the concentration of glucose falls below a lower threshold, glucose from an external source can be supplied. If the concentration of glucose increases above an upper threshold, insulin from an external source can be supplied. In some embodiments, glucose or insulin may be infused in a patient continuously over a certain time interval or may be injected in a large quantity at once (referred to as "bolus injection").

In some embodiments, a glycemic control system may be capable of delivering glucose, dextrose, glycogen, and/or glucagon from an external source relatively quickly in the event of hypoglycemia. As discussed, embodiments of the glycemic control system may be capable of delivering insulin from an external source relatively quickly in the event of hyperglycemia.

Returning to FIGS. 5 and 6, these figures schematically illustrate embodiments of a fluid handling system that comprise optional analyte control subsystems 2780. The analyte control subsystem 2780 may be used for providing control of an analyte such as, e.g., glucose, and may provide delivery of the analyte and/or related substances (e.g., dextrose solution and/or insulin in the case of glucose). The analyte control subsystem 2780 comprises a source 2782 such as, for example, the analyte (or a suitable compound related to the analyte) dissolved in water or saline. For example, if the analyte is glucose, the source 2782 may comprise a bag of dextrose solution (e.g., Dextrose or Dextrose 50%). The source 2782 can be coupled to an infusion pump (not shown). The source 2782 and the infusion pump can be provided separately from the analyte control subsystem 2780. For example, a hospital advantageously can use existing dextrose bags and infusion pumps with the subsystem 2780.

As schematically illustrated in FIGS. 5 and 6, the source 2782 is in fluid communication with the patient tube 512 via a tube 2784 and suitable connectors. A pinch valve 2786 may be disposed adjacent the tube 2784 to regulate the flow of fluid from the source 2782. A patient injection port can be located at a short distance from the proximal port of the central venous catheter or some other catheter connected to the patient.

In an example implementation for glycemic control, if the analyte detection system determines that the level of glucose has fallen below a lower threshold value (e.g., the patient is hypoglycemic), a control system (e.g., the fluid system controller 405 in some embodiments) controlling an infusion delivery system may close the pinch valves 521 and/or 542 to prevent infusion of insulin and/or saline into the patient.

The control system may open the pinch valve 2786 and dextrose solution from the source 2782 can be infused (or alternatively injected as a bolus) into the patient. After a suitable amount of dextrose solution has been infused to the patient, the pinch valve 2786 can be closed, and the pinch valves 521 and/or 542 can be opened to allow flow of insulin and/or saline. In some systems, the amount of dextrose solution for infusion (or bolus injection) may be calculated based on one or more detected concentration levels of glucose. The source 2782 advantageously may be located at a short enough fluidic distance from the patient such that dextrose can be delivered to the patient within a time period of about one to about ten minutes. In other embodiments, the source 2782 can be located at the site where the patient tube 512 interfaces with the patient so that dextrose can be delivered within about one minute.

If the analyte detection system determines that the level of glucose has increased above an upper threshold value (e.g., the patient is hyperglycemic), the control system may close the pinch valves 542 and/or 2786 to prevent infusion of saline and/or dextrose into the patient. The control system may open the pinch valve 521, and insulin can be infused (or alternatively injected as a bolus) into the patient. After a suitable amount of insulin has been infused (or bolus injected) to the patient, the control system can close the pinch valve 521 and open the pinch valves 542 and/or 2786 to allow flow of saline and/or glucose. The suitable amount of insulin may be calculated based on one or more detected concentration levels of glucose in the patient. The insulin source 518 advantageously may be located at a short enough fluidic distance from the patient such that insulin can be delivered to the patient within about one to about ten minutes. In other embodiments, the insulin source 518 may be located at the site where the patient tube 512 interfaces with the patient so that insulin can be delivered to the patient within about one minute.

In some embodiments, sampling bodily fluid from a patient and providing medication to the patient may be achieved through the same lines of the fluid handling system. For example, in some embodiments, a port to a patient can be shared by alternately drawing samples and medicating through the same line. In some embodiments, a bolus can be provided to the patient at regular intervals (in the same or different lines). For example, a bolus of insulin can be provided to a patient after meals. In another embodiment comprising a shared line, a bolus of medication can be delivered when returning part of a body fluid sample back to the patient. In some implementations, the bolus of medication is delivered midway between samples (e.g., every 7.5 minutes if samples are drawn every 15 minutes). In other embodiment, a dual lumen tube can be used, wherein one lumen is used for the sample and the other lumen to medicate. In yet another embodiment, an analyte detection system (e.g., an "OptiScanner®" monitor) may provide suitable commands to a separate insulin pump (on a shared port or different line).

Example Method for Glycemic Control

Figure 27:
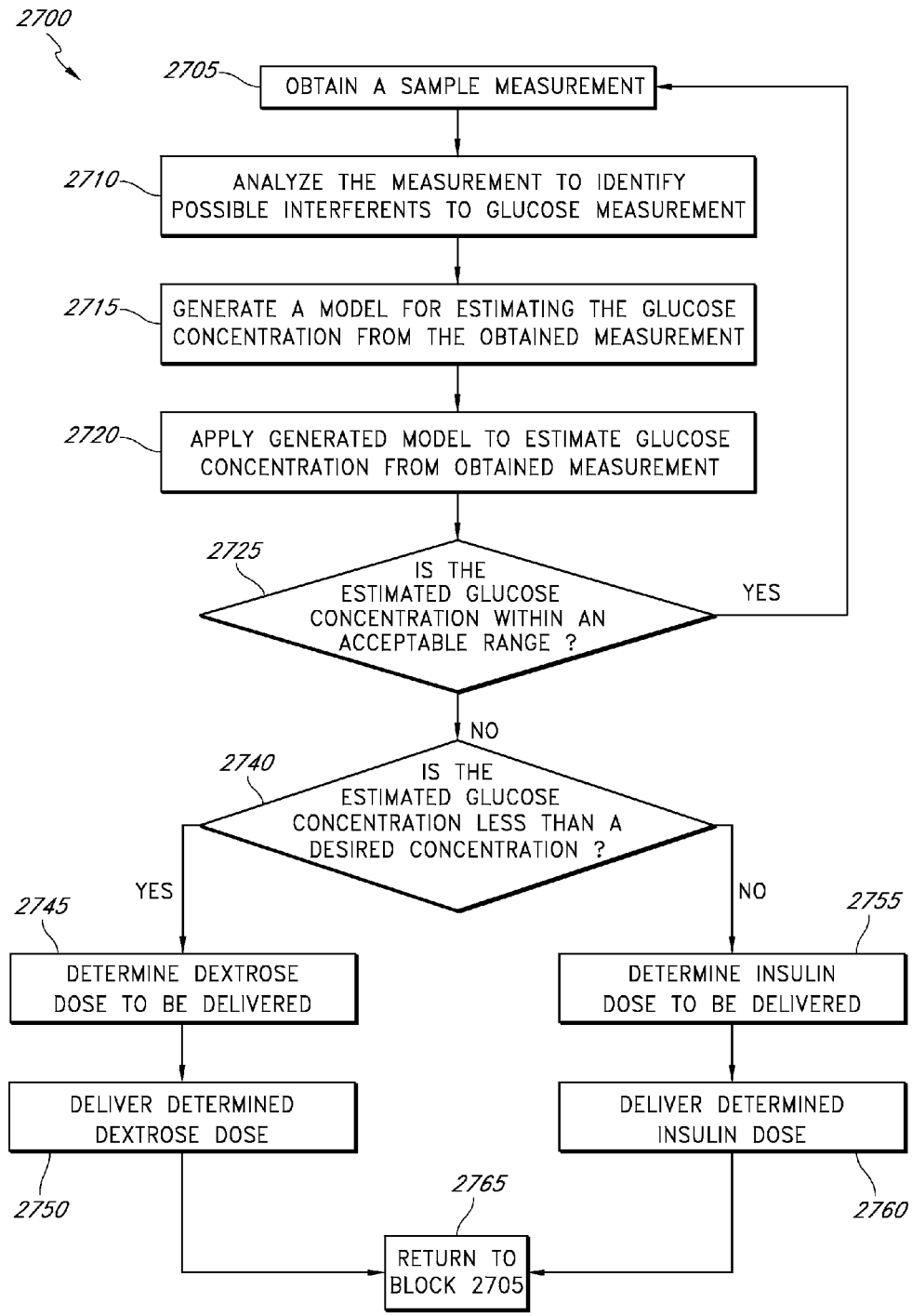
FIG. 27 is a flowchart that schematically illustrates an embodiment of a method of providing glycemic control.

FIG. 27 is a flowchart that schematically illustrates an example embodiment of a method 2700 of providing analyte control. The example embodiment is directed toward one possible implementation for glycemic control (including but not limited to tight glycemic control) and is intended to illustrate certain aspects of the method 2700 and is not intended to limit the scope of possible analyte control methods. In block 2705, a glucose monitoring apparatus (e.g., the monitoring apparatus 2632 of FIG. 26) draws a sample (e.g., a blood or blood plasma sample) from a sample source (e.g., a patient) and obtains a measurement from the sample (e.g., a portion of the drawn sample). The measurement may comprise an optical measurement such as, for example, an infrared spectrum of the sample. In block 2710, the measurement sample is analyzed to identify possible interferents to an estimation of the glucose concentration in the measurement sample. In block 2715, a model is generated for estimating the glucose concentration from the obtained measurement. In some embodiments, models developed from the algorithms describe above with reference to FIGS. 21-23 are used. The generated model may reduce or minimize effects of the identified interferents on the estimated glucose concentration, in certain embodiments. In block 2720, an estimated glucose concentration is determined from the model and the obtained measurement. In block 2725, the estimated glucose concentration in the sample is compared to an acceptable range of concentrations. The acceptable range may be determined according to a suitable glycemic control protocol such as, for example, a TGC protocol. For example, in certain TGC protocols the acceptable range may be a glucose concentration in a range from about 70 mg/dL to about 110 mg/dL. If the estimated glucose concentration lies within the acceptable range, the method 2700 returns to block 2705 to obtain the next sample measurement, which may be made within about one to about thirty minutes (e.g., every fifteen minutes).

In block 2725, if the estimated glucose concentration is outside the acceptable range of concentrations, then the method 2700 proceeds to block 2740 in which the estimated glucose concentration is compared with a desired glucose concentration. The desired glucose concentration may be based on, for example, the acceptable range of glucose concentrations, the parameters of the particular glycemic protocol, the patient's estimated glucose concentration, and so forth. If the estimated glucose concentration is below the desired concentration (e.g., the patient is hypoglycemic), a dose of dextrose to be delivered to the patient is calculated in block 2745. This calculation may take into account various factors including, for example, one or more estimated glucose concentrations, presence of additional drugs in the patient's system, time taken for dextrose to be assimilated by the patient, and the delivery method (e.g., continuous infusion or bolus injection). In block 2750, a fluid delivery system (e.g., a system such as the optional subsystem 2780 shown in FIGS. 5 and 6) delivers the calculated dose of dextrose to the patient.

In block 2740, if the estimated glucose concentration is greater than the desired concentration (e.g., the patient is hyperglycemic), a dose of insulin to be delivered is calculated in block 2755. The dose of insulin may depend on various factors including, for example, one or more estimated glucose concentrations in the patient, presence of other drugs, type of insulin used, time taken for insulin to be assimilated by the patient, method of delivery (e.g., continuous infusion or bolus injection), etc. In block 2750, a fluid delivery system (e.g., the optional subsystem 2780 shown in FIGS. 5 and 6) delivers the calculated dose of insulin to the patient.

In block 2765, the method 2700 returns to block 2705 to await the start of the next measurement cycle, which may be within about one to about thirty minutes (e.g., every fifteen minutes). In some embodiments, the next measurement cycle begins at a different time than normally scheduled in cases in which the estimated glucose concentration lies outside the acceptable range of concentrations under the glycemic protocol. Such embodiments advantageously allow the system to monitor response of the patient to the delivered dose of dextrose (or insulin). In some such embodiments, the time between measurement cycles is reduced so the system can more accurately monitor analyte levels in the patient.

Examples of Some Possible Additional or Alternative Analytes

Although examples of control and/or monitoring has been described in the illustrative context of glycemic control, embodiments of the systems and methods can be configured for control and/or monitoring of one or more of many possible analytes, in addition to or instead of glucose. Monitor and/or control of analytes may be particularly helpful in ICUs, which receive patients experiencing trauma. For example, another parameter that can be monitored is level of Hemoglobin (Hb). If the Hb level of a patient goes down without an apparent external reason, the patient could be suffering from internal bleeding. Indeed, many ICU patients (some estimate as many as 10%) suffer from what appears to be spontaneous internal bleeding that may not be otherwise detectable until the consequences are too drastic to easily overcome. In some embodiments, level of Hb can be measured indirectly, because its relationship to oxygen in the veins and arteries (at different points in the vasculature with respect to the heart and lungs) is understood. In some embodiments, the apparatus, systems and methods described herein can be useful for measuring a level of Hb.

Another parameter that can be monitored is lactate level, which can be related to sepsis or toxic shock. Indeed, high levels and/or rapid rise in lactate levels can be correlated to organ failure and oxygenation problems in the blood and organs. However, other direct measures of the biological effects related to lactate level problems can be difficult to measure, for example, only becoming measurable with a delay (e.g., 2-6 hours later). Thus, measurement of lactate level can help provide a valuable early warning of other medical problems. Indeed, if a problem with lactate levels is detected, a nurse or doctor may be able to prevent the correlated problems by providing more fluids.

Another parameter that can be monitored is central venous oxygen saturation (ScvO2). It can be advantageous to try to maintain an ScvO2 of 65-70% or greater in ICU patients (to help avoid sepsis, for example). In some embodiments, the apparatus, systems, and methods described herein can be useful for measuring a level of ScvO2.

Levels of lactate and ScvO2 in a patient can be used together to provide information and/or warnings to a health care provider, which can be especially useful in an ICU setting. For example, if lactate and ScvO2 are both high, a warning can be provided (e.g., automatically using an alarm). If lactate is high, but ScvO2 is low, a patient may benefit from additional fluids. If ScvO2 is high, but lactate is low, a cardiac problem may be indicated. Thus, a system that provides information about both lactate and ScvO2 can be very beneficial to a patient, especially, for example, in the ICU environment. Although lactate and ScvO2 have been used as an illustrative example, in other embodiments different combinations of analytes may be monitored and used to provide information and/or warnings to a health care provider.

Sample Fluids

In many of the embodiments discussed herein, measurements can be taken from a sample of bodily fluid. In some embodiments whole blood can be used. For some analyte measurements, characteristics of the sample can impede measurement. For example, blood can include some analytes in the red blood cells and some analytes in white blood cells. Some analytes can be present in the blood and not present within either type of blood cell. Other, non-analyte components in whole blood may have chemical bonds with similar vibrational frequencies to those of the analyte. Analytes can be unhelpfully shielded (optically, physically, or both) by non-analyte components. Indeed, in some cases analytes can be located within cell membranes and therefore more difficult to measure or quantify, either because they are not evenly distributed, because they are chemically bound, or for some other reason. Other particles within a sample (e.g., blood) can interfere with the measurement, thereby reducing accuracy of the system. For example, in embodiments that use an optical measurement system (e.g., 412) red blood cells, or other particles, can absorb, reflect, scatter, or otherwise interfere with the light that is transferred through the sample. Thus, in some embodiments, it can be advantageous to remove these interfering particles or to mitigate or suppress their adverse effects on the measurement. Similarly, it can be advantageous to break down or adjust biological or physiological structures in order to remove optical or physical barriers to measurement, evenly distribute analytes, or otherwise improve analyte detection and measurement. For example, blood can be separated using a centrifuge or filter into components that are organized by similar mass. Blood can also be separated using a lysing process that breaks down the blood's structure on a more fundamental level, breaking cell membranes and causing the contents of cells to be released into a more general suspension. Separation and/or lysing can occur using many mechanical and chemical approaches. For example, cells can be broken down using sonication, heat, lasers, ultrasound, physical shaking, homogenization, freeze-thaw procedures, grinding, detergents or other chemical approaches, enzymatic cell disruption, buffers, bacterial or other biological cell lysates, etc. Separation into components by mass can occur through settling, centrifugation, etc. Separation by mass can occur before or after cell disruption (e.g., by lysing).

A fluid handling system (e.g., 404) can prepare a sample for measurement. For example, a sample can be prepared by causing interfering substances or particles to move away from an analyte. In some embodiments, the fluid handling system can lyse the red blood cells in a portion of bodily fluid that will be used for the measurement, thereby releasing analytes from being confined within cells. The fluid handling system can include an ultrasound source configured to direct ultrasound energy into the bodily fluid to lyse the red blood cells. The red blood cells can be lysed using any other suitable manner as well, such as the mechanical, sonic, chemical, or optical approaches listed above. Particles other than red blood cells in the sample fluid can also be lysed or broken up using the ultrasound energy or in another manner. In some embodiments, the lysed red blood cells (or other particles) interfere less with the measurement than in their whole state.

Once the red blood cells have been lysed, the cells' cytoplasm and other contents can be released and intermingle with other blood components (e.g., the blood plasma). In some embodiments, the cytoplasm and other lysed components of the red blood cells (or other lysed particles) can interfere with the measurement. Thus, it can be advantageous in some embodiments to remove the red blood cells, or other undesirable particles, from the blood plasma (e.g., using filtering or centrifuging). In some embodiments, the separation of the blood plasma can be performed by the fluid handling system in lieu of lysing the particles as discussed above. In other embodiments, the fluid handling system can be configured to both lyse particles in the sample fluid and also separate the sample into components (e.g., by centrifuging) before or after lysing.

Figure 37:
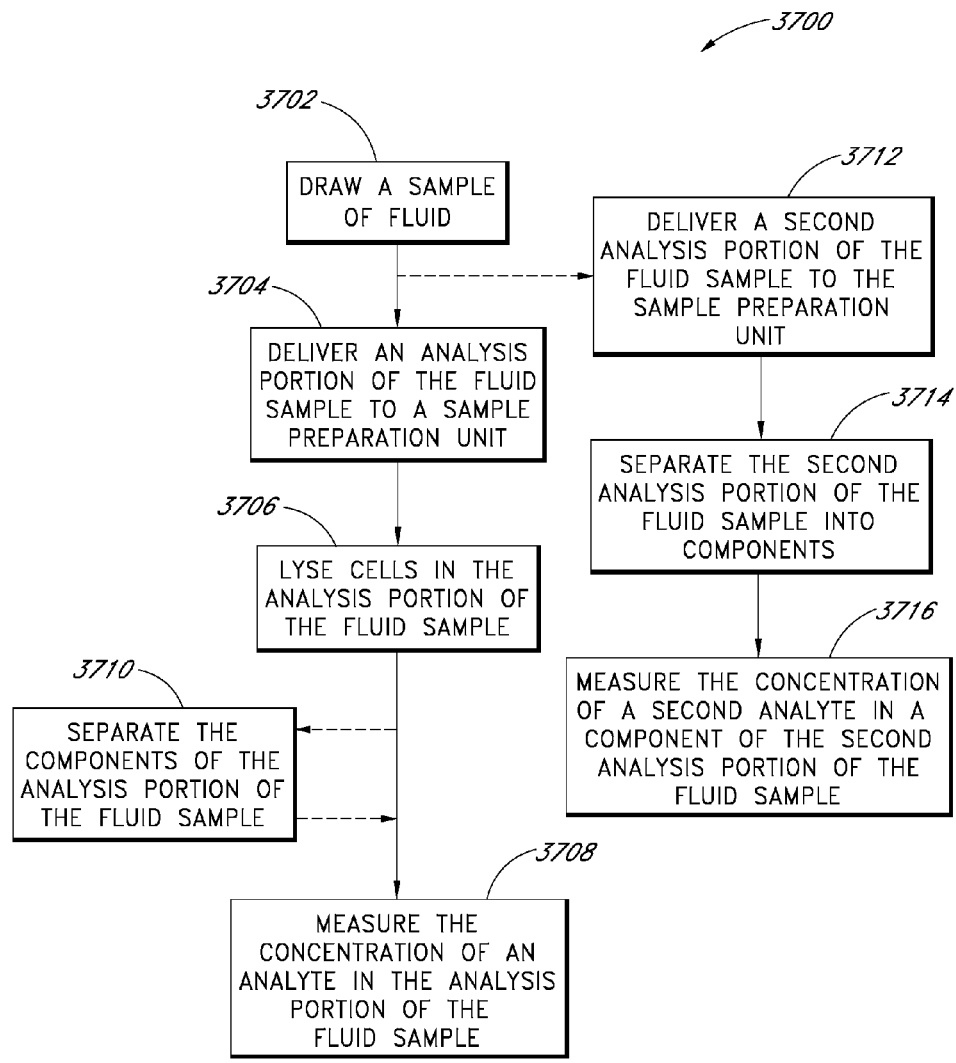
FIG. 37 is a flowchart illustrating example methods for measuring analytes in fluid samples.

FIG. 37 is a flowchart showing example embodiments of methods 3700 for measuring concentrations of analytes. The methods 3700 disclosed by FIG. 37 can be performed by an analyte (e.g., glucose) monitoring apparatus (e.g., the monitoring apparatus 2632 of FIG. 26), or by any other suitable device. At block 3702, a sample of fluid is drawn. The fluid sample can be drawn from a patient or other fluid source, and the fluid can be blood, for example. At block 3704, an analysis portion of the fluid sample is delivered to a sample preparation unit. At block 3706, the sample preparation unit lyses cells (e.g., blood cells) in the analysis portion of the fluid sample. And at block 3708, the monitoring system measures the concentration of an analyte in the analysis portion of the fluid sample. In some embodiments, additional steps can be performed. For example, in block 3710, the sample preparation unit can separate the analysis portion of the fluid sample into components after the cells have been lysed. This can provide the advantage of substantially isolating a component of the fluid so that a measurement can be made in a component of the fluid without other components influencing the measurement. If the lysed cells are blood cells, for example, lysing can release cytoplasm and other cell contents from the cell membranes into the blood plasma. Then by centrifugation or filtering, one component of the cells (e.g., the cytoplasm) can be substantially isolated, thereby improving the ability to measure one component (e.g., the cytoplasm) without being interference or obstruction from other components (e.g., cell membranes). Centrifugation can stratify the components into layers. However, centrifugation before lysing can form different layers than centrifugation after lysing. For example, centrifugation after lysing may involve additional substances having their own distinct mass or other physical qualities, resulting in additional strata containing particular cell components of similar mass. In some embodiments, if the cells are not lysed, the accuracy of measurements taken on components inside the cells (e.g., cytoplasm) can be reduced by the cell membranes or other cell components. By lysing the cells, a cell component to be measured (e.g., cytoplasm) can be more easily isolated and measured. In the flowchart, the lines leading to and from the block 3710 are dotted lines to show that block 3710 is an optional feature of the method 3700.

In some embodiments, the system can deliver a second analysis portion of the fluid sample to the sample preparation unit (block 3712). Then, at block 3714, the sample preparation unit can separate the second analysis portion of the fluid sample into a plurality of components (e.g., by centrifugation or filtering). At block 3716, the concentration of a second analyte is measured in a component of the second analysis portion of the fluid sample. Thus, in some embodiments, a first analysis portion of the fluid sample is prepared for analysis by lysing cells, and a second analysis portion of the fluid sample is prepared for analysis by separating the fluid into a plurality of components (e.g., by centrifugation, filtering, or some other selective process based on mass, size, magnetics, electrical qualities, etc.). In some embodiments, a single analysis portion of the fluid sample can be prepared for analysis by both lysing cells in the fluid and by separating the fluid into a plurality of components. Thus, the lysing and the component separating (e.g., by centrifuging) can be performed in series on the same portion of the sample or in parallel on different portions of the sample, or on different samples.

The line leading to block 3712 is dotted to indicate that the features of blocks 3712, 3714, and 3716 are optional to the method 3700. Although FIG. 37 shows a single flowchart, the method 3700 can follow several different possible paths. For example, the method can include blocks 3702, 3704, 3706, and 3708. In some embodiments, the method can include blocks, 3702, 3704, 3706, 3710, and 3708. In some embodiments, the method can include blocks, 3702, 3704, 3706, 3710, 3708, 3712, 3714, and 3716. In some embodiments, the method can include blocks, 3702, 3704, 3706, 3708, 3712, 3714, and 3716.

Sample Cell Holder

Figure 28A:
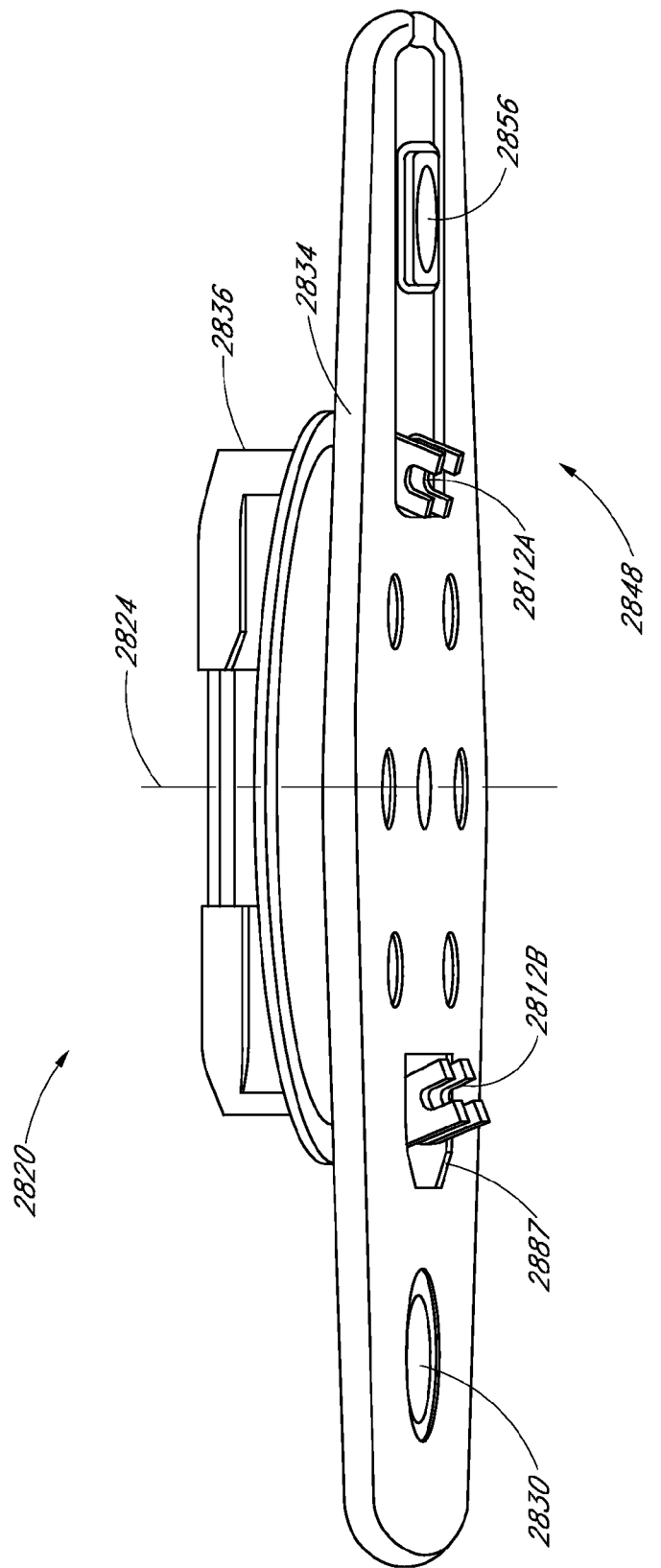
FIG. 28A illustrates an example embodiment of a sample cell holder.
Figure 28B:
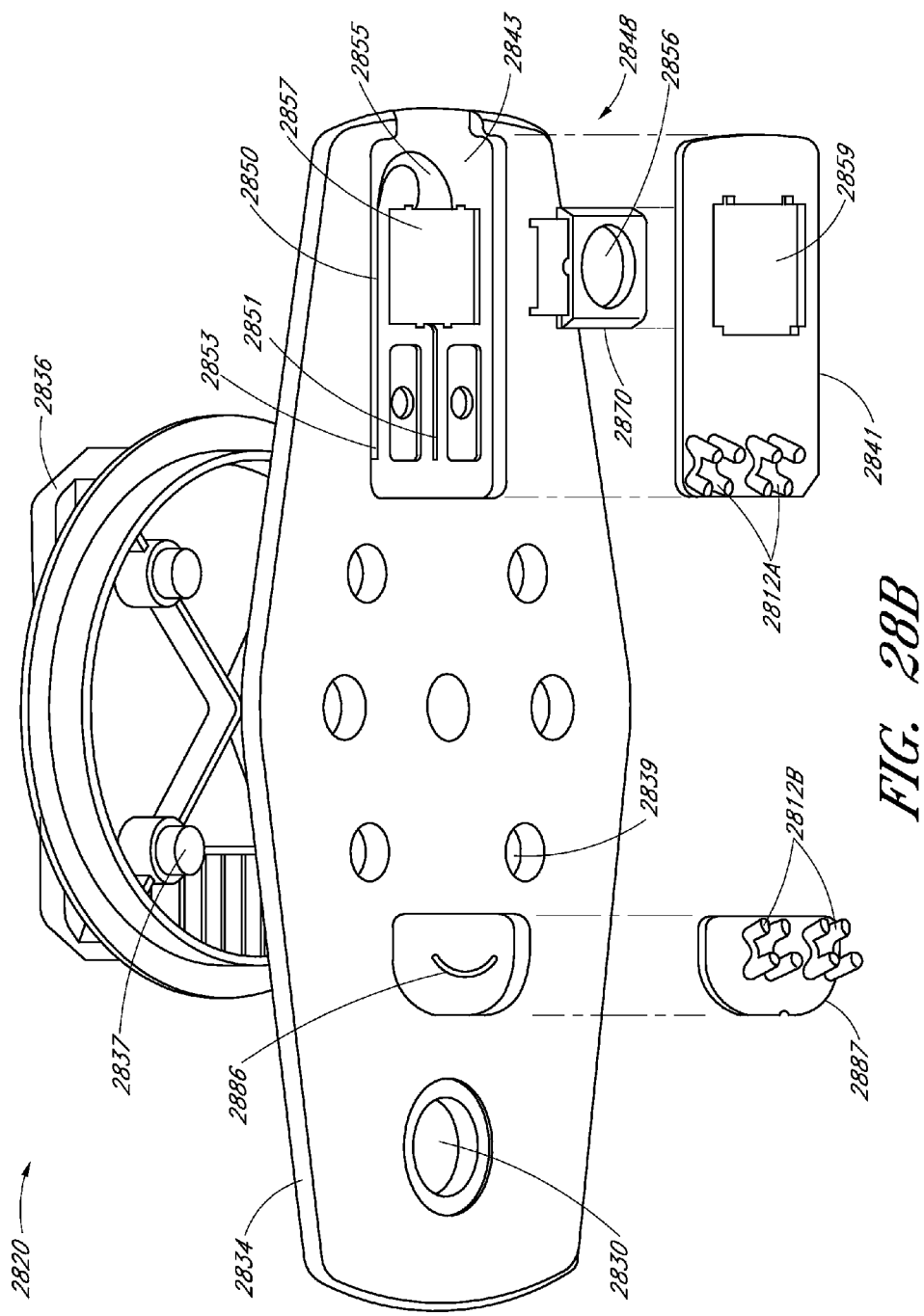
FIG. 28B is an exploded view o the sample cell holder of FIG. 28A.

FIG. 28A shows a sample cell holder 2820, which can be similar to or the same as the sample cell holder 820, or any other sample cell holder disclosed herein. FIG. 28B is an exploded view of the sample cell holder 2820. The sample cell holder 2820 can include a rotor housing 2834 that can be mounted (e.g., onto an optical interface portion 1030 of a cartridge 1000) such that the rotor housing 2834 can rotate about the axis 2824. A centrifuge interface 2836 can be attached to the rotor housing 2834. In some embodiments, posts 2837 formed on the centrifuge interface piece 2836 can mount into holes 2839 formed in the rotor housing 2834, and can be secured thereto using an adhesive, a snap fit connection, a friction fit connection, or any other suitable fastening mechanism. The centrifuge interface 2836 can engage a centrifuge motor (not shown) when the cartridge (e.g., 1000) is inserted into the body of the monitoring system (e.g., 700). The centrifuge motor can be configured to rotate the sample cell holder 2820 at least at about 7200 RPM, 5000 RPM, or 4500 RPM. Other rotational speeds can also be used, such as 1000 RPM, 2000 RPM, 3000 RPM, or 4000 RPM. The rotational speed can be sufficiently large to separate a sample fluid (e.g., blood) into a plurality of components (e.g., plasma, red blood cells, buffy coat, etc.).

The rotor housing 2834 can include a sample cell 2848 that includes a sample cell cover 2841, a recessed portion 2843 of the rotor housing 2834, and a cuvette 2870. The cuvette 2870 can provide a window 2856 configured to allow radiation from the optical system (e.g., optical system 412) to pass through the sample contained in the sample cell 2848. The sample cell cover 2841 can be secured to the rotor housing 2834 using an adhesive, a snap fit connection, sonic welding, or any other suitable fastening mechanism, and the cuvette 2870 can be sandwiched between the sample cell cover 2841 and the rotor housing 2834. In some embodiments, the cuvette 2870 can be secured directly to the rotor housing 2834 and/or the sample cell cover 2841 using an adhesive or sonic welding or any other suitable connection mechanism. The cuvette 2870 can be positioned so as to be aligned with holes 2857, 2859 formed in the rotor housing 2834 and the sample cell cover 2841 so that radiation from the optical system can reach the window and pass through the sample cell 2848.

The sample cell cover 2841 can include two receiving nubs 2812A that provide inlet and outlet fluid pathways for fluid to enter and leave the sample cell 2848. The recessed portion 2843 of the rotor housing 2834 can include channels 2850 to provide a fluid flow path from an inlet point 2851 associated with the inlet receiving nub 2812A, to the cuvette 2870, and to an outlet point 2853 associated with the outlet receiving nub 2812A. It will be understood that the fluid pathway through the sample cell 2848 can be provided by channels formed in the back of the sample cell cover, or by tubing, or any other suitable manner. It will also be understood that, in some cases, fluid may be directed into the sample cell 2848 through the outlet and may exit the sample cell 2848 through the inlet (e.g., when flushing the sample cell 2848 with saline or cleaning solution). In some embodiments, the channel 2850 can include a wide portion 2855 located adjacent to the cuvette 2870 such that the wide portion 2855 can collect particles (e.g., red blood cells) that are isolated during centrifuging and moved out of the optical pathway of the optical system.

The rotor housing 2834 can include an opening 2830 positioned generally at the opposite end of the rotor housing 2834 from the sample cell 2848. The opening 2830 can provide an alternative optical pathway between a radiation source and a radiation detector of the optical system. The alternate optical pathway through the opening 2830 may be used, for example, for obtaining a calibration measurement of the source and detector without an intervening window or sample. The rotor housing 2834 can include a shunt 2886, and a shunt cover 2887. The shunt cover 2887 can include two receiving nubs 2812B to provide an inlet and outlet for fluid to enter and leave the shunt 2886.

Figure 29B:
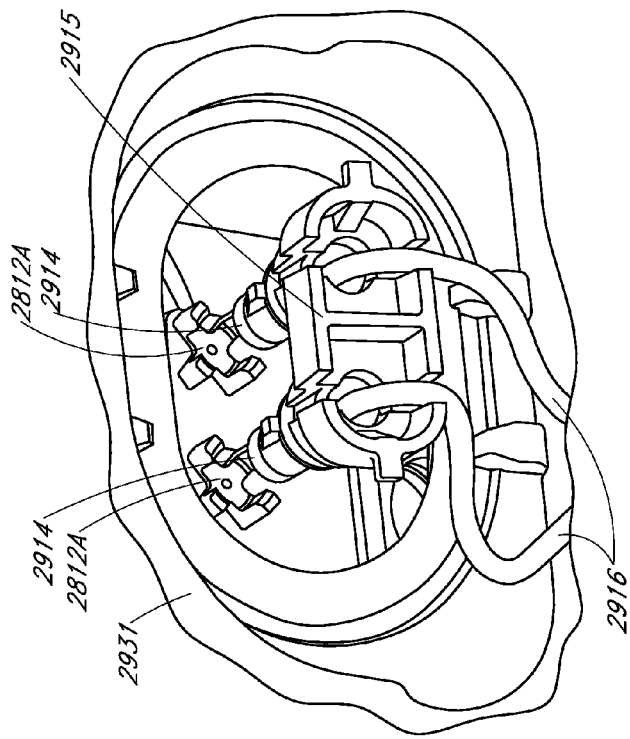
FIG. 29B is a close-up view of a portion of the cartridge of FIG. 29A showing the fluid injectors.
Figure 29A:
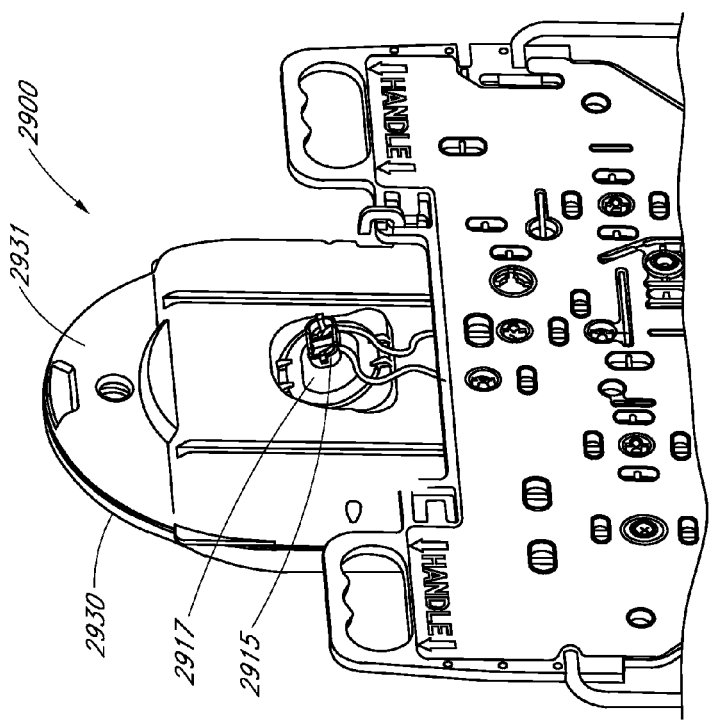
FIG. 29A illustrates an example embodiment of a cartridge that includes the sample cell holder of FIG. 28A.

With reference now to FIGS. 29A and 29B, the receiving nubs 2812A, 2812B of the sample cell colder 2820 can be configured to engage or dock with fluid nipples 2914 of a fluid injector 2915 to provide a fluid connection between tubes 2916 of the fluid handling system and the sample cell 2848 or the shunt 2886. FIG. 29A is a partial perspective view of a cartridge 2900 which can be similar to or the same as the cartridge 1000 of FIG. 10 in many regards. FIG. 29B is a partial view of the injector 2915 and receiving nubs 2812A in a disengaged configuration with the injector seal omitted.

The cartridge 2900 can have an optical interface portion 2930 which can include the sample cell holder 2820 rotatably mounted to an outer housing 2931. The fluid injector 2915 can receive tubes 2916 that provide a fluid connection between the fluid injector 2915 and the rest of the fluidics system (e.g., via interface tubes 582 and 584). The fluid injector 2915 can be movable between engaged and disengaged positions. The fluid injector 2915 can be attached to the outer housing 2931 by an injector seal 2917 that can be resiliently deformable and configured to bias the injector 2915 to the disengaged position (as shown in FIGS. 29A and 29B).

FIG. 29B shows the fluid injector 2915 in the disengaged position, and the injector seal 1917 is omitted to allow a view into the inside of the outer housing 2931. The receiving numbs 2812A can include a number of guide posts (e.g., four posts each) configured to guide the fluid nipples 2914 of the fluid injector 2915 as it transitions from the disengaged position to the engaged position. In some embodiments, an actuator (not shown) can be driven by a motor to press against the fluid injector 2915 and drive the fluid nipples 2914 toward the receiving nubs 2812A until a fluid connection is established between the fluid nipples 2914 and the receiving nubs 2812A. When the actuator (not shown) is retracted, the injector seal 2917 can resiliently return the fluid injector 2915 to the disengaged position, pulling the fluid nipples 2914 away from, and breaking the fluid connection with, the receiving nubs 2912A. Thus, the fluid injector 2915 can be retracted to a position that is clear from contact with the sample cell holder 2820 when the centrifuge motor spins the sample cell holder 2820. It will be understood that the sample cell holder 2820 can be rotated to a position in which the receiving nubs 2812B associated with the shunt 2886 can aligned with the fluid injector 2915 so that the fluid nipples 2914 can engage the receiving nubs 2912B to provide a fluid connection to the shunt 2886.

Figure 30:
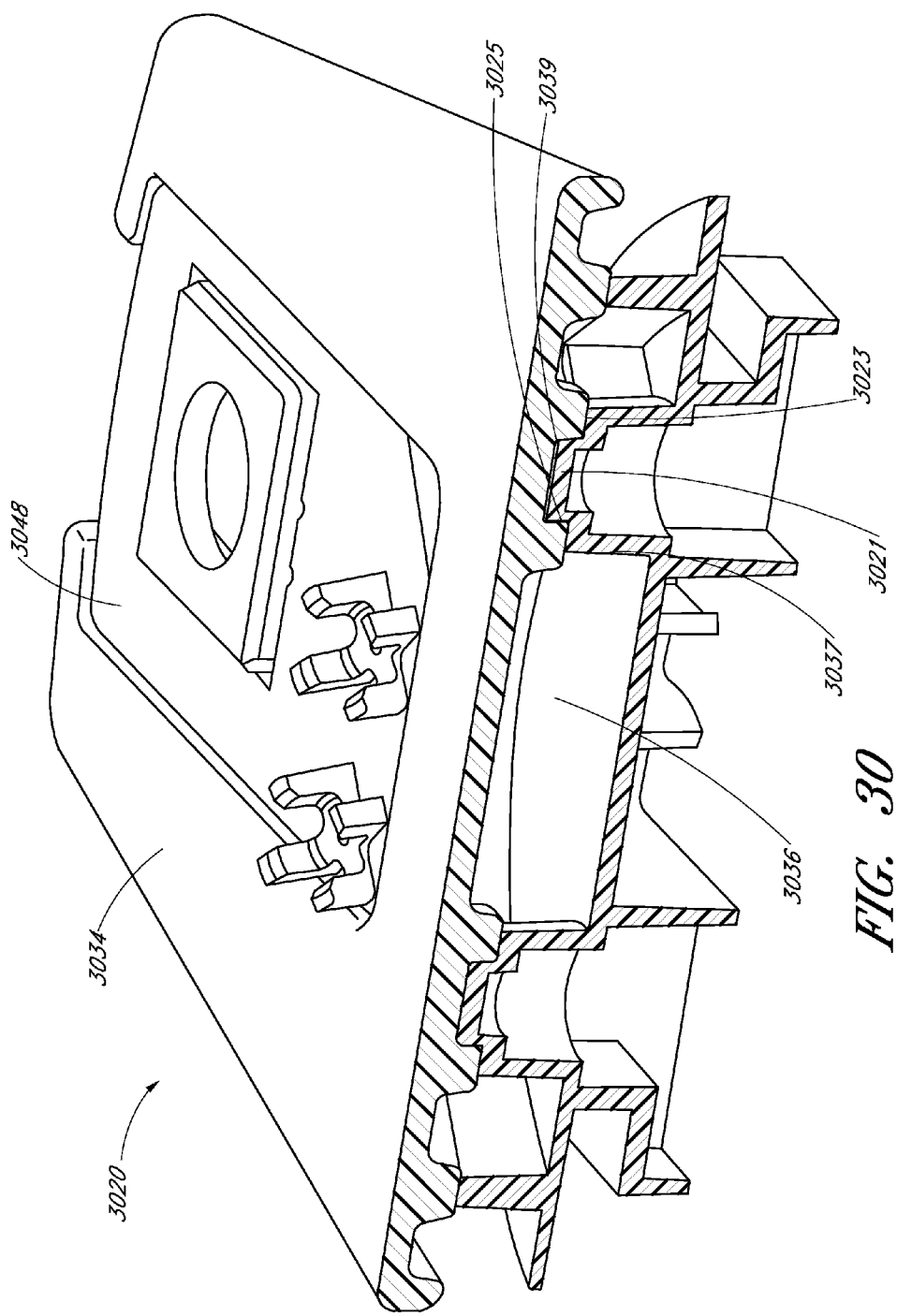
FIG. 30 illustrates an example embodiment of a sample cell.

FIG. 30 shows a perspective cross-sectional view of another embodiment of a sample cell holder 3020 that can include a sample cell 3048, a rotor housing 3034, and a centrifuge interface 3036. In the embodiment shown in FIG. 30, the centrifuge interface piece 3036 can be laser welded to the rotor housing 3034. The centrifuge interface 3036 can include posts 3037 (e.g., four posts) that are configured to engage holes 3039 formed in the rotor housing 3034. The posts 3037 can include studs 3021 that form a step 3023 at the periphery of the posts 3037. The studs 3021 can be configured to fit into the holes 3039 such that the steps 3023 engage the shoulders 3025 of the holes 3039. The studs 3021 can be laser welded to the rotor housing 3034, and the stress on the connection between the rotor housing 3034 and the centrifuge interface 3036 that is caused by the centrifuge motor (not shown) rotating the sample cell holder 3020 are kept generally localized to the locations that are laser welded together, thereby preventing warping or other deformation that can occur as a result of the force introduced by the centrifuge motor. The portions where the centrifuging stress is focused can be fortified to prevent deformation, or they can located where minor deformation does not significantly affect the positioning of the sample cell 3048 or otherwise adversely affect the operation of the monitoring system.

Figure 31:
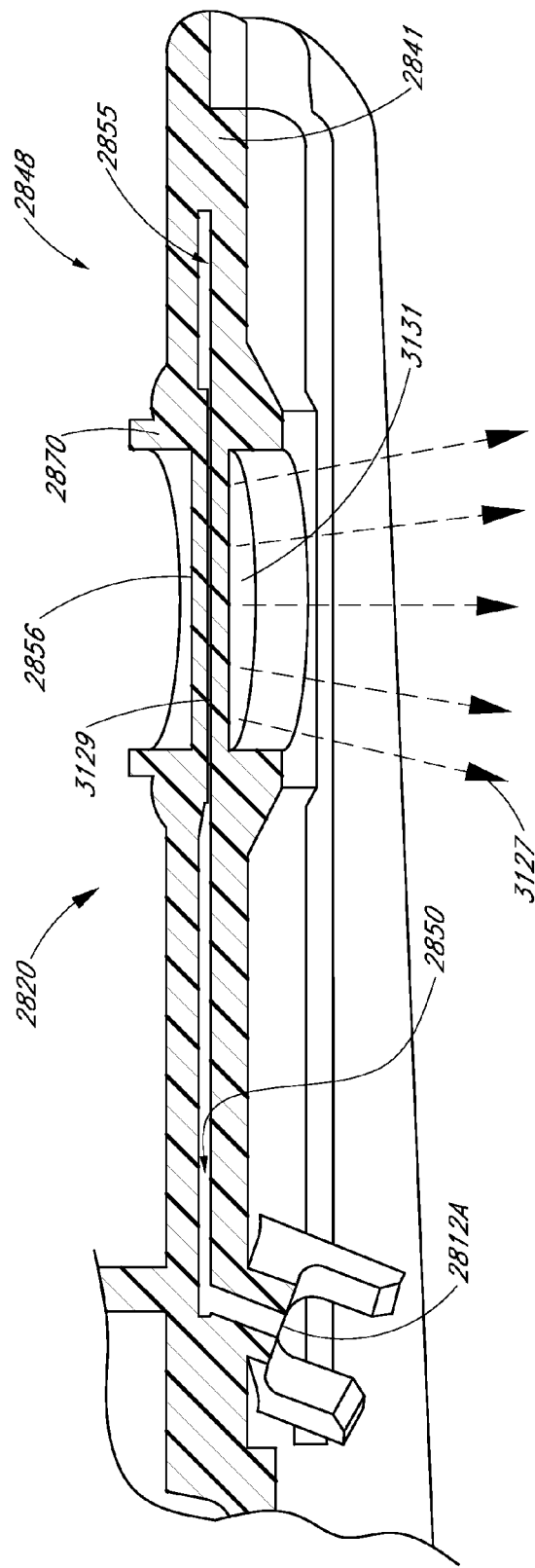
FIG. 31 is a partial cross-sectional view of the sample cell holder of FIG. 28A.

FIG. 31 is a partial cross-sectional view of the sample cell holder 2820 that includes the sample cell 2848. Fluid can enter the sample cell 2848 via the inlet receiving nub 2812A and travel toward the cuvette 2870 via the channel 2850. When the sample cell holder 2820 is rotated by the centrifuge motor, the fluid sample contained in the sample cell 2848 can be separated such that heavier particles (e.g., red blood cells) are pulled radially outwardly (toward the right in FIG. 31) into the bloodtrap 2855 and lighter particles (e.g., blood plasma) remain in the cuvette 2870 aligned with the window 2856.

A beam of light 3127 can be directed from a light source to an optical detector such that the beam of light 3127 passes through the window 2856 and through the fluid (e.g., plasma) contained in the sample portion 3129 of the sample cell 2848. The sample portion 3129 can be significantly thinner than the channels 2850 that lead to and from the cuvette 2870. In some embodiments, the path length of the light through the fluid sample contained in the sample portion 3129 is at least about 0.001 inches and/or no more than about 0.003 inches, and can be about 0.002 inches, although path lengths outside these ranges can also be used. The window 2856 can provide an aperture 3131 for the light beam 3127 that is at least about 0.25 inches wide and/or no more than about 0.50 inches wide, and can be about 0.31 inches wide, although widths outside these ranges can also be used. The aperture 3131 size can be larger than the beam of light 3127 that passes through the sample portion 3129. In some embodiments, the use of laser welding for features on the rotor can widen the process window.

Cuvette

Figure 32:
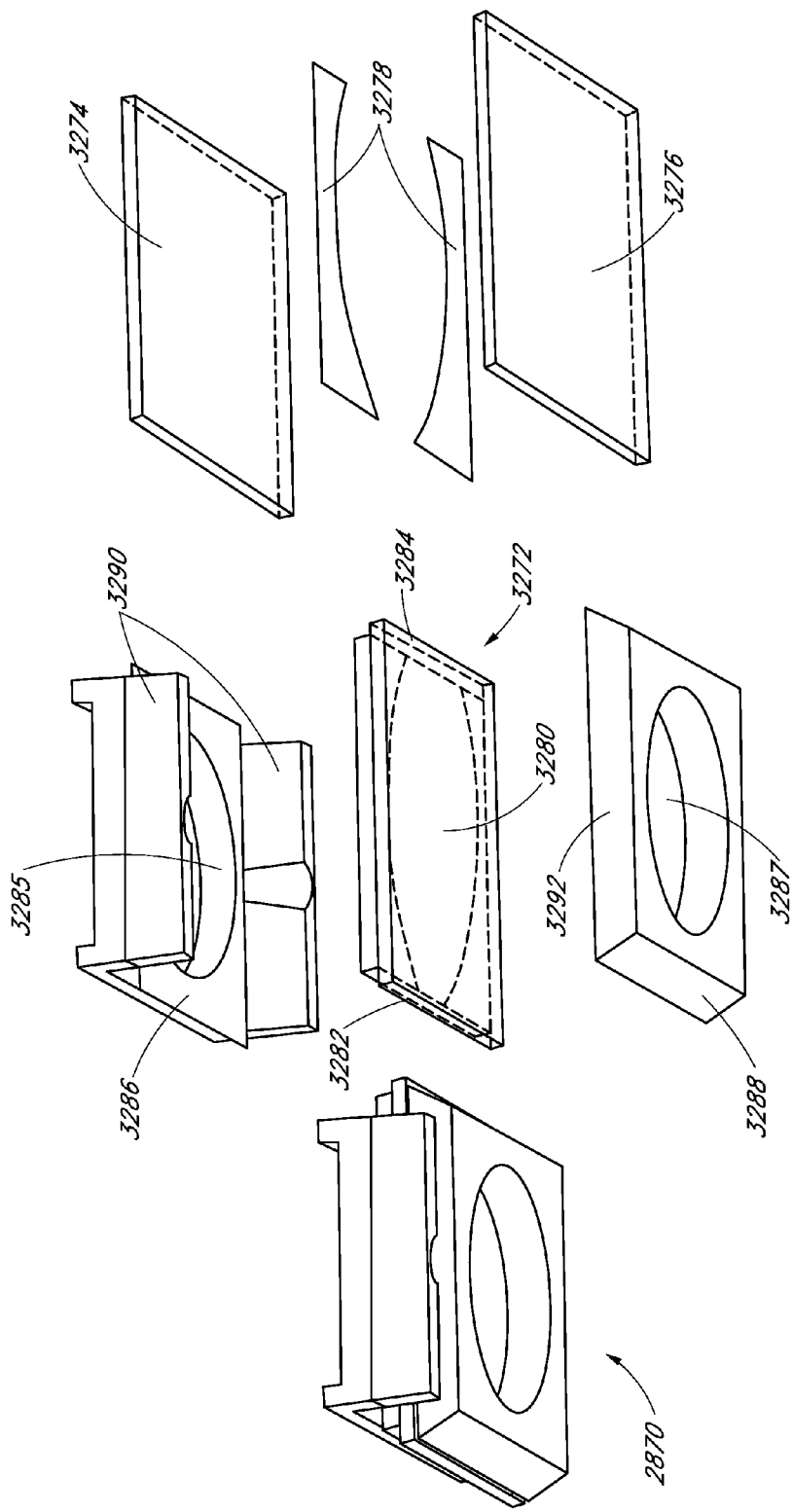
FIG. 32A illustrates an example embodiment of a cuvette for use with the sample cell holder of FIG. 28A.
FIG. 32B is an exploded view of the cuvette of FIG. 32A.
FIG. 32C is an exploded view of the insert portion of the cuvette of FIG. 32A.

FIG. 32A is a perspective view of the cuvette 2870, FIG. 32B is an exploded view of the cuvette 2870, and FIG. 32C is an exploded view of the insert portion 3272 of the cuvette. The insert portion 3272 includes an upper window piece 3274 and a lower window piece 3276 sandwiched together with an adhesive layer 3278 formed therebetween to secure the upper window piece 3274 to the lower window piece 3276. The window pieces 3274, 3276 can be made from Calcium Fluoride or other suitably transparent material. As can be seen in FIG. 32B, in some cases, the loser window piece 3276 can be somewhat longer than the upper window piece 3274. In some embodiments, the lower window piece 3276 can be longer than the upper window piece 3274 by a distance of at least about 0.25 mm and/or by less than or equal to about 2.0 mm, although distances outside these ranges can also be used. In some embodiments, the lower window piece 3276 can be longer than the upper window piece 3274 by a distance of about 1.0 mm. The window pieces 3274, 3276 can be relatively thin to conserve on the cost of Calcium Fluoride. The window pieces 3274, 3276 can be at least about 0.015 inches thick, and or no more than about 0.025 inches thick, and can be about 0.02 inches thick, although other thicknesses outside these ranges can be used.

The adhesive 3278 can be positioned at the sides of the insert portion 3272, such that a generally round aperture portion 3280 of the insert portion 3272 does not contain any adhesive between the window pieces 3274, 3276, thereby forming a gap between the window pieces 3274 at the aperture portion 3280. The gap provides the thin sample portion 3129 discussed above in connection with FIG. 31. The thickness of the adhesive layer 3278 can set the width of the gap (and the sample portion 3129) between the window pieces 3274, 3276. Thus, the adhesive layer can have a thickness of at least about 0.001 inches and/or no more than about 0.003 inches, and can be about 0.002 inches, although thicknesses outside these ranges can also be used. The adhesive 3278 can substantially completely cover two opposing sides of the insert portion 3272. The other two sides of the insert portion 3272 can be partially covered by the adhesive 3278, forming an inlet 3282 at one end of the insert portion 3272 and an outlet 3284 at the opposing side of the insert portion 3272. In some embodiments, the outlet 3284 can be wider than the inlet 3282. The width of the outlet 3284 can be at least about 2 times the width of the inlet 3282 and/or no more than about 3 times the width of the inlet 3282, and can be about 2.5 times the width of the inlet 3282. Other dimensions may also be used for the inlet 3282 and outlet 3284. The adhesive can be an epoxy resin, such as Delo-Monopox 1197 provided by Delo Industrial Adhesives LLC of Hauppauge, N.Y.

The insert portion 3272 can be sandwiched between an upper clamshell piece 3286 and a lower clamshell piece 3288. The clamshell pieces 3286, 3288 can be injection molded rigid plastic pieces and may be formed of polycarbonate or any other suitably rigid material. The upper clamshell 3286 and lower clamshell 3288 can include holes 3285 and 3287 configured to align with the aperture portion 3280 of the insert portion 3272 such that light from the optical system can pass through the cuvette 3270. The upper clamshell piece 3286 can include arms 3290 that extend toward the lower clamshell piece 3288 and are configured to engage the lower clamshell piece 3288 so as to secure the upper clamshell piece 3286 to the lower clamshell piece 3288 with the insert portion 3272 sandwiched therebetween. The lower clamshell piece 3288 can include tapered walls 3292 that are configured to engage the arms 3290 to maintain a pressure exerted on the insert portion 3272. In some embodiments, the upper clamshell piece 3286 can be secured to the lower clamshell piece 3288 using an adhesive. In some cases, no adhesive is used. The clamshell pieces 3286, 3288 can provide additional support to the cuvette 3270 so as to maintain the cuvette's 3270 integrity during repeated centrifuging, for example, at about 5000 RPM (or other speeds disclosed herein). The clamshell pieces 3286, 3288 can also stabilize the spacing between the window pieces 3274, 3276 so as to maintain a substantially constant optical path length through the sample portion of the cuvette 3270. In some embodiments, the clamshell pieces 3286, 3288 can be made from a glass-filled material (e.g., a polymer or other plastic material), such as glass-filled nylon or glass-filled polypropylene. In some embodiments, the material can be 30% glass-filled. In some embodiments, the material can be at least about 10% glass-filled and/or less than or equal to about 50% glass filled, although values outside these ranges may also be used.

Figure 33:
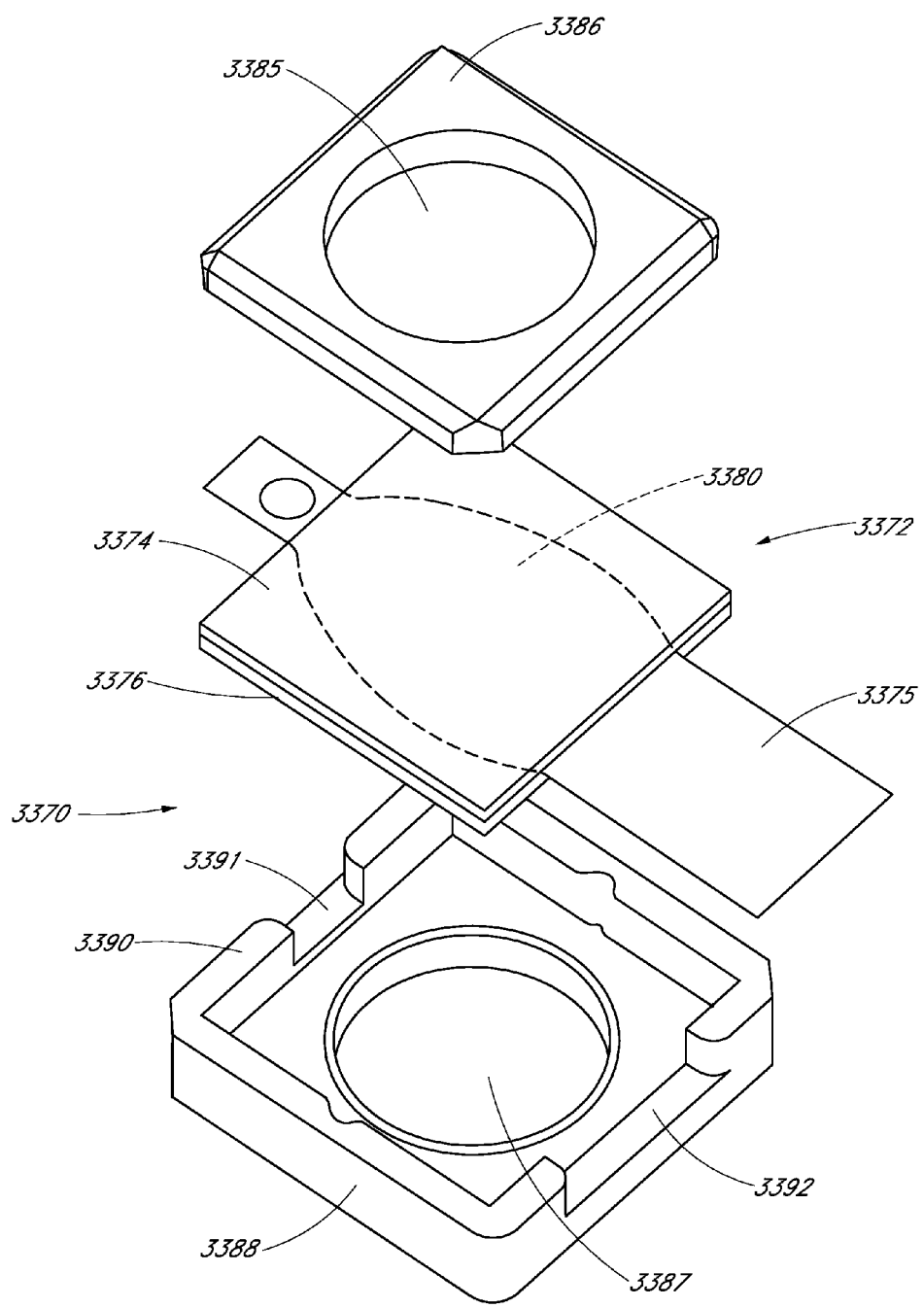
FIG. 33 is an exploded view of another embodiment of a cuvette.

FIG. 33 is an exploded view of another embodiment of a cuvette 3370 that can be similar to or the same as the cuvette 2870, or any other cuvette described herein, in many regards. The cuvette 3370 includes an insert portion 3372 that can have two window pieces 3374, 3376 sandwiched together with an adhesive formed therebetween, similar to the cuvette 2870 described above. The window pieces 3374, 3376 can be made from Calcium Fluoride. The windows pieces 3374, 3376 can be of the same size, and can be square or rectangular in shape. In some embodiments, the window pieces 3374, 3376 can have side lengths between about 8 mm and 15 mm, and can have dimensions of about 11 mm by 11 mm, although other dimensions can be used. The window pieces 3374, 3376 can be at least about 0.015 inches thick, and or no more than about 0.025 inches thick, and can be about 0.02 inches thick, although other thicknesses outside these ranges can be used. An aperture portion 3380 can be formed in the center where no adhesive is present and there is a gap between the window pieces 3374, 3376. In some embodiments, an insert 3375 can be positioned between the window pieces 3374, 3376 when the window pieces 3374, 3376 are adhered to each other to maintain a constant gap size and form a precise optical path length through the sample portion. The insert 3375 can be removed from the insert portion 3372 once the adhesive cures.

In some embodiments, no adhesive is applied between the window pieces 3374, 3376. A spacer (not shown) can be positioned between the upper window piece 3374 and the lower window piece 3376 such that a thin gap is maintained therebetween. The spacer can have a thickness that is configured to provide a path length between the window pieces of at least about 0.001 inches and/or no more than about 0.003 inches, and in some cases of about 0.002 inches, although other path lengths can be used. The spacer can be made from Teflon or other suitable material. Thus, the window pieces 3374, 3376 are not directly adhered or otherwise secured to each other, but are pressed together by the two clamshell pieces 3386, 3388 which are secured to each other. This can simplify the construction of the cuvette since no hand application of the epoxy resin to the window pieces is required. In some cases, the clamshell pieces can be secured using an adhesive, but application of the adhesive to the clamshell pieces can simpler than gluing the window pieces directly.

The insert portion 3372 can be sandwiched between the upper clamshell piece 3386 and the lower clamshell piece 3388, which can each include an opening 3385, 3387 that aligns with the aperture portion 3380 of the insert portion 3372. The lower clamshell piece 3388 can include raised sidewalls 3390 that extend substantially around the entire periphery except for an inlet gap 3391 and an outlet gap 3392. The sidewalls 3390 can extend around each of the corners of the lower clamshell piece 3388. This can provide rigidity to the cuvette 3370 and aid in maintaining the integrity of the cuvette 3370 when it spins at high speeds during repeated centrifuging. Thus, the same cuvette 3370 can be used for many different samples, where the cuvette 3370 is subjected to centrifuging stresses for each sample. It will be understood that although the cuvette illustrated in FIG. 33 is generally square-shaped and has four corners, a cuvette having a different number of corners and sides can be used.

In some embodiments, the top clamshell piece 3386 can be secured to the lower clamshell piece 3388 using an adhesive that extends substantially around the entire periphery of the cuvette 3370, except for the inlet and outlet. The seal formed between polycarbonate and the epoxy resin adhesive can be significantly stronger than the seal formed between Calcium Fluoride and the adhesive. Thus, by providing a polycarbonate to adhesive seal surrounding substantially the entire periphery of the insert portion 3372 except at the inlet and outlet, the cuvette 3370 can prevent fluid from leaking out of the cuvette 3370 more effectively than a cuvette in which the boarders of the cuvette are sealed using a Calcium Fluoride to epoxy resin bond. This is especially the case since gamma sterilization or electromagnetic radiation that passes through the cuvette can break adhesive bonds to Calcium Fluoride causing delamination.

Figure 34B:
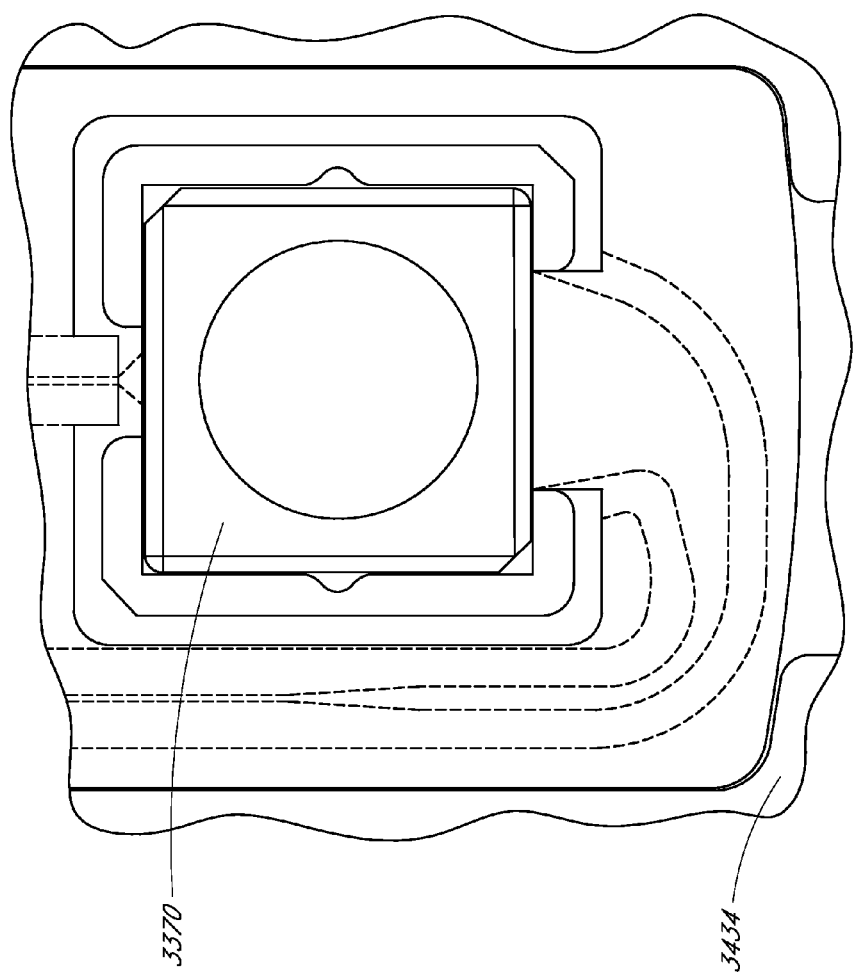

FIG. 34A is a partial perspective view of the cuvette 3370 incorporated into a rotor housing 3434 which can be similar to the rotor housing 2834 discussed above in many regards. FIG. 34B is a partial plan view of the cuvette 3370 incorporated into the rotor housing 3434. FIG. 34C is a partial cross-sectional view of the cuvette 3370 incorporated into the rotor housing 3434. In FIGS. 34A-34C, the rotor housing 3434 is shown as being partially transparent such that feature of the rotor housing 3434 are visible that would otherwise be hidden from view.

In some embodiments, the sample cell cover 3441 and the rotor housing 3434 contact the clamshell pieces 3386, 3388 to secure the cuvette 3370 in place, and they do not directly apply pressure to the window pieces 3374, 3376. This reduces the occurrence of occlusion in the sample portion between the window pieces 3374, 3376 and aids in maintaining a constant optical path length through the sample portion.

Dead Space and Sealing Mass

Analyte monitoring systems can be connected to a source of bodily fluid (e.g., blood) that may be susceptible to clotting. If clotting occurs in the analyte monitoring system, a fluid pathway may be obstructed or otherwise compromised. In some instances, if clotting occurs, the disposable cartridge must be replaced. Thus, by reducing the occurrence of clotting, the cartridge may be used for a longer period of time before replacement, thereby reducing cost, reducing waste, reducing time required of the medical professionals, and reducing agitation of the patient. Blood clotting risk can be reduced, for example, by employing coatings in or on portions of the Analyte monitoring system and/or by reducing dead space volume. As used herein, the term "dead space" is a broad term and is used in accordance with its ordinary meaning to refer to any unwanted or unproductive areas that do not allow efficient and/or smooth fluid flow. For example, a widened portion, a peripheral opening or cavity that is located out of a main fluid flow path can be "dead space" because fluid can get caught in that space and either form eddy currents, turbulence, or stagnation, which can increase the risk of clotting. Also, in some instances, a portion of the fluid being transferred can remain trapped in the dead space, thereby preventing the desired volume of fluid from reaching the desired destination, and possibly contaminating later samples of fluid that come into contact with the fluid retained in the dead space. The problems presented by dead space can be exaggerated in a low volume system (e.g., the analyte monitoring system) because even a small amount of fluid that is diverted or unintentionally mixed can compromise a fluid sample and the resulting analyte measurements. Also, in a small volume system, tubes having small diameters can more easily be occluded by clots of small sizes.

In medical systems and devices used in hospitals it can be useful to use anticoagulants (e.g. heparin) to help prevent deposits from building up in fluid systems, especially those that contain bodily fluids such as blood. In some medical devices connected to the vasculature of a patient, anticoagulants (e.g., heparin) can be used to prevent blood clotting in a patient and/or to keep the fluid lines open (e.g., by preventing fluids from coagulating in dead spaces of connectors). However, if excessive amounts of these anticoagulants are infused into a patient—for example, when the line is flushed—the patient may lose some clotting capability and Heparin Induced Thrombocytopenia (HIT) can result in many or all heparin-sensitive patients. HIT can be a very dangerous condition, and may lead to loss of vision, loss of a limb, or even death. Systems and methods of preventing accidental injection into the patient are described in U.S. Patent Publication No. 2009/0036764, published on Feb. 5, 2009, which corresponds to U.S. patent application Ser. No. 12/123,422, filed on May 19, 2008, and which is hereby incorporated by reference herein in its entirety and made a part of this specification. Another approach of preventing infusion of heparin into a patient is to avoid the use of anticoagulants (e.g. heparin) in portions of devices that may be connected to or in fluid communication with a patient's vasculature. However, not using anticoagulants can result in fluid pathways that are attached to a patient's vasculature being blocked over time due to clotting and/or accumulation of deposits.

For at least these reasons there is a need for fluid transfer/ handling systems that can provide a continuous flow path with minimized change in the cross-sectional area of various points along the flow path and with reduced dead space. Such fluid transfer systems can promote smooth flow and reduce unwanted turbulence and stagnation in fluid systems, leading to reduced medical risk. Such systems may have coatings on the inner or outer walls of the connecting tubes or other components. The coatings can be designed to provide various benefits such as delivering therapeutic compounds or other additives to the fluid flowing through the system, reducing friction and improving fluid flow, protecting sidewall materials from prolonged contact with the fluid; and/or decreasing the occurrence of blood clotting and lengthening the useful life of the fluid transfer/handling system such as may be included in a removable cartridge.

One way to reduce dead space is to include a sealing mass at or near an interface where fluid flows across a junction between two components. For example, a sealing mass can be placed on a tube so that it partially or fully surrounds the tube. The sealing mass may be placed at specific locations along the tube where it may be most effective in reducing dead space. For example, the sealing mass may be placed such that it encircles a connecting tube near the tip of the tube that is inserted into, or otherwise interface with, a connector or other component to help reduce dead space at the connection between the tube and the connector or other component. The sealing mass can resiliently deform to fill cavities or crevices that may otherwise allow fluid pooling, stagnation, eddy currents, etc. a sealing mass can be used in various locations in the analyte detection system.

A sealing mass may be made out of any type of material. The material used for a sealing mass may be chosen based upon any number of desirable characteristics, such as biological neutrality (or biological activity), affinity for the fluid in the fluid path (or lack of affinity), impermeability, resilience, compressibility, cost, ease of manufacture, ease of attaching to a tube, or other reasons. Various approaches can improve the sealing ability of a sealing mass. For example, a sealing mass may be made from the same type of material as the tube it surrounds. This can allow the mass and the tube to resiliently abut or conform to other surfaces and to each other in a similar manner. A sealing mass may be joined to the tube it surrounds. This can reduce the likelihood of fluid leakage between the sealing mass and the tube and also assist in urging the sealing mass against a mating component. A sealing mass may be a unitary piece with the tube that it surrounds for similar reasons. It can be beneficial to make a sealing mass from a resilient or compressible material, as these materials may be useful to more effectively fill dead space and thereby reduce turbulence in a fluid path. These materials may be used to form a fluid-tight seal around the fluid path between the tubing and a mating component. In one particularly useful example, a sealing mass may be a plug or roughly frustoconical body made out of silicone.

If a sealing mass is placed such that it encircles a tube near a tip, a resilient or compressible material can help to create a seal between the connecting tube and another component. Compressible or resilient material may be preferable because such material may be able to form a tighter or larger seal near the connection between the connecting tube and the other component. This tighter or larger seal may restrict a fluid traveling through the tube from entering dead space that may otherwise be present near the connection between the connecting tube and the other component. A resilient or compressible sealing mass placed near the tip of a connecting tube may be especially effective in forming a tight, large seal in the presence of a force-exerting or an actuating member. A force-exerting member may be designed to apply pressure to firmly seat the connecting tube and the other component. Such pressure may be sufficient to partially compress a resilient or compressible sealing mass that encircles the tip of the connecting tube.

A sealing mass that is placed around a tube may be any shape. The shape of the sealing mass may depend upon what type of material is used, where it is placed, and the anticipated use of the sealing mass. For example, if a sealing mass is placed encircling the tip of a tube which will connect to another tube, this may make some shapes more advantageous. A sealing mass with a radially symmetric shape may be desirable in order to create a larger or better seal. This can be especially helpful in a common medical setting where the component receiving the tubing or other piece that has the sealing mass is radially symmetric. Thus, the shape, surface angles, and symmetries of the sealing mass can be made compatible with a wide variety of interfaces. If it is known what type of interface a tube will connect to, the shape of the sealing mass may be based upon the shape of the corresponding interface. Additional details relating to the structure and functionality of the sealing mass are disclosed in U.S. Patent Application Publication No. 2011/0313317, published on Dec. 22, 2011, which corresponds to U.S. patent application Ser. No. 13/068,121, filed on May 3, 2011, the entirety of which is hereby incorporated herein by reference and made a part of this disclosure.

Figure 35:
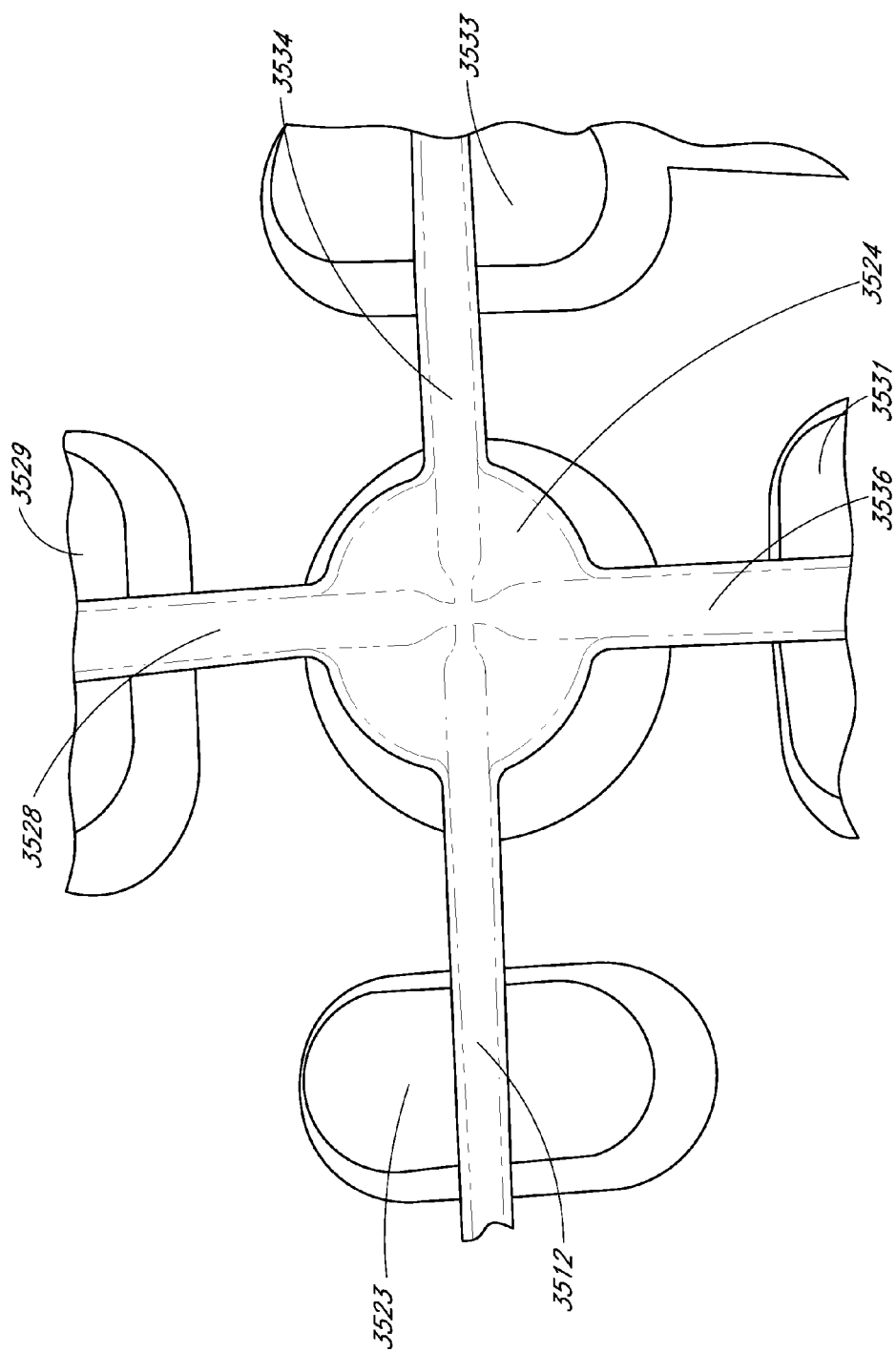
FIG. 35 illustrates an example embodiment of a juncture between components in an analyte monitoring system.

A sealing mass can be used at various different positions in the analyte monitoring system. For example, with reference to FIG. 5, the fluid handling network can include various junctions (e.g., at connectors C1, C2, C3, etc.) between portions of fluid transport tubing. FIG. 35 shows an example embodiment of a junction (which can be similar to, or the same as the connector C1) between tubing elements 3512, 3528, 3534, and 3536. The connector 3524 can be a rigid plastic connector with through holes to provide fluid pathways for fluid to pass through the connector. In the illustrated embodiment, the connector 3524 can be a 4-way connector, but other configurations (e.g., 3-way connectors) are possible. The end of the tubing 3512 can be inserted into the corresponding hole in the connector 3524. In some embodiments, the through hole can include a wide portion configured to receive the end of the tubing 3512 therein so that the inner surface of the through hole generally aligns with the inner surface of the tubing 3512, thereby providing a substantially linear non-turbulent flow path through from the tubing 3512 to the connector 3524. A sealing mass can be positioned near the tip of the tubing 3512 and/or on the inside of the through hole. The sealing mass can be configured to expand to fill area that would otherwise be dead space, thereby reducing turbulence in the flow of fluid and reducing the amount of fluid that can be retained stagnant in dead space. The other tubing elements, 3528, 3534, and 3536 can be connected to the connector 3512 in a similar manner.

If the sealing mass is placed near the tip of a connecting tube 3512, it may be desirable to minimize the distance between the sealing mass and the tip of the connecting tube 3512 because fluid may be more likely to leak out of the tip, so stopping the flow of leaked fluid advantageously occurs close to the original leak. For example, it may be advantageous to place a sealing mass within 0.001, 0.005, 0.01, 0.05 or 0.1 inches from, or completely flush with, the tip of a connecting tube 3512.

A sealing mass may be especially useful on connections which are intended to be engaged and disengaged multiple times. For example, with reference to FIG. 29B, the fluid nipples 2914 of a fluid injector 2915 can be configured to interface with the two receiving nubs 2812A (as well as the receiving nubs 2812B in similar manner). The fluid nipples 2914 can disengage from the receiving nubs 2812A (as shown in the configuration illustrated in FIG. 29B), for example, to allow the rotor to spin without contacting the fluid nipples 2914. The fluid injector 2915 can be moved forward by an actuator to engage the receiving nubs 2812A, thereby forming a fluid connecting that allows fluid to flow between the tubing 2916 and a flow cell by passing through the interface between the fluid nipples 2914 and the receiving nubs 2812A. The fluid nipples 2914 and/or the receiving nubs 2812A can include one or more sealing masses configured to occupy area at the interface that would otherwise result in dead space.

FIG. 36 is a close up view of two fluid nipples 3619A, 3619B that include sealing masses 3620A, 3620B and tubing ends 3622A, 3622B. In the fluid nipple, 3619A, the edge of the sealing mass 3620A is space back from the end of the tubing 3622A by a distance 3624A, and in the fluid nipple 3619B, the edge of the sealing mass 3620B is space back from the end of the tubing 3622B by a distance 3624B. The distances 3624A, 3624B can cause dead space in the interface between the fluid nipples 3619A and 3629B and the corresponding receiving nubs. It may be desirable to minimize the distances 3624A, 3624B between the sealing masses 3620A, 3620B and the ends of the tubing 3622A, 3622B to prevent dead space from forming. For example, it may be advantageous to place the sealing masses 3620A, 3620B within 0.001, 0.005, 0.01, 0.05 or 0.1 inches from, or completely flush with, the edge of a connecting tubing 3622A, 3622B. The sealing masses 3620A, 3620B can be shaped and configured to interface with the receiving nubs (e.g., 2812A or 2812B) to reduce dead space and form substantially linear non-turbulent flow paths between the fluid nipples 3619A and 3619B and the corresponding receiving nubs.

Coatings

One or more coatings may be applied to any surface of an analyte monitoring system. For example, coatings may be applied to the inner or outer walls of a sample cell, of connecting tubes, of a sealing mass, or of other connecting structures in the analyte monitoring system. Such coatings may serve any number of purposes, such as making the components last longer, preventing materials used in the tubing or other components from entering the fluid contained in a fluid path, increasing the accuracy of an analyte measurement, allowing for more flexibility in which materials are used in the components, or reducing blood clotting. The purpose of a coating may determine where on an analyte monitoring system the coating is applied. For example, if a coating is designed to reduce or eliminate blood clotting, it may be advantageous to apply the coating to the inner and outer walls of a connecting tube, to a sealing mass placed near the tip of the connecting tube, and/or to any other surface that blood may come into contact with. A coating that is designed to reduce or eliminate blood clotting may be applied to any surface in an analyte monitoring system that may come into contact with blood. For example, a coating may be applied to an analyte monitoring system that is situated outside the body, either in the analyte monitoring system or in a tube that leads to the analyte monitoring system.

There are a number of ways that a coating may assist in reducing or eliminating blood clotting in an analyte monitoring system. For example, lubricious coatings can be used to reduce friction between the flowing fluid and the side-walls of the tubing or other components. Therapeutic drug delivery coatings can also be used (e.g., drug-eluting coatings). Some useful coatings include those that comprise heparin, which can be designed to reduce blood clotting against the side-walls of the connector by acting as an anticoagulant. A coating may be applied to the inner or outer walls of various components. A reduction in friction may reduce the shear stress on blood that flows in a boundary area near the side-walls of the connector. The blood coagulation cascade is a very delicate process, and a reduction in shear stress can decrease the tendency for blood to begin to coagulate by reducing the turbulence in blood passing through the tubing or other components. Any number of lubricating agents may be suitable to form a lubricious coating on the inner or outer walls of the connecting tubes and other components. A number of companies provide a wide array of active or inactive haemocompatible coatings that can be used in this context. Such companies include: AdvanSource biomaterials (e.g., HydroMed); AorTech Biomaterials; Applied Membrane Technology (e.g., Silglide, Fluorocarb); AST Products Inc. (LubriLAST); Bayer (e.g., Baymedix CL); Biocoat, Inc. (e.g., HYDAK); BioInteractions Ltd. (e.g., Assist); Cadence Inc.; Carmeda (e.g., CBAS); Coatings2Go LLC; Covalon Technologies Ltd.; Demax Medical; DSM Biomedical (e.g., ComfortCoat); Hemoteq (e.g., Lubriteq); Medkote; Merit Medical Systems Inc. (e.g., Endotek); SurModics Inc. (e.g., Rejoice, Harmony); and Tegra Medical. Lubricious coatings can be used to coat the inner or outer walls of the connecting tubes or other components. Lubricious coatings such as this can dramatically reduce the friction between blood and the inner walls of the connecting tubes, and therefore reduce the shear stress on the blood. Lubricious coatings may be advantageous because they are less likely than some other coatings to interfere with analyte detection and measurement. Lubricious coatings may also be easier to apply to the inner and outer walls of a connecting tube, and may be more cost-effective than other types of coatings. Lubricious coatings may also present less danger than some types of drug-eluting coatings, and therefore be easier to work with or more desirable than other types of coatings. Lubricious coatings can work with interfaces between components in the analyte monitoring system that are configured to minimize dead space to reduce the incidents of clotting on the inner walls of the connecting interfaces. In some embodiments, such a coating can be applied to surfaces of components of the analyte monitoring system as one of the later steps in their production, as coatings may be somewhat more sensitive to temperatures encountered during manufacturing. For example, it maybe desirable to apply a coating to a component as a final step in manufacturing the component, to ensure that heat used to shape the component does not adversely affect the coating and inhibit its function.

Coatings may reduce the need for detergent and/or heparin to flush the fluid system between draws and may allow for more frequent measurements. For example, a lubricious coating may cause less blood or other fluid to remain in the fluid system after blood is drawn. If less blood remains in the fluid system after blood is drawn, this may reduce the amount of detergent (such as tergazyme A) and/or heparin that are needed to flush the system between blood draws, or may even eliminate the need to use detergent and/or heparin during flushing. This may simplify the design of the system, may create less waste, and/or may make the system less expensive to create and to operate. Coatings may also allow for more frequent measurements, as less time may be needed between measurements to flush the system.

Coating (e.g., lubricious coatings) can be applied at transitions and junctures between components in the analyte monitoring system. For example, a coating may be applied near an intersection, such as the juncture shown in FIG. 35. As discussed above, the connector 3524 can be the same as, or similar to, the first connector 524 (C1) as illustrated in FIG. 5. A coating can be applied to the inner walls and/or the ends of the tubes 3512, 3528, 3534, and 3536 as well as to the portions of the connector 3524 that are configured to receive the tubes 3512, 3528, 3534, and 3536. It may also be beneficial to apply a coating to sealing masses that can be positioned at the interface between the connector 3524 and the tubes 3512, 3528, 3534, and 3536. Thus, in some embodiments, as fluid flows from a tube (e.g., 3512) and into the connector 3524, each surface that the fluid contacts can have a coating (e.g., a lubricious coating) applied thereto, thereby reducing the likelihood that blood will start to clot at the interface between the tube (e.g., 3512) and the connector 3524. An intersection such the one shown in FIG. 35 may be especially prone to turbulence because fluid flowing through the connector 3524 may be required to make a sharp 90-degree turn. Thus, in some embodiments, all the inner walls of the connector 3524 can have a coating applied thereto to reduce clotting. Also, fluid that flows through the connector 3524 (e.g., from tube 3512 to tube 3534) may be especially prone to turbulence when a neighboring valve (e.g., pinch valves 3529 and/or 3531) is closed, if the valve is some distance away from the connector 3524. For example, when the valve (e.g., pinch valve 3531, or a rotary valve, shuttle valve, etc.) is placed some distance from the connector 3524, fluid that passes through connector (e.g., from tube 3512 to tube 3534) and fluid that is in the tube 3536 leading to the closed valve 3531 may be more likely to be turbulent. Therefore, to avoid such turbulence, it may be useful to apply a coating to some or all of the surfaces of the intersection, especially when a valve is placed further away from the connector 3524. For example, a coating can be applied to some or all of the internal surfaces of the fluid pathways through the connector 3524, and to the internal walls of the tubing 3512, 3528, 3534, and 3536 between the connector 3524 and the valves 3523, 3529, 3531, 3533. In some embodiments, coating can be applied to the full inner surfaces of the tubing 3512, 3528, 3534, and 3536 (or other tubing in the system).

A coating may be applied to an analyte monitoring system that is designed to take multiple readings of analyte levels. Such a coating may be applied to components that are used during multiple readings from a medical device, and over multiple fluid withdrawal cycles. A coating may also be applied to an analyte monitoring system that is situated at least partly inside the patient's body to reduce or prevent the formation of clots thereon. A coating may also be applied to other systems that may come into contact with blood where it is desired to reduce friction and/or avoid blood clotting.

For example, in some embodiments, the sample cell 2848 can have a coating (e.g., a lubricious coating) applied thereto. The sample cell 2848 can be flushed (e.g., between measurements). In some embodiments, saline can be used to flush the sample cell 2848. A cleaning solution, such as a detergent (e.g., tergazyme), can be used to flush the sample cell 2848 and can facilitate the removal of blood or blood components from the sample cell 2848. In some embodiments in which the sample cell 2848 is coated with the lubricious coating, no detergent or other cleaning solution is used, or a reduced amount of detergent or other cleaning solution can be used. The coating can prevent the blood or blood components or other substances from sticking to the sample cell 2848, thereby facilitating the flushing with a reduce amount of, or without, a cleaning solution. In some embodiments, saline or water can be used. Various portions of the sample cell 2848 can be coated. For example, the sample portion 3129, the channels 2850, the inlet, and/or the outlet have the coating applied thereto. Also, tubing or other portions of the system can be coated (e.g., with a lubricant) to facilitate flushing.

With reference again to FIG. 36, the fluid nipples 3619A, 3619B can have a coating (e.g., a lubricious coating) applied thereto. For example, the inner and/or outer surfaces of the tube ends 3622A, 3622B and/or the sealing masses 3620A, 3620B can be coated with a lubricious coating to reduce or prevent the formation of clots at the interface between the fluid nipples 3619A, 3619B and the receiving nubs (e.g., 2812A or 2812B). Various other coatings can also be used, as discussed herein.

An analyte monitoring apparatus can be usefully configured to draw blood from the body and analyze a portion of that blood. One useful assumption to make is that the drawn and analyzed blood is representative of the other blood that remains in the body and is not analyzed. This can be a valid assumption in many cases because blood flow in the body is a turbulent process, with the heart urging the blood through vessels and organs and tissue having various diameters and various levels of flow resistance. Indeed, there can be a great amount of variation in the flow rate of blood as it passes through the many regions of the body. This turbulence and variation of flow rates will tend to mix blood within the body, which will prevent blood in one part of the body from having a substantially different composition than blood in other parts of the body.

An analyte monitoring apparatus can also be usefully configured to be inserted into the body, and, for example, into the blood stream. This can have the advantage of eliminating any need to transport the blood out of the body; it can also introduce other potential risks. However, even if a monitoring device is inserted into the body, at any given time the device is likely only capable of measuring an analyte in a limited portion of the blood—for example, the blood that is in contact with (or within the view of) a sensor in the device. Thus, even in this case it is useful to assume that this limited portion of the blood is representative of the other blood in the body.

Some systems do not measure over a fixed amount of blood, but instead assume a constant relationship between the analyte in local blood and the amount of blood overall in the body. Such a constant relationship can be referred to as a stoichiometric relationship. If this assumption is inaccurate, results of the analysis can be inaccurate. This potential problem can be amplified when measurements are taken, for example, in a portion of the blood flow that has a varying rate of the analyte (e.g., for physiological reasons). For example, measurement of oxygen in the blood inside the lungs can be difficult over time because the lungs introduce blood into the oxygen periodically but at relatively short intervals. An indwelling system that is constantly measuring the glucose level of the blood that flows by and/or through its sensors may provide a reading that is too local and not provide a consistently useful overview of the amount of analyte generally present in the body as a whole. One way to avoid inaccuracies due to failures of this assumption is to measure an amount of analyte in a fixed amount of blood, drawn from a portion of the bloodstream that is physiologically likely to maintain a relatively constant level of the analyte in question. In many cases, the larger the blood sample, the less likely it will be to reflect misleading and/or temporary local distortions in an analyte level. Accordingly, ex-vivo systems that withdraw blood can have some advantages over systems with sensors that are inserted into the body notwithstanding the potential difficulties of repeatedly withdrawing blood out of the body and reducing clot risk in ex-vivo fluid systems.

Reducing Fluid Contamination During Withdrawal

As discussed above, various embodiments of analyte monitoring systems such as the analyte monitoring system 100 (e.g. an "OptiScanner®") can be attached or connected to a patient. In various embodiments, a patient connection can be achieved through a patient tube (e.g. patient tube 512) having an inner lumen which is configured to be connected to a patient catheter. In various embodiments, the inner lumen of the patient tube can have a small inner diameter—e.g., without limitation, a diameter in the range of approximately 0.01 inches to approximately 0.04 inches. In various embodiments, the outer diameter of the patient tube can be less than or equal to approximately 0.06 inches. In a hospital or an ICU setting, the analyte monitoring system can be connected to a patient through a variety of patient catheters such as, for example, a central venous catheter (CVC), a peripherally inserted central catheter (PICC), and/or other central or peripheral IV catheters. Other catheters not described herein can also be used to connect patients to devices such as an analyte monitoring system (e.g., the system(s) described herein). CVCs can generally be used when fluid is desired to be regularly inserted into a patient and/or the vascular access is compromised or unavailable for repeated insertions (e.g. if peripheral veins are collapsed, difficult to find, not available in sufficient quantity, etc.).

FIGS. 38A-38D illustrate various embodiments of multi-lumen catheters 3800 that can be used to attach analyte monitoring systems to patients. The multi-lumen catheter 3800 can be representative of any of the patient catheters described above. The multi-lumen catheter 3800 can in general include multiple lumina (e.g. 2 lumina, 3 lumina, 5 lumina, etc.). Often, one of the lumina of the catheter is longer than another; accordingly, the lumina do not open into a blood vessel directly adjacent to one another. As illustrated, the multi-lumen catheter 3800 comprises an elongated tubular structure 3802 that comprises three lumina 3802a, 3802b and 3802c, and multiple external ports 3804, 3806 and 3808 that connect to the elongated tubular structure 3802 through a fitting or a hub 3805. The elongated tubular structure 3802 can be much longer than shown in FIG. 38A, as indicated schematically with a break.

The elongated tubular structure 3802 can comprise a bio-compatible material and include a proximal end (closer to the fitting 3805) and a distal end (at the right in FIG. 38A) that is configured to be inserted into a blood vessel (e.g. an artery or a vein) or a body portion of the patient. In various embodiments, the elongated tubular structure 3802 can be flexible. In some embodiments, the elongated tubular structure 3802 can comprise a stiff material that provides structural stability to the elongated tubular structure 3802. In various embodiments, the diameter of the proximal end of the elongated tubular structure 3802 can be approximately equal to the diameter of the distal end. In contrast, in some embodiments the diameter of the proximal end of the elongated tubular structure 3802 can be larger or smaller than the diameter of the distal end. In some embodiments, the distal end of the elongated tubular structure 3802 can be tapered. In some embodiments, the lumina of the elongated tubular structure can have different lengths such that each internal tube terminates at a different position to create the staggered effect illustrated in FIG. 38A with the openings 3814, 3816, and 3818. In some embodiments, the lumina of the elongated tubular structure can have the same lengths (not shown).

The multiple lumina 3802a, 3802b and 3802c may be separated from each other by an internal partition or membrane such that fluid integrity and separation is maintained within the multi-lumen catheter. In various embodiments, the internal partition or membrane may comprise materials that generally prevent the mixing of the different fluids flowing through the multiple lumina. Each of the multiple (e.g., three) ports can be configured to be in fluid communication with one of the lumina of the elongated tubular structure 3802. For example, in the illustrated embodiment, the proximal port 3804 is configured to be in fluid communication with the lumen 3802a, which in turn corresponds to the proximal opening 3814. The medial port 3806 is configured to be in fluid communication with the lumen 3802b, which in turn corresponds to the medial opening 3816, and the port 3808 is configured to be in fluid communication with the lumen 3802c, which in turn corresponds to the distal opening 3818. The proximal port is referred to in this way because a health care provider often can determine, using a color code, for example, which external port corresponds to the internal opening that is "proximal" of (or nearer to the health care provider than) the openings corresponding to the other ports. In many cases, this type of staggered internal port arrangement is configured by users such that the "proximal" port (e.g., the proximal opening 3814) is upstream from the other ports (e.g., medial opening 3816 and distal opening 3818) relative to the expected or typical flow of body fluid (e.g., blood). This convention can be useful because a "distal" port can be used to administer therapeutic compounds to the blood stream, for example, which carries those compounds further downstream, thus reducing the risk that those compounds will flow upstream into the other ports. Because of the useful convention assuming that these staggered catheters place the proximal port upstream and the distal port downstream, in this description, it will be generally assumed that this convention is followed.

Figure 38A:
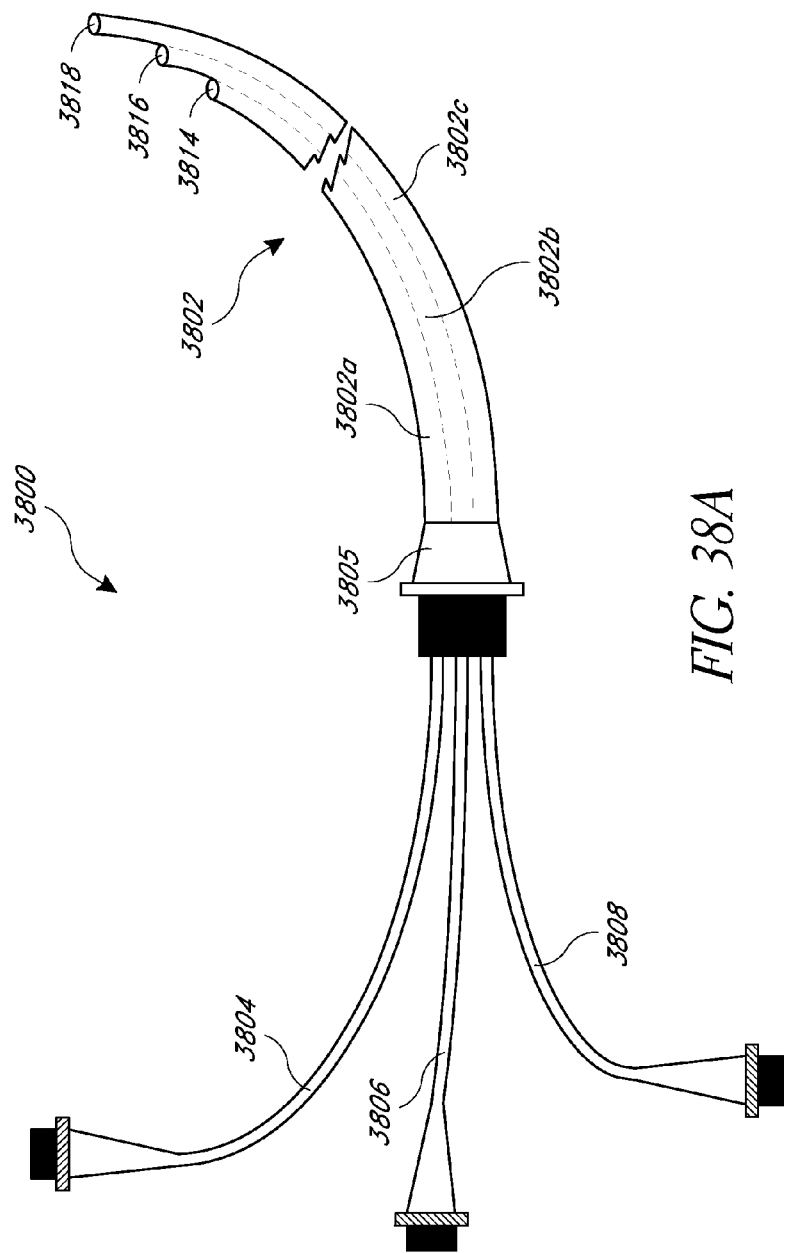
FIGS. 38A-38D schematically illustrate various embodiments of multi-lumen catheters.
Figure 38B:
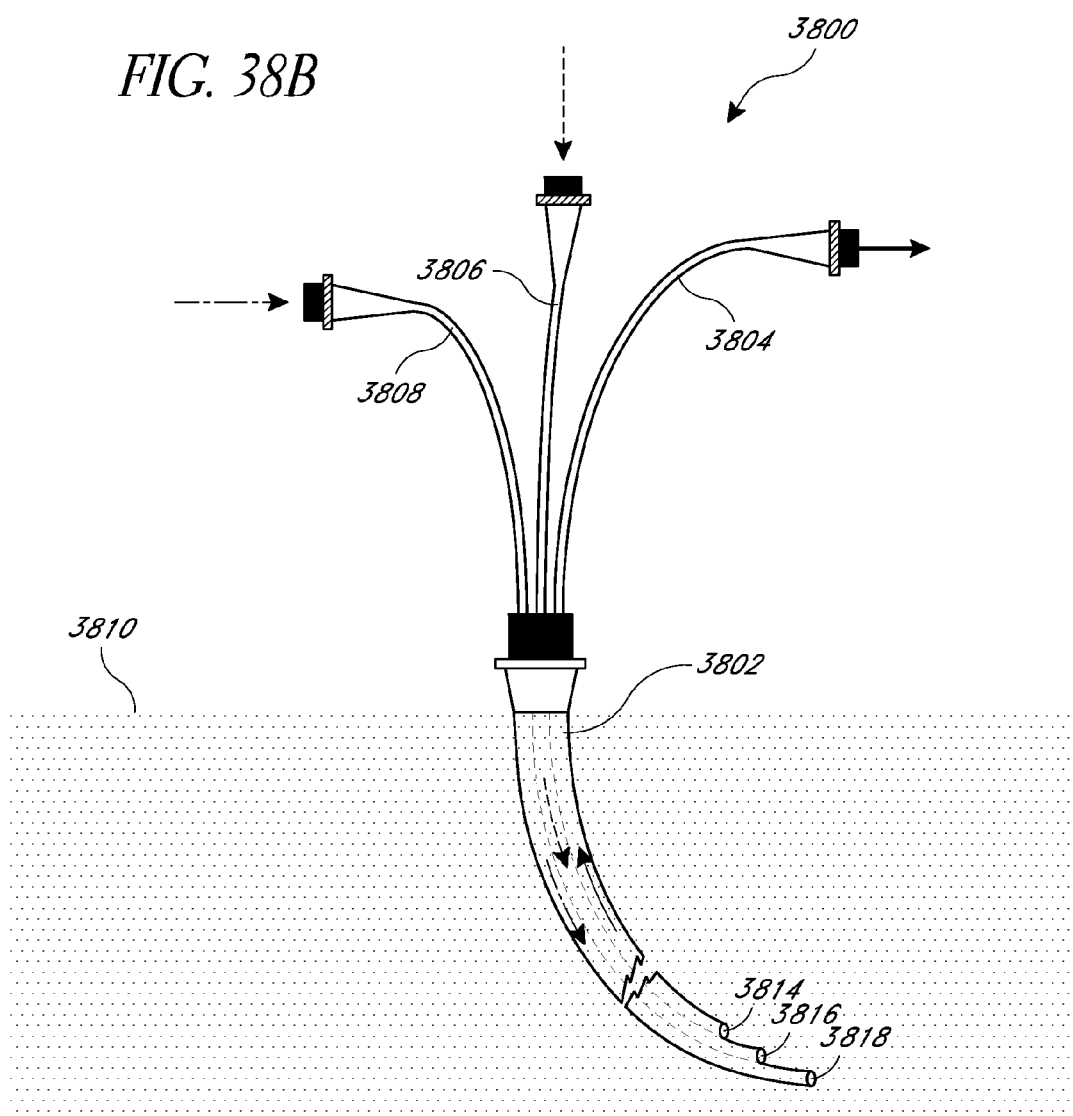
Figure 38C:
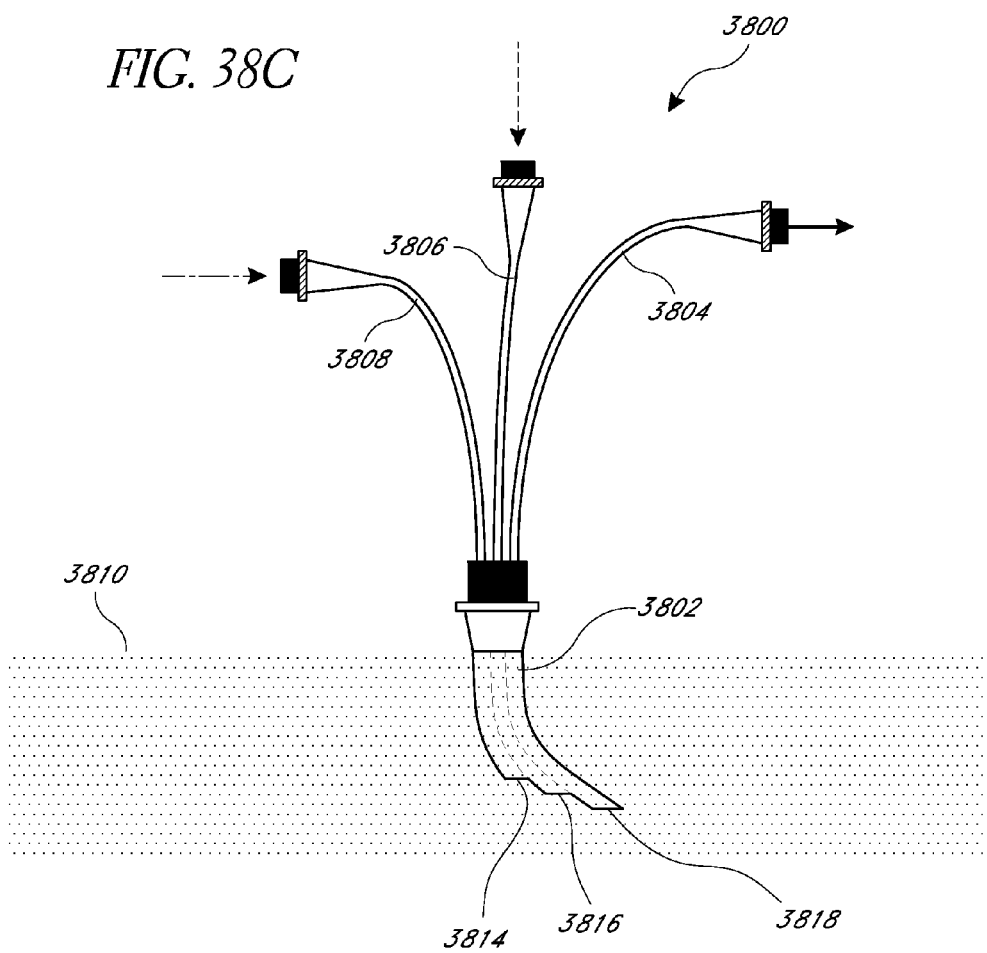

At the generally distal end of the elongated tubular structure 3802, the openings of the various lumina can be staggered and/or configured such that a certain minimum distance is maintained between the three in-patient openings. In various embodiments, the proximal port can be the port that communicates with an outlet (here illustrated as the opening 3814) for infusate is the closest of the in-patient openings to the caregiver or medical practitioner. In some embodiments, the proximal port can be the port wherein the outlet of the infusate is farthest from the extreme tip of the catheter 3800 that is typically configured to enter the patient first. As illustrated in FIG. 38A, this extreme tip corresponds to the distal opening 3818.

In various embodiments, the analyte monitoring system described above can be connected to the proximal port 3804 of the multi-lumen catheter 3800. In various embodiments, an advantage of using the proximal port 3804 of the catheter is that under many hospital protocols, this port can be reserved for a dedicated connection to a device (such as an analyte monitor that also infuses substances such as insulin, dextrose, saline, etc.), but no non-controlled medications or drugs—other than those controlled and tracked by the analyte monitor and infusion system—are infused through this port. In some embodiments, it may be advantageous to use the "proximal" port of a CVC to withdraw blood because that port typically has an opening into a patient's bloodstream that is upstream (with respect to blood flow in a vein, for example) from the openings into the bloodstream of any other ports. Accordingly, and because the blood flow rate can be relatively high (e.g. 4-6 liters/minute), downstream infusions (entering the blood stream from the medial or the distal port) are unlikely to flow upstream and substantially mix with the blood in the area of the proximal port. Thus the withdrawn blood from the proximal port can be substantially undiluted (or "uncontaminated" by other infusates). This can be advantageous because it can reduce the likelihood that recently-infused compounds are sucked into the proximal port and lead to inaccuracies in measurements of analytes present in the withdrawn fluid (e.g., blood). These and other advantages will be described further below.

For the reasons described above, it is wise for health care practitioners to withdraw from the proximal port when drawing blood for analysis. It may also be advisable to clamp the other ports of the CVC (e.g. distal or medial ports) while blood is being drawn from the proximal port. However, this can be cumbersome and impractical. Accordingly, in various embodiments of the apparatus, systems and methods described herein, fluid can be withdrawn from one port (e.g., the proximal port of the CVC) while other ports (e.g., the medial or distal ports) are still in use, while still reducing likelihood of contamination in the withdrawn fluid. As used in this context, the term "contamination" can refer to inclusion of any unwanted or unexpected substance in a withdrawn sample, the inclusion of which may lead to an inaccurate analysis and false measurement of analyte levels in a body fluid (e.g., in the blood flow). One useful aspect includes the described push/pull fluidics systems, which can use gravity systems, valves, fine motors and/or precision controls to enable withdrawal of a sample at a slow, steady rate (e.g., a slower, steadier rate than that achievable through manual withdrawal by a health care practitioner).

Ordinarily, the human heart pumps the blood around the vascular system such that the rate of flow of blood is approximately 5-6 liters/minute. The blood flow rate can be higher or lower depending on the physical condition of the human. For example, during or after a period vigorous cardio-vascular activity the blood flow rate may be higher. To take another example, a human who is critically ill or has suffered significant blood loss can have a blood flow rate as low as 2 liters/minute. The pressure in the vascular system can be between approximately 1-3 psi.

As discussed above, the different lumina of a multi-lumen catheter may be separated internally—e.g., by walls or membrane(s)—such that the fluids introduced in each of the multiple lumina are kept separated from each other and do not mix as they flow through the lumina. In certain embodiments, it may be beneficial to reduce the likelihood of inter-mixing between the different fluids even after they are introduced into a patient's vasculature. The ordinary rate of flow of blood—about 5-6 liters/minute—in the patient's vasculature can be sufficient to prevent or substantially reduce mixing of the different fluids (e.g. medications, drugs, saline, control fluids, etc.) that are being infused through the various lumina of the multi-lumen even after they are introduced into the patient's vasculature because the "current" of the blood flow sweeps away infusates so quickly downstream that they are often rapidly well dispersed into the bloodstream before they have a chance to directly intermix with other infusates that may be coming through catheter ports into the blood stream. For example, generally, fluids can be introduced into the patient's vasculature at a rate of between approximately 300 ml/hour to approximately 1 liter/hour—rates that are substantially lower than the typical rates of flow of blood in the patient's vasculature.

Figure 38D:
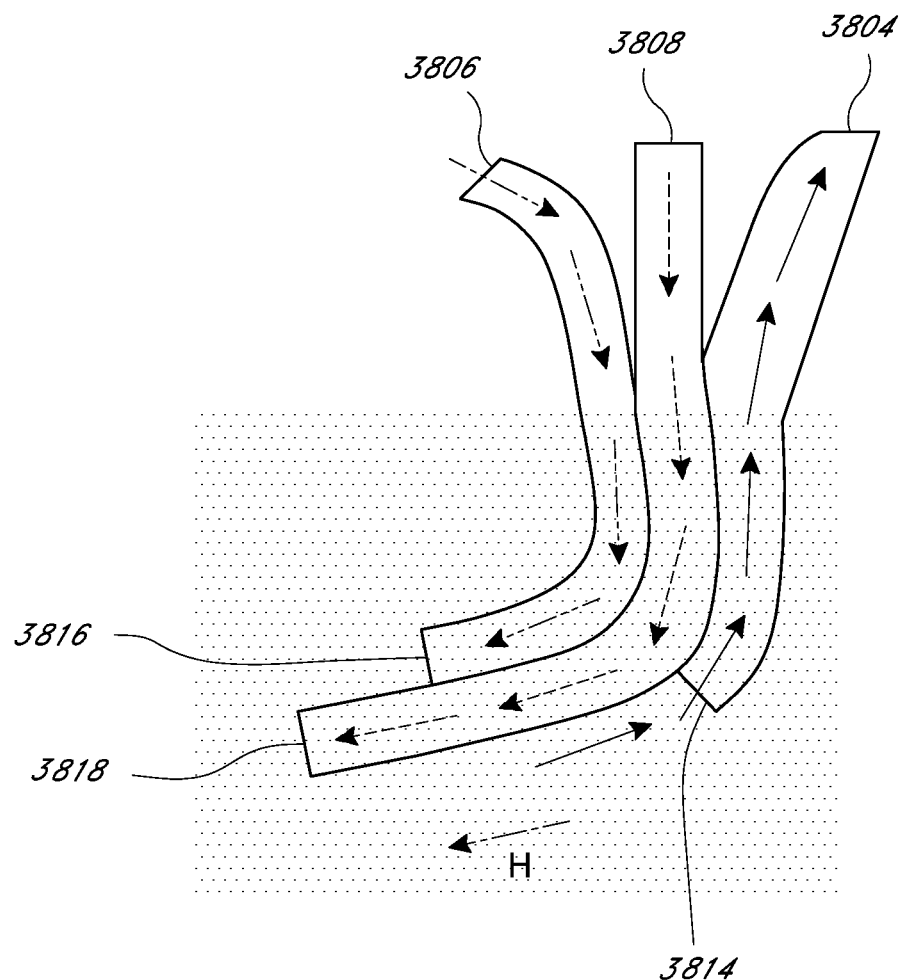

In some embodiments, as illustrated in FIG. 38D, each of the lumina of the multi-lumen catheter can be further configured to have different lengths (and possibly even different diameters) such that the fluids are introduced in different regions of the patient's vasculature—some farther upstream, and some farther downstream—to further reduce the possibility of inter-mixing between the different fluids. In FIG. 38D, the proximal port is 3804 because the opening 3814 is located proximally when compared to the more distal openings 3816 and 3818. Another method to reduce or prevent intermixing between the different fluids that can be used instead of or in addition to having lumina with different lengths can be to control the pressure and/or the flow rate at which the different fluids are introduced into the patient's vasculature.

Various blood withdrawal techniques can require high pressures (e.g. as high as 3000 psi) and/or high flow rates to withdraw blood from a patient's vasculature. Systems comprising a multi-lumen catheter may be configured such that blood can be withdrawn through one of the ports (e.g. the proximal port 3804) while infusates/infusion fluids can be infused through the other ports (e.g., medial port 3806 and distal port 3808). Withdrawing blood using high pressures and/or high flow rates can cause some of the infusates/infusion fluid to be drawn or pulled into a withdrawal port along with the withdrawn blood. This can "contaminate" the withdrawn blood. In a system where the withdrawn blood is used to determine the presence and/or the concentration of various analytes, contamination of the withdrawn blood with the infusate/infusion fluid can affect the measurement results. Thus, it may be advantageous to clamp the infusion ports (e.g. medial 3806 and distal 3808 ports) while blood is being withdrawn from the proximal port 3804 under high pressure and/or at a high flow rate since such a technique can advantageously prevent or substantially reduce the risk of contamination or mixing of the withdrawn blood with the fluids being infused.

But even clamping may not minimize or avoid undesired reversal of flow and withdrawal of substances that were located downstream of the withdrawal port (e.g., substances present in or near the infusion ports). Moreover, it may be advantageous to avoid clamping the infusion ports while blood is being withdrawn. Methods of and systems for preventing or substantially reducing the inter-mixing between the different fluids introduced into the patients' vasculature can be also useful in preventing or substantially reducing the contamination of the withdrawn blood without clamping the infusion ports.

For example, blood can be withdrawn through one of the ports of the multi-lumen catheter using an automated blood withdrawal system (e.g. an "OptiScanner®") at a controlled flow rate. For example, the system may control the flow rate such that a low flow rate and/or low pressure is used to withdraw blood. The automated blood withdrawal system can be configured to withdraw blood using a pressure between approximately 1 psi and approximately 10 psi or lower. The automated blood withdrawal system can be configured to create a pressure in the proximal port of the catheter (through which blood is withdrawn) that is between approximately 40% to approximately 99% of the pressure of blood in the vasculature thereby allowing withdrawal of blood under negative pressure. This pressure may be monitored in order to gauge whether blood or other fluids are being withdrawn at a low flow rate. A pressure sensor may be attached at various points in the system, to determine the pressure in the system and assist in maintaining it at desirable levels. The automated system can be configured to withdraw blood at a rate that is between approximately 1 mL/minute and approximately 10 mL/minute. These flow rates may be monitored directly or indirectly. Flow parameters (e.g., a pump setting) can be adjusted accordingly to allow the system to withdraw fluid at the desired rate. The automated blood withdrawal system may also use other methods to ensure blood is withdrawn at the desired flow rate and/or pressure. As discussed above, withdrawing blood rapidly at relatively high pressures (e.g. 1000-3000 psi) and/or relatively high flow rates (e.g. >10 mL/minute) from the proximal port—which is often configured to be upstream of the other port(s)—can draw the fluids being infused through the other—often downstream—ports. This can be especially likely if the rapid blood withdrawal is fast enough to cause a temporary flow reversal in the local blood stream and/or if any infusion ports are in the process of infusing (or are at least open or not clamped, for example). Indeed, rapid blood withdrawal can often result in the "contamination" of the withdrawn fluid—by inclusion of higher concentrations of the substances being infused, by unwanted dilution, etc. In contrast, the ability of the automated blood withdrawal systems described herein to withdraw blood at low pressures and/or flow rates can substantially reduce the possibility that the withdrawn blood will be "contaminated," for example by an infused fluid. Withdrawing fluid at a lower flow rate may also improve the accuracy of analyte readings if the amount of analyte in the blood at one point is not representative of the total amount of analyte in the body (e.g., for physiological reasons), as discussed supra.

In some embodiments, it may be advantageous to use a multi-lumen catheter wherein the multiple lumina can be further configured to have different lengths and different diameters such that in combination with low withdrawal pressures and/or withdrawal rates, a small negative pressure can be created in the proximal port and/or region surrounding the proximal port which can further reduce or eliminate the contamination of the withdrawn fluid from the fluids infused in the other lumina of the catheter.

It can be advantageous to measure dilution of withdrawn fluids in order to determine the effectiveness of systems and methods for minimizing dilution. For example, the systems and methods described herein can reduce dilution to 20%, to 10%, to 5%, or, in some embodiments, to approximately 0%, effectively eliminating dilution. These results can be achieved by withdrawing blood at a location far from an infusion port, or by controlling—usually by lowering—the rate of withdrawal. Automated blood withdrawal systems can be especially helpful in achieving steady, low flow rates and/or pressures at the proximal port (through which blood is withdrawn), since a motor controlling a pump, for example, can be more precisely and systematically controlled than the movements of a nurse's muscles in withdrawing fluids into a syringe. Accordingly, the automated systems described herein can reduce the risk that infusate contaminants from the medial and/or distal ports are included in withdrawn blood.

Automated fluid withdrawal may be measured, controlled, or described according to flow rate. Withdrawal can be achieved at a constant rate, where the rate of withdrawing blood is low enough to reduce the presence of infusate contaminants being withdrawn through the proximal port. The withdrawal of blood may also be done at a variable rate to reduce the presence of infusate contaminants being withdrawn through the proximal port. The rate at which blood is withdrawn may be controlled to correspond to activity at other lumina of a multi-lumen catheter. For example, a system may reduce the rate of blood withdrawal when large amounts of infusates are being infused into the blood stream at another port. A system may also adjust the rate at which blood is withdrawn based upon the type of infusates that are being infused at other ports. For example, the system may withdraw blood at a lower rate when infusates that are more likely to affect the accuracy of an analyte measurement are being infused.

Automated fluid withdrawal may be measured, controlled, or described according to pressure. For example, blood withdrawal can be achieved at a constant pressure. The pressure at the proximal port or within an inner lumen of a tube attached to the proximal port may be maintained at some fixed pressure, where the pressure is low enough to reduce the presence of infusate contaminants being withdrawn through the proximal port. A pressure monitor may be used to help maintain pressure at a desirable level. Blood may also be withdrawn at variable pressures to reduce the presence of infusate contaminants being withdrawn through the proximal port. For example, the pressure at which blood is withdrawn may be automatically controlled to correspond to activity at other lumina of a multi-lumen catheter. It may be useful to use a system that is able to adjust the pressure that blood is withdrawn according to the rate that infusates are being infused into the blood stream from other lumina. A system may also adjust the pressure at which blood is withdrawn based upon the type of infusates that are being infused at other ports. For example, the system may withdraw blood at a lower pressure when infusates that are more likely to affect the accuracy of an analyte measurement are being infused.

Controlling the rate and/or pressure at which fluid is withdrawn may reduce or avoid contamination, and thereby reduce any effect that potential infusate contaminants may have on an analyte reading taken on withdrawn fluid. Infusate contaminants can be especially troublesome in a system where the infused substance is, or directly affects, the analyzed substance. For example, a glucose measurement system drawing blood from a withdrawal port can produce very inaccurate readings if nearby infusion ports are concurrently infusing glucose, dextrose, insulin, etc. Accordingly, it can be very advantageous to lower the effect of such contamination and achieve a 20% difference in the accuracy of the analyte reading due to contamination effects. It can be even more advantageous to achieve even better accuracy and reduce contamination effects further yet. For example, the infusate contaminants may cause only a 2, 4, 5, 10, 15, or 20% difference in the accuracy of the analyte reading from the withdrawn fluid.

The flow rate and/or pressure that is needed to achieve a certain difference in the accuracy of the analyte reading from the withdrawn fluid may depend upon numerous factors. For example, the distance between the proximal port and the other ports may impact the flow rate and/or pressure needed to achieve a certain accuracy of the analyte reading. If the proximal port is further away from the other ports, a somewhat higher pressure and/or flow rate may be used to withdraw fluid without creating excessive infusate contamination. The analyte that is being measured may affect the flow rate and/or pressure needed to maintain a certain accuracy in analyte readings. Some analytes may be more or less prone to inaccurate analyte measurements due to the presence of contaminants. The type of infusates being infused may impact the flow rate and/or pressure that fluid may be withdrawn at. Certain infusates may be more likely to promote inaccurate analyte readings than others. For example, if the analyte that is being measured is the same as an infusate that is being infused in another port, it may be necessary to use even lower flow rates and/or pressures than normal in order to achieve analyte readings with a desired level of accuracy. For example, if the analyte to be measured is glucose, and if glucose is being infused at a downstream port, it may be useful to withdraw fluid at a very low pressure and/or flow rate because if the withdrawn fluid contains infused glucose, the glucose reading may be too high. The amount of infusate being infused may affect the flow rate and/or pressure needed to maintain a certain accuracy in analyte readings. For example, if a relatively large amount of infusate is being infused at a high rate, it may be necessary to withdraw fluid at a lower pressure and/or flow rate than if a smaller amount of infusate is being infused at a lower rate. The flow rate of the fluid may also affect the flow rate and/or pressure that fluid may be withdrawn at. If a fluid has a high flow rate, infusates that enter at a downstream port may be carried away from the proximal port more quickly and effectively, and therefore, a slightly higher flow rate and/or pressure may be used to withdraw fluid without adversely affecting the accuracy of the analyte reading.

The expected level of the analyte to be measured may also affect the flow rate and/or pressure at which fluid may with withdrawn. If the levels of an analyte in the bloodstream is extremely low, for example 50 ppm, then in may be more important to avoid infusate contamination in the withdrawn fluid. This may be especially true when the infusate is the same chemical as the analyte to be measured. In this instance, if even a small amount of infusate from a downstream port traveled to the proximal port and into the withdrawn fluid, it could dramatically alter the accuracy of the analyte reading. In this situation, infusate contamination is a much more serious problem, as it will cause a much higher error in the analyte measurement than would be caused when the infusate is merely diluting the withdrawn fluid (which may slightly decrease the analyte reading). Thus, if an analyte level is very low, it may be useful to use a very low flow rate and/or pressure when withdrawing fluid from the proximal port. For example, if the infusate and the analyte being measured are glucose, and if the level of glucose in a blood stream is extremely low, it can be vitally important to be able to accurately measure glucose levels as discussed above under the heading ANALYTE CONTROL MONITORING.

Therefore, it may be necessary in this situation to withdraw fluid at a very low flow rate and/or pressure, to minimize contamination in the withdrawn fluid. There may also be other factors that affect the pressure and/or flow rate that fluid should be withdrawn at in order to achieve the desired level of accuracy in an analyte reading.

In various methods and systems as described herein, it can be observed that by using the fluid withdrawal techniques discussed herein, the amount of infusate contaminants in the withdrawn blood can be very low—for example in the range of 10, 20, 30, 100, or 1000 parts per million. However, such volumetric expressions of contamination reduction can be less useful than percentage expressions, since, as noted above, some contaminants affect an analyte measurement more directly (e.g., if glucose is the analyte and glucose, dextrose, and/or insulin are the contaminant, for example). Thus, one useful measure of the advantages of the described systems and methods is by how they improve the accuracy of an analyte measurement itself. The systems and methods described herein can reduce the effects of contaminants in the withdrawn fluid such that there is only a 20%, 15%, 10%, 5%, 4%, 2%, and/or 0% difference in the underlying analyte measurement.

The relative sizes of adjoining tubular structures can be used to provide desired changes in fluid velocity and/or pressure. For example, a tube with a small inner diameter may have a lower flow rate than a larger tube at the same pressure. A system may be designed which uses a variety of diameters of tubes in order to achieve desirable flow rates. In some cases, however, the relative sizes of adjoining tubular structures can introduce factors that must be overcome or compensated for using other aspects of the device, method, or system. For example, if a tube to which a fluid pump is immediately attached later communicates with a tube having a smaller diameter, a pumping action can cause a pressure in the immediately attached tube that is lower than the pressure in the more distant tube. Indeed, if the proper conditions are met (e.g., laminar flow, presence or absence of other flow paths, etc.), the relative fluid velocities, pressures, etc. in connected tubes can be determined using Bernoulli's equations, in a similar fashion as flow in a Venturi tube is calculated and modeled using principles of hydraulic systems. The practical consequence of this can be that a system of tubes having a greater diameter at the in-patient opening than at the immediate pump interface can have a lower pressure at the in-patient opening than at the immediate pump interface. In this way, system design having a larger opening in the patient can allow even lower pressures at that point than may otherwise be possible using the same pump. On the other hand, a system of tubes having a smaller diameter at the in-patient opening than at the immediate pump interface can have a higher pressure at the in-patient opening than at the immediate pump interface. Thus, in order to have a low pressure for fluid intake at a relatively very small in-patient opening, the pump may need to operate at an even lower pressure than would be called for if the tube had the same diameter at the pump and at the in-patient opening.

Free Flow Protection Subsystem

As discussed above, various embodiments of analyte monitoring systems such as the analyte monitoring system 100 (e.g. an "OptiScanner®") can be attached or connected to a patient. When the fluid source is a living entity such as a patient, a low flow of saline (e.g., 1-5 mL/hr) is preferably moved through the patient tube 512 (T1) of FIG. 5 and into the patient to keep the patient's vessel open (e.g., to establish a keep vessel open, or "KVO" flow). This KVO flow can be temporarily interrupted when fluid is drawn into the fluid system 510 illustrated in FIG. 5. The source of this KVO flow can be the infusion pump 518 shown in FIG. 5, the third pump 568 (pump #3) shown in FIG. 5, or the first pump 522 (pump #1) shown in FIG. 5. In various embodiments, a flow of an infusion fluid including infusates such as glucose, insulin or other medications can be also provided to the patient through the patient tube 512 of FIG. 5. The flow of the KVO fluid and/or the infusion fluid can be controlled by various valves e.g. pinch valve 521 and 542 shown in FIG. 5. As discussed above with reference to FIG. 6, in some embodiments, the pinch valves 521 and 542 may be located on the door of the analyte monitoring system. In some embodiments, when the door of the analyte monitoring system is open, the pinch valves may not be capable of controlling the flow of the KVO and/or the infusion fluid. In such instances, to prevent the free flow of the KVO and/or the infusion fluid into the patient, a free flow protection sub-system may be provided. The free flow protection sub-system is further described below with reference to FIGS. 39-42.

Figure 39:
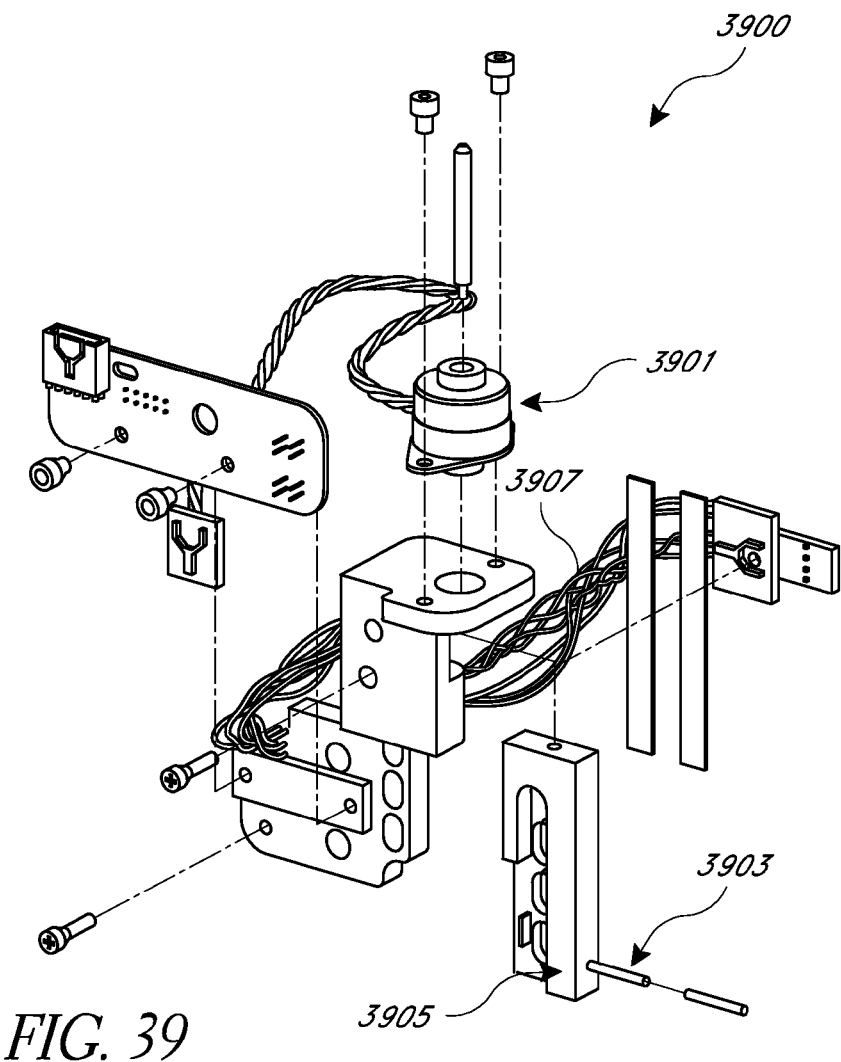
FIG. 39 schematically illustrates an embodiment of a free flow protection sub-system.

The free flow protection (FFP) sub-system 3900 illustrated in FIG. 39 comprises a motor 3901 which moves a pin 3903 that pushes on a FFP device 3905. In various embodiments, the FFP device 3905 may interface with a disposable (e.g. disposable system 408 of FIG. 4, removable portion 710 of FIG. 7, disposable portion 804 of FIG. 8, etc.) and be configured to pinch off or control the flow of fluids through the patient tube 3907 (which can be similar to the patient tube 512 (T1) of FIG. 5). In various embodiments, the FFP device 3905 can be configured to shut-off or control the flow of KVO and/or infusion fluids through the patient and thus avoid or substantially reduce free flow of infusion fluids.

Figure 40A:
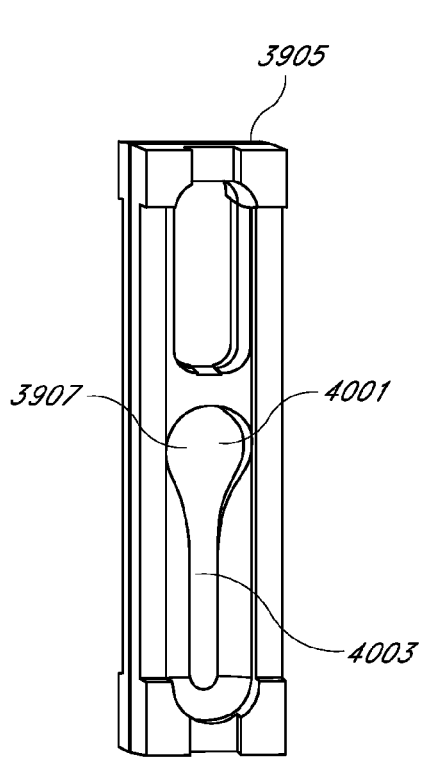
FIGS. 40A and 40B schematically illustrate embodiments of a free flow protection device which is included in the free flow protection system.
Figure 40B:
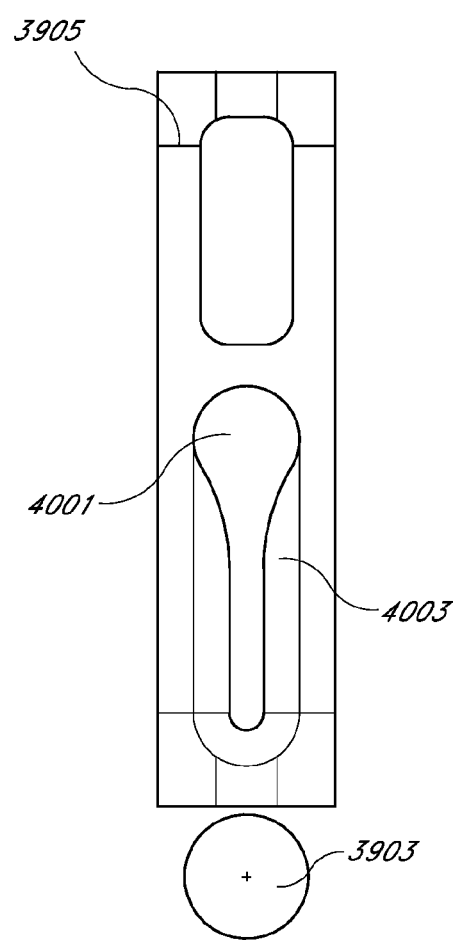

FIGS. 40A and 40B schematically illustrate an embodiment of the FFP device 3905. The FFP device 3905 can include a widened portion 4001 and a narrowed portion 4003. In the normal, non-actuated or load position of the FFP device 3905, the pin 3903 (also referred to as the trigger pin) is configured to slide underneath the FFP device 3905 as shown in FIG. 40B and the patient tube 3907 (e.g. tube 512 of FIG. 5) runs through the widened portion 4001 of the FFP device such that the flow through the tube is not restricted as shown in FIGS. 40 A and 40 B.

When the FFP device is actuated (e.g. when the door is opened), the pin 3903 is configured to move upwards to an actuated position and pushes the FFP device 3905 upwards, such that the patient tube 3907 is crimped by the narrowed portion 4003 of the FFP device 3905 thus restricting the flow of fluid through the patient tube 3907. When the door is closed the pin 3903 goes back to its normal, non-actuated position.

Figure 41A:
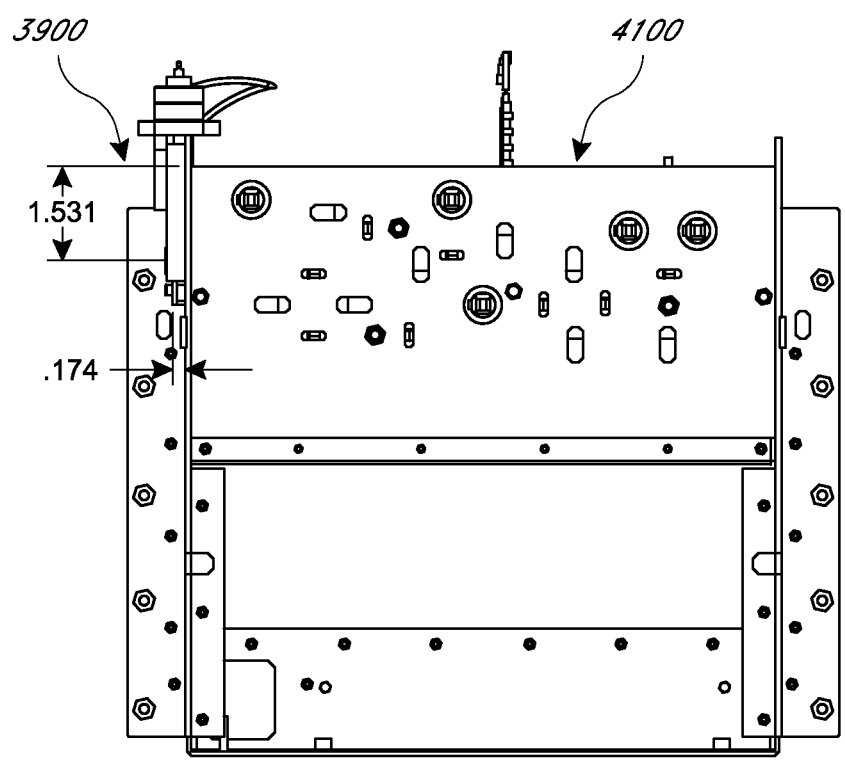
FIGS. 41A and 41B schematically illustrate embodiments of a free flow protection system interfaced with a disposable.
Figure 41B:
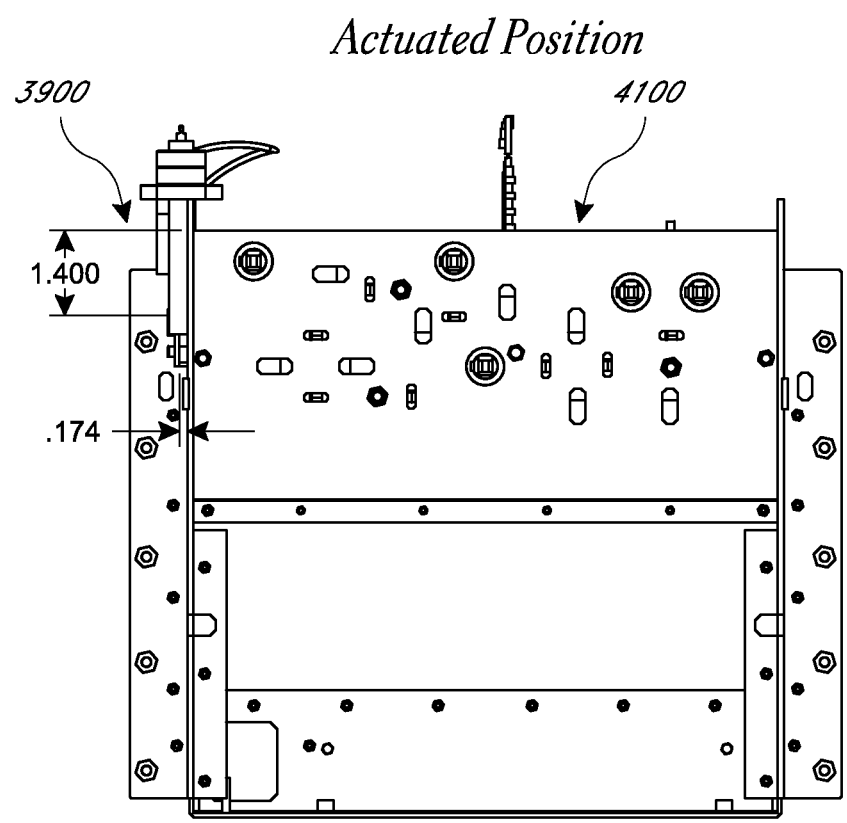

FIGS. 41A and 41B schematically illustrate an embodiment of the FFP sub-system 3900 interfaced with a disposable 4100. The FFP sub-system interfaces with the disposable 4100 such that the FFP device 3905 is located in the tubing carrier portion of the disposable that interfaces or includes the patient tube 3907 (e.g. tube 512 of FIG. 5). As illustrated in FIGS. 41A and 41B, the pin 3903 of the FFP sub-system 3900 is configured to move between two positions: a load position and an actuated position. In various embodiments, the difference between the load and the actuated positions can be approximately 0.1 inches to approximately 0.15 inches. As described above, in its normal position, non-actuated or load position the FFP device 3905 does not interfere with the disposable the loading process. While it is in its actuated position, the FFP device is configured to pinch the patient tube 3907. Upon loading, the tube sections in the tubing carrier portion of the disposable align with (e.g., can register off of) the pins in the pinch zone assembly of the analyte monitoring system.

Figure 42A:
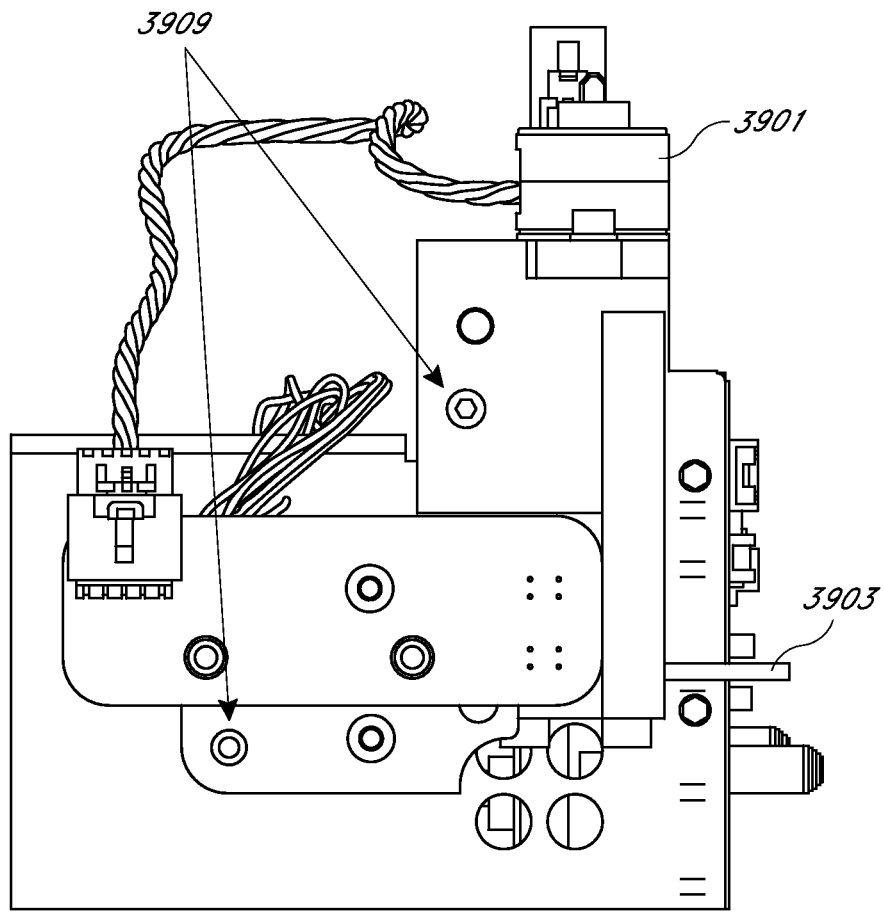
FIGS. 42A-42C schematically illustrate embodiments of a free flow protection system interfaced with an analyte monitoring system.
Figure 42B:
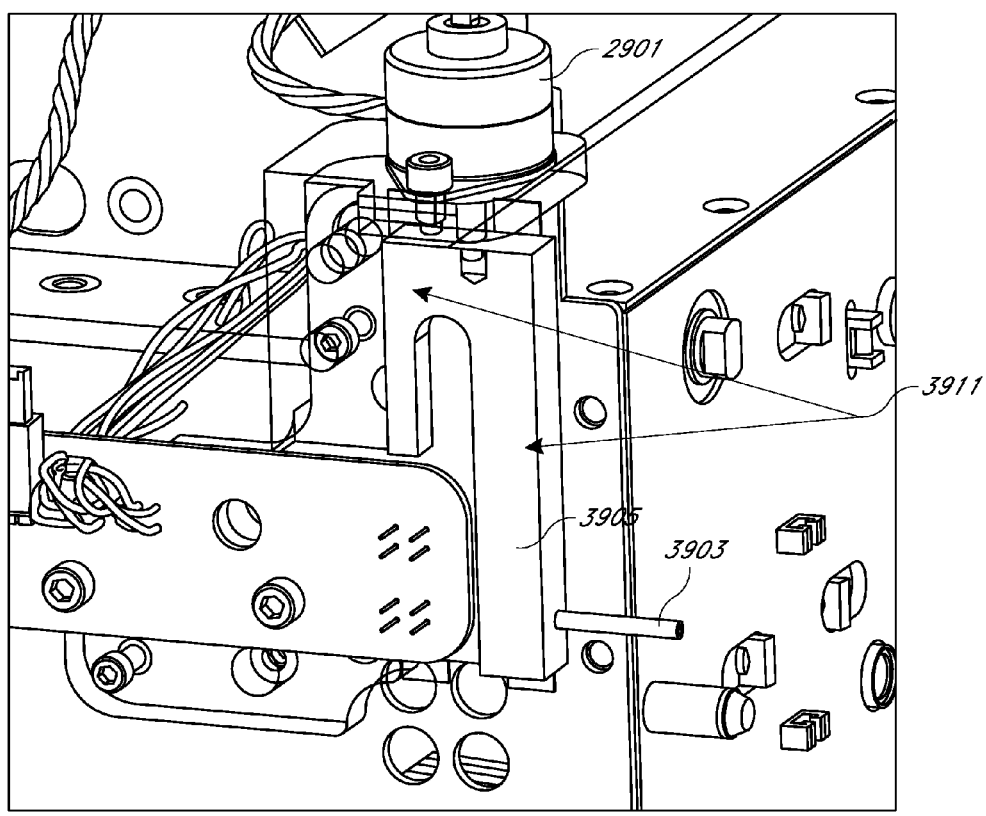
Figure 42C:
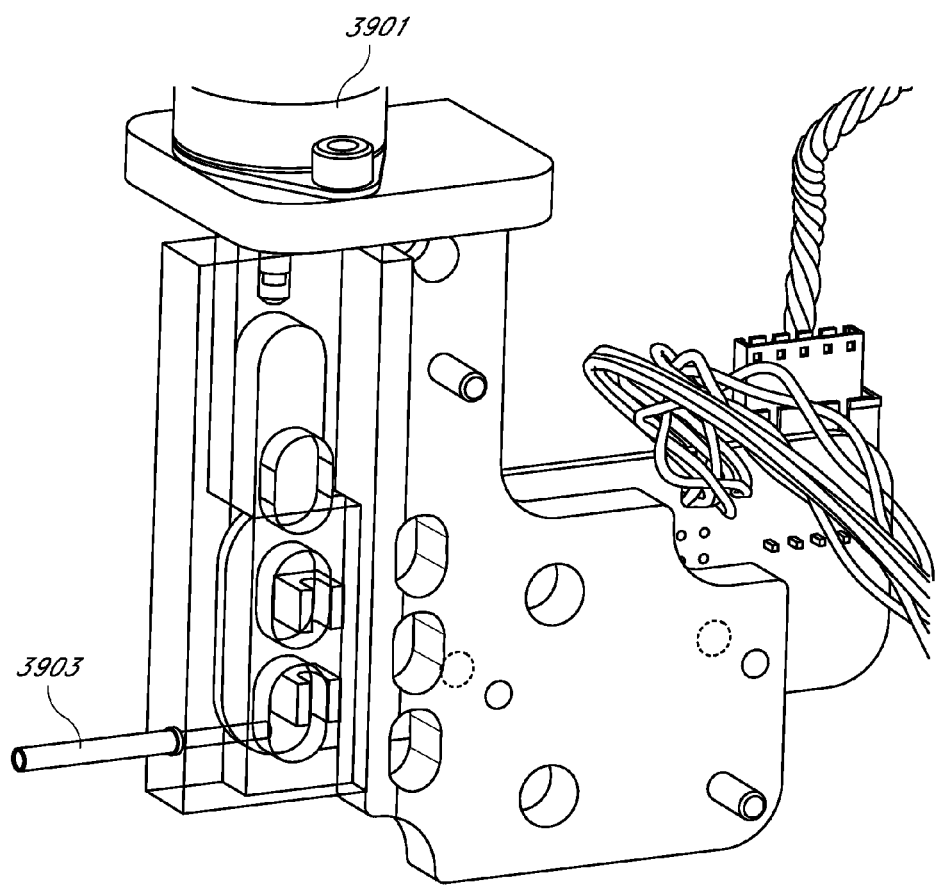

FIGS. 42A-42C schematically illustrate a FFP sub-system mounted to the analyte monitoring system. As illustrated in FIG. 42A, in some embodiments, the FFP sub-system comprises a variety of mounting points 3909 which are used to mount the FFP sub-system to a side of the analyte monitoring system by using bolts. In various embodiments, as illustrated in FIG. 42A, Teflon tape 3911 may be provided between the FFP device 3905 and the surface of the analyte monitoring system to prevent from wearing the FFP device down by the rough surface of the analyte monitoring system. In some embodiments, the FFP subsystem may comprise optical sensors 3913 as shown in FIG. 42C which are located at the load and the actuated positions of the FFP device 3905. The optical sensors can be used to control the movement of the FFP device 3905 between the load and the actuated positions. For example, in some embodiments, the FFP device 3905 moves from the load position to the actuated position and/or from the actuated position to the load position until one of the optical sensors is tripped (or changes state).

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Embodiments of the disclosed systems and methods may be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may be comprised of connected logic units, such as gates and flip-flops, and/or may be comprised of programmable units, such as programmable gate arrays, application specific integrated circuits, and/or processors. The modules described herein are preferably implemented as software modules, but may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

A number of applications, publications, and external documents may be incorporated by reference herein. Any conflict or contradiction between a statement in the body text of this specification and a statement in any of the incorporated documents is to be resolved in favor of the statement in the body text.

Although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. A fluid analysis system comprising:
a fluid handling system that includes a patient end configured to provide access to a bodily fluid of a patient, wherein the fluid handling system is configured to draw a sample of bodily fluid from the patient through the patient end;
a sample preparation system in fluid communication with the fluid handling system, the sample preparation system comprising a cuvette, the cuvette comprising:
a first window piece;
a second window piece;
a spacer positioned between the first window piece and the second window piece to provide a gap between the first window piece and the second window piece; and
a first clamping element and a second clamping element positioned on opposite sides of the window pieces, wherein the first and second clamping elements are secured to each other to provide support to the first and second window pieces;
wherein the sample preparation system is configured to:
receive a portion of the sample of bodily fluid from the fluid handling system; and
separate the portion of the sample of bodily fluid into a plurality of components; and
a fluid measurement system configured to measure the concentration of an analyte in the portion of the sample of bodily fluid.

2. The fluid analysis system of claim 1, wherein the bodily fluid comprises blood that includes red blood cells.

3. The fluid analysis system of claim 2, wherein the sample preparation system comprises a filter configured to separate the red blood cells from plasma of the blood.

4. The fluid analysis system of claim 2, wherein the sample preparation system comprises a centrifuge configured to separate the red blood cells from plasma of the blood.

5. The fluid analysis system of claim 1, wherein the fluid measurement system comprises an optical measurement system.

6. The fluid analysis system of claim 5, wherein the first window piece comprises an aperture portion that is transparent to light emitted by the optical measurement system, and wherein the second window piece comprises an aperture that is transparent to light emitted by the optical measurement system.

7. The fluid analysis system of claim 6, wherein the first and second clamping elements comprise openings that align with the transparent aperture portions of the first and second window pieces such that the light emitted by the optical measurement system can pass through the cuvette.

8. The fluid analysis system of claim 1, comprising:
a fluid passage having a tip configured to mate with a multi-lumen catheter without leaking, the multi-lumen catheter having:
a proximal port communicating with a proximal port lumen that provides a fluid path to a proximal intravascular opening that is configured to open into a vessel having a fluid flow; and
a distal port communicating with a distal port lumen that is independent from and not in fluid communication with the proximal port lumen and that provides a fluid path to a distal intravascular opening that is configured to open into the vessel distal of and downstream from the proximal intravascular opening to infuse infusates;
a fluid pressure system in fluid communication with the fluid passage, the fluid pressure system configured to periodically automatically draw fluid from the vessel through the proximal intravascular opening and the proximal port and through the tip back into the fluid passage while maintaining a low pressure and/or flow rate to thereby reduce risk of reversing the fluid flow in the vessel and drawing infusates back upstream into the proximal intravascular opening.

9. The fluid analysis system of claim 8, wherein the fluid pressure system comprises a controller and a pressure monitor that provides feedback to the controller.

10. The fluid analysis system of claim 9, wherein the controller is configured to maintain the withdrawal pressure below 99% of the pressure of blood in the vessel.

11. The fluid analysis system of claim 9, further comprising a patient blood pressure monitor that provides feedback to the controller to allow a baseline for comparison to the withdrawal pressure.

12. The fluid analysis system of claim 9, wherein the pressure monitor is configured to monitor the pressure at or near the proximal port.

13. The fluid analysis system of claim 8, wherein the fluid pressure system is configured to maintain a constant rate for the majority of the time blood is being withdrawn through the proximal port.

14. The fluid analysis system of claim 8, wherein the fluid pressure system is configured to adjust the withdrawal rate to be lower when infusates are being infused through the distal port.

15. The fluid analysis system of claim 1, wherein the aperture portions of the first and second window pieces are transparent to mid-infrared light.

16. The fluid analysis system of claim 1, wherein the openings in the first and second clamping elements comprise holes with closed edges.

17. The fluid analysis system of claim 1, wherein the entire periphery of the window pieces except for an inlet and an outlet are covered by the first or second clamping elements.

18. The fluid analysis system of claim 1, wherein the window pieces have a plurality of corners and wherein the window pieces are bound on each corner by a side wall of the first or second clamping element such that the window pieces are held securely in place.

19. The fluid analysis system of claim 1, wherein the first and second clamping elements are secured using an adhesive that extends substantially around the entire periphery of the window pieces except for at an inlet and at an outlet.

20. The fluid analysis system of claim 1, wherein the first and second clamping elements apply a force to press the first and second window pieces towards each other.

* * * * *